(12) United States Patent
Chakraborty et al.

(10) Patent No.: US 11,970,699 B2
(45) Date of Patent: Apr. 30, 2024

(54) KINETICALLY ENHANCED ENGINEERED FNCAS9 AND ITS USES THEREOF

(71) Applicant: COUNCIL OF SCIENTIFIC & INDUSTRIAL RESEARCH, New Delhi (IN)

(72) Inventors: Debojyoti Chakraborty, Delhi (IN); Souvik Maiti, Delhi (IN); Sundaram Acharya, Delhi (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 18/049,291

(22) Filed: Oct. 25, 2022

(65) Prior Publication Data

US 2023/0146664 A1     May 11, 2023

Related U.S. Application Data

(63) Continuation of application No. 17/853,353, filed on Jun. 29, 2022, now abandoned.

(30) Foreign Application Priority Data

Jun. 29, 2021  (IN) .............................. 202111029109

(51) Int. Cl.
*C12N 15/52*     (2006.01)
*C12N 9/22*      (2006.01)

(52) U.S. Cl.
CPC ............... *C12N 15/52* (2013.01); *C12N 9/22* (2013.01); *C12N 2310/20* (2017.05)

(58) Field of Classification Search
CPC ...... C12N 15/52; C12N 9/22; C12N 2310/20; C12N 9/52; C12N 15/113
See application file for complete search history.

(56) References Cited

U.S. PATENT DOCUMENTS

2021/0269801 A1* 9/2021 Weiss .................. C12N 15/102
2021/0309995 A1* 10/2021 Rawlings ............... C12N 15/11

OTHER PUBLICATIONS

Addgene plasmid # 130969 (Year: 2019).*
Hirano, Hisato, et al. "Structure and engineering of Francisella novicida Cas9." Cell 164.5 (2016): 950-961 (Year: 2016).*
RCSB Accession 5B2O (Year: 2016).*
Sander, et al., "CRISPR-Cas systems for editing, regulating and targeting genomes", Nature Biotechnology, vol. 32, No. 4, pp. 347-355, 2014.
Doudna, et al., "The new frontier of genome engineering with CRISPR-Cas9", Genome Editing, vol. 346, Issue 6213, pp. 1-11, Nov. 2014.
Mojica, et al., "Short motif sequences determine the targets of the prokaryotic CRISPR defence system", Microbiology, vol. 155, pp. 733-740, pp. 1-8, 2009.
Shah, et al., "Protospacer recognition motifs", RNA Biology, vol. 10, No. 5, pp. 891-899, May 2013.
Jinek, et al., "A programmable dual RNA-guided DNA endonuclease in adaptive bacterial immunity", Science, Howard Hughes Medical institute, vol. 337, No. 6096, pp. 816-821, Aug. 17, 2012.
Sternberg, et al., "DNA interrogation by the CRISPR RNA-guided endonuclease Cas9", Nature Article, vol. 507, pp. 1-17, Mar. 6, 2014.
Acharya, et al., "Francisella novicida Cas9 interrogates genomic DNA with very high specificity and can be used for mammalian genome editing", PNAS, vol. 116, No. 42, pp. 1-10, Oct. 15, 2019.
Hirano, et al., "Structure and Engineering of Francisella novicida Cas9", Cell, vol. 164, No. 5, pp. 950-961, Feb. 25, 2016.
Nishimasu, et al., "engineered CRISPR-Cas9 nuclease with expanded targeting space", Biotechnology, vol. 361, pp. 1259-1262, Sep. 21, 2018.

* cited by examiner

*Primary Examiner* — Neil P Hammell
*Assistant Examiner* — Kyle Thomas Rega
(74) *Attorney, Agent, or Firm* — Dinsmore & Shohl, LLP

(57) ABSTRACT

Engineered FnCas9 variants are provided that have an enhanced kinetic activity and a broader PAM recognition. The protein engineering methodology introduced specific mutations that stabilized interaction between Cas9 enzyme and target DNA. The enhanced kinetic activity increases NHEJ-mediated editing, owing to more efficient DSB generation potential than WT FnCas9, and the broadened PAM specificity increases the target range of FnCas9 variants. Thus, the scope and accessibility of CRISPR-Cas9 system targets are widened, along with generating robust and highly specific engineered FnCas9 variants.

8 Claims, 23 Drawing Sheets

Specification includes a Sequence Listing.

FC - Full Complement

An example for a hemoglobin disorder is as follows:

KINETICALLY ENHANCED ENGINEERED FNCAS9 AND ITS USES THEREOF

CROSS-REFERENCES TO RELATED APPLICATIONS

This application is a continuation under 35 U.S.C. § 111(a) of U.S. patent application Ser. No. 17/853,353, filed Jun. 29, 2022, which claims benefit of priority under 35 U.S.C. § 119 to Indian Patent Application No. 202111029109, filed Jun. 29, 2021, both of which applications are incorporated by reference herein in their entireties.

SEQUENCE LISTING

The contents of the electronic sequence listing having file name EnFnCas9-CSIR0078NA.xml (701,842 bytes), created Oct. 25, 2022, is incorporated herein by reference. The nucleic acid sequences and amino acid sequences listed in the accompanying sequence listing are shown using standard abbreviations as defined in 37 C.F.R. § 1.822.

TECHNICAL FIELD

The present disclosure provides a kinetically enhanced engineered fncas9 and a method for gene editing using the engineered Cas9 protein obtained from *Francisella novicida*. This engineered version of FnCas9 (enFnCas9) has a faster kinetics, stronger binding and a broader PAM binding specificity compared to wild type FnCas9 which widens the use of CRISPR-Cas for gene targeting. The applications of enFnCas9 are diverse and have potential impact for advancements in the following but not limited to these settings: health sector, pharmaceuticals, agriculture, biotechnology, and food sector.

BACKGROUND

CRISPR-Cas system has revolutionized the gene editing technology making it easier to dissect out molecular pathways, understanding functions by controlling expression and correcting mutations with a potential to treat multiple genetic diseases. The major limitations of the CRISPR-Cas system include the off-target effects and the limitation of targeting being restricted by the requirement of a specific PAM sequence.

SUMMARY

Accordingly, the present disclosure relates to an engineered Cas9 protein from *Francisella novicida* (FnCas9) that has enhanced kinetic activity. The engineered Cas9 has higher activity on a polynucleotide with respect to binding and cleavage of the target. The engineered variant will also have a very high specificity to mismatches in the target making it suitable for fields such as but not limited to therapeutic genome editing, disease diagnosis and genome regulation. The higher kinetic activity of the engineered protein will enable editing of nucleotide loci previously inaccessible to the enzyme.

The principal objective of this disclosure is to provide a kinetically enhanced engineered fncas9.

Another objective of this disclosure is to provide a method for gene editing using the engineered Cas9 protein obtained from *Francisella novicida* and develop a highly precise, efficient, and PAM-flexible gene editing method.

Another objective of this disclosure is to provide use of the gene editing tools to correct pathogenic mutations inside eukaryotic cells.

Another objective of this disclosure is to use the gene editing method for modifying nucleic acids under in vivo conditions.

Another objective of this disclosure is to use the method for detecting the presence of pathogenic nucleotide sequences.

Another objective of this disclosure is to use the method for discriminating between two similar nucleotide sequences.

DETAILED DESCRIPTION

Figure 1:
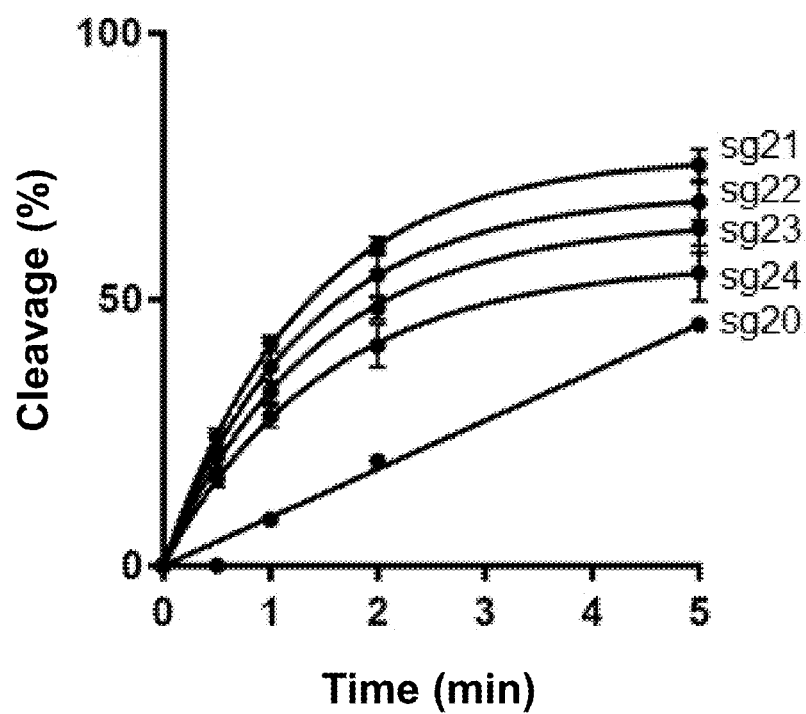
FIG. 1: In-vitro cleavage activities of Wild-type (WT) FnCas9 (SEQ ID NO:1) with sgRNA bearing 20-24-nt long guide-RNA (sg20-24, SEQ ID NOS:198-202). Cleavage activity is shown by percent cleavage (y-axis) as a function of time (x-axis).
Figure 2:
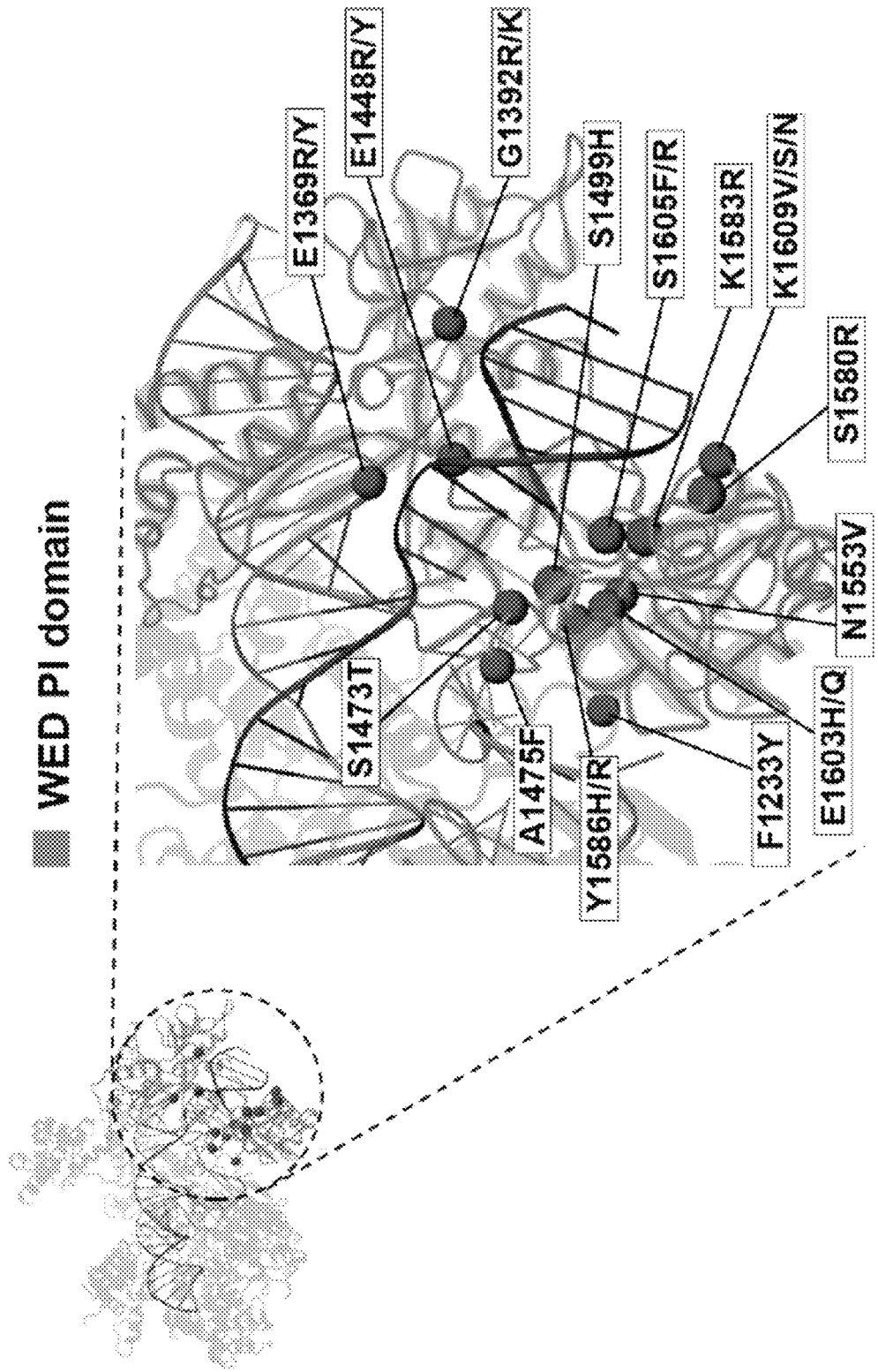
FIG. 2: Crystal structure of FnCas9 (PDB: 5B2O) with highlighted WED-PI domain. WED-PI domain is zoomed in to show amino acid residues changed for engineering purposes.
Figure 3:
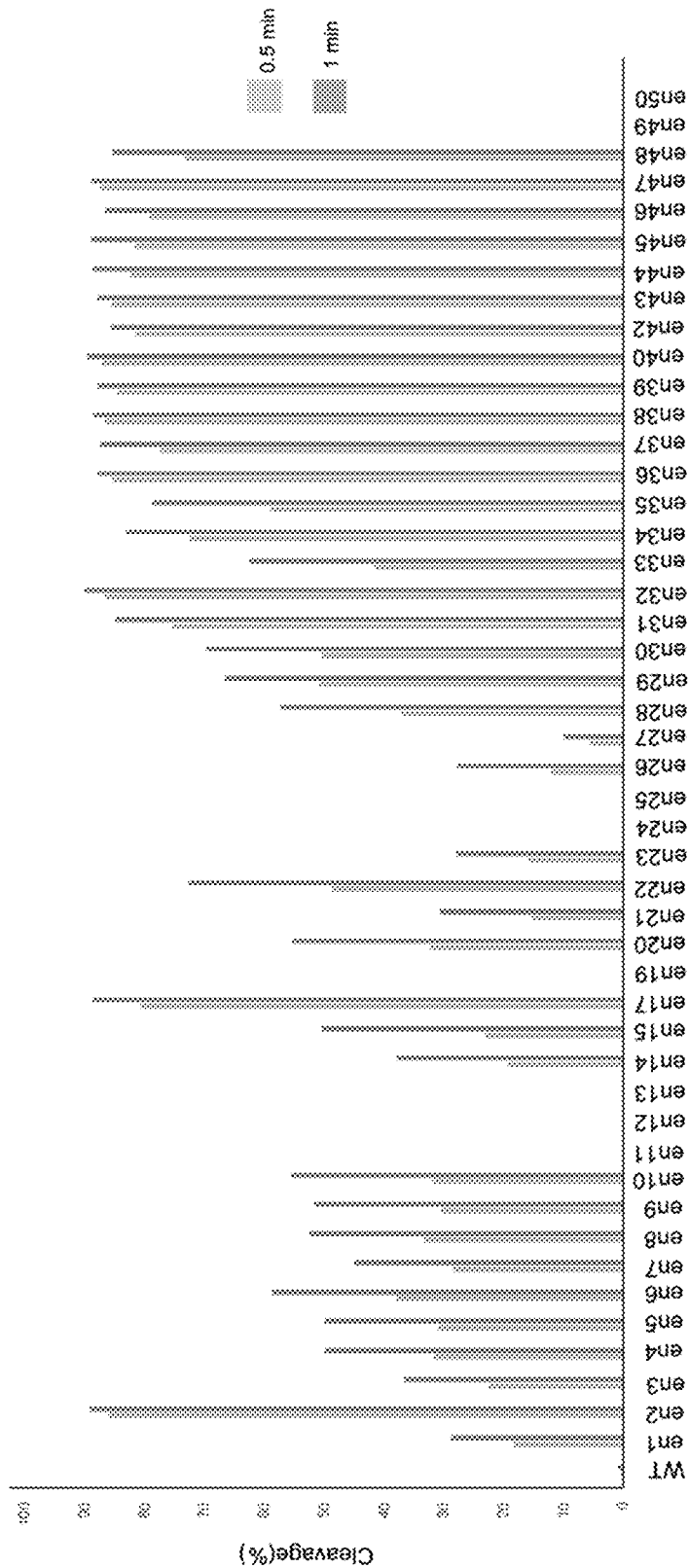
FIG. 3: Bar Plot of percent cleavage (y-axis) vs time (x-axis) showing the in vitro cleavage screening of FnCas9 (WT; SEQ ID NO:1) and enFn variants (en1 (SEQ ID NO:2), en2 (SEQ ID NO:3), en3 (SEQ ID NO:4), en4 (SEQ ID NO:5), en5 (SEQ ID NO:6), en6 (SEQ ID NO:7), en7 (SEQ ID NO:8), en8 (SEQ ID NO:9), en9 (SEQ ID NO:10), en10 (SEQ ID NO:11), en11 (SEQ ID NO:12), en12 (SEQ ID NO:13), en13 (SEQ ID NO:14), en14 (SEQ ID NO:15), en 15 (SEQ ID NO:16), en17 (SEQ ID NO:17), en19 (SEQ ID NO:19), en20 (SEQ ID NO:20), en21 (SEQ ID NO:21), en22 (SEQ ID NO:22), en23 (SEQ ID NO:23), en24 (SEQ ID NO:24), en25 (SEQ ID NO:25), en26 (SEQ ID NO:26), en27 (SEQ ID NO:27), en28 (SEQ ID NO:28), en29 (SEQ ID NO:29), en30 (SEQ ID NO:30), en31 (SEQ ID NO:31), en32 (SEQ ID NO:32), en33 (SEQ ID NO:33), en34 (SEQ ID NO:34), en35 (SEQ ID NO:35), en36 (SEQ ID NO:36), en37 (SEQ ID NO:37), en38 (SEQ ID NO:38), en39 (SEQ ID NO:39), en40 (SEQ ID NO:40), en42 (SEQ ID NO:42), en43 (SEQ ID NO:43), en44 (SEQ ID NO:44), en45 (SEQ ID NO:45), en46 (SEQ ID NO:46), en47 (SEQ ID NO:47), en48 (SEQ ID NO:48), en49 (SEQ ID NO:49), and en50 (SEQ ID NO:50))) using GGG PAM containing DNA substrate expressed as cleavage percentage for 0.5 and 1 min.
Figure 4:
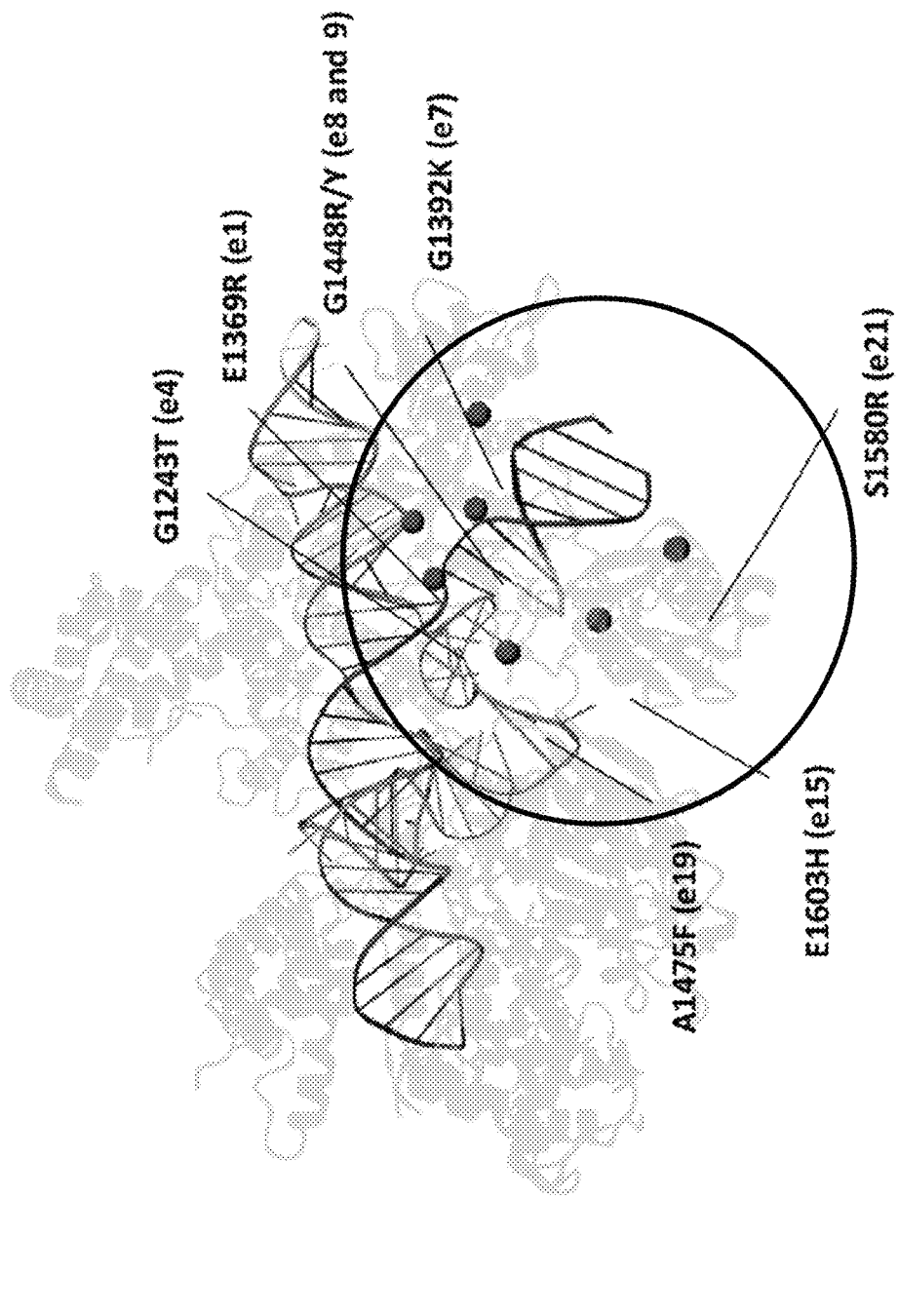
FIG. 4: Crystal structure of FnCas9 (PDB: 5B2O) showing amino acid positions of chosen FnCas9 variants from in-vitro cleavage screening assay. The WED-PI domain is highlighted by a dotted circle.

Embodiments herein are directed to ribonucleoprotein complexes for gene editing, to variants including the ribonucleoprotein complexes, to methods for gene editing by the ribonucleoprotein complex, to methods for base editing by the ribonucleoprotein complex, and to kits for gene editing including the ribonucleoprotein complexes.

Ribonucleoprotein complexes comprise or consist of (a) an engineered FnCas9 protein effector selected from the group consisting of SEQ ID NOS:2-197; and (b) a chimeric single guide RNA (sgRNA), comprising: a crispr RNA (crRNA), wherein the crRNA is transcribed in vitro using a DNA sequence selected from the group consisting of SEQ ID NOS:198-215, and a trans-activating crispr RNA (tracrRNA) having SEQ ID NO:305.

In non-limiting examples, the ribonucleoprotein complex may be bound to a PAM sequence selected from the group consisting of NGG, NGA, GGA, and GGG.

In non-limiting examples, the engineered FnCas9 protein effector of the ribonucleoprotein complex is SEQ ID NO:2. The engineered FnCas9 protein effector sequence having SEQ ID NO:2 has a point mutation, such that a glutamic acid (glu; E) at amino acid position 1369 of wild type FnCas9 is replaced by arginine (arg; R).

In non-limiting examples, the engineered FnCas9 protein effector of the ribonucleoprotein complex is SEQ ID NO:3. The engineered FnCas9 protein effector sequence having SEQ ID NO:3 has a point mutation, such that at amino acid position 1449 of wild type FnCas9 (SEQ ID NO:1) a glutamic acid (glu; E) is replaced by histidine (his; H).

In non-limiting examples, the engineered FnCas9 protein effector of the ribonucleoprotein complex is ID NO:4. The engineered FnCas9 protein effector sequence having SEQ ID NO:4 has a point mutation, such that at amino acid position 1369 of wild type FnCas9 (SEQ ID NO:1) a glutamic acid (glu; E) is replaced by arginine (arg; R) and at amino acid position 1449 of wild type FnCas9 (SEQ ID NO:1) a glutamic acid is replaced by histidine.

In non-limiting examples, the engineered FnCas9 protein effector of the ribonucleoprotein complex is SEQ ID NO:5. The engineered FnCas9 protein effector sequence having SEQ ID NO:5 has a point mutation, such that at amino acid position 1243 of wild type FnCas9 (SEQ ID NO:1) a glycine (gly; G) is replaced by threonine (thr; T).

In non-limiting examples, the engineered FnCas9 protein effector of the ribonucleoprotein complex is SEQ ID NO:16. The engineered FnCas9 protein effector sequence having SEQ ID NO:16 has a point mutation, such that at amino acid position 1603 of wild type FnCas9 (SEQ ID NO:1) a glutamic acid (glu; E) is replaced by histidine (his; H).

In non-limiting examples, the engineered FnCas9 protein effector of the ribonucleoprotein complex is SEQ ID NO: 31. The engineered FnCas9 protein effector sequence having SEQ ID NO:31 has a point mutation, such that at amino acid position 1369 of wild type FnCas9 (SEQ ID NO:1) a glutamic acid (glu; E) is replaced by arginine (arg; R), and at amino acid position 1449 of wild type FnCas9 (SEQ ID NO:1) a glutamic acid (glu; E) is replaced by histidine (his; H), and at amino acid position 1243 of wild type FnCas9 (SEQ ID NO:1) a glycine (gly; G) is replaced by threonine (thr; T).

In non-limiting examples, the engineered FnCas9 protein effector of the ribonucleoprotein complex is SEQ ID NO:40. The engineered FnCas9 protein effector sequence having SEQ ID NO:40 has a point mutation, such that at amino acid position 1369 of wild type FnCas9 (SEQ ID NO:1) a glutamic acid (glu; E) is replaced by arginine (arg; R) and at position 1243 of wild type FnCas9 (SEQ ID NO:1) a glycine (gly; G) is replaced by threonine (thr; T).

In non-limiting examples, the engineered FnCas9 protein effector of the ribonucleoprotein complex is SEQ ID NO:47. The engineered FnCas9 protein effector sequence having SEQ ID NO:47 has a point mutation, such that at amino acid position 1603 of wild type FnCas9 (SEQ ID NO:1) a glutamic acid (glu; E) is replaced by histidine (his; H), and at amino acid position 1243 of wild type FnCas9a (SEQ ID NO:1) glycine (gly; G) is replaced by threonine (thr; T).

In non-limiting examples, the engineered FnCas9 protein effector of the ribonucleoprotein complex is selected from the group consisting of SEQ ID NOS:51-99. The engineered FnCas9 protein effector sequences having SEQ ID NOS:51-99 have a REC2 deletion.

Example variants comprise a ribonucleoprotein complex, as described herein, where the ribonucleoprotein complex is bound to a PAM sequence selected from the group consisting of NGG, NGA, GGA, and GGG.

Methods for gene editing by the ribonucleoprotein complexes described herein include delivering the engineered FnCas9 protein effector to living cells. The engineered FnCas9 protein effector may be selected from the group consisting of SEQ ID NOS:2-99. The methods for gene editing further include breaking DNA at a genetic target using the sgRNA, where the crRNA is transcribed with a DNA sequence selected from the group consisting of SEQ ID NOS:198-211. The methods for gene editing further include sealing the break by repair machinery of the cell, optionally comprising a repair DNA template.

Methods for base editing by the ribonucleoprotein complexes described herein include delivering the engineered FnCas9 protein effector to living cells. The engineered FnCas9 protein effector is selected from the group consisting of SEQ ID NOS:100-197. The methods for base editing further include modifying a target base using the sgRNA, where the crRNA is transcribed with a DNA sequence selected from the group consisting of SEQ ID NOS:212-215, and wherein modifying the target base is accomplished without breaking the DNA.

Kits for gene editing, according to embodiments herein, may comprise or consist of (a) an engineered FnCas9 protein effector selected from the group consisting of SEQ ID NOS:2-197; and (b) a chimeric single guide RNA (sgRNA). The sgRNA comprises or consists of a crispr RNA (crRNA), wherein the crRNA is transcribed in vitro using a DNA sequence selected from the group consisting of SEQ ID NOS:198-215, and a trans-activating crispr RNA (tracrRNA) having SEQ ID NO:305. The kits may further include a Homology Directed Repair (HDR) template. The kits may further include at least one buffer or buffer solution suitable for performing a gene editing using the components of the kit in combination.

EXAMPLES

The following examples are given by way of illustration and therefore should not be constructed to limit the scope of the present disclosure or the appended claims.

All materials reported in this disclosure have been synthesized in lab, no biological materials in its natural form have been used.

Example 1

Plasmid Construction for Engineering FnCas9

Point mutations and deletions were done by inverse PCR method on FnCas9 (SEQ ID NO:1) cloned in pE-Sumo vector backbone (LifeSensors) (Hirano et al., 2016) where changes were made on the forward primer and the entire plasmid and amplified (FIGS. 2,4, and 10-12). The variants generated are shown in TABLE 1 below.

TABLE 1

| Fn variants | Amino acid position | Primers used for SDM | amino acid change |
|---|---|---|---|
| en1 (SEQ ID NO: 2) | 1369 | SEQ ID NOS: 216 and 217 | E > R |
| en2 (SEQ ID NO: 3) | 1449 | SEQ ID NOS: 218 and 219 | E > H |
| en3 (SEQ ID NO: 4) | 1369, 1449 | SEQ ID NOS: 216 to 220 | E > R, E > H |
| en4 (SEQ ID NO: 5) | 1243 | SEQ ID NOS: 221 and 222 | G > T |
| en5 (SEQ ID NO: 6) | 1369 | SEQ ID NOS: 222 and 223 | E > Y |
| en6 (SEQ ID NO: 7) | 1392 | SEQ ID NOS: 224 and 225 | G > R |
| en7 (SEQ ID NO: 8) | 1392 | SEQ ID NOS: 225 and 226 | G > K |
| en8 (SEQ ID NO: 9) | 1448 | SEQ ID NOS: 227 and 228 | N > R |
| en9 (SEQ ID NO: 10) | 1448 | SEQ ID NOS: 228 and 229 | N > Y |
| en10 (SEQ ID NO: 11) | 1451_1452 | SEQ ID NOS: 230 and 231 | ins V |
| en11 (SEQ ID NO: 12) | 1473 | SEQ ID NOS: 232 and 233 | S > T |
| en12 (SEQ ID NO: 13) | 1553 | SEQ ID NOS: 234 and 235 | N > V |
| en13 (SEQ ID NO: 14) | 1586 | SEQ ID NOS: 236 and 237 | Y > H |
| en14 (SEQ ID NO: 15) | 1586 | SEQ ID NOS: 237 and 238 | Y > R |
| en15 (SEQ ID NO: 16) | 1603 | SEQ ID NOS: 239 and 240 | E > H |
| en17 (SEQ ID NO: 17) | 1369, 1449, 1556 | SEQ ID NOS: 241 and 242 | E > R, E > H, R > T |
| en18 (SEQ ID NO: 18) | 1233 | SEQ ID NOS: 243 and 244 | F > Y |
| en19 (SEQ ID NO: 19) | 1475 | SEQ ID NOS: 245 and 246 | A > F |
| en20 (SEQ ID NO: 20) | 1499 | SEQ ID NOS: 247 and 248 | S > H |
| en21 (SEQ ID NO: 21) | 1580 | SEQ ID NOS: 249 and 250 | S > R |
| en22 (SEQ ID NO: 22) | 1583 | SEQ ID NOS: 251 and 252 | K > R |
| en23 (SEQ ID NO: 23) | 1609 | SEQ ID NOS: 253 and 254 | K > V |
| en24 (SEQ ID NO: 24) | 1609 | SEQ ID NOS: 254 and 255 | K > S |
| en25 (SEQ ID NO: 25) | 1609 | SEQ ID NOS: 254 and 256 | K > N |
| en26 (SEQ ID NO: 26) | 1605 | SEQ ID NOS: 257 and 258 | S > F |
| en27 (SEQ ID NO: 27) | 1605 | SEQ ID NOS: 258 and 259 | S > R |
| en28 (SEQ ID NO: 28) | 1386_1387 | SEQ ID NOS: 260 and 261 | ins RR |
| en29 (SEQ ID NO: 29) | 1586, 1603 | SEQ ID NOS: 236, 237, 239 and 240 | Y > H, E > H |
| en30 (SEQ ID NO: 30) | 1392, 1448 | SEQ ID NOS: 226, 227, 229 and 230 | G > K, N > Y |
| en31 (SEQ ID NO: 31) | 1369, 1449, 1243 | SEQ ID NOS: 216 to 222 | E > R, E > H, G > T |
| en32 (SEQ ID NO: 32) | 1369, 1449, 1392 | SEQ ID NOS: 216 to 219, 225 and 226 | E > R, E > H, G > K |
| en33 (SEQ ID NO: 33) | 1369, 1449, 1448 | SEQ ID NOS: 216 to 219, 228 and 229 | E > R, E > H, N > Y |
| en34 (SEQ ID NO: 34) | 1369, 1603 | SEQ ID NOS: 216, 217, 239 and 240 | E > R, E > H |
| en35 (SEQ ID NO: 35) | 1369, 1392 | SEQ ID NOS: 216, 217, 225 and 226 | E > R, G > K |
| en36 (SEQ ID NO: 36) | 1369, 1448 | SEQ ID NOS: 216, 217, 227 and 228 | E > R, N > R |
| en37 (SEQ ID NO: 37) | 1369, 1448 | SEQ ID NOS: 216, 217, 228 and 229 | E > R, N > Y |
| en38 (SEQ ID NO: 38) | 1369, 1475 | SEQ ID NOS: 216, 217, 244 and 245 | E > R, A > F |
| en39 (SEQ ID NO: 39) | 1369, 1580 | SEQ ID NOS: 216, 217, 249 and 250 | E > R, S > R |
| en40 (SEQ ID NO: 40) | 1369, 1243 | SEQ ID NOS: 216, 217, 221 and 222 | E > R, G > T |
| en41 (SEQ ID NO: 41) | 1369, 1556 | SEQ ID NOS: 216, 217, 225 and 226 | E > R, R > Q |
| en42 (SEQ ID NO: 42) | 1603, 1392 | SEQ ID NOS: 239, 240, 225 and 226 | E > H, G > K |
| en43 (SEQ ID NO: 43) | 1603, 1448 | SEQ ID NOS: 239, 240, 227 and 228 | E > H, N > R |
| en44 (SEQ ID NO: 44) | 1603, 1448 | SEQ ID NOS: 239, 240, 228 and 229 | E > H, N > Y |
| en45 (SEQ ID NO: 45) | 1603, 1475 | SEQ ID NOS: 239, 240, 245 and 246 | E > H, A > F |
| en46 (SEQ ID NO: 46) | 1603, 1580 | SEQ ID NOS: 239, 240, 239 and 250 | E > H, S > R |
| en47 (SEQ ID NO: 47) | 1603, 1243 | SEQ ID NOS: 239, 240, 221 and 222 | E > H, G > T |
| en48 (SEQ ID NO: 48) | 1603, 1556 | SEQ ID NOS: 239, 240, 242 and 262 | E > H, R > Q |
| en49 (SEQ ID NO: 49) | 1556 | SEQ ID NOS: 242 and 262 | R > Q |
| en50 (SEQ ID NO: 50) | 1369, 1449, 1556 | SEQ ID NOS: 216 to 219, 242 and 262 | E > R, E > H, R > Q |

Figure 17:
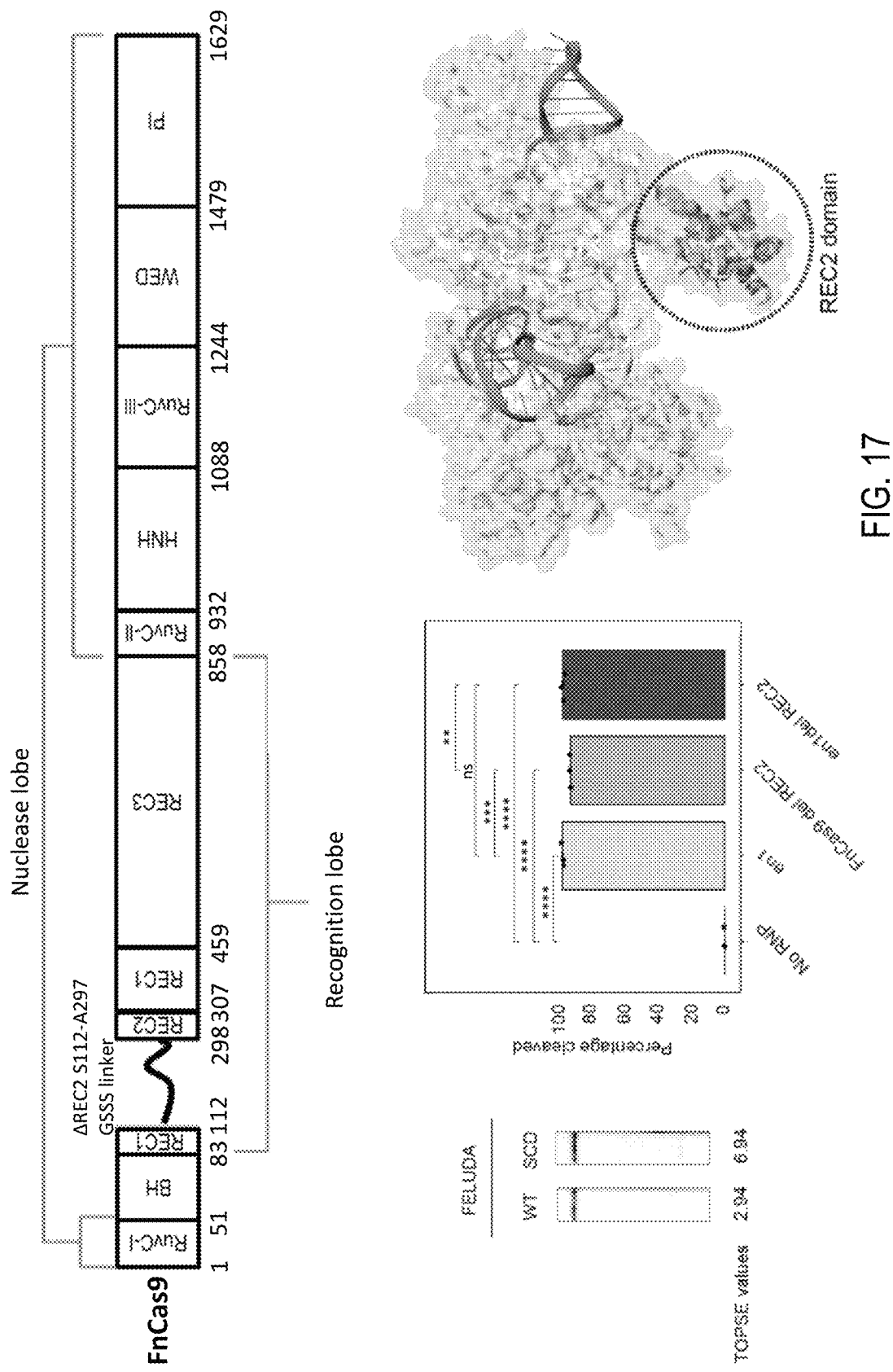
FIG. 17: REC2 truncation (using SEQ ID NOS:275, 276) retains activity and specificity of enFnCas9 variants. (A) Schematics of FnCas9 domain organization with partial REC2 deletion. (B) Crystal structure of FnCas9 in complex with DNA and RNA (PDB: 52BO) is shown in ribbon model with space fill overlay. Truncated REC2 domain (ΔS112-A297) is highlighted in red and marked by a dotted circle. (C) Bar plot showing in vitro cleavage efficiency of en1 (SEQ ID NO:2), FnCas9ΔREC2 and en1ΔREC2 (SEQ ID NO:51) on GGG PAM containing DNA substrate. The 5 nM DNA substrate was incubated with 100 nM RNPs for 1 hr at 37° C. Error bars represent SD (three independent experiments). Student's unpaired t-test p-values are represented for <0.01, *<0.001. (D) Outcome of lateral flow assay (LFA) for SCD detection by FELUDA using en1ΔREC2. Corresponding TOPSE values are given at the bottom.

Point mutations on synthetically constructed pET-His6-dFnCas9GFP backbone and PX458-3xHA-FnCas9 backbone (Addgene 130969) was done by essentially following the method described in (Acharya et al., 2019). Mammalian specific sequences were generated using SEQ ID NOS:263-274. FnCas9 truncations shown in FIG. 17, parts A and B (SEQ ID NOS:51-99) were generated using SEQ ID NO:275 and SEQ ID NO:276. Fn/enFnCas9 base editors were also synthetically constructed and cloned in PX458-3xHA-FnCas9 backbone (SEQ ID NOS:100-197).

Example 2

Cas9 Protein and sgRNA Purification [PK1]

The proteins used in this study were purified as reported previously (Nishimasu et al., 2018; Acharya et al., 2019) Briefly, plasmids for Cas9 from *Francisella novicida* were expressed in *Escherichia coli* Rosetta2 (DE3) (Novagen). The protein expressing Rosetta2 (DE3) cells were cultured at 37° C. in LB medium (supplemented with 50 mg/L kanamycin) until $OD_{600}$ reached 0.6 and protein expression was induced by addition of 0.5 mM isopropyl-β-D-thiogalactopyranoside (IPTG).

Figure 5:
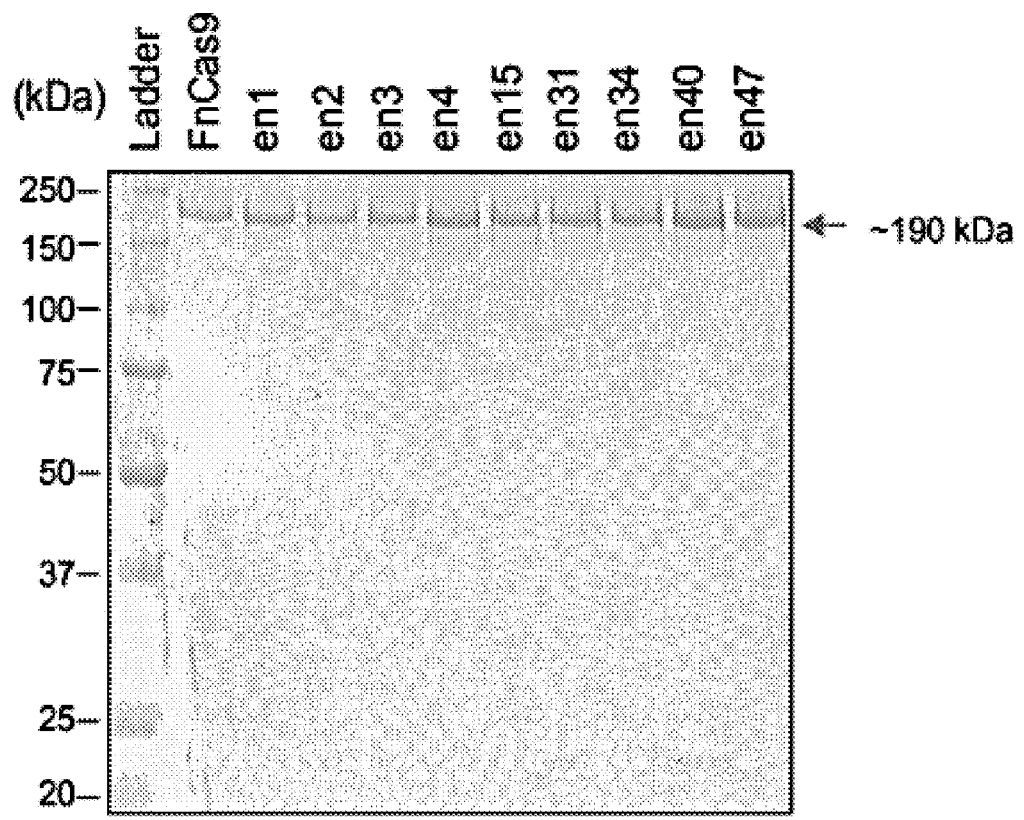
FIG. 5: Coomassie gel showing purified FnCas9 (Seq ID No. 1) and enFnCas9 protein variants (en1 (SEQ ID NO:2), en2 (SEQ ID NO:3), en3 (SEQ ID NO:4), en4 (SEQ ID NO:5), en15 (SEQ ID NO:16), en31 (SEQ ID NO:31), en34 (SEQ ID NO:34), en40 (SEQ ID NO:40), and en47 (SEQ ID NO:47)) used in the study.
Figure 6:
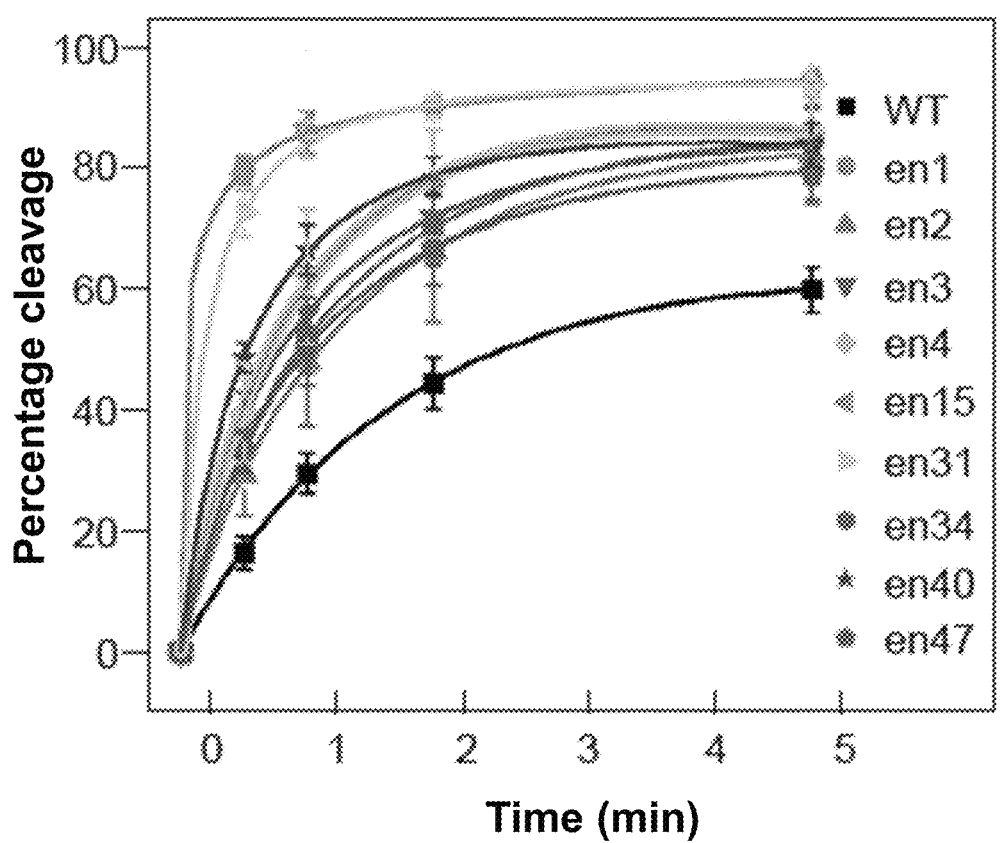
FIG. 6: In vitro cleavage assay of FnCas9 (Seq ID No.1) and a subset of nine enFnCas9 variants (en1 (SEQ ID NO:2), en2 (SEQ ID NO:3), en3 (SEQ ID NO:4), en4 (SEQ ID NO:5), en15 (SEQ ID NO:16), en31 (SEQ ID NO:31), en34 (SEQ ID NO:34), en40 (SEQ ID NO:40), and en47 (SEQ ID NO:47)) on GGG PAM containing PCR linearized DNA substrate expressed as percentage cleavage (y-axis) as a function of time (x-axis). Error bars represent SD (three independent experiments).
Figure 7:
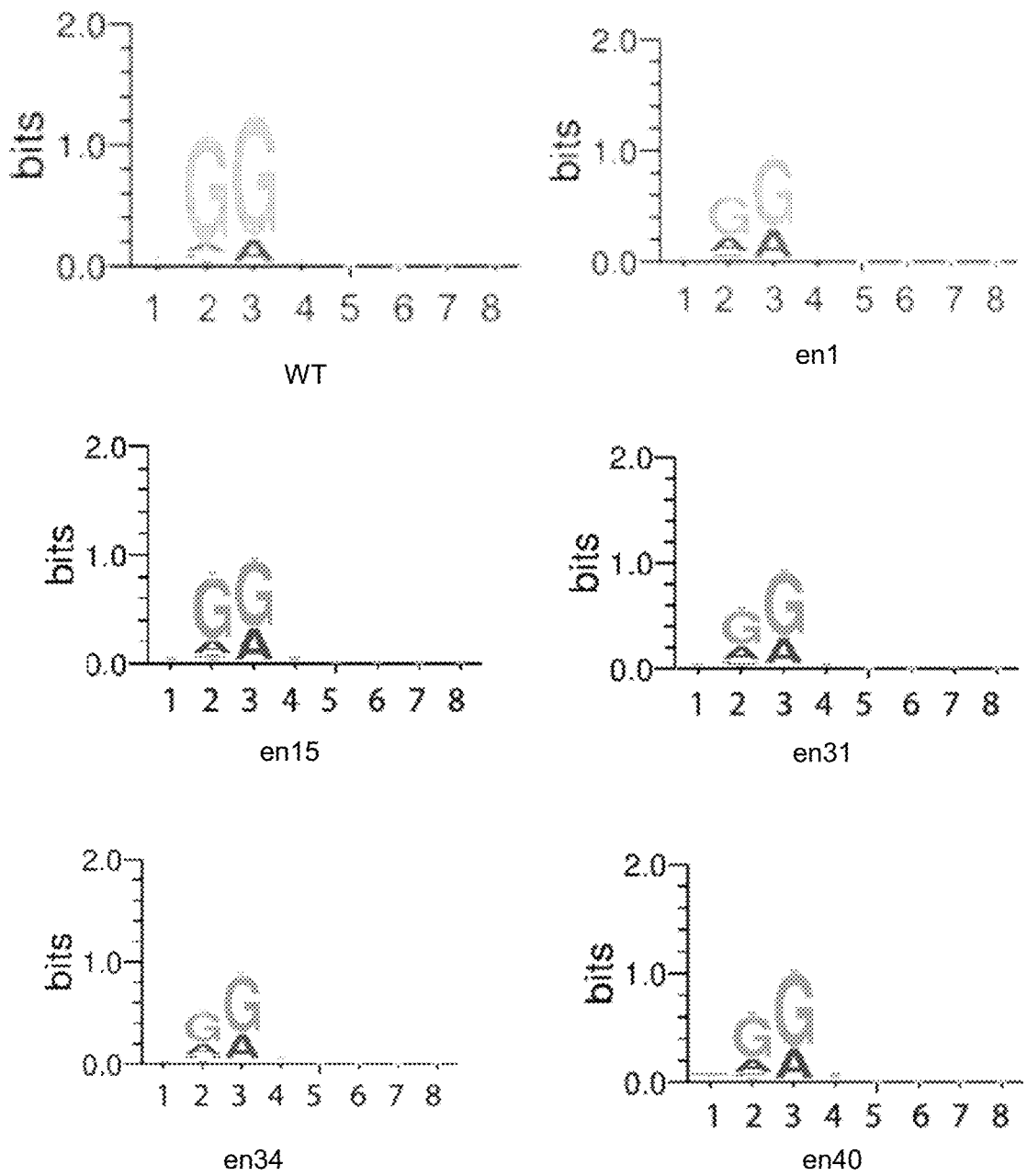
FIG. 7: Sequence logos showing the results obtained after PAM discovery assay for WT (SEQ ID NO:1) and enFn variants (en1 (SEQ ID NO:2), en15 (SEQ ID NO:16), en31 (SEQ ID NO:31), en34 (SEQ ID NO:34), en40 (SEQ ID NO:40)). Bases showing up in the logos represent the preference of the PAM bases recognition by Cas9.
Figure 8:
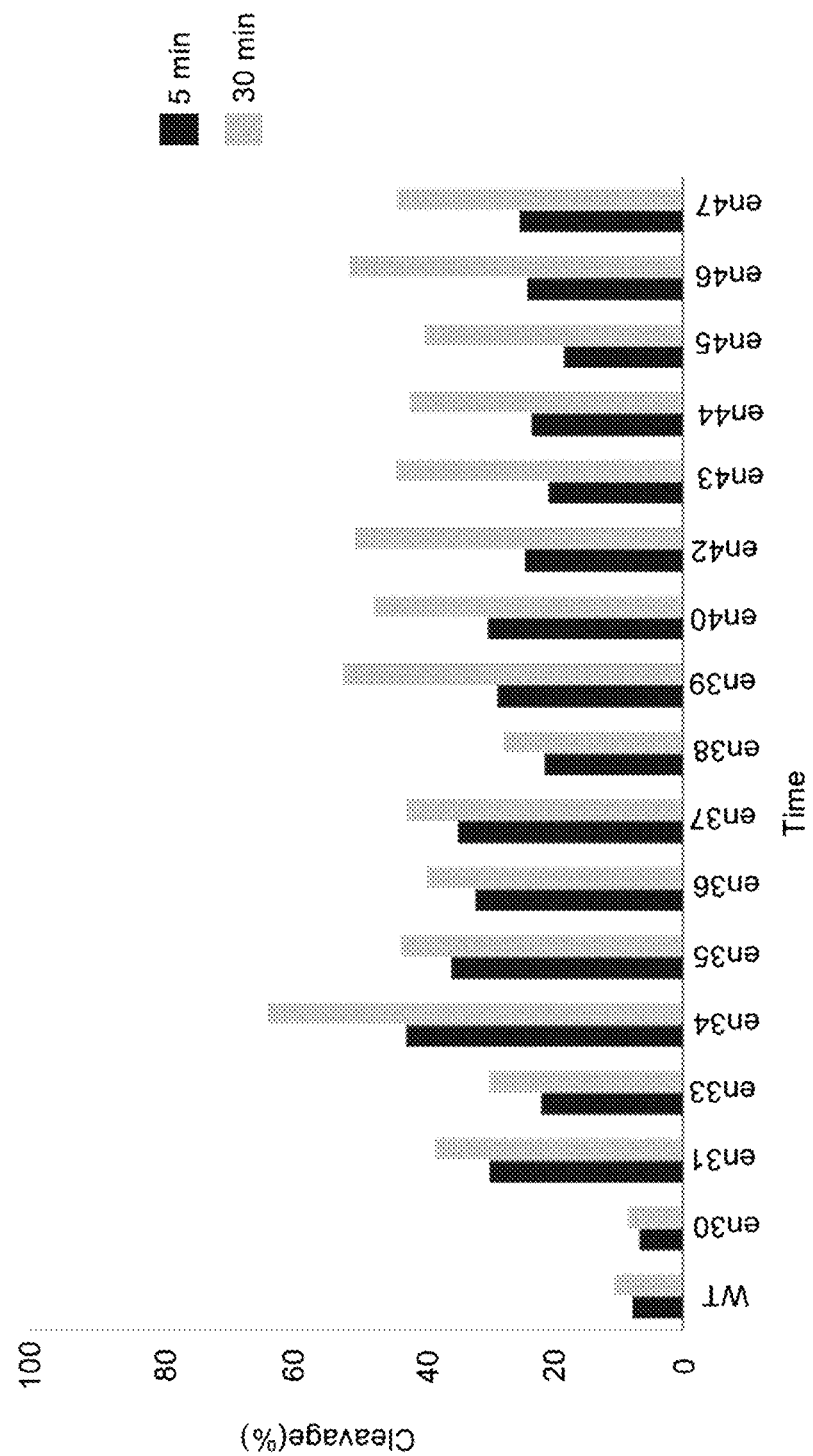
FIG. 8: Bar Plot of percent cleavage (y-axis) vs time (x-axis) showing the in vitro cleavage screening of FnCas9 (WT; SEQ ID NO:1) and enFn variants (en30 (SEQ ID NO:30), en31 (SEQ ID NO:31), en33 (SEQ ID NO:33), en34 (SEQ ID NO:34), en35 (SEQ ID NO:35), en36 (SEQ ID NO:36), en37 (SEQ ID NO:37), en38 (SEQ ID NO:38), en39 (SEQ ID NO:39), en40 (SEQ ID NO:40), en42 (SEQ ID NO:42), en43 (SEQ ID NO:43), en44 (SEQ ID NO:44), en45 (SEQ ID NO:45), en46 (SEQ ID NO:46), and en47 (SEQ ID NO:47))) using GGA PAM containing DNA substrate.
Figure 9:
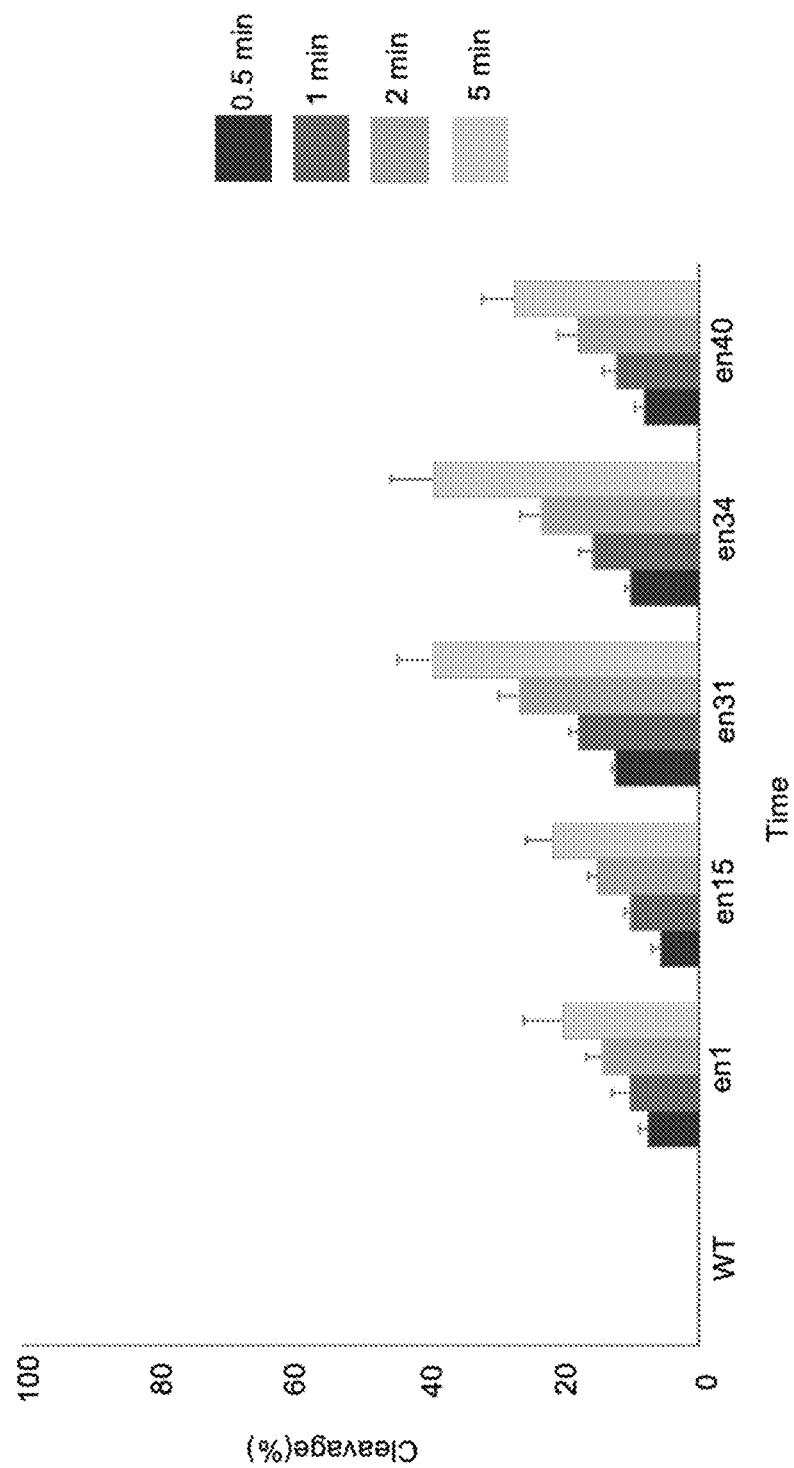
FIG. 9: Bar plot showing in vitro cleavage assay using GGA PAM containing DNA substrate expressed as cleavage percentage (y-axis) as a function of time (x-axis). Error bars represent SD (three independent experiments).
Figure 10:
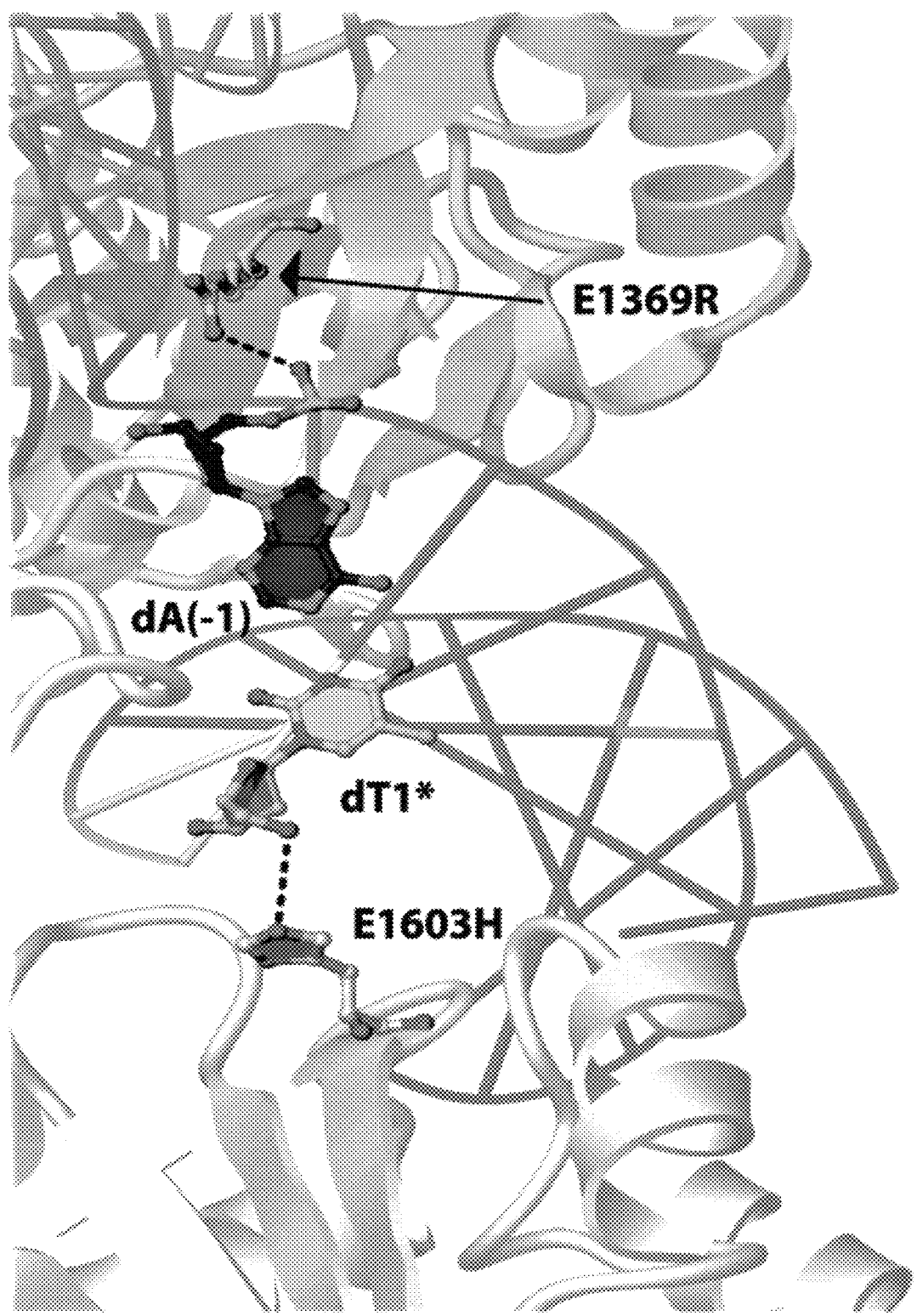
FIG. 10: Structural models showing interaction between substituted amino acids and PAM duplex. Interactions of en1 (E1369R, SEQ ID NO:2) and en15 (E1603H, SEQ ID NO:16) are shown.
Figure 11:
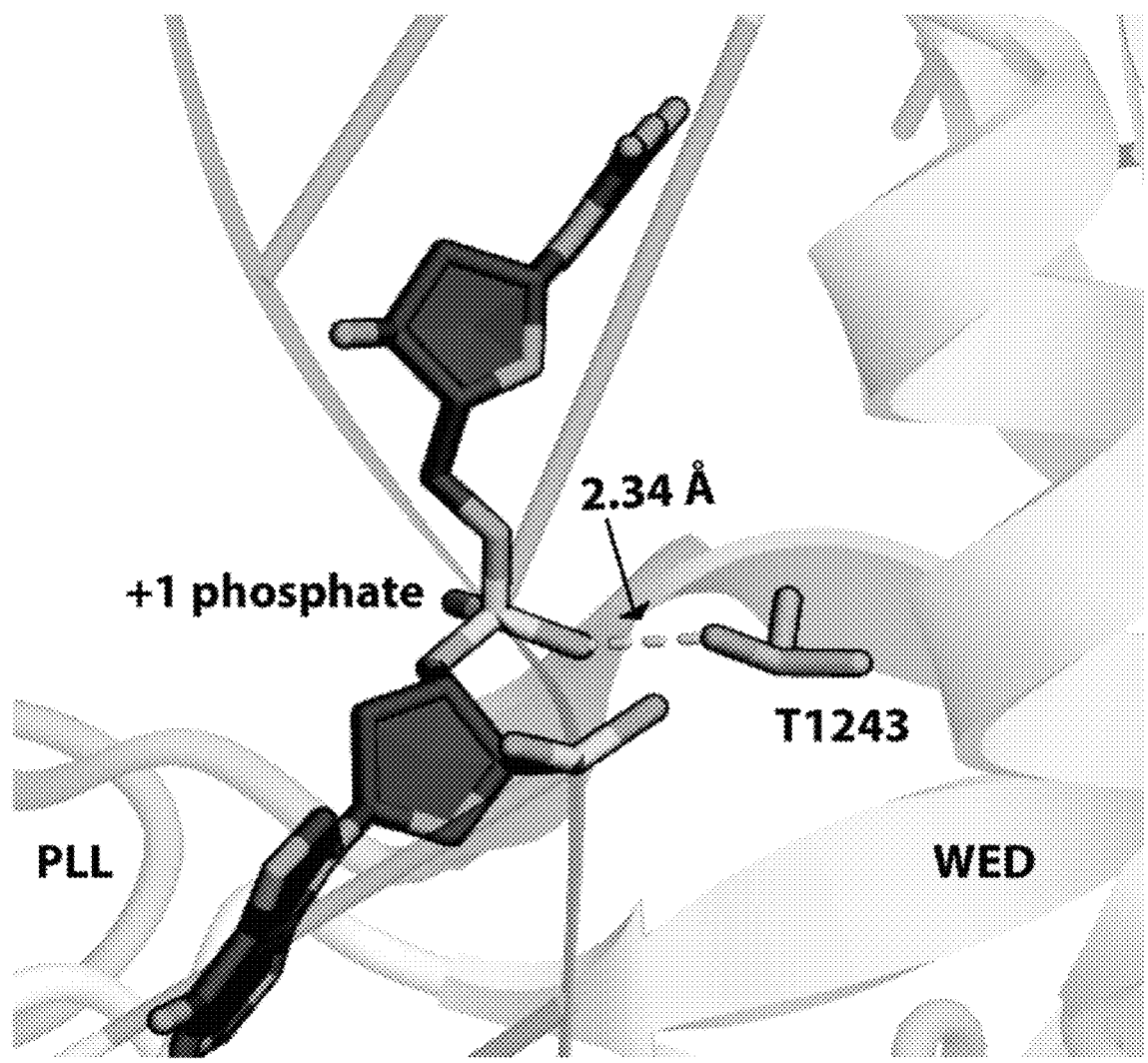
FIG. 11: Structural models showing interaction between substituted amino acids and PAM duplex. Interaction of en4 (G1243T, SEQ ID NO:5) with +1 Phosphate group.
Figure 12:
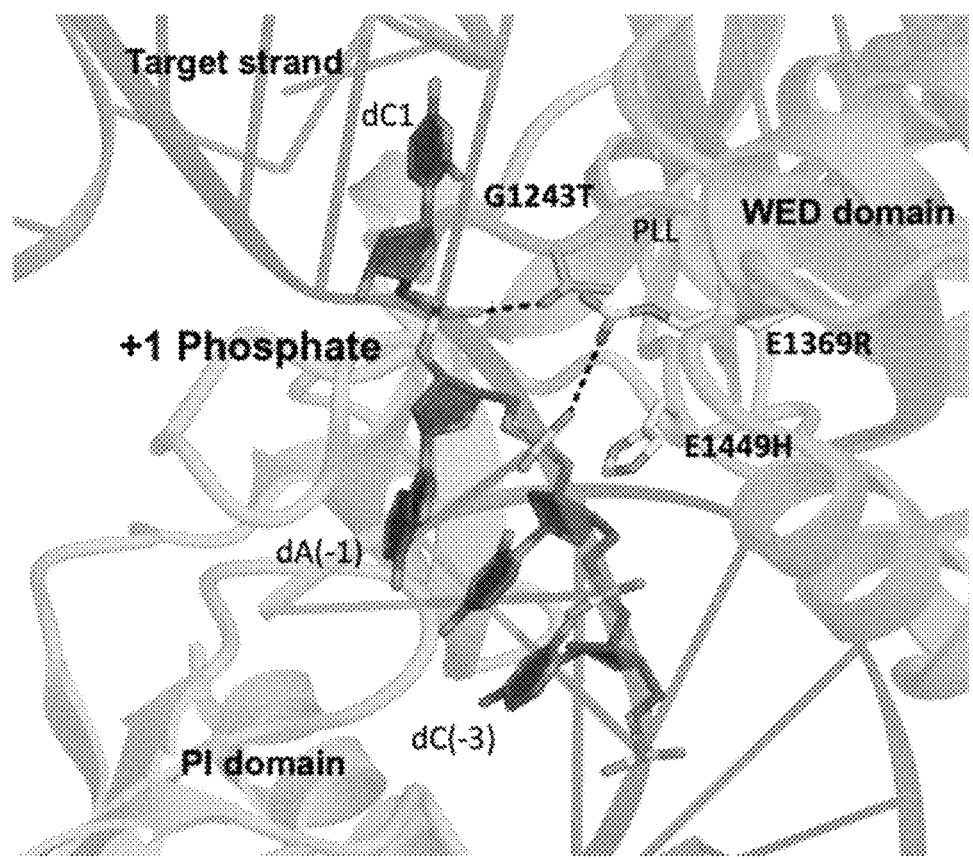
FIG. 12: Structural models showing interaction between substituted amino acids and PAM duplex. Interactions of en31 (E1369R/E1449H/G1243T, SEQ ID NO:31) with PAM duplex and PLL loop.
Figure 13A:
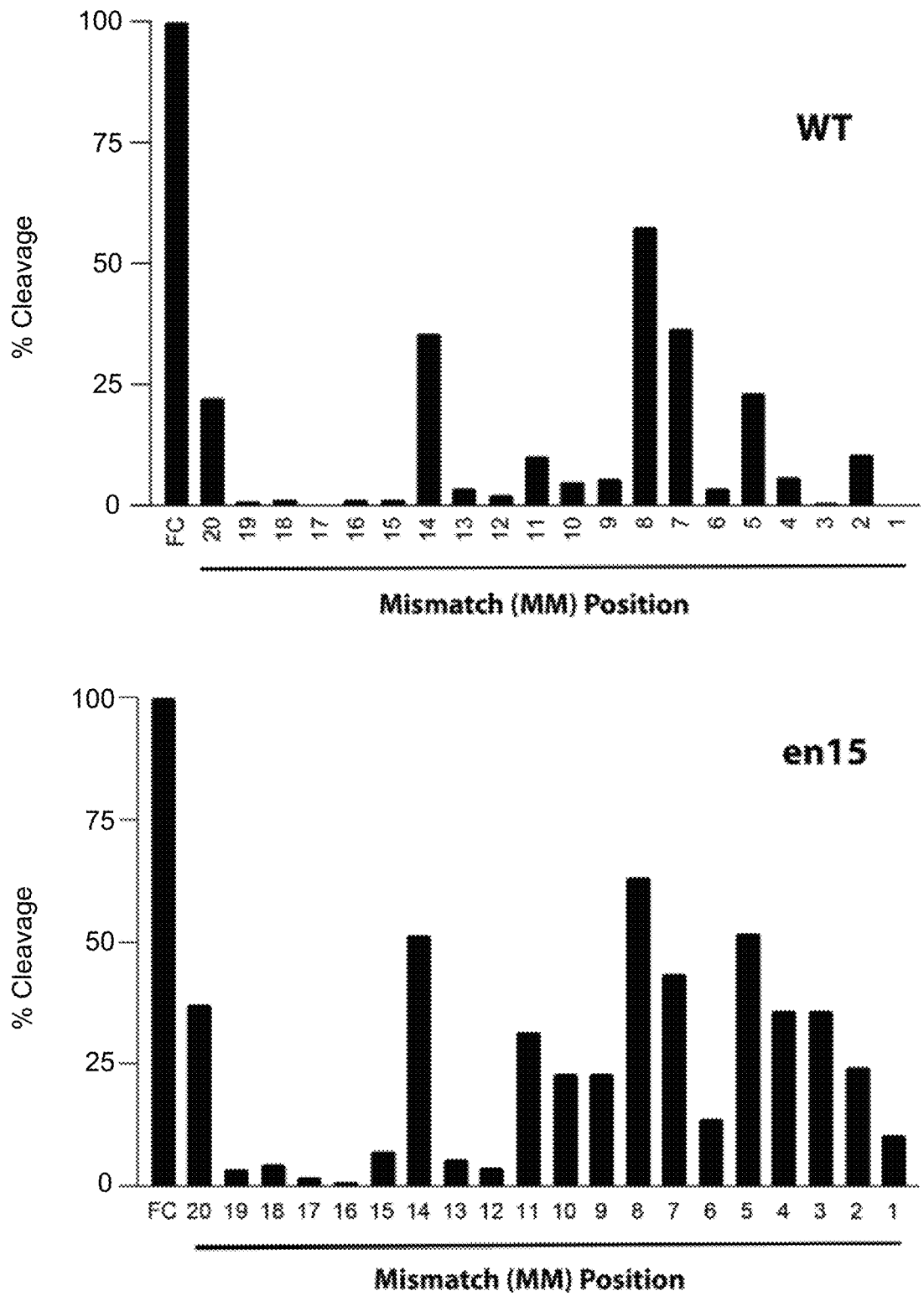
FIGS. 13A and 13B: Bar plots showing the in vitro cleavage outcome of FnCas9 (SEQ ID NO:1), en1 (SEQ ID NO:2), en15 (SEQ ID NO:16) and en31 (SEQ ID NO:31) on HBB and its mutant substrates (SEQ ID NOS:283, 284). Each substrate is harbouring a single mutation (position is indicated by counting away from PAM) across the target length. 25 nM of DNA substrates was incubated with respective 100 nM RNPs for 15 min at 37° C.
Figure 13B:
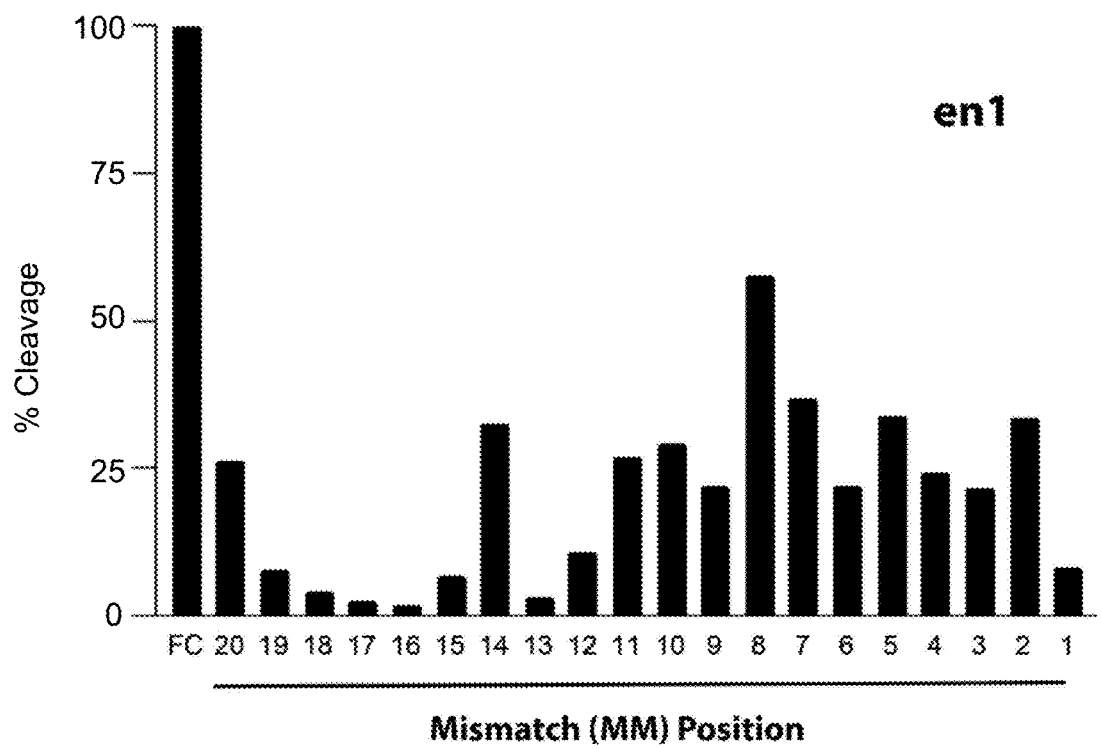
Figure 13B:
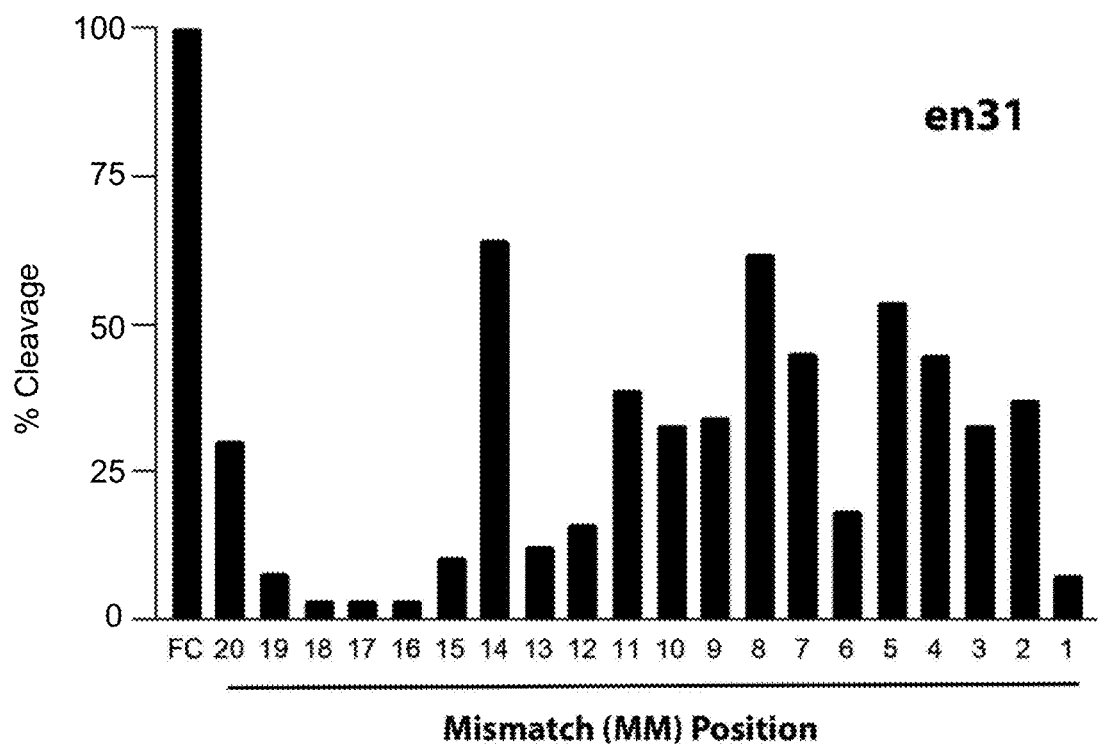
Figure 14A:
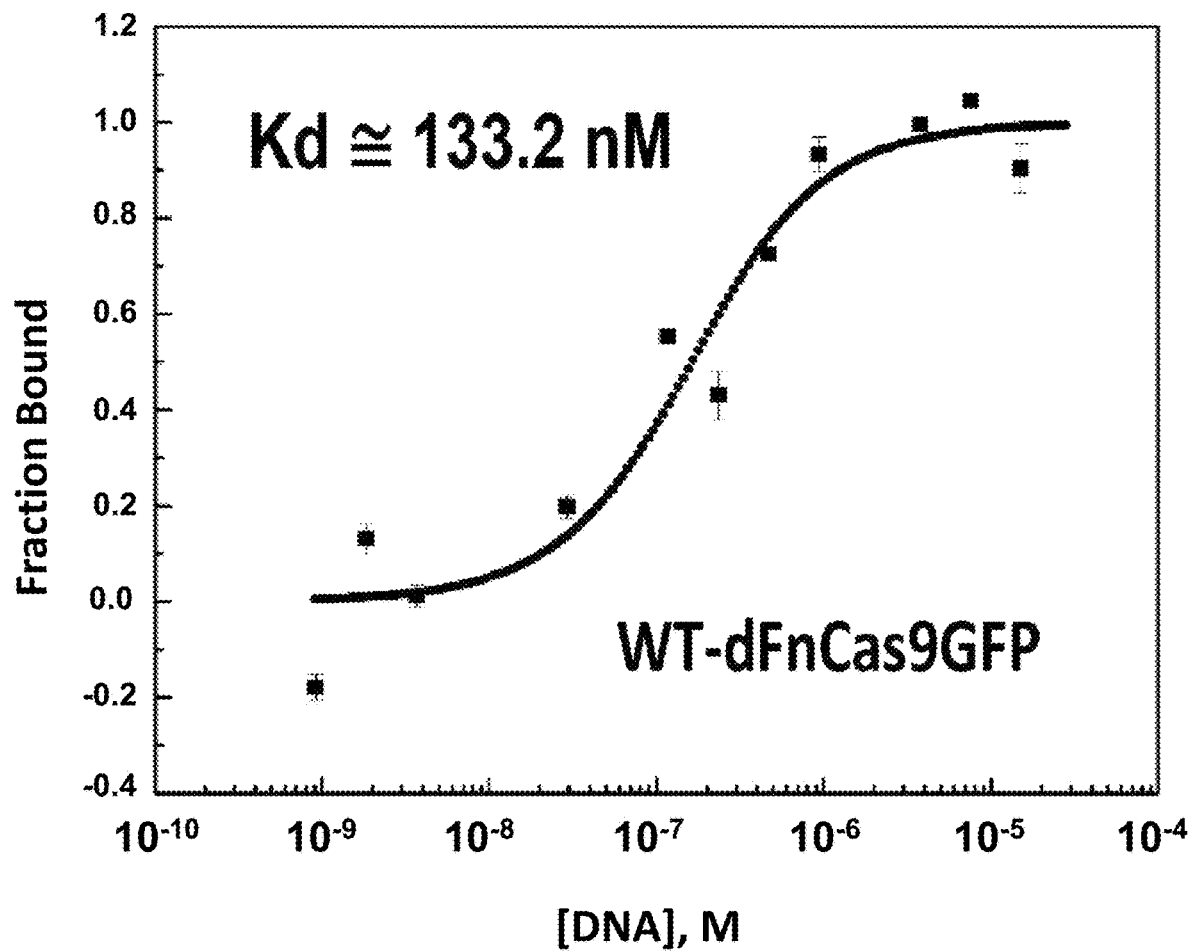
FIGS. 14A, 14B, and 14C: Micro Scale Thermophoresis results showing affinity of WT dFnCas9GFP and variants to VEGFA3 DNA substrate, expressed as fraction bound (y-axis) as a function of varying concentrations of DNA substrate (x-axis) Seq ID No. 281, 282.
Figure 14B:
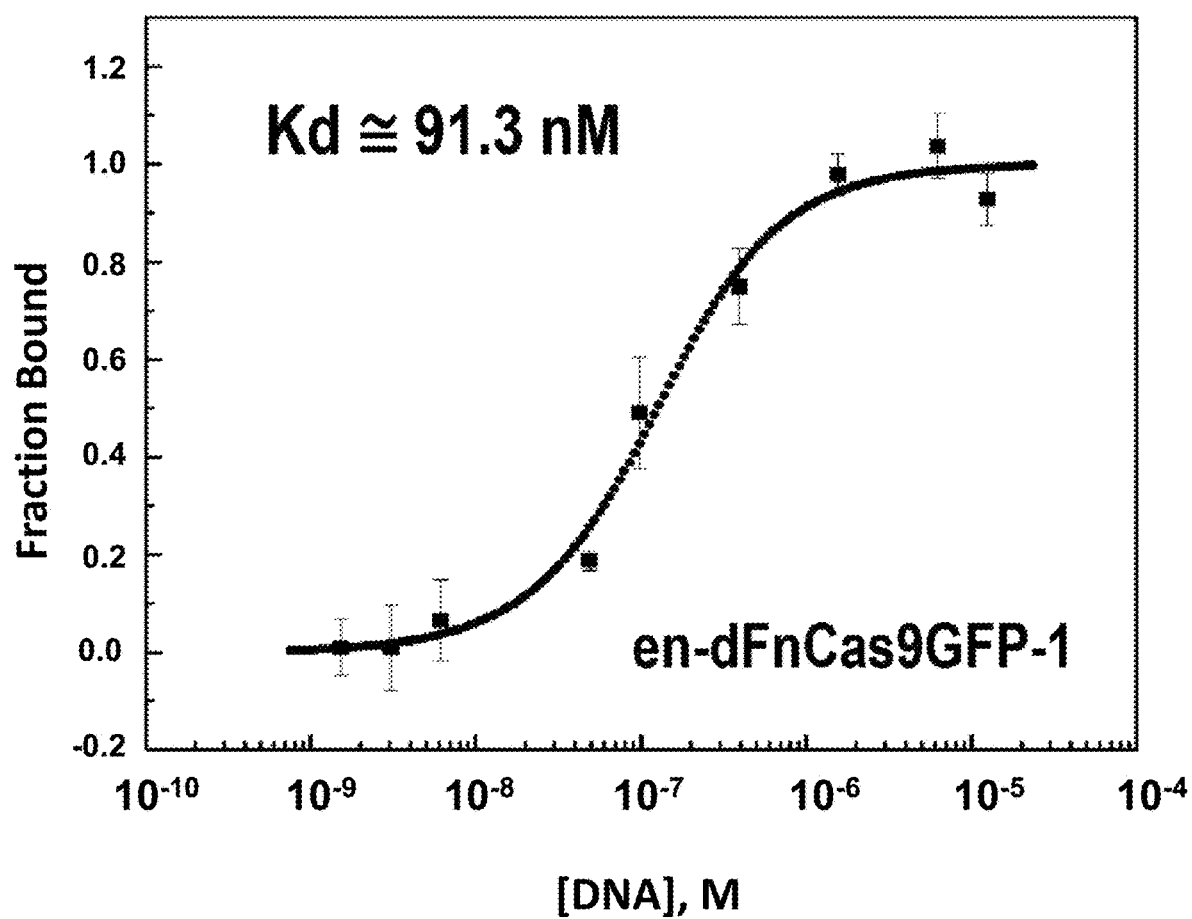
Figure 14C:
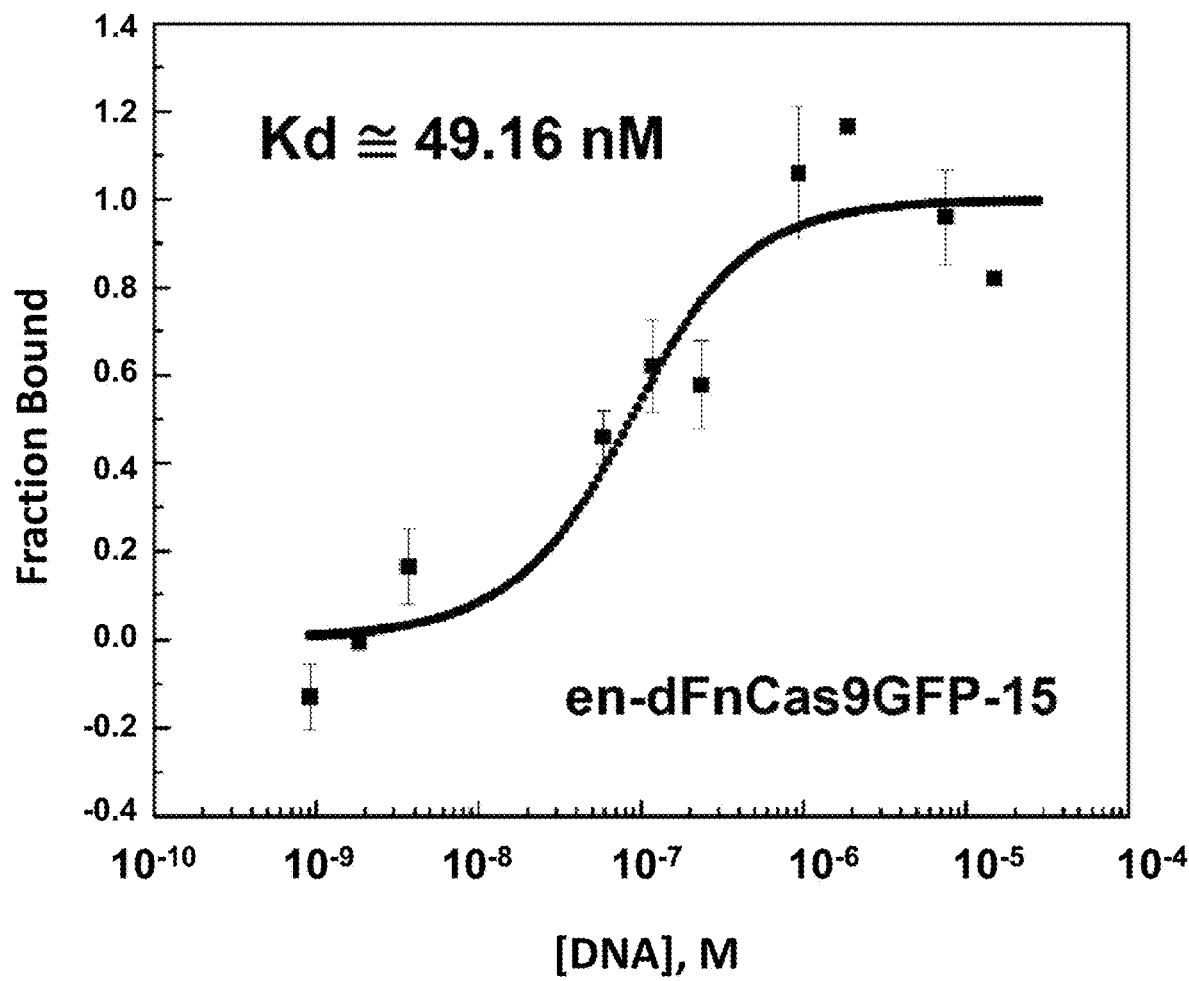

The Rosetta2 (DE3) cells (DSS Takara) were further cultured at 18° C. overnight and harvested by centrifugation. The *E. coli* cells were resuspended in buffer A (20 mM Tris-HCl, pH 8.0, 20 mM imidazole, and 1 M NaCl), and lysed by sonication and centrifuged. The lysate was mixed with Ni-NTA beads (Roche), the mixture was loaded into a Poly-Prep Column (BioRad) and the protein was eluted by buffer B (20 mM Tris-HCl, pH 8.0, 0.3 M imidazole, and 0.3 M NaCl). The affinity eluted protein was mixed with ion-exchange beads (SP Sepharose Fast Flow, GE Healthcare) equilibrated with buffer C (20 mM Tris-HCl, pH 8.0, and 0.15 M NaCl) and the protein was eluted by buffer D (20 mM Tris-HCl, pH 8.0, and 1 M NaCl). The concentration of purified protein was measured by Pierce BCA protein assay kit (Thermo Fisher Scientific). The purified proteins were stored at −80° C. until further use. Some of the purified FnCas9/en FnCas9 variant proteins (SEQ ID NOS:1-50) can be seen on polyacrylamide gel in FIG. 5.

In vitro transcribed sgRNAs were synthesized using MegaScript T7 Transcription kit (Thermo Fisher Scientific) using T7 promoter containing template as substrates. IVT reactions were incubated overnight at 37° C. followed by NucAway spin column (Thermo Fisher Scientific) purification as described earlier (Acharya et al., 2019). IVT sgRNAs were stored at −20° C. until further use. Primers used SEQ ID NOS:198-202, 277.

Example 3

In Vitro Cleavage (IVC) Assay

For kinetic study, the pUC119 plasmid (Nureki lab, Japan) containing the target sequence and the respective PAM sequence (generated by PCR based cloning) (mentioned in respective legends) was used as the substrate for in vitro cleavage experiments. The linearized pUC119 plasmid (50 ng or ~5 nM) was incubated at 37° C. for 0.5-5 min with the Cas9-sgRNA complex (50 nM) in 10 µL of reaction buffer, containing 20 mM HEPES, pH 7.5, 150 mM KCl, 10 mM $MgCl_2$, 1 mM DTT, and 5% glycerol.

The reaction was stopped by the addition of quenching buffer, containing EDTA (20 mM nal concentration) and Proteinase K (40 ng). The reaction products were resolved, visualized, and quantified with a MultiNA microchip electrophoresis device (SHIMADZU) (Nishimasu et al., 2018). FIGS. 1, 3, 6-9, and 13 illustrate some of the IVC experiments performed for the screening of guide RNAs, enFnCas9 variants, and PAM flexibility.

Rest of the IVC assays were done as described earlier (Acharya et al., 2019). Details of substrates, concentrations, and incubation time are mentioned in respective figure legends.

Example 4

PAM Discovery Assay

The PAM discovery assays (FIG. 7) were performed, as previously described (Nishimasu et al., 2018). Briefly, a library of pUC119 plasmids containing eight randomized nucleotides downstream of the target sequence was incubated at 37° C. for 5 min with the FnCas9-sgRNA complex (50 nM), in 50 µL of the reaction buffer. The reactions were quenched by the addition of Proteinase K, and then purified using a Wizard DNA Clean-Up System (Promega). The purified DNA samples were amplified for 25 cycles, using primers containing common adapter sequences. After column purification, each PCR product (~5 ng) was subjected to a second round of PCR for 15 cycles, to add custom Illumina TruSeq adapters and sample indices.

The sequencing libraries were quantified by qPCR (KAPA Biosystems), and then subjected to paired-end sequencing on a MiSeq sequencer (Illumina) with 20% PhiX spike-in (Illumina). The sequencing reads were demultiplexed by primer sequences and sample indices, using NCBI Blast+ (version 2.8.1) with the blastn-short option. For each sequencing sample, the number of reads for every possible 8-nt PAM sequence pattern ($4^8$=65,536 patterns in total) was counted and normalized by the total number of reads in each sample. For a given PAM sequence, the enrichment score was calculated as log 2-fold enrichment as compared to the untreated sample. PAM sequences with enrichment scores of −2.0 or less were used to generate the sequence logo representation, using WebLogo (version 3.7.1).

Example 5

Binding Assay

Micro Scale Thermophoresis (FIGS. 14A, 14B, 14C, and 16) was performed as described previously (Acharya et al., 2019). Briefly, dFnCas9-GFP protein was complexed with PAGE purified respective IVT sgRNAs (purified by 12% Urea-PAGE). The binding affinities of the Cas9 proteins and sgRNA RNP complexes were calculated using Monolith NT. 115 (NanoTemper Technologies GmbH, Munich, Germany). RNP complex (Protein:sgRNA molar ratio, 1:1) was reconstituted at 25 for 10 mins in reaction buffer (20 mM HEPES, pH 7.5, 150 mM KCl, 1 mM DTT, 10 mM $MgCl_2$) HPLC purified 30 bp dsDNA (IDT) of different genomic loci with varying concentrations (ranging from 0.09 nM to 30 µM) were incubated with RNP complex at 37° C. temperature for 30 minutes in reaction buffer. The sample was loaded into NanoTemper standard treated capillaries and measurements were performed at 25° C. using 20% LED power and 40% MST power. Data analyses were done using NanoTemper analysis software. Oligos are SEQ ID NO:281 and SEQ ID NO:282.

Example 6

In Cellulo Genome Editing Analysis

HEK293T cells (ATCC) were grown in DMEM media supplemented with high glucose (Invitrogen), 2 mM GlutaMax, 10% FBS (Invitrogen), 1× antibiotic and antimycotic (Invitrogen) at 37° C. in 5% $CO_2$. Transfections of mammalian cells were performed using Lipofectamine 3000 Reagent (Invitrogen) following the manufacturer's protocol. 48 hrs post-transfection GFP-positive cells were FACS sorted (BD FACS Melody Cell Sorter) and gDNA was isolated (Lucigen QuickExtract Extraction solution).

The respective loci were PCR amplified using forward and reverse primers containing overhang adapter sequences using Phusion High-Fidelity DNA polymerase (Thermo Fisher). The 16S Metagenomic sequencing library preparation protocol was adapted for library preparation. Briefly, AMPure XP beads (A63881, Beckman Coulter) were used to separate out amplicons from free primers and primer dimers.

Figure 15:
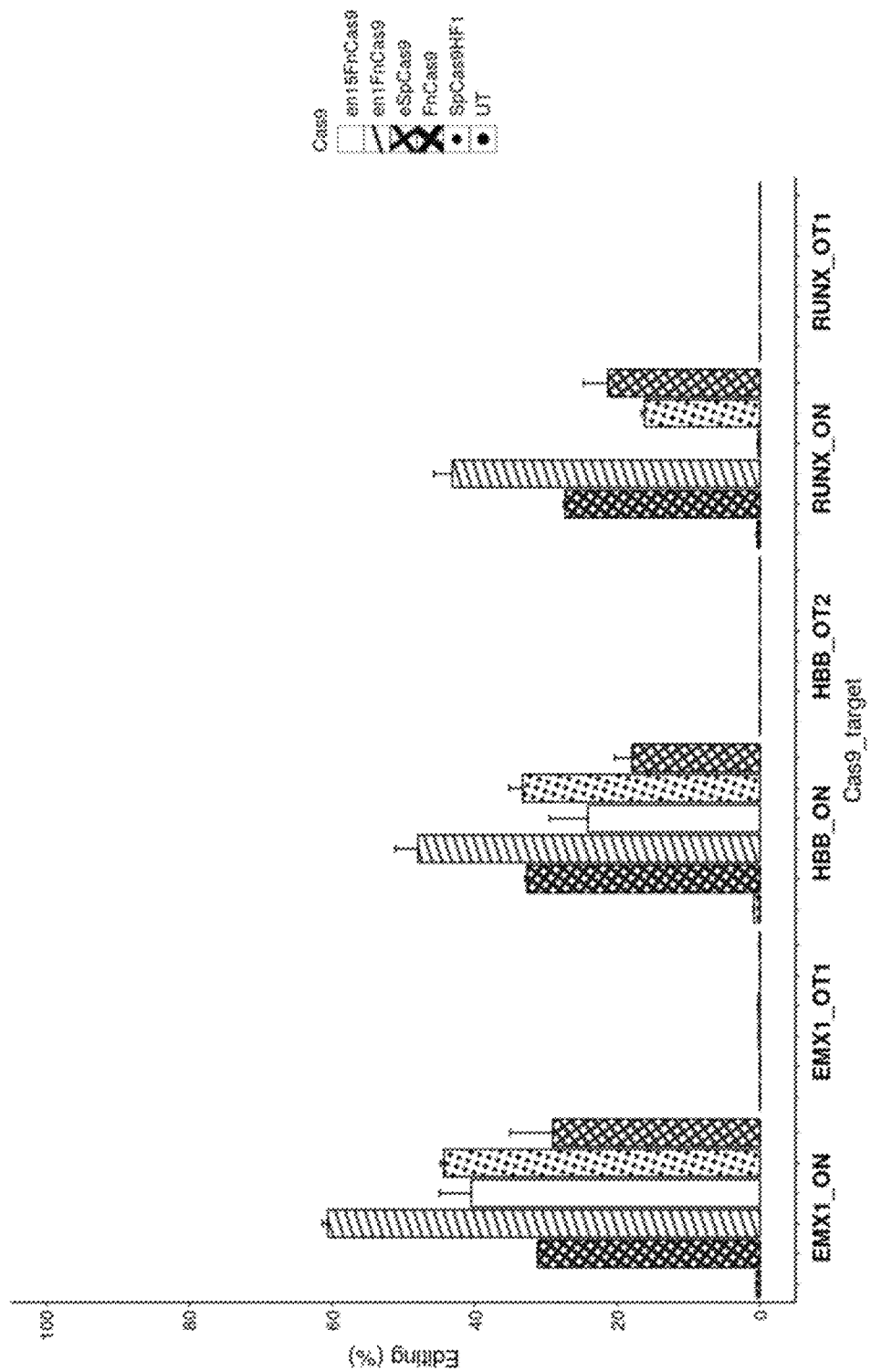
FIG. 15: INDEL events as percent editing in HEK293T cells by respective Cas9s on EMX1, HBB and RUNX1 loci and respective off-targets (OTs). SEQ ID NOS:285-300. Error bars represent SEM (three independent experiments).
Figure 16:
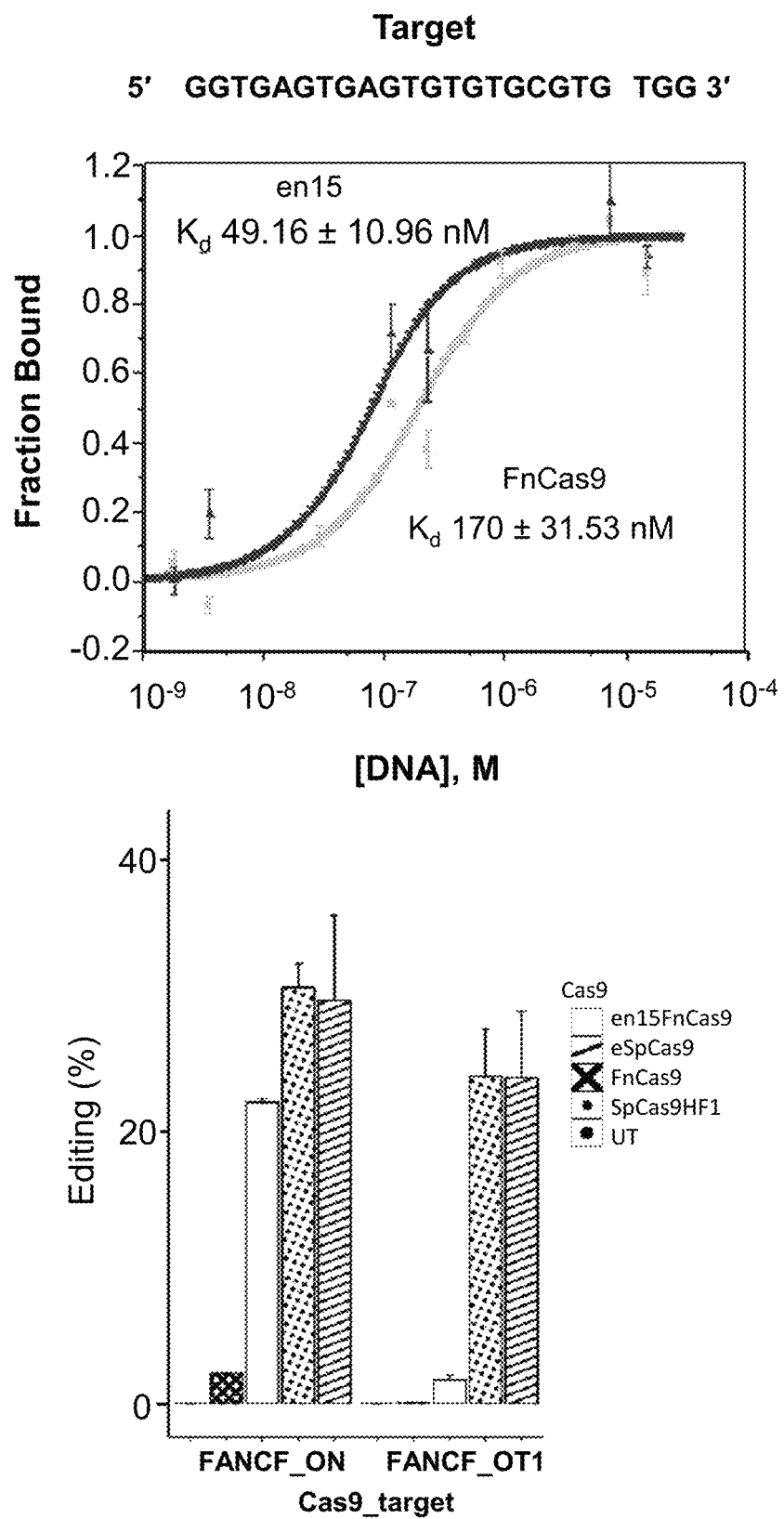
FIG. 16: Micro Scale Thermophoresis result showing the comparative binding affinity between FnCas9 and en15 on VEGFA3 substrate DNA (SEQ ID NOS:281, 282). Data is represented as a fraction bound RNP (y-axis) with respect to purified DNA substrate (Molar units M, x-axis). Error bars represent SD (three independent experiments). Indel events (expressed in percentage) as obtained from amplicon sequencing upon targeting FANCF locus in HEK293T cells (SEQ ID NOS:297-300). Untransfected cells serve as control. Error bars represent SEM (three independent experiments).
Figure 18:
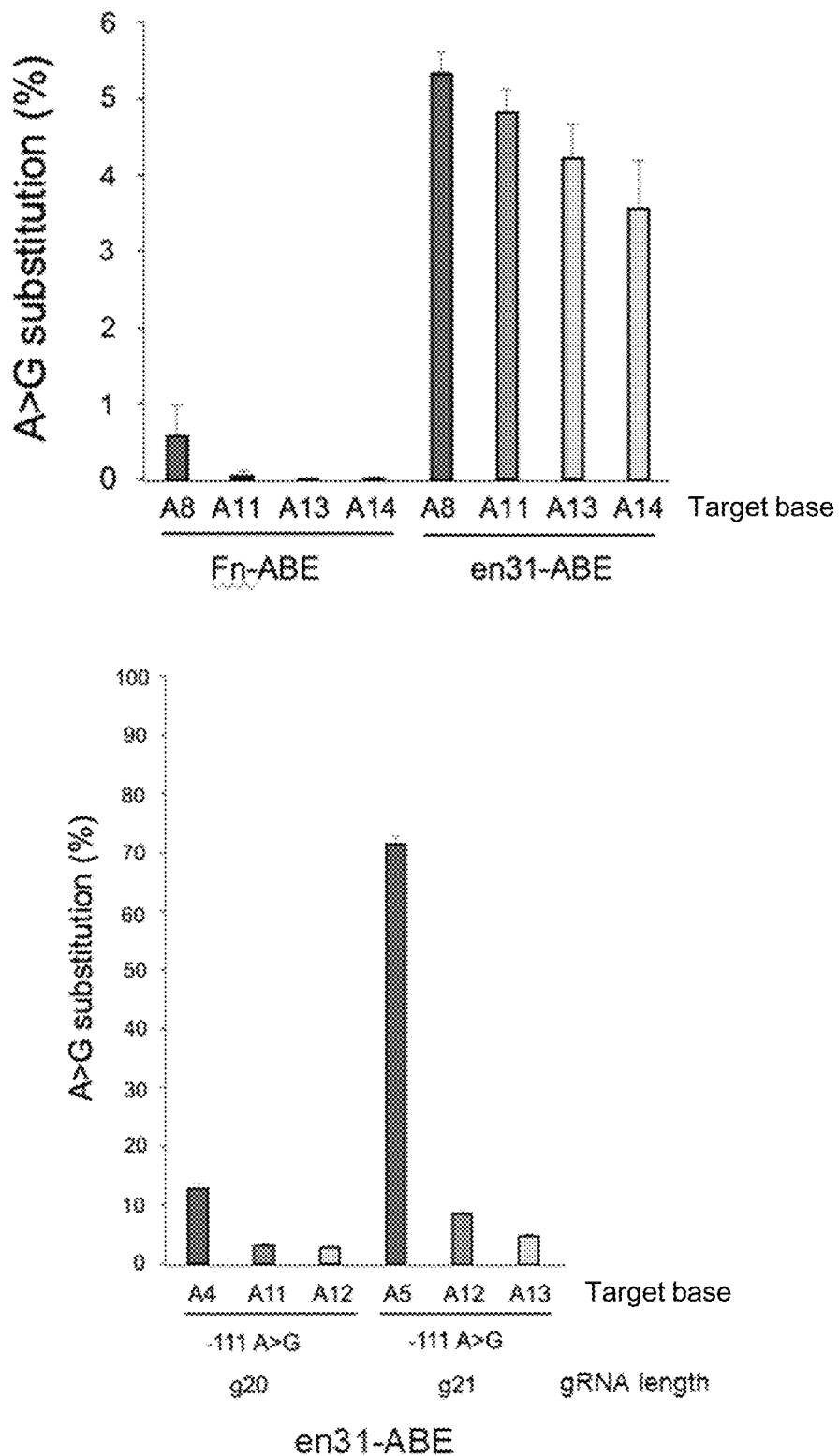
FIG. 18: (A) Control subtracted A>G base substitution percentage as obtained from amplicon sequencing upon targeting EMX1 (using) in HEK293T cells by Fn-ABE and en31-ABE (SEQ ID NO:129). (B) Control subtracted A>G base substitution percentage as obtained from amplicon sequencing (SEQ ID NOS:301, 302) upon targeting—111 HBG1/2 promoter (using SEQ ID NOS:212, 213) responsible for recreating Hereditary Persistence of Fetal Hemoglobin (HPFH) in HEK293T cells by en31-ABE.
Figure 19:
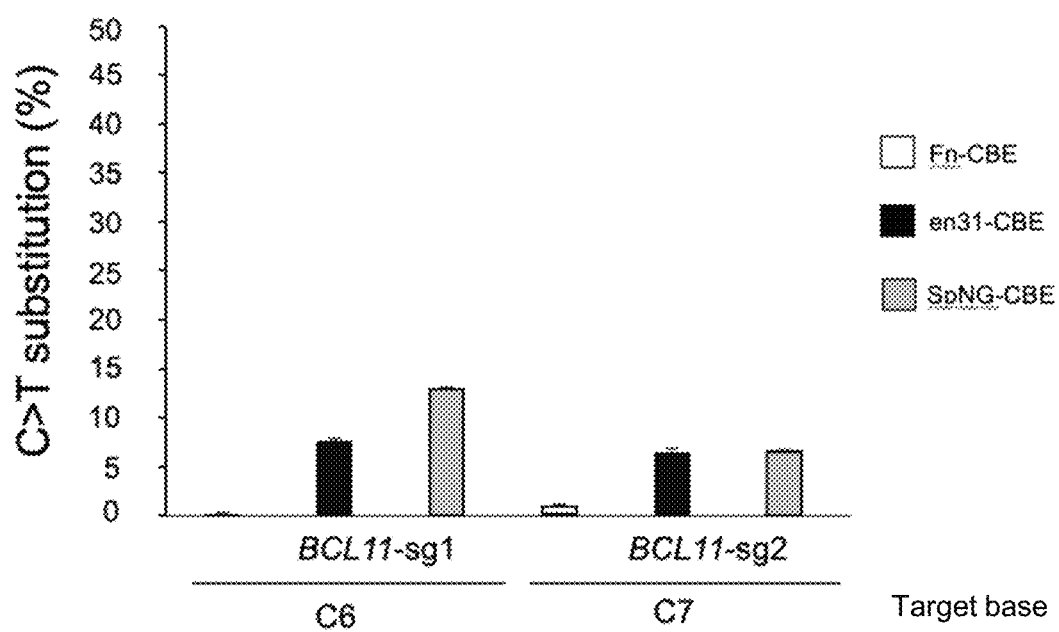
FIG. 19: Control subtracted C>T base substitution percentage as obtained from amplicon sequencing (using SEQ ID NOS:303, 304) upon targeting BCL11A enhancer by two different gRNAs (sg1 and sg2; SEQ ID NOS:214, 215) in HEK293T cells for respective Cas9-CBEs.

Dual indexing was done using Nextera XT V2 index kit followed by another round of bead-based purification. The libraries were quantified using a Qubit dsDNA HS Assay kit (Invitrogen, Q32853) and 1 µL was run on a Bioanalyzer (Agilent 2100 Bioanalyzer) for quality check. Libraries were normalized, pooled and were loaded onto illumina MiniSeq platform for a 150-bp paired-end sequencing run (FIGS. 15, 18, and 19).

Example 7

Method of Gene Editing

Figure 20:
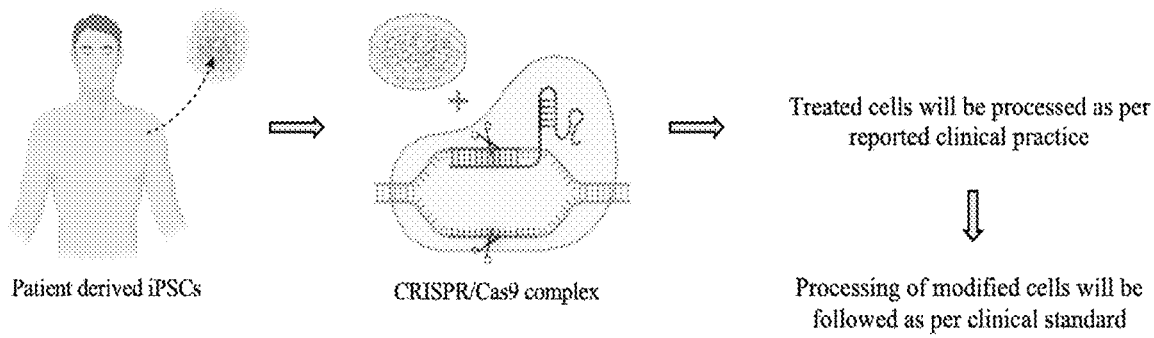
FIG. 20: Ex-vivo method for gene editing. Patient derived iPSCs are cultured. Proliferated cells after incubation are exposed to the CRISPR-Cas9 engineering. The complex induces double-strand DNA breaks in the targeted genomic region. The modification is corrected via the natural DNA-repair mechanisms. Successfully treated cells are then processed as per clinical standards. For example, in case of a hemoglobin disorder, CD34+ HSCs are isolated and cultured in appropriate media such as TeSR, DMEM under defined incubation conditions. Following expansion of cells, electroporation is conducted creating pores in the cell membrane through which CRISPR/Cas9 complex can be introduced. This complex will target the sequence in the gene to be edited and make desired cuts. Repair mechanisms such as HDR or NHEJ will support correction. Once expressed, successfully edited cells will undergo expansion and will be introduced again to the recipient following clinically approved practices.
Figure 20:
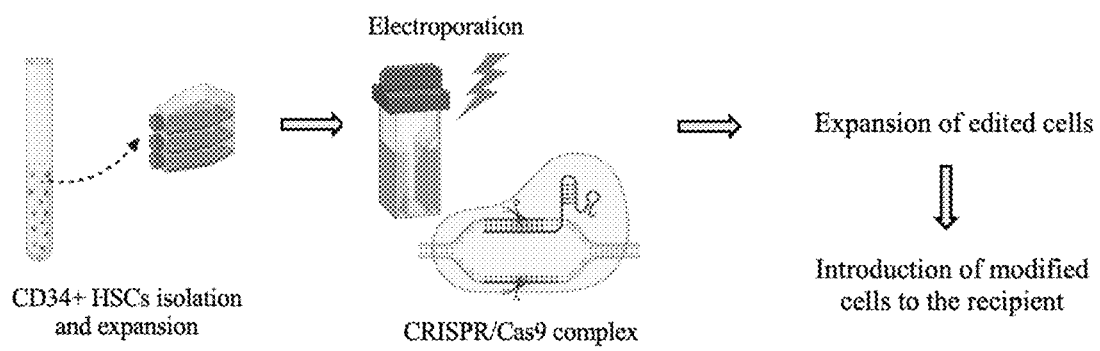
Figure 21:
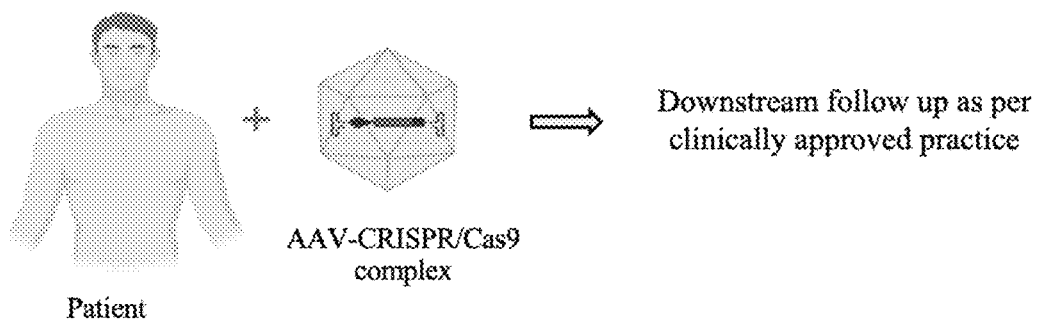
FIG. 21: In-vivo method for gene editing. The patient is introduced the CRISPR-Cas9 construct, specifically designed to target the gene to be edited via the AAV vector. The complex after associating with the targeted cells could result in desired transgene expression. A downstream follow-up of symptom-reversal or desired phenotype via correct protein formation in the patient can be observed while adhering to clinically approved practices.

As mentioned in Example 6, a kit for gene editing can be prepared using the following to perform ex vivo (FIGS. 20 and 21):
1. Cas9 effector.
2. single-guide(sg)RNA or dual crRNA:tracrRNA dissolved in nuclease free water (NFW).
3. Homology Directed Repair (HDR) template dissolved in NFW if nuclease in '1' is used.
4. NFW is present if DNA is used in '1'.

5. 10 mM Tris-HCl, pH 7.5 is present if mRNA is used in '1'.
6. Protein storage buffer (20 mM HEPES pH 7.5, 150 mM KCl, 10% glycerol, 1 mM DTT) is present if protein is used in '1'.

Thus, the present disclosure provides, among other features:
1. An engineered FnCas9 variant having higher specificity owing to its stable binding to DNA and undetectable off-target editing;
2. The broader PAM recognition widening the scope of FnCas9 variant for targeting sequences that the wild type enzyme cannot recognize; and
3. Engineered FnCas9 variants and derivatives ensuring that both double strand-break based editing as well as break-free editing works with high efficiency inside cells.

REFERENCES

1. Sander, J. D. & Joung, J. K. CRISPR-Cas systems for editing, regulating and targeting genomes. Nature Biotechnol. 32, 347-355 (2014).
2. Doudna, J. A. & Charpentier, E. Genome editing. The new frontier of genome engineering with CRISPR-Cas9. Science 346, 1258096 (2014).
3. Mojica, F. J., Diez-Villasenor, C., Garcia-Martinez, J. & Almendros, C. Short motif sequences determine the targets of the prokaryotic CRISPR defence system. Microbiology 155, 733-740 (2009).
4. Shah, S. A., Erdmann, S., Mojica, F. J. & Garrett, R. A. Protospacer recognition motifs: mixed identities and functional diversity. RNA Biol. 10, 891-899 (2013).
5. Jinek, M. et al. A programmable dual-RNA-guided DNA endonuclease in adaptive bacterial immunity. Science 337, 816-821 (2012).
6. Sternberg, S. H., Redding, S., Jinek, M., Greene, E. C. & Doudna, J. A. DNA interrogation by the CRISPR RNA-guided endonuclease Cas9. Nature 507, 62-67 (2014).
7. Acharya, S. et al. (2019) 'Cas9 interrogates genomic DNA with very high specificity and can be used for mammalian genome editing', Proceedings of the National Academy of Sciences of the United States of America, 116(42), pp. 20959-20968.
8. Hirano, H. et al. (2016) 'Structure and Engineering of Francisella novicida Cas9', Cell, 164(5), pp. 950-961.
9. Nishimasu, H. et al. (2018) 'Engineered CRISPR-Cas9 nuclease with expanded targeting space', Science, 361 (6408), pp. 1259-1262.

We claim:

1. A ribonucleoprotein complex for gene editing comprising:
   (a) an engineered FnCas9 protein effector selected from the group consisting of SEQ ID NO:16 and SEQ ID NO:31; and
   (b) a crispr RNA (crRNA) having from 20 to 24 nucleotides, wherein the crRNA binds to a nucleotide sequence located upstream and adjacent to a protospacer adjacent motif (PAM) sequence selected from the group consisting of NGG, NGA, GGA, and GGG; and
   (c) a trans-activating crispr RNA (tracrRNA) having SEQ ID NO:305.

2. The ribonucleoprotein complex of claim 1, wherein the engineered FnCas9 protein effector is SEQ ID NO:16.

3. The ribonucleoprotein complex of claim 1, wherein the engineered FnCas9 protein effector is SEQ ID NO:31.

4. The ribonucleoprotein complex of claim 1, wherein the crRNA of the ribonucleoprotein complex is transcribed in vitro using a DNA sequence selected from the group consisting of SEQ ID NOS:203-215.

5. A method for gene editing by the ribonucleoprotein complex of claim 1, the method comprising:
   (a) delivering the ribonucleoprotein complex to living cells;
   (b) breaking DNA at a genetic target using the crRNA of the ribonucleoprotein complex, wherein the crRNA is transcribed with a DNA sequence selected from the group consisting of SEQ ID NOS: 203-215; and
   (c) sealing the DNA break by repair machinery of the cell, optionally comprising a repair DNA template.

6. A method for base editing by the ribonucleoprotein complex of claim 1, the method comprising:
   (a) delivering the ribonucleoprotein complex to living cells;
   (b) modifying a target base using the crRNA of the ribonucleoprotein complex, wherein the crRNA is transcribed with a DNA sequence selected from the group consisting of SEQ ID NOS:212-215, and wherein modifying the target base is accomplished without breaking the DNA.

7. A kit for gene editing, comprising:
   (a) the ribonucleoprotein complex according to claim 1
   (b) a Homology Directed Repair (HDR) template; and
   (c) at least one buffer.

8. The kit of claim 7, wherein the crRNA of the ribonucleoprotein complex is transcribed in vitro using a DNA sequence selected from the group consisting of SEQ ID NOS:203-215.

* * * * *

SEQUENCE LISTING

```
Sequence total quantity: 305
SEQ ID NO: 1            moltype = AA  length = 1629
FEATURE                 Location/Qualifiers
source                  1..1629
                        mol_type = protein
                        organism = Francisella novicida
SEQUENCE: 1
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YSPEYLNIVP  120
EQVKAILMDI FDDYNGEDDL DSYLKLATEQ ESKISEIYNK LMQKILEFKL MKLCTDIKDD  180
KVSTKTLKEI TSYEFELLAD YLANYSESLK TQKFSYTDKQ GNLKELSYYH HDKYNIQEFL  240
KRHATINDRI LDTLLTDDLD IWNFNFEKFD FDKNEEKLQN QEDKDHIQAH LHHFVFAVNK  300
IKSEMASGGR HRSQYFQEIT NVLDENNHQE GYLKNFCENL HNKKYSNLSV KNLVNLIGNL  360
SNLELKPLRK YFNDKIHAKA DHWDEQKFTE TYCHWILGEW RVGVKDQDKK DGAKYSYKDL  420
CNELKQKVTK AGLVDFLLEL DPCRTIPPYL DNNNRKPPKC QSLILNPKFL DNQYPNWQQY  480
LQELKKLQSI QNYLDSFETD LKVLKSSKDQ PYFVEYKSSN QQIASGQRDY KDLDARILQF  540
IFDRVKASDE LLLNEIYFQA KKLKQKASSE LEKLESSKKL DEVIANSQLS QILKSQHTNG  600
IFEQGTFLHL VCKYYKQRQR ARDSRLYIMP EYRYDKKLHK YNNTGRFDDD NQLLTYCNHK  660
PRQKRYQLLN DLAGVLQVSP NFLKDKIGSD DDLFISKWLV EHIRGFKKAC EDSLKIQKDN  720
RGLLNHKINI ARNTKGKCEK EIFNLICKIE GSEDKKGNYK HGLAYELGVL LFGEPNEASK  780
PEFDRKIKKF NSIYSFAQIQ QIAFAERKGN ANTCAVCSAD NAHRMQQIKI TEPVEDNKDK  840
IILSAKAQRL PAIPTRIVDG AVKKMATILA KNIVDDNWQN IKQVLSAKHQ LHIPIITESN  900
AFEFEPALAD VKGKSLKDRR KKALERISPE NIFKDKNNRI KEFAKGISAY SGANLTDGDF  960
DGAKEELDHI IPRSHKKYGT LNDEANLICV TRGDNKNKGN RIFCLRDLAD NYKLKQFETT 1020
DDLEIEKKIA DTIWDANKKD FKFGNYRSFI NLTPQEQKAF RHALFLADEN PIKQAVIRAI 1080
NNRNRTFVNG TQRYFAEVLA NNIYLRAKKE NLNTDKISFD YFGIPTIGNG RGIAEIRQLY 1140
EKVDSDIQAY AKGDKPQASY SHLIDAMLAF CIAADEHRND GSIGLEIDKN YSLYPLDKNT 1200
GEVFTKDIFS QIKITDNEFS DKKLVRKKAI EGFNTHRQMT RDGIYAENYL PILIHKELNE 1260
VRKGYTWKNS EEIKIFKGKK YDIQQLNNLV YCLKFVDKPI SIDIQISTLE ELRNILTTNN 1320
IAATAEYYYI NLKTQKLHEY YIENYNTALG YKKYSKEMEF LRSLAYRSER VKIKSIDDVK 1380
QVLDKDSNFI IGKITLPFKK EWQRLYREWQ NTTIKDDYEF LKSFFNVKSI TKLHKKVRKD 1440
FSLPISTNEG KFLVKRKTWD NNFIYQILND SDSRADGTKP FIPAFDISKN EIVEAIIDSF 1500
TSKNIFWLPK NIELQKVDNK NIFAIDTSKW FEVETPSDLR DIGIATIQYK IDNNSRPKVR 1560
VKLDYVIDDD SKINYFMNHS LLKSRYPDKV LEILKQSTII EFESSGFNKT IKEMLGMKLA 1620
GIYNETSNN                                                        1629

SEQ ID NO: 2            moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 2
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YSPEYLNIVP  120
```

```
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSRR VKIKSIDDVK   1380
QVLDKDSNFI IGKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNKT IKEMLGMKLA   1620
GIYNETSNN                                                         1629

SEQ ID NO: 3           moltype = AA  length = 1629
FEATURE                Location/Qualifiers
REGION                 1..1629
                       note = engineered FnCas9
source                 1..1629
                       mol_type = protein
                       organism = synthetic construct
SEQUENCE: 3
MNFKILPIAI DLGVKNTGVF SAFYQKGTSL ERLDNKNGKV YELSKDSYTL LMNNRTARRH     60
QRRGIDRKQL VKRLFKLIWT EQLNEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSER VKIKSIDDVK   1380
QVLDKDSNFI IGKITLPFKK EWQRLYREWQ NTTIKDDYEF LKSFFNVKSI TKLHKKVRKD   1440
FSLPISTNHG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNKT IKEMLGMKLA   1620
GIYNETSNN                                                         1629

SEQ ID NO: 4           moltype = AA  length = 1629
FEATURE                Location/Qualifiers
REGION                 1..1629
                       note = engineered FnCas9
source                 1..1629
                       mol_type = protein
                       organism = synthetic construct
SEQUENCE: 4
MNFKILPIAI DLGVKNTGVF SAFYQKGTSL ERLDNKNGKV YELSKDSYTL LMNNRTARRH     60
QRRGIDRKQL VKRLFKLIWT EQLNEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
```

```
CNELKQKVTK AGLVDFLLEL DPCRTIPPYL DNNNRKPPKC QSLILNPKFL DNQYPNWQQY      480
LQELKKLQSI QNYLDSFETD LKVLKSSKDQ PYFVEYKSSN QQIASGQRDY KDLDARILQF      540
IFDRVKASDE LLLNEIYFQA KKLKQKASSE LEKLESSKKL DEVIANSQLS QILKSQHTNG      600
IFEQGTFLHL VCKYYKQRQR ARDSRLYIMP EYRYDKKLHK YNNTGRFDDD NQLLTYCNHK      660
PRQKRYQLLN DLAGVLQVSP NFLKDKIGSD DDLFISKWLV EHIRGFKKAC EDSLKIQKDN      720
RGLLNHKINI ARNTKGKCEK EIFNLICKIE GSEDKKGNYK HGLAYELGVL LFGEPNEASK      780
PEFDRKIKKF NSIYSFAQIQ QIAFAERKGN ANTCAVCSAD NAHRMQQIKI TEPVEDNKDK      840
IILSAKAQRL PAIPTRIVDG AVKKMATILA KNIVDDNWQN IKQVLSAKHQ LHIPIITESN      900
AFEFEPALAD VKGKSLKDRR KKALERISPE NIFKDKNNRI KEFAKGISAY SGANLTDGDF      960
DGAKEELDHI IPRSHKKYGT LNDEANLICV TRGDNKNKGN RIFCLRDLAD NYKLKQFETT     1020
DDLEIEKKIA DTIWDANKKD FKFGNYRSFI NLTPQEQKAF RHALFLADEN PIKQAVIRAI     1080
NNRNRTFVNG TQRYFAEVLA NNIYLRAKKE NLNTDKISFD YFGIPTIGNG RGIAEIRQLY     1140
EKVDSDIQAY AKGDKPQASY SHLIDAMLAF CIAADEHRND GSIGLEIDKN YSLYPLDKNT     1200
GEVFTKDIFS QIKITDNEFS DKKLVRKKAI EGFNTHRQMT RDGIYAENYL PILIHKELNE     1260
VRKGYTWKNS EEIKIFKGKK YDIQQLNNLV YCLKFVDKPI SIDIQISTLE ELRNILTTNN     1320
IAATAEYYYI NLKTQKLHEY YIENYNTALG YKKYSKEMEF LRSLAYRSRR VKIKSIDDVK     1380
QVLDKDSNFI IGKITLPFKK EWQRLYREWQ NTTIKDDYEF LKSFFNVKSI TKLHKKVRKD     1440
FSLPISTNHG KFLVKRKTWD NNFIYQILND SDSRADGTKP FIPAFDISKN EIVEAIIDSF     1500
TSKNIFWLPK NIELQKVDNK NIFAIDTSKW FEVETPSDLR DIGIATIQYK IDNNSRPKVR     1560
VKLDYVIDDD SKINYFMNHS LLKSRYPDKV LEILKQSTII EFESSGFNKT IKEMLGMKLA     1620
GIYNETSNN                                                            1629

SEQ ID NO: 5            moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 5
MNFKILPIAI DLGVKNTGVF SAFYQKGTSL ERLDNKNGKV YELSKDSYTL LMNNRTARRH       60
QRRGIDRKQL VKRLFKLIWT EQLNLEWDKD TQQAISFLFN RRGFSFITDG YSPEYLNIVP      120
EQVKAILMDI FDDYNGEDDL DSYLKLATEQ ESKISEIYNK LMQKILEFKL MKLCTDIKDD      180
KVSTKTLKEI TSYEFELLAD YLANYSESLK TQKFSYTDKQ GNLKELSYYH HDKYNIQEFL      240
KRHATINDRI LDTLLTDDLD IWNFNFEKFD FDKNEEKLQN QEDKDHIQAH LHHFVFAVNK      300
IKSEMASGGR HRSQYFQEIT NVLDENNHQE GYLKNFCENL HNKKYSNLSV KNLVNLIGNL      360
SNLELKPLRK YFNDKIHAKA DHWDEQKFTE TYCHWILGEW RVGVKDQDKK DGAKYSYKDL      420
CNELKQKVTK AGLVDFLLEL DPCRTIPPYL DNNNRKPPKC QSLILNPKFL DNQYPNWQQY      480
LQELKKLQSI QNYLDSFETD LKVLKSSKDQ PYFVEYKSSN QQIASGQRDY KDLDARILQF      540
IFDRVKASDE LLLNEIYFQA KKLKQKASSE LEKLESSKKL DEVIANSQLS QILKSQHTNG      600
IFEQGTFLHL VCKYYKQRQR ARDSRLYIMP EYRYDKKLHK YNNTGRFDDD NQLLTYCNHK      660
PRQKRYQLLN DLAGVLQVSP NFLKDKIGSD DDLFISKWLV EHIRGFKKAC EDSLKIQKDN      720
RGLLNHKINI ARNTKGKCEK EIFNLICKIE GSEDKKGNYK HGLAYELGVL LFGEPNEASK      780
PEFDRKIKKF NSIYSFAQIQ QIAFAERKGN ANTCAVCSAD NAHRMQQIKI TEPVEDNKDK      840
IILSAKAQRL PAIPTRIVDG AVKKMATILA KNIVDDNWQN IKQVLSAKHQ LHIPIITESN      900
AFEFEPALAD VKGKSLKDRR KKALERISPE NIFKDKNNRI KEFAKGISAY SGANLTDGDF      960
DGAKEELDHI IPRSHKKYGT LNDEANLICV TRGDNKNKGN RIFCLRDLAD NYKLKQFETT     1020
DDLEIEKKIA DTIWDANKKD FKFGNYRSFI NLTPQEQKAF RHALFLADEN PIKQAVIRAI     1080
NNRNRTFVNG TQRYFAEVLA NNIYLRAKKE NLNTDKISFD YFGIPTIGNG RGIAEIRQLY     1140
EKVDSDIQAY AKGDKPQASY SHLIDAMLAF CIAADEHRND GSIGLEIDKN YSLYPLDKNT     1200
GEVFTKDIFS QIKITDNEFS DKKLVRKKAI EGFNTHRQMT RDTIYAENYL PILIHKELNE     1260
VRKGYTWKNS EEIKIFKGKK YDIQQLNNLV YCLKFVDKPI SIDIQISTLE ELRNILTTNN     1320
IAATAEYYYI NLKTQKLHEY YIENYNTALG YKKYSKEMEF LRSLAYRSER VKIKSIDDVK     1380
QVLDKDSNFI IGKITLPFKK EWQRLYREWQ NTTIKDDYEF LKSFFNVKSI TKLHKKVRKD     1440
FSLPISTNEG KFLVKRKTWD NNFIYQILND SDSRADGTKP FIPAFDISKN EIVEAIIDSF     1500
TSKNIFWLPK NIELQKVDNK NIFAIDTSKW FEVETPSDLR DIGIATIQYK IDNNSRPKVR     1560
VKLDYVIDDD SKINYFMNHS LLKSRYPDKV LEILKQSTII EFESSGFNKT IKEMLGMKLA     1620
GIYNETSNN                                                            1629

SEQ ID NO: 6            moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 6
MNFKILPIAI DLGVKNTGVF SAFYQKGTSL ERLDNKNGKV YELSKDSYTL LMNNRTARRH       60
QRRGIDRKQL VKRLFKLIWT EQLNLEWDKD TQQAISFLFN RRGFSFITDG YSPEYLNIVP      120
EQVKAILMDI FDDYNGEDDL DSYLKLATEQ ESKISEIYNK LMQKILEFKL MKLCTDIKDD      180
KVSTKTLKEI TSYEFELLAD YLANYSESLK TQKFSYTDKQ GNLKELSYYH HDKYNIQEFL      240
KRHATINDRI LDTLLTDDLD IWNFNFEKFD FDKNEEKLQN QEDKDHIQAH LHHFVFAVNK      300
IKSEMASGGR HRSQYFQEIT NVLDENNHQE GYLKNFCENL HNKKYSNLSV KNLVNLIGNL      360
SNLELKPLRK YFNDKIHAKA DHWDEQKFTE TYCHWILGEW RVGVKDQDKK DGAKYSYKDL      420
CNELKQKVTK AGLVDFLLEL DPCRTIPPYL DNNNRKPPKC QSLILNPKFL DNQYPNWQQY      480
LQELKKLQSI QNYLDSFETD LKVLKSSKDQ PYFVEYKSSN QQIASGQRDY KDLDARILQF      540
IFDRVKASDE LLLNEIYFQA KKLKQKASSE LEKLESSKKL DEVIANSQLS QILKSQHTNG      600
IFEQGTFLHL VCKYYKQRQR ARDSRLYIMP EYRYDKKLHK YNNTGRFDDD NQLLTYCNHK      660
PRQKRYQLLN DLAGVLQVSP NFLKDKIGSD DDLFISKWLV EHIRGFKKAC EDSLKIQKDN      720
```

```
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSYR VKIKSIDDVK   1380
QVLDKDSNFI IGKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNKT IKEMLGMKLA   1620
GIYNETSNN                                                          1629

SEQ ID NO: 7             moltype = AA  length = 1629
FEATURE                  Location/Qualifiers
REGION                   1..1629
                         note = engineered FnCas9
source                   1..1629
                         mol_type = protein
                         organism = synthetic construct
SEQUENCE: 7
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSER VKIKSIDDVK   1380
QVLDKDSNFI IRKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNKT IKEMLGMKLA   1620
GIYNETSNN                                                          1629

SEQ ID NO: 8             moltype = AA  length = 1629
FEATURE                  Location/Qualifiers
REGION                   1..1629
                         note = engineered FnCas9
source                   1..1629
                         mol_type = protein
                         organism = synthetic construct
SEQUENCE: 8
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
```

```
DDLEIEKKIA DTIWDANKKD FKFGNYRSFI NLTPQEQKAF RHALFLADEN PIKQAVIRAI 1080
NNRNRTFVNG TQRYFAEVLA NNIYLRAKKE NLNTDKISFD YFGIPTIGNG RGIAEIRQLY 1140
EKVDSDIQAY AKGDKPQASY SHLIDAMLAF CIAADEHRND GSIGLEIDKN YSLYPLDKNT 1200
GEVFTKDIFS QIKITDNEFS DKKLVRKKAI EGFNTHRQMT RDGIYAENYL PILIHKELNE 1260
VRKGYTWKNS EEIKIFKGKK YDIQQLNNLV YCLKFVDKPI SIDIQISTLE ELRNILTTNN 1320
IAATAEYYYI NLKTQKLHEY YIENYNTALG YKKYSKEMEF LRSLAYRSER VKIKSIDDVK 1380
QVLDKDSNFI IKKITLPFKK EWQRLYREWQ NTTIKDDYEF LKSFFNVKSI TKLHKKVRKD 1440
FSLPISTNEG KFLVKRKTWD NNFIYQILND SDSRADGTKP FIPAFDISKN EIVEAIIDSF 1500
TSKNIFWLPK NIELQKVDNK NIFAIDTSKW FEVETPSDLR DIGIATIQYK IDNNSRPKVR 1560
VKLDYVIDDD SKINYFMNHS LLKSRYPDKV LEILKQSTII EFESSGFNKT IKEMLGMKLA 1620
GIYNETSNN                                                       1629

SEQ ID NO: 9           moltype = AA   length = 1629
FEATURE                Location/Qualifiers
REGION                 1..1629
                       note = engineered FnCas9
source                 1..1629
                       mol_type = protein
                       organism = synthetic construct
SEQUENCE: 9
MNFKILPIAI DLGVKNTGVF SAFYQKGTSL ERLDNKNGKV YELSKDSYTL LMNNRTARRH 60
QRRGIDRKQL VKRLFKLIWT EQLNLEWDKD TQQAISFLFN RRGFSFITDG YSPEYLNIVP 120
EQVKAILMDI FDDYNGEDDL DSYLKLATEQ ESKISEIYNK LMQKILEFKL MKLCTDIKDD 180
KVSTKTLKEI TSYEFELLAD YLANYSESLK TQKFSYTDKQ GNLKELSYYH HDKYNIQEFL 240
KRHATINDRI LDTLLTDDLD IWNFNFEKFD FDKNEEKLQN QEDKDHIQAH LHHFVFAVNK 300
IKSEMASGGR HRSQYFQEIT NVLDENNHQE GYLKNFCENL HNKKYSNLSV KNLVNLIGNL 360
SNLELKPLRK YFNDKIHAKA DHWDEQKFTE TYCHWILGEW RVGVKDQDKK DGAKYSYKDL 420
CNELKQKVTK AGLVDPLLEL DPCRTIPPYL DNNNRKPPKC QSLILNPKFL DNQYPNWQQY 480
LQELKKLQSI QNYLDSFETD LKVLKSSKDQ PYFVEYKSSN QQIASGQRDY KDLDARILQF 540
IFDRVKASDE LLLNEIYFQA KKLKQKASSE LEKLESSSKKL DEVIANSQLS QILKSQHTNG 600
IFEQGTFLHL VCKYYKQRQR ARDSRLYIMP EYRYDKKLHK YNNTGRFDDD NQLLTYCNHK 660
PRQKRYQLLN DLAGVLQVSP NFLKDKIGSD DDLFISKWLV EHIRGFKKAC EDSLKIQKDN 720
RGLLNHKINI ARNTKGKCEK EIFNLICKIE GSEDKKGNYK HGLAYELGVL LFGEPNEASK 780
PEFDRKIKKF NSIYSFAQIQ QIAFAERKGN ANTCAVCSAD NAHRMQQIKI TEPVEDNKDK 840
IILSAKAQRL PAIPTRIVDG AVKKMATILA KNIVDDNWQN IKQVLSAKHQ LHIPIITESN 900
AFEFEPALAD VKGKSLKDRR KKALERISPE NIFKDKNNRI KEFAKGISAY SGANLTGDGF 960
DGAKEELDHI IPRSHKKYGT LNDEANLICV TRGDNKNKGN RIFCLRDLAD NYKLKQFETT 1020
DDLEIEKKIA DTIWDANKKD FKFGNYRSFI NLTPQEQKAF RHALFLADEN PIKQAVIRAI 1080
NNRNRTFVNG TQRYFAEVLA NNIYLRAKKE NLNTDKISFD YFGIPTIGNG RGIAEIRQLY 1140
EKVDSDIQAY AKGDKPQASY SHLIDAMLAF CIAADEHRND GSIGLEIDKN YSLYPLDKNT 1200
GEVFTKDIFS QIKITDNEFS DKKLVRKKAI EGFNTHRQMT RDGIYAENYL PILIHKELNE 1260
VRKGYTWKNS EEIKIFKGKK YDIQQLNNLV YCLKFVDKPI SIDIQISTLE ELRNILTTNN 1320
IAATAEYYYI NLKTQKLHEY YIENYNTALG YKKYSKEMEF LRSLAYRSER VKIKSIDDVK 1380
QVLDKDSNFI IGKITLPFKK EWQRLYREWQ NTTIKDDYEF LKSFFNVKSI TKLHKKVRKD 1440
FSLPISTREG KFLVKRKTWD NNFIYQILND SDSRADGTKP FIPAFDISKN EIVEAIIDSF 1500
TSKNIFWLPK NIELQKVDNK NIFAIDTSKW FEVETPSDLR DIGIATIQYK IDNNSRPKVR 1560
VKLDYVIDDD SKINYFMNHS LLKSRYPDKV LEILKQSTII EFESSGFNKT IKEMLGMKLA 1620
GIYNETSNN                                                       1629

SEQ ID NO: 10          moltype = AA   length = 1629
FEATURE                Location/Qualifiers
REGION                 1..1629
                       note = engineered FnCas9
source                 1..1629
                       mol_type = protein
                       organism = synthetic construct
SEQUENCE: 10
MNFKILPIAI DLGVKNTGVF SAFYQKGTSL ERLDNKNGKV YELSKDSYTL LMNNRTARRH 60
QRRGIDRKQL VKRLFKLIWT EQLNLEWDKD TQQAISFLFN RRGFSFITDG YSPEYLNIVP 120
EQVKAILMDI FDDYNGEDDL DSYLKLATEQ ESKISEIYNK LMQKILEFKL MKLCTDIKDD 180
KVSTKTLKEI TSYEFELLAD YLANYSESLK TQKFSYTDKQ GNLKELSYYH HDKYNIQEFL 240
KRHATINDRI LDTLLTDDLD IWNFNFEKFD FDKNEEKLQN QEDKDHIQAH LHHFVFAVNK 300
IKSEMASGGR HRSQYFCENL NVLDENNHQE GYLKNFCENL HNKKYSNLSV KNLVNLIGNL 360
SNLELKPLRK YFNDKIHAKA DHWDEQKFTE TYCHWILGEW RVGVKDQDKK DGAKYSYKDL 420
CNELKQKVTK AGLVDPLLEL DPCRTIPPYL DNNNRKPPKC QSLILNPKFL DNQYPNWQQY 480
LQELKKLQSI QNYLDSFETD LKVLKSSKDQ PYFVEYKSSN QQIASGQRDY KDLDARILQF 540
IFDRVKASDE LLLNEIYFQA KKLKQKASSE LEKLESSKKL DEVIANSQLS QILKSQHTNG 600
IFEQGTFLHL VCKYYKQRQR ARDSRLYIMP EYRYDKKLHK YNNTGRFDDD NQLLTYCNHK 660
PRQKRYQLLN DLAGVLQVSP NFLKDKIGSD DDLFISKWLV EHIRGFKKAC EDSLKIQKDN 720
RGLLNHKINI ARNTKGKCEK EIFNLICKIE GSEDKKGNYK HGLAYELGVL LFGEPNEASK 780
PEFDRKIKKF NSIYSFAQIQ QIAFAERKGN ANTCAVCSAD NAHRMQQIKI TEPVEDNKDK 840
IILSAKAQRL PAIPTRIVDG AVKKMATILA KNIVDDNWQN IKQVLSAKHQ LHIPIITESN 900
AFEFEPALAD VKGKSLKDRR KKALERISPE NIFKDKNNRI KEFAKGISAY SGANLTGDGF 960
DGAKEELDHI IPRSHKKYGT LNDEANLICV TRGDNKNKGN RIFCLRDLAD NYKLKQFETT 1020
DDLEIEKKIA DTIWDANKKD FKFGNYRSFI NLTPQEQKAF RHALFLADEN PIKQAVIRAI 1080
NNRNRTFVNG TQRYFAEVLA NNIYLRAKKE NLNTDKISFD YFGIPTIGNG RGIAEIRQLY 1140
EKVDSDIQAY AKGDKPQASY SHLIDAMLAF CIAADEHRND GSIGLEIDKN YSLYPLDKNT 1200
GEVFTKDIFS QIKITDNEFS DKKLVRKKAI EGFNTHRQMT RDGIYAENYL PILIHKELNE 1260
VRKGYTWKNS EEIKIFKGKK YDIQQLNNLV YCLKFVDKPI SIDIQISTLE ELRNILTTNN 1320
```

```
IAATAEYYYI NLKTQKLHEY YIENYNTALG YKKYSKEMEF LRSLAYRSER VKIKSIDDVK   1380
QVLDKDSNFI IGKITLPFKK EWQRLYREWQ NTTIKDDYEF LKSFFNVKSI TKLHKKVRKD   1440
FSLPISTYEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNKT IKEMLGMKLA   1620
GIYNETSNN                                                         1629

SEQ ID NO: 11           moltype = AA  length = 1630
FEATURE                 Location/Qualifiers
REGION                  1..1630
                        note = engineered FnCas9
source                  1..1630
                        mol_type = protein
                        organism = synthetic construct
SEQUENCE: 11
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEV RVGVKDQDKK DGAKYSYKDL   420
CNELKQKVTK AGLVDFLLEL DPCRTIPPYL DNNNRKPPKC QSLILNPKFL DNQYPNWQQY   480
LQEELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
APEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KVFLVKRKTW DNNFIYQILN DSDSRADGTK PFIPAFDISK NEIVEAIIDS  1500
FTSKNIFWLP KNIELQKVDN KNIFAIDTSK WFEVETPSDL RDIGIATIQY KIDNNSRPKV  1560
RVKLDYVIDD DSKINYFMNH SLLKSRYPDK VLEILKQSTI IEFESSGFNK TIKEMLGMKL  1620
AGIYNETSNN                                                        1630

SEQ ID NO: 12           moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 12
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEV RVGVKDQDKK DGAKYSYKDL   420
CNELKQKVTK AGLVDFLLEL DPCRTIPPYL DNNNRKPPKC QSLILNPKFL DNQYPNWQQY   480
LQEELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
APEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDTRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFESSGFNKT IKEMLGMKLA  1620
```

```
GIYNETSNN                                                                    1629

SEQ ID NO: 13           moltype = AA   length = 1629
FEATURE                 Location/Qualifiers
REGION                  1..1629
                        note = engineered FnCas9
source                  1..1629
                        mol_type = protein
                        organism = synthetic construct
SEQUENCE: 13
MNFKILPIAI DLGVKNTGVF SAFYQKGTSL ERLDKNGKV  YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
APEFEPALAD VKGKSLRDRR KKALERISPE NIFKDKNNRI KEFAKGISAY SGANLTDGF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRNTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFPKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDVNSRPKVR  1560
VKLDYVIDDD SKINYFMNHS LLKSRYPDKV LEILKQSTII EFESSGFNKT IKEMLGMKLA  1620
GIYNETSNN                                                          1629

SEQ ID NO: 14           moltype = AA   length = 1629
FEATURE                 Location/Qualifiers
REGION                  1..1629
                        note = engineered FnCas9
source                  1..1629
                        mol_type = protein
                        organism = synthetic construct
SEQUENCE: 14
MNFKILPIAI DLGVKNTGVF SAFYQKGTSL ERLDKNGKV  YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
APEFEPALAD VKGKSLRDRR KKALERISPE NIFKDKNNRI KEFAKGISAY SGANLTDGF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRNTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFPKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRHPDKV LEILKQSTII EFESSGFNKT IKEMLGMKLA  1620
GIYNETSNN                                                          1629

SEQ ID NO: 15           moltype = AA   length = 1629
FEATURE                 Location/Qualifiers
REGION                  1..1629
```

|  | note = engineered FnCas9 |
| --- | --- |
| source | 1..1629 |
|  | mol_type = protein |
|  | organism = synthetic construct |

SEQUENCE: 15

```
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSITDG  YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRRPDKV LEILKQSTII EFESSGFNKT IKEMLGMKLA  1620
GIYNETSNN                                                         1629
```

| SEQ ID NO: 17 | moltype = AA  length = 1629 |
| --- | --- |
| FEATURE | Location/Qualifiers |
| REGION | 1..1629 |
|  | note = engineered FnCas9 |
| source | 1..1629 |
|  | mol_type = protein |
|  | organism = synthetic construct |

SEQUENCE: 16

```
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSITDG  YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFHSSGFNKT IKEMLGMKLA  1620
GIYNETSNN                                                         1629
```

| SEQ ID NO: 17 | moltype = AA  length = 1629 |
| --- | --- |
| FEATURE | Location/Qualifiers |
| REGION | 1..1629 |
|  | note = engineered FnCas9 |
| source | 1..1629 |
|  | mol_type = protein |
|  | organism = synthetic construct |

SEQUENCE: 17

```
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKRS SIDIQISTLE ELRNILTTNN  1320
IAATAEYYYI NLKTQKLHEY YIENYNTALG YKKYSKEMEF LRSLAYRSRR VKIKSIDDVK  1380
QVLDKDSNFI IGKITLPFKK EWQRLYREWQ NTTIKDDYEF LKSFFNVKSI TKLHKKVRKD  1440
FSLPISTNHG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSTPKVR  1560
VKLDYVIDDD SKINYFMNHS LLKSRYPDKV LEILKQSTII EFESSGFNKT IKEMLGMKLA  1620
GIYNETSNN                                                         1629

SEQ ID NO: 18         moltype = AA   length = 1629
FEATURE               Location/Qualifiers
REGION                1..1629
                      note = engineered FnCas9
source                1..1629
                      mol_type = protein
                      organism = synthetic construct
SEQUENCE: 18
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKYLVRKKAI EGFNTHRQMT RDGIYAENYL PILIHKELNE  1260
VRKGYTWKNS EEIKIFKGKK YDIQQLNNLV YCLKFVDKRS SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFESSGFNKT IKEMLGMKLA  1620
GIYNETSNN                                                         1629

SEQ ID NO: 19         moltype = AA   length = 1629
FEATURE               Location/Qualifiers
REGION                1..1629
                      note = engineered FnCas9
source                1..1629
                      mol_type = protein
                      organism = synthetic construct
SEQUENCE: 19
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
```

```
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQEELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRFDGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFESSGFNKT IKEMLGMKLA  1620
GIYNETSNN                                                         1629

SEQ ID NO: 20             moltype = AA  length = 1629
FEATURE                   Location/Qualifiers
REGION                    1..1629
                          note = engineered FnCas9
source                    1..1629
                          mol_type = protein
                          organism = synthetic construct
SEQUENCE: 20
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQEELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDHF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFESSGFNKT IKEMLGMKLA  1620
GIYNETSNN                                                         1629

SEQ ID NO: 21             moltype = AA  length = 1629
FEATURE                   Location/Qualifiers
REGION                    1..1629
                          note = engineered FnCas9
source                    1..1629
                          mol_type = protein
                          organism = synthetic construct
SEQUENCE: 21
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQEELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
```

```
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSER VKIKSIDDVK   1380
QVLDKDSNFI IGKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHR LLKSRYPDKV LEILKQSTII EFESSGFNKT IKEMLGMKLA   1620
GIYNETSNN                                                          1629

SEQ ID NO: 22           moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 22
MNFKILPIAI DLGVKNTGVF SAFYQKGTSL ERLDNKNGKV YELSKDSYTL LMNNRTARRH     60
QRRGIDRKQL VKRLFKLIWT EQLNEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSER VKIKSIDDVK   1380
QVLDKDSNFI IGKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLRSRYPDKV LEILKQSTII EFESSGFNKT IKEMLGMKLA   1620
GIYNETSNN                                                          1629

SEQ ID NO: 23           moltype = AA  length = 1629
FEATURE                 Location/Qualifiers
source                  1..1629
                        mol_type = protein
                        organism = synthetic construct
SEQUENCE: 23
MNFKILPIAI DLGVKNTGVF SAFYQKGTSL ERLDNKNGKV YELSKDSYTL LMNNRTARRH     60
QRRGIDRKQL VKRLFKLIWT EQLNEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
```

```
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSER VKIKSIDDVK   1380
QVLDKDSNFI IGKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNVT IKEMLGMKLA   1620
GIYNETSNN                                                          1629

SEQ ID NO: 24          moltype = AA  length = 1629
FEATURE                Location/Qualifiers
REGION                 1..1629
                       note = engineered FnCas9
source                 1..1629
                       mol_type = protein
                       organism = synthetic construct
SEQUENCE: 24
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
APEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFESSGFNST IKEMLGMKLA  1620
GIYNETSNN                                                         1629

SEQ ID NO: 25          moltype = AA  length = 1629
FEATURE                Location/Qualifiers
source                 1..1629
                       mol_type = protein
                       organism = synthetic construct
SEQUENCE: 25
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
APEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
```

```
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFESSGFNNT IKEMLGMKLA  1620
GIYNETSNN                                                         1629

SEQ ID NO: 26           moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 26
MNFKILPIAI DLGVKNTGVF SAFYQKGTSL ERLDNKNGKV YELSKDSYTL LMNNRTARRH  60
QRRGIDRKQL VKRLFKLIWT EQLNLEWDKD TQQAISFLFN RRGFSFITDG YSPEYLNIVP  120
EQVKAILMDI FDDYNGEDDL DSYLKLATEQ ESKISEIYNK LMQKILEFKL MKLCTDIKDD  180
KVSTKTLKEI TSYEFELLAD YLANYSESLK TQKFSYTDKQ GNLKELSYYH HDKYNIQEFL  240
KRHATINDRI LDTLLTDDLD IWNFNFEKFD FDKNEEKLQN QEDKDHIQAH LHHFVFAVNK  300
IKSEMASGGR HRSQYFQEIT NVLDENNHQE GYLKNFCENL HNKKYSNLSV KNLVNLIGNL  360
SNLELKPLRK YFNDKIHAKA DHWDEQKFTE TYCHWILGEW RVGVKDQDKK DGAKYSYKDL  420
CNELKQKVTK AGLVDFLLEL DPCRTIPPYL DNNNRKPPKC QSLILNPKFL DNQYPNWQQY  480
LQELKKLQSI QNYLDSFETD LKVLKSSKDQ PYFVEYKSSN QQIASGQRDY KDLDARILQF  540
IFDRVKASDE LLLNEIYFQA KKLKQKASSE LEKLESSKKL DEVIANSQLS QILKSQHTNG  600
IFEQGTFLHL VCKYYKQRQR ARDSRLYIMP ERYRDKKLHK YNNTGRFDDD NQLLTYCNHK  660
PRQKRYQLLN DLAGVLQVSP NFLKDKIGSD DDLFISKWLV EHIRGFKKAC EDSLKIQKDN  720
RGLLNHKINI ARNTKGKCEK EIFNLICKIE GSEDKKGNYK HGLAYELGVL LFGEPNEASK  780
PEFDRKIKKF NSIYSFAQIQ QIAFAERKGN ANTCAVCSAD NAHRMQQIKI TEPVEDNKDK  840
IILSAKAQRL PAIPTRIVDG AVKKMATILA KNIVDDNWQN IKQVLSAKHQ LHIPIITESN  900
AFEFEPALAD VKGKSLKDRR KKALERISPE NIFKDKNNRI KEFAKGISAY SGANLTDGDF  960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFESFGFNKT IKEMLGMKLA  1620
GIYNETSNN                                                         1629

SEQ ID NO: 27           moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 27
MNFKILPIAI DLGVKNTGVF SAFYQKGTSL ERLDNKNGKV YELSKDSYTL LMNNRTARRH  60
QRRGIDRKQL VKRLFKLIWT EQLNLEWDKD TQQAISFLFN RRGFSFITDG YSPEYLNIVP  120
EQVKAILMDI FDDYNGEDDL DSYLKLATEQ ESKISEIYNK LMQKILEFKL MKLCTDIKDD  180
KVSTKTLKEI TSYEFELLAD YLANYSESLK TQKFSYTDKQ GNLKELSYYH HDKYNIQEFL  240
KRHATINDRI LDTLLTDDLD IWNFNFEKFD FDKNEEKLQN QEDKDHIQAH LHHFVFAVNK  300
IKSEMASGGR HRSQYFQEIT NVLDENNHQE GYLKNFCENL HNKKYSNLSV KNLVNLIGNL  360
SNLELKPLRK YFNDKIHAKA DHWDEQKFTE TYCHWILGEW RVGVKDQDKK DGAKYSYKDL  420
CNELKQKVTK AGLVDFLLEL DPCRTIPPYL DNNNRKPPKC QSLILNPKFL DNQYPNWQQY  480
LQELKKLQSI QNYLDSFETD LKVLKSSKDQ PYFVEYKSSN QQIASGQRDY KDLDARILQF  540
IFDRVKASDE LLLNEIYFQA KKLKQKASSE LEKLESSKKL DEVIANSQLS QILKSQHTNG  600
IFEQGTFLHL VCKYYKQRQR ARDSRLYIMP ERYRDKKLHK YNNTGRFDDD NQLLTYCNHK  660
PRQKRYQLLN DLAGVLQVSP NFLKDKIGSD DDLFISKWLV EHIRGFKKAC EDSLKIQKDN  720
RGLLNHKINI ARNTKGKCEK EIFNLICKIE GSEDKKGNYK HGLAYELGVL LFGEPNEASK  780
PEFDRKIKKF NSIYSFAQIQ QIAFAERKGN ANTCAVCSAD NAHRMQQIKI TEPVEDNKDK  840
IILSAKAQRL PAIPTRIVDG AVKKMATILA KNIVDDNWQN IKQVLSAKHQ LHIPIITESN  900
AFEFEPALAD VKGKSLKDRR KKALERISPE NIFKDKNNRI KEFAKGISAY SGANLTDGDF  960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFESRGFNKT IKEMLGMKLA  1620
GIYNETSNN                                                         1629
```

```
SEQ ID NO: 28            moltype = AA   length = 1630
FEATURE                  Location/Qualifiers
REGION                   1..1630
                         note = engineered FnCas9
source                   1..1630
                         mol_type = protein
                         organism = synthetic construct
SEQUENCE: 28
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
APEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFPKGK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDRSNF IIGKITLPFK KEWQRLYREW QNTTIKDDYE FLKSFFNVKS ITKLHKKVRK  1440
DFSLPISTNE GKFLVKRKTW DNNFIYQILN DSDSRADGTK PFIPAFDISK NEIVEAIIDS  1500
FTSKNIFWLP KNIELQKVDN KNIFAIDTSK WFEVETPSDL RDIGIATIQY KIDNNSRPKV  1560
RVKLDYVIDD DSKINYFMNH SLLKSRYPDK VLEILKQSTI IEFESSGFNK TIKEMLGMKL  1620
AGIYNETSNN                                                        1630

SEQ ID NO: 29            moltype = AA   length = 1629
FEATURE                  Location/Qualifiers
source                   1..1629
                         mol_type = protein
                         organism = synthetic construct
SEQUENCE: 29
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
APEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFPKGK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRHPDKV LEILKQSTII EFHSSGFNKT IKEMLGMKLA  1620
GIYNETSNN                                                         1629

SEQ ID NO: 30            moltype = AA   length = 1629
FEATURE                  Location/Qualifiers
REGION                   1..1629
                         note = engineered FnCas9
source                   1..1629
                         mol_type = protein
                         organism = synthetic construct
```

```
SEQUENCE: 30
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YSPEYLNIVP  120
EQVKAILMDI FDDYNGEDDL DSYLKLATEQ ESKISEIYNK LMQKILEFKL MKLCTDIKDD  180
KVSTKTLKEI TSYEFELLAD YLANYSESLK TQKFSYTDKQ GNLKELSYYH HDKYNIQEFL  240
KRHATINDRI LDTLLTDDLD IWNFNFEKFD FDKNEEKLQN QEDKDHIQAH LHHFVFAVNK  300
IKSEMASGGR HRSQYFQEIT NVLDENNHQE GYLKNFCENL HNKKYSNLSV KNLVNLIGNL  360
SNLELKPLRK YFNDKIHAKA DHWDEQKFTE TYCHWILGEW RVGVKDQDKK DGAKYSYKDL  420
CNELKQKVTK AGLVDFLLEL DPCRTIPPYL DNNNRKPPKC QSLILNPKFL DNQYPNWQQY  480
LQELKKLQSI QNYLDSFETD LKVLKSSSKDQ PYFVEYKSSN QQIASGQRDY KDLDARILQF  540
IFDRVKASDE LLLNEIYFQA KKLKQKASSE LEKLESSKKL DEVIANSQLS QILKSQHTNG  600
IFEQGTFLHL VCKYYKQRQR ARDSRLYIMP EYRYDKKLHK YNNTGRFDDD NQLLTYCNHK  660
PRQKRYQLLN DLAGVLQVSP NFLKDKIGSD DDLFISKWLV EHIRGFKKAC EDSLKIQKDN  720
RGLLNHKINI ARNTKGKCEK EIFNLICKIE GSEDKKGNYK HGLAYELGVL LFGEPNEASK  780
PEFDRKIKKF NSIYSFAQIQ QIAFAERKGN ANTCAVCSAD NAHRMQQIKI TEPVEDNKDK  840
IILSAKAQRL PAIPTRIVDG AVKKMATILA KNIVDDNWQN IKQVLSAKHQ LHIPIITESN  900
AFEFEPALAD VKGKSLKDRR KKALERISPE NIFKDKNNRI KEFAKGISAY SGANLTDGDF  960
DGAKEELDHI IPRSHKKYGT LNDEANLICV TRGDNKNKGN RIFCLRDLAD NYKLKQFETT 1020
DDLEIEKKIA DTIWDANKKD FKFGNYRSFI NLTPQEQKAF RHALFLADEN PIKQAVIRAI 1080
NNRNRTFVNG TQRYFAEVLA NNIYLRAKKE NLNTDKISFD YFGIPTIGNG RGIAEIRQLY 1140
EKVDSDIQAY AKGDKPQASY SHLIDAMLAF CIAADEHRND GSIGLEIDKN YSLYPLDKNT 1200
GEVFTKDIFS QIKITDNEFS DKKLVRKKAI EGFNTHRQMT RDGIYAENYL PILIHKELNE 1260
VRKGYTWKNS EEIKPFKGKK YDIQQLNNLV YCLKFVDKPI SIDIQISTLE ELRNILTTNN 1320
IAATAEYYYI NLKTQKLHEY YIENYNTALG YKKYSKEMEF LRSLAYRSER VKIKSIDDVK 1380
QVLDKDSNFI IKKITLPFKK EWQRLYREWQ NTTIKDDYEF LKSFFNVKSI TKLHKKVRKD 1440
FSLPISTYEG KFLVKRKTWD NNFIYQILND SDSRADGTKP FIPAFDISKN EIVEAIIDSF 1500
TSKNIFWLPK NIELQKVDNK NIFAIDTSKW FEVETPSDLR DIGIATIQYK IDNNSRPKVR 1560
VKLDYVIDDD SKINYFMNHS LLKSRYPDKV LEILKQSTII EFESSGFNKT IKEMLGMKLA 1620
GIYNETSNN                                                       1629

SEQ ID NO: 31           moltype = AA   length = 1629
FEATURE                 Location/Qualifiers
REGION                  1..1629
                        note = engineered FnCas9
source                  1..1629
                        mol_type = protein
                        organism = synthetic construct
SEQUENCE: 31
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YSPEYLNIVP  120
EQVKAILMDI FDDYNGEDDL DSYLKLATEQ ESKISEIYNK LMQKILEFKL MKLCTDIKDD  180
KVSTKTLKEI TSYEFELLAD YLANYSESLK TQKFSYTDKQ GNLKELSYYH HDKYNIQEFL  240
KRHATINDRI LDTLLTDDLD IWNFNFEKFD FDKNEEKLQN QEDKDHIQAH LHHFVFAVNK  300
IKSEMASGGR HRSQYFQEIT NVLDENNHQE GYLKNFCENL HNKKYSNLSV KNLVNLIGNL  360
SNLELKPLRK YFNDKIHAKA DHWDEQKFTE TYCHWILGEW RVGVKDQDKK DGAKYSYKDL  420
CNELKQKVTK AGLVDFLLEL DPCRTIPPYL DNNNRKPPKC QSLILNPKFL DNQYPNWQQY  480
LQELKKLQSI QNYLDSFETD LKVLKSSSKDQ PYFVEYKSSN QQIASGQRDY KDLDARILQF  540
IFDRVKASDE LLLNEIYFQA KKLKQKASSE LEKLESSKKL DEVIANSQLS QILKSQHTNG  600
IFEQGTFLHL VCKYYKQRQR ARDSRLYIMP EYRYDKKLHK YNNTGRFDDD NQLLTYCNHK  660
PRQKRYQLLN DLAGVLQVSP NFLKDKIGSD DDLFISKWLV EHIRGFKKAC EDSLKIQKDN  720
RGLLNHKINI ARNTKGKCEK EIFNLICKIE GSEDKKGNYK HGLAYELGVL LFGEPNEASK  780
PEFDRKIKKF NSIYSFAQIQ QIAFAERKGN ANTCAVCSAD NAHRMQQIKI TEPVEDNKDK  840
IILSAKAQRL PAIPTRIVDG AVKKMATILA KNIVDDNWQN IKQVLSAKHQ LHIPIITESN  900
AFEFEPALAD VKGKSLKDRR KKALERISPE NIFKDKNNRI KEFAKGISAY SGANLTDGDF  960
DGAKEELDHI IPRSHKKYGT LNDEANLICV TRGDNKNKGN RIFCLRDLAD NYKLKQFETT 1020
DDLEIEKKIA DTIWDANKKD FKFGNYRSFI NLTPQEQKAF RHALFLADEN PIKQAVIRAI 1080
NNRNRTFVNG TQRYFAEVLA NNIYLRAKKE NLNTDKISFD YFGIPTIGNG RGIAEIRQLY 1140
EKVDSDIQAY AKGDKPQASY SHLIDAMLAF CIAADEHRND GSIGLEIDKN YSLYPLDKNT 1200
GEVFTKDIFS QIKITDNEFS DKKLVRKKAI EGFNTHRQMT RDTIYAENYL PILIHKELNE 1260
VRKGYTWKNS EEIKPFKGKK YDIQQLNNLV YCLKFVDKPI SIDIQISTLE ELRNILTTNN 1320
IAATAEYYYI NLKTQKLHEY YIENYNTALG YKKYSKEMEF LRSLAYRSRR VKIKSIDDVK 1380
QVLDKDSNFI IGKITLPFKK EWQRLYREWQ NTTIKDDYEF LKSFFNVKSI TKLHKKVRKD 1440
FSLPISTNHG KFLVKRKTWD NNFIYQILND SDSRADGTKP FIPAFDISKN EIVEAIIDSF 1500
TSKNIFWLPK NIELQKVDNK NIFAIDTSKW FEVETPSDLR DIGIATIQYK IDNNSRPKVR 1560
VKLDYVIDDD SKINYFMNHS LLKSRYPDKV LEILKQSTII EFESSGFNKT IKEMLGMKLA 1620
GIYNETSNN                                                       1629

SEQ ID NO: 32           moltype = AA   length = 1629
FEATURE                 Location/Qualifiers
REGION                  1..1629
                        note = engineered FnCas9
source                  1..1629
                        mol_type = protein
                        organism = synthetic construct
SEQUENCE: 32
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YSPEYLNIVP  120
EQVKAILMDI FDDYNGEDDL DSYLKLATEQ ESKISEIYNK LMQKILEFKL MKLCTDIKDD  180
KVSTKTLKEI TSYEFELLAD YLANYSESLK TQKFSYTDKQ GNLKELSYYH HDKYNIQEFL  240
```

```
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSRR VKIKSIDDVK   1380
QVLDKDSNFI IKKITLPFKK EWQRLYREWQ NTTIKDDYEF LKSFFNVKSI TKLHKKVRKD   1440
FSLPISTNHG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNKT IKEMLGMKLA   1620
GIYNETSNN                                                          1629
```

SEQ ID NO: 33        moltype = AA   length = 1629
FEATURE              Location/Qualifiers
REGION               1..1629
                     note = engineered FnCas9
source               1..1629
                     mol_type = protein
                     organism = synthetic construct
SEQUENCE: 33

```
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSRR VKIKSIDDVK   1380
QVLDKDSNFI IGKITLPFKK EWQRLYREWQ NTTIKDDYEF LKSFFNVKSI TKLHKKVRKD   1440
FSLPISTYHG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNKT IKEMLGMKLA   1620
GIYNETSNN                                                          1629
```

SEQ ID NO: 34        moltype = AA   length = 1629
FEATURE              Location/Qualifiers
REGION               1..1629
                     note = engineered FnCas9
source               1..1629
                     mol_type = protein
                     organism = synthetic construct
SEQUENCE: 34

```
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
```

```
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSRR VKIKSIDDVK   1380
QVLDKDSNFI IGKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFHSSGFNKT IKEMLGMKLA   1620
GIYNETSNN                                                          1629

SEQ ID NO: 35           moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 35
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSRR VKIKSIDDVK   1380
QVLDKDSNFI IKKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNKT IKEMLGMKLA   1620
GIYNETSNN                                                          1629

SEQ ID NO: 36           moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 36
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
```

```
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSRR VKIKSIDDVK   1380
QVLDKDSNFI IGKITLPFKK EWQRLYREWQ NTTIKDDYEF LKSFFNVKSI TKLHKKVRKD   1440
FSLPISTREG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNKT IKEMLGMKLA   1620
GIYNETSNN                                                          1629

SEQ ID NO: 37           moltype = AA   length = 1629
FEATURE                 Location/Qualifiers
REGION                  1..1629
                        note = engineered FnCas9
source                  1..1629
                        mol_type = protein
                        organism = synthetic construct
SEQUENCE: 37
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEV RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSRR VKIKSIDDVK   1380
QVLDKDSNFI IGKITLPFKK EWQRLYREWQ NTTIKDDYEF LKSFFNVKSI TKLHKKVRKD   1440
FSLPISTYEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFESSGFNKT IKEMLGMKLA   1620
GIYNETSNN                                                          1629

SEQ ID NO: 38           moltype = AA   length = 1629
FEATURE                 Location/Qualifiers
REGION                  1..1629
                        note = engineered FnCas9
source                  1..1629
                        mol_type = protein
                        organism = synthetic construct
SEQUENCE: 38
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
```

```
EKVDSDIQAY AKGDKPQASY SHLIDAMLAF CIAADEHRND GSIGLEIDKN YSLYPLDKNT    1200
GEVFTKDIFS QIKITDNEFS DKKLVRKKAI EGFNTHRQMT RDGIYAENYL PILIHKELNE    1260
VRKGYTWKNS EEIKIFKGKK YDIQQLNNLV YCLKFVDKPI SIDIQISTLE ELRNILTTNN    1320
IAATAEYYYI NLKTQKLHEY YIENYNTALG YKKYSKEMEF LRSLAYRSRR VKIKSIDDVK    1380
QVLDKDSNFI IGKITLPFKK EWQRLYREWQ NTTIKDDYEF LKSFFNVKSI TKLHKKVRKD    1440
FSLPISTNEG KFLVKRKTWD NNFIYQILND SDSRFDGTKP FIPAFDISKN EIVEAIIDSF    1500
TSKNIFWLPK NIELQKVDNK NIFAIDTSKW FEVETPSDLR DIGIATIQYK IDNNSRPKVR    1560
VKLDYVIDDD SKINYFMNHS LLKSRYPDKV LEILKQSTII EFESSGFNKT IKEMLGMKLA    1620
GIYNETSNN                                                            1629

SEQ ID NO: 39          moltype = AA   length = 1629
FEATURE                Location/Qualifiers
REGION                 1..1629
                       note = engineered FnCas9
source                 1..1629
                       mol_type = protein
                       organism = synthetic construct
SEQUENCE: 39
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
APEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSRR VKIKSIDDVK   1380
QVLDKDSNFI IGKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHR LLKSRYPDKV LEILKQSTII EFESSGFNKT IKEMLGMKLA   1620
GIYNETSNN                                                           1629

SEQ ID NO: 40          moltype = AA   length = 1629
FEATURE                Location/Qualifiers
REGION                 1..1629
                       note = engineered FnCas9
source                 1..1629
                       mol_type = protein
                       organism = synthetic construct
SEQUENCE: 40
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
APEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDTIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSRR VKIKSIDDVK   1380
QVLDKDSNFI IGKITLPFKK EWQRLYREWQ NTTIKDDYEF LKSFFNVKSI TKLHKKVRKD   1440
```

```
FSLPISTNEG KFLVKRKTWD NNFIYQILND SDSRADGTKP FIPAFDISKN EIVEAIIDSF    1500
TSKNIFWLPK NIELQKVDNK NIFAIDTSKW FEVETPSDLR DIGIATIQYK IDNNSRPKVR    1560
VKLDYVIDDD SKINYFMNHS LLKSRYPDKV LEILKQSTII EFESSGFNKT IKEMLGMKLA    1620
GIYNETSNN                                                           1629

SEQ ID NO: 41           moltype = AA   length = 1629
FEATURE                 Location/Qualifiers
REGION                  1..1629
                        note = engineered FnCas9
source                  1..1629
                        mol_type = protein
                        organism = synthetic construct
SEQUENCE: 41
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP ERYRDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT    1020
DDLEIEKKIA DTIWDANKKD FKFGNYRSFI NLTPQEQKAF RHALFLADEN PIKQAVIRAI    1080
NNRNRTFVNG TQRYFAEVLA NNIYLRAKKE NLNTDKISFD YFGIPTIGNG RGIAEIRQLY    1140
EKVDSDIQAY AKGDKPQASY SHLIDAMLAF CIAADEHRND GSIGLEIDKN YSLYPLDKNT    1200
GEVFTKDIFS QIKITDNEFS DKKLVRKKAI EGFNTHRQMT RDGIYAENYL PILIHKELNE    1260
VRKGYTWKNS EEIKIFKGKK YDIQQLNNLV YCLKFVDKPI SIDIQISTLE ELRNILTTNN    1320
IAATAEYYYI NLKTQKLHEY YIENYNTALG YKKYSKEMEF LRSLAYRSRR VKIKSIDDVK    1380
QVLDKDSNFI IGKITLPFKK EWQRLYREWQ NTTIKDDYEF LKSFFNVKSI TKLHKKVRKD    1440
FSLPISTNEG KFLVKRKTWD NNFIYQILND SDSRADGTKP FIPAFDISKN EIVEAIIDSF    1500
TSKNIFWLPK NIELQKVDNK NIFAIDTSKW FEVETPSDLR DIGIATIQYK IDNNSQPKVR    1560
VKLDYVIDDD SKINYFMNHS LLKSRYPDKV LEILKQSTII EFESSGFNKT IKEMLGMKLA    1620
GIYNETSNN                                                           1629

SEQ ID NO: 42           moltype = AA   length = 1629
FEATURE                 Location/Qualifiers
REGION                  1..1629
                        note = engineered FnCas9
source                  1..1629
                        mol_type = protein
                        organism = synthetic construct
SEQUENCE: 42
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP ERYRDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT    1020
DDLEIEKKIA DTIWDANKKD FKFGNYRSFI NLTPQEQKAF RHALFLADEN PIKQAVIRAI    1080
NNRNRTFVNG TQRYFAEVLA NNIYLRAKKE NLNTDKISFD YFGIPTIGNG RGIAEIRQLY    1140
EKVDSDIQAY AKGDKPQASY SHLIDAMLAF CIAADEHRND GSIGLEIDKN YSLYPLDKNT    1200
GEVFTKDIFS QIKITDNEFS DKKLVRKKAI EGFNTHRQMT RDGIYAENYL PILIHKELNE    1260
VRKGYTWKNS EEIKIFKGKK YDIQQLNNLV YCLKFVDKPI SIDIQISTLE ELRNILTTNN    1320
IAATAEYYYI NLKTQKLHEY YIENYNTALG YKKYSKEMEF LRSLAYRSER VKIKSIDDVK    1380
QVLDKDSNFI IKKITLPFKK EWQRLYREWQ NTTIKDDYEF LKSFFNVKSI TKLHKKVRKD    1440
FSLPISTNEG KFLVKRKTWD NNFIYQILND SDSRADGTKP FIPAFDISKN EIVEAIIDSF    1500
TSKNIFWLPK NIELQKVDNK NIFAIDTSKW FEVETPSDLR DIGIATIQYK IDNNSRPKVR    1560
VKLDYVIDDD SKINYFMNHS LLKSRYPDKV LEILKQSTII EFHSSGFNKT IKEMLGMKLA    1620
GIYNETSNN                                                           1629
```

```
SEQ ID NO: 43          moltype = AA   length = 1629
FEATURE                Location/Qualifiers
REGION                 1..1629
                       note = engineered FnCas9
source                 1..1629
                       mol_type = protein
                       organism = synthetic construct
SEQUENCE: 43
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YSPEYLNIVP  120
EQVKAILMDI FDDYNGEDDL DSYLKLATEQ ESKISEIYNK LMQKILEFKL MKLCTDIKDD  180
KVSTKTLKEI TSYEFELLAD YLANYSESLK TQKFSYTDKQ GNLKELSYYH HDKYNIQEFL  240
KRHATINDRI LDTLLTDDLD IWNFNFEKFD FDKNEEKLQN QEDKDHIQAH LHHFVFAVNK  300
IKSEMASGGR HRSQYFQEIT NVLDENNHQE GYLKNFCENL HNKKYSNLSV KNLVNLIGNL  360
SNLELKPLRK YFNDKIHAKA DHWDEQKFTE TYCHWILGEW RVGVKDQDKK DGAKYSYKDL  420
CNELKQKVTK AGLVDFLLEL DPCRTIPPYL DNNRKPPKC QSLILNPKFL DNQYPNWQQY   480
LQELKKLQSI QNYLDSFETD LKVLKSSKDQ PYFVEYKSSN QQIASGQRDY KDLDARILQF  540
IFDRVKASDE LLLNEIYFQA KKLKQKASSE LEKLESSKKL DEVIANSQLS QILKSQHTNG  600
IFEQGTFLHL VCKYYKQRQR ARDSRLYIMP EYRYDKKLHK YNNTGRFDDD NQLLTYCNHK  660
PRQKRYQLLN DLAGVLQVSP NFLKDKIGSD DDLFISKWLV EHIRGFKKAC EDSLKIQKDN  720
RGLLNHKINI ARNTKGKCEK EIFNLICKIE GSEDKKGNYK HGLAYELGVL LFGEPNEASK  780
PEFDRKIKKF NSIYSFAQIQ QIAFAERKGN ANTCAVCSAD NAHRMQQIKI TEPVEDNKDK  840
IILSAKAQRL PAIPTRIVDG AVKKMATILA KNIVDDNWQN IKQVLSAKHQ LHIPIITESN  900
APEFEPALAD VKGKSLKDRR KKALERISPE NIFKDKNNRI KEFAKGISAY SGANLTGDF   960
DGAKEELDHI IPRSHKKYGT LNDEANLICV TRGDNKNKGN RIFCLRDLAD NYKLKQFETT 1020
DDLEIEKKIA DTIWDANKKD FKFGNYRSFI NLTPQEQKAF RHALFLADEN PIKQAVIRAI 1080
NNRNRTFVNG TQRYFAEVLA NNIYLRAKKE NLNTDKISFD YFGIPTIGNG RGIAEIRQLY 1140
EKVDSDIQAY AKGDKPQASY SHLIDAMLAF CIAADEHRND GSIGLEIDKN YSLYPLDKNT 1200
GEVFTKDIFS QIKITDNEFS DKKLVRKKAI EGFNTHRQMT RDGIYAENYL PILIHKELNE 1260
VRKGYTWKNS EEIKIFKGKK YDIQQLNNLV YCLKFVDKPI SIDIQISTLE ELRNILTTNN 1320
IAATAEYYYI NLKTQKLHEY YIENYNTALG YKKYSKEMEF LRSLAYRSER VKIKSIDDVK 1380
QVLDKDSNFI IGKITLPFKK EWQRLYREWQ NTTIKDDYEF LKSFFNVKSI TKLHKKVRKD 1440
FSLPISTREG KFLVKRKTWD NNFIYQILND SDSRADGTKP FIPAFDISKN EIVEAIIDSF 1500
TSKNIFWLPK NIELQKVDNK NIFAIDTSKW FEVETPSDLR DIGIATIQYK IDNNSRPKVR 1560
VKLDYVIDDD SKINYFMNHS LLKSRYPDKV LEILKQSTII EFHSSGFNKT IKEMLGMKLA 1620
GIYNETSNN                                                         1629

SEQ ID NO: 44          moltype = AA   length = 1629
FEATURE                Location/Qualifiers
REGION                 1..1629
                       note = engineered FnCas9
source                 1..1629
                       mol_type = protein
                       organism = synthetic construct
SEQUENCE: 44
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YSPEYLNIVP  120
EQVKAILMDI FDDYNGEDDL DSYLKLATEQ ESKISEIYNK LMQKILEFKL MKLCTDIKDD  180
KVSTKTLKEI TSYEFELLAD YLANYSESLK TQKFSYTDKQ GNLKELSYYH HDKYNIQEFL  240
KRHATINDRI LDTLLTDDLD IWNFNFEKFD FDKNEEKLQN QEDKDHIQAH LHHFVFAVNK  300
IKSEMASGGR HRSQYFQEIT NVLDENNHQE GYLKNFCENL HNKKYSNLSV KNLVNLIGNL  360
SNLELKPLRK YFNDKIHAKA DHWDEQKFTE TYCHWILGEW RVGVKDQDKK DGAKYSYKDL  420
CNELKQKVTK AGLVDFLLEL DPCRTIPPYL DNNRKPPKC QSLILNPKFL DNQYPNWQQY   480
LQELKKLQSI QNYLDSFETD LKVLKSSKDQ PYFVEYKSSN QQIASGQRDY KDLDARILQF  540
IFDRVKASDE LLLNEIYFQA KKLKQKASSE LEKLESSKKL DEVIANSQLS QILKSQHTNG  600
IFEQGTFLHL VCKYYKQRQR ARDSRLYIMP EYRYDKKLHK YNNTGRFDDD NQLLTYCNHK  660
PRQKRYQLLN DLAGVLQVSP NFLKDKIGSD DDLFISKWLV EHIRGFKKAC EDSLKIQKDN  720
RGLLNHKINI ARNTKGKCEK EIFNLICKIE GSEDKKGNYK HGLAYELGVL LFGEPNEASK  780
PEFDRKIKKF NSIYSFAQIQ QIAFAERKGN ANTCAVCSAD NAHRMQQIKI TEPVEDNKDK  840
IILSAKAQRL PAIPTRIVDG AVKKMATILA KNIVDDNWQN IKQVLSAKHQ LHIPIITESN  900
APEFEPALAD VKGKSLKDRR KKALERISPE NIFKDKNNRI KEFAKGISAY SGANLTGDF   960
DGAKEELDHI IPRSHKKYGT LNDEANLICV TRGDNKNKGN RIFCLRDLAD NYKLKQFETT 1020
DDLEIEKKIA DTIWDANKKD FKFGNYRSFI NLTPQEQKAF RHALFLADEN PIKQAVIRAI 1080
NNRNRTFVNG TQRYFAEVLA NNIYLRAKKE NLNTDKISFD YFGIPTIGNG RGIAEIRQLY 1140
EKVDSDIQAY AKGDKPQASY SHLIDAMLAF CIAADEHRND GSIGLEIDKN YSLYPLDKNT 1200
GEVFTKDIFS QIKITDNEFS DKKLVRKKAI EGFNTHRQMT RDGIYAENYL PILIHKELNE 1260
VRKGYTWKNS EEIKIFKGKK YDIQQLNNLV YCLKFVDKPI SIDIQISTLE ELRNILTTNN 1320
IAATAEYYYI NLKTQKLHEY YIENYNTALG YKKYSKEMEF LRSLAYRSER VKIKSIDDVK 1380
QVLDKDSNFI IGKITLPFKK EWQRLYREWQ NTTIKDDYEF LKSFFNVKSI TKLHKKVRKD 1440
FSLPISTYEG KFLVKRKTWD NNFIYQILND SDSRADGTKP FIPAFDISKN EIVEAIIDSF 1500
TSKNIFWLPK NIELQKVDNK NIFAIDTSKW FEVETPSDLR DIGIATIQYK IDNNSRPKVR 1560
VKLDYVIDDD SKINYFMNHS LLKSRYPDKV LEILKQSTII EFHSSGFNKT IKEMLGMKLA 1620
GIYNETSNN                                                         1629

SEQ ID NO: 45          moltype = AA   length = 1629
FEATURE                Location/Qualifiers
REGION                 1..1629
                       note = engineered FnCas9
source                 1..1629
```

```
                      mol_type = protein
                      organism = synthetic construct
SEQUENCE: 45
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQLHEY  YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRFDGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFHSSGFNKT IKEMLGMKLA  1620
GIYNETSNN                                                         1629

SEQ ID NO: 46           moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 46
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQLHEY  YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHR LLKSRYPDKV LEILKQSTII EFHSSGFNKT IKEMLGMKLA  1620
GIYNETSNN                                                         1629

SEQ ID NO: 47           moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 47
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YSPEYLNIVP   120
```

```
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDTIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLRYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFHSSGFNKT IKEMLGMKLA  1620
GIYNETSNN                                                         1629

SEQ ID NO: 48           moltype = AA  length = 1629
FEATURE                 Location/Qualifiers
REGION                  1..1629
                        note = engineered FnCas9
source                  1..1629
                        mol_type = protein
                        organism = synthetic construct
SEQUENCE: 48
MNFKILPIAI DLGVKNTGVF SAFYQKGTSL ERLDNKNGKV YELSKDSYTL LMNNRTARRH    60
QRRGIDRKQL VKRLFKLIWT EQLNEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLRYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSQPKVR  1560
VKLDYVIDDD SKINYFMNHS LLKSRYPDKV LEILKQSTII EFHSSGFNKT IKEMLGMKLA  1620
GIYNETSNN                                                         1629

SEQ ID NO: 49           moltype = AA  length = 1628
FEATURE                 Location/Qualifiers
REGION                  1..1628
                        note = engineered FnCas9
source                  1..1628
                        mol_type = protein
                        organism = synthetic construct
SEQUENCE: 49
MNFKILPIAI DLGVKNTGVF SAFYQKGTSL ERLDNKNGKV YELSKDSYTL LMNNRTARRH    60
QRRGIDRKQL VKRLFKLIWT EQLNEWDKD TQQAISFLFN RRGFSFITDG YSPEYLNIVP   120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
```

```
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ERLNILTTNN   1320
IAATAEYYYI NLKTQKLHEY YIENYNTALG YKKYSKEMEF LRSLAYRSER VKIKSIDDVK   1380
QVLDKDSNFI IGKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSQKVRV   1560
KLDYVIDDDS KINYFMNHSL LKSRYPDKVL EILKQSTIIE FESSGFNKTI KEMLGMKLAG   1620
IYNETSNN                                                           1628

SEQ ID NO: 50           moltype = AA   length = 1629
FEATURE                 Location/Qualifiers
REGION                  1..1629
                        note = engineered FnCas9
source                  1..1629
                        mol_type = protein
                        organism = synthetic construct
SEQUENCE: 50
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YSPEYLNIVP    120
EQVKAILMDI FDDYNGEDDL DSYLKLATEQ ESKISEIYNK LMQKILEFKL MKLCTDIKDD    180
KVSTKTLKEI TSYEFELLAD YLANYSESLK TQKFSYTDKQ GNLKELSYYH HDKYNIQEFL    240
KRHATINDRI LDTLLTDDLD IWNFNFEKFD FDKNEEKLQN QEDKDHIQAH LHHFVFAVNK    300
IKSEMASGGR HRSQYFQEIT NVLDENNHQE GYLKNFCENL HNKKYSNLSV KNLVNLIGNL    360
SNLELKPLRK YFNDKIHAKA DHWDEQKFTE TYCHWILGEW RVGVKDQDKK DGAKYSYKDL    420
CNELKQKVTK AGLVDFLLEL DPCRTIPPYL DNNNRKPPKC QSLILNPKFL DNQYPNWQQY    480
LQELKKLQSI QNYLDSFETD LKVLKSSKDQ PYFVEYKSSN QQIASGQRDY KDLDARILQF    540
IFDRVKASDE LLLNEIYFQA KKLKQKASSE LEKLESSKKL DEVIANSQLS QILKSQHTNG    600
IFEQGTFLHL VCKYYKQRQR ARDSRLYIMP EYRYDKKLHK YNNTGRFDDD NQLLTYCNHK    660
PRQKRYQLLN DLAGVLQVSP NFLKDKIGSD DDLFISKWLV EHIRGFKKAC EDSLKIQKDN    720
RGLLNHKINI ARNTKGKCEK EIFNLICKIE GSEDKKGNYK HGLAYELGVL LFGEPNEASK    780
PEFDRKIKKF NSIYSFAQIQ QIAFAERKGN ANTCAVCSAD NAHRMQQIKI TEPVEDNKDK    840
IILSAKAQRL PAIPTRIVDG AVKKMATILA KNIVDDNWQN IKQVLSAKHQ LHIPIITESN    900
AFEFEPALAD VKGKSLKDRR KKALERISPE NIFKDKNNRI KEFAKGISAY SGANLTDGDF    960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ERLNILTTNN   1320
IAATAEYYYI NLKTQKLHEY YIENYNTALG YKKYSKEMEF LRSLAYRSRR VKIKSIDDVK   1380
QVLDKDSNFI IGKITLPFKK EWQRLYREWQ NTTIKDDYEF LKSFFNVKSI TKLHKKVRKD   1440
FSLPISTNHG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSQPKVR   1560
VKLDYVIDDD SKINYFMNHS LLKSRYPDKV LEILKQSTII EFESSGFNKT IKEMLGMKLA   1620
GIYNETSNN                                                          1629

SEQ ID NO: 51           moltype = AA   length = 1447
FEATURE                 Location/Qualifiers
REGION                  1..1447
                        note = engineered FnCas9 truncations
source                  1..1447
                        mol_type = protein
                        organism = synthetic construct
SEQUENCE: 51
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
```

```
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSRRVK IKSIDDVKQV   1200
LDKDSNFIIG KITLPFKKEW QRLYREWQNT TIKDDYEFLK SFFNVKSITK LHKKVRKDFS   1260
LPISTNEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                             1447

SEQ ID NO: 52           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 52
MNFKILPIAI DLGVKNTGVF SAFYQKGTSL ERLDNKNGKV YELSKDSYTL LMNNRTARRH     60
QRRGIDRKQL VKRLFKLIWT EQLNEWDKD TQQAISFLFN RRGFSITDG YGGGSVNKIK     120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIIITESNAF   720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSERVK IKSIDDVKQV   1200
LDKDSNFIIG KITLPFKKEW QRLYREWQNT TIKDDYEFLK SFFNVKSITK LHKKVRKDFS   1260
LPISTNHGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                             1447

SEQ ID NO: 53           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 53
MNFKILPIAI DLGVKNTGVF SAFYQKGTSL ERLDNKNGKV YELSKDSYTL LMNNRTARRH     60
QRRGIDRKQL VKRLFKLIWT EQLNEWDKD TQQAISFLFN RRGFSITDG YGGGSVNKIK     120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIIITESNAF   720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSRRVK IKSIDDVKQV   1200
LDKDSNFIIG KITLPFKKEW QRLYREWQNT TIKDDYEFLK SFFNVKSITK LHKKVRKDFS   1260
LPISTNHGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
```

```
LDYVIDDDSK INYFMNHSLL KSRYPDKVLE ILKQSTIIEF ESSGFNKTIK EMLGMKLAGI    1440
YNETSNN                                                             1447

SEQ ID NO: 54           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 54
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE    1020
VFTKDIFSQI KITDNEFSDK KLVRKKAIEG FNTHRQMTRD TIYAENYLPI LIHKELNEVR    1080
KGYTWKNSEE IKIFKGKKYD IQQLNNLVYC LKFVDKPISI DIQISTLEEL RNILTTNNIA    1140
ATAEYYYINL KTQKLHEYYI ENYNTALGYK KYSKEMEFLR SLAYRSERVK IKSIDDVKQV    1200
LDKDSNFIIG KITLPFKKEW QRLYREWQNT TIKDDYEFLK SFFNVKSITK LHKKVRKDFS    1260
LPISTNEGKF LVKRKTWDNN FIYQILNDSD SRADGTKPFI PAFDISKNEI VEAIIDSFTS    1320
KNIFWLPKNI ELQKVDNKNI FAIDTSKWFE VETPSDLRDI GIATIQYKID NNSRPKVRVK    1380
LDYVIDDDSK INYFMNHSLL KSRYPDKVLE ILKQSTIIEF ESSGFNKTIK EMLGMKLAGI    1440
YNETSNN                                                             1447

SEQ ID NO: 55           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 55
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE    1020
VFTKDIFSQI KITDNEFSDK KLVRKKAIEG FNTHRQMTRD GIYAENYLPI LIHKELNEVR    1080
KGYTWKNSEE IKIFKGKKYD IQQLNNLVYC LKFVDKPISI DIQISTLEEL RNILTTNNIA    1140
ATAEYYYINL KTQKLHEYYI ENYNTALGYK KYSKEMEFLR SLAYRSERVK IKSIDDVKQV    1200
LDKDSNFIIG KITLPFKKEW QRLYREWQNT TIKDDYEFLK SFFNVKSITK LHKKVRKDFS    1260
LPISTNEGKF LVKRKTWDNN FIYQILNDSD SRADGTKPFI PAFDISKNEI VEAIIDSFTS    1320
KNIFWLPKNI ELQKVDNKNI FAIDTSKWFE VETPSDLRDI GIATIQYKID NNSRPKVRVK    1380
LDYVIDDDSK INYFMNHSLL KSRYPDKVLE ILKQSTIIEF ESSGFNKTIK EMLGMKLAGI    1440
YNETSNN                                                             1447

SEQ ID NO: 56           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 56
```

```
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE  1020
VFTKDIFSQI KITDNEFSDK KLVRKKAIEG FNTHRQMTRD GIYAENYLPI LIHKELNEVR  1080
KGYTWKNSEE IKIFKGKKYD IQQLNNLVYC LKFVDKPISI DIQISTLEEL RNILTTNNIA  1140
ATAEYYYINL KTQKLHEYYI ENYNTALGYK KYSKEMEFLR SLAYRSERVK IKSIDDVKQV  1200
LDKDSNFIIR KITLPFKKEW QRLYREWQNT TIKDDYEFLK SFFNVKSITK LHKKVRKDFS  1260
LPISTNEGKF LVKRKTWDNN FIYQILNDSD SRADGTKPFI PAFDISKNEI VEAIIDSFTS  1320
KNIFWLPKNI ELQKVDNKNI FAIDTSKWFE VETPSDLRDI GIATIQYKID NNSRPKVRVK  1380
LDYVIDDDSK INYFMNHSLL KSRYPDKVLE ILKQSTIIEF ESSGFNKTIK EMLGMKLAGI  1440
YNETSNN                                                           1447

SEQ ID NO: 57          moltype = AA  length = 1447
FEATURE                Location/Qualifiers
REGION                 1..1447
                       note = FnCas9 truncations
source                 1..1447
                       mol_type = protein
                       organism = synthetic construct
SEQUENCE: 57
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE  1020
VFTKDIFSQI KITDNEFSDK KLVRKKAIEG FNTHRQMTRD GIYAENYLPI LIHKELNEVR  1080
KGYTWKNSEE IKIFKGKKYD IQQLNNLVYC LKFVDKPISI DIQISTLEEL RNILTTNNIA  1140
ATAEYYYINL KTQKLHEYYI ENYNTALGYK KYSKEMEFLR SLAYRSERVK IKSIDDVKQV  1200
LDKDSNFIIR KITLPFKKEW QRLYREWQNT TIKDDYEFLK SFFNVKSITK LHKKVRKDFS  1260
LPISTNEGKF LVKRKTWDNN FIYQILNDSD SRADGTKPFI PAFDISKNEI VEAIIDSFTS  1320
KNIFWLPKNI ELQKVDNKNI FAIDTSKWFE VETPSDLRDI GIATIQYKID NNSRPKVRVK  1380
LDYVIDDDSK INYFMNHSLL KSRYPDKVLE ILKQSTIIEF ESSGFNKTIK EMLGMKLAGI  1440
YNETSNN                                                           1447

SEQ ID NO: 58          moltype = AA  length = 1447
FEATURE                Location/Qualifiers
REGION                 1..1447
                       note = FnCas9 truncations
source                 1..1447
                       mol_type = protein
                       organism = synthetic construct
SEQUENCE: 58
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
```

```
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSERVK IKSIDDVKQV   1200
LDKDSNFIIG KITLPFKKEW QRLYREWQNT TIKDDYEFLK SFFNVKSITK LHKKVRKDFS   1260
LPISTREGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                            1447

SEQ ID NO: 59           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 59
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKDKG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSERVK IKSIDDVKQV   1200
LDKDSNFIIG KITLPFKKEW QRLYREWQNT TIKDDYEFLK SFFNVKSITK LHKKVRKDFS   1260
LPISTYEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                            1447

SEQ ID NO: 60           moltype = AA  length = 1448
FEATURE                 Location/Qualifiers
REGION                  1..1448
                        note = FnCas9 truncations
source                  1..1448
                        mol_type = protein
                        organism = synthetic construct
SEQUENCE: 60
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKDKG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSERVK IKSIDDVKQV   1200
LDKDSNFIIG KITLPFKKEW QRLYREWQNT TIKDDYEFLK SFFNVKSITK LHKKVRKDFS   1260
LPISTNEGKV FLVKRKTWDN NFIYQILNDS DSRADGTKPF IPAFDISKNE IVEAIIDSFT   1320
```

```
SKNIFWLPKN IELQKVDNKN IFAIDTSKWF EVETPSDLRD IGIATIQYKI DNNSRPKVRV   1380
KLDYVIDDDS KINYFMNHSL LKSRYPDKVL EILKQSTIIE FESSGFNKTI KEMLGMKLAG   1440
IYNETSNN                                                           1448

SEQ ID NO: 61           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 61
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE  1020
VFTKDIFSQI KITDNEFSDK KLVRKKAIEG FNTHRQMTRD GIYAENYLPI LIHKELNEVR  1080
KGYTWKNSEE IKIFKGKKYD IQQLNNLVYC LKFVDKPISI DIQISTLEEL RNILTTNNIA  1140
ATAEYYYINL KTQKLHEYYI ENYNTALGYK KYSKEMEFLR SLAYRSERVK IKSIDDVKQV  1200
LDKDSNFIIG KITLPFKKEW QRLYREWQNT TIKDDYEFLK SFFNVKSITK LHKKVRKDFS  1260
LPISTNEGKF LVKRKTWDNN FIYQILNDSD TRADGTKPPI PAPDISKNEI VEAIIDSFTS  1320
KNIFWLPKNI ELQKVDNKNI FAIDTSKWFE VETPSDLRDI GIATIQYKID NNSRPKVRVK  1380
LDYVIDDDSK INYFMNHSLL KSRYPDKVLE ILKQSTIIEF ESSGFNKTIK EMLGMKLAGI  1440
YNETSNN                                                            1447

SEQ ID NO: 62           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 62
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE  1020
VFTKDIFSQI KITDNEFSDK KLVRKKAIEG FNTHRQMTRD GIYAENYLPI LIHKELNEVR  1080
KGYTWKNSEE IKIFKGKKYD IQQLNNLVYC LKFVDKPISI DIQISTLEEL RNILTTNNIA  1140
ATAEYYYINL KTQKLHEYYI ENYNTALGYK KYSKEMEFLR SLAYRSERVK IKSIDDVKQV  1200
LDKDSNFIIG KITLPFKKEW QRLYREWQNT TIKDDYEFLK SFFNVKSITK LHKKVRKDFS  1260
LPISTNEGKF LVKRKTWDNN FIYQILNDSD SRADGTKPPI PAPDISKNEI VEAIIDSFTS  1320
KNIFWLPKNI ELQKVDNKNI FAIDTSKWFE VETPSDLRDI GIATIQYKID VNSRPKVRVK  1380
LDYVIDDDSK INYFMNHSLL KSRYPDKVLE ILKQSTIIEF ESSGFNKTIK EMLGMKLAGI  1440
YNETSNN                                                            1447

SEQ ID NO: 63           moltype = AA  length = 1447
FEATURE                 Location/Qualifiers
REGION                  1..1447
                        note = FnCas9 truncations
source                  1..1447
                        mol_type = protein
                        organism = synthetic construct
```

```
SEQUENCE: 63
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE  1020
VFTKDIFSQI KITDNEFSDK KLVRKKAIEG FNTHRQMTRD GIYAENYLPI LIHKELNEVR  1080
KGYTWKNSEE IKIFKGKKYD IQQLNNLVYC LKFVDKPISI DIQISTLEEL RNILTTNNIA  1140
ATAEYYYINL KTQKLHEYYI ENYNTALGYK KYSKEMEFLR SLAYRSERVK IKSIDDVKQV  1200
LDKDSNFIIG KITLPFKKEW QRLYREWQNT TIKDDYEFLK SFFNVKSITK LHKKVRKDFS  1260
LPISTNEGKF LVRKRKTWDNN FIYQILNDSD SRADGTKPFI PAFDISKNEI VEAIIDSFTS  1320
KNIFWLPKNI ELQKVDNKNI FAIDTSKWFE VETPSDLRDI GIATIQYKID NNSRPKVRVK  1380
LDYVIDDDSK INYFMNHSLL KSRHPDKVLE ILKQSTIIEF ESSGFNKTIK EMLGMKLAGI  1440
YNETSNN                                                            1447

SEQ ID NO: 64           moltype = AA   length = 1447
FEATURE                 Location/Qualifiers
REGION                  1..1447
                        note = FnCas9 truncations
source                  1..1447
                        mol_type = protein
                        organism = synthetic construct
SEQUENCE: 64
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE  1020
VFTKDIFSQI KITDNEFSDK KLVRKKAIEG FNTHRQMTRD GIYAENYLPI LIHKELNEVR  1080
KGYTWKNSEE IKIFKGKKYD IQQLNNLVYC LKFVDKPISI DIQISTLEEL RNILTTNNIA  1140
ATAEYYYINL KTQKLHEYYI ENYNTALGYK KYSKEMEFLR SLAYRSERVK IKSIDDVKQV  1200
LDKDSNFIIG KITLPFKKEW QRLYREWQNT TIKDDYEFLK SFFNVKSITK LHKKVRKDFS  1260
LPISTNEGKF LVRKRKTWDNN FIYQILNDSD SRADGTKPFI PAFDISKNEI VEAIIDSFTS  1320
KNIFWLPKNI ELQKVDNKNI FAIDTSKWFE VETPSDLRDI GIATIQYKID NNSRPKVRVK  1380
LDYVIDDDSK INYFMNHSLL KSRRPDKVLE ILKQSTIIEF ESSGFNKTIK EMLGMKLAGI  1440
YNETSNN                                                            1447

SEQ ID NO: 65           moltype = AA   length = 1447
FEATURE                 Location/Qualifiers
REGION                  1..1447
                        note = FnCas9 truncations
source                  1..1447
                        mol_type = protein
                        organism = synthetic construct
SEQUENCE: 65
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
```

```
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE    1020
VFTKDIFSQI KITDNEFSDK KLVRKKAIEG FNTHRQMTRD GIYAENYLPI LIHKELNEVR    1080
KGYTWKNSEE IKIFKGKKYD IQQLNNLVYC LKFVDKPISI DIQISTLEEL RNILTTNNIA    1140
ATAEYYYINL KTQKLHEYYI ENYNTALGYK KYSKEMEFLR SLAYRSERVK IKSIDDVKQV    1200
LDKDSNFIIG KITLPFKKEW QRLYREWQNT TIKDDYEFLK SFFNVKSITK LHKKVRKDFS    1260
LPISTNEGKF LVKRKTWDNN FIYQILNDSD SRADGTKPFI PAFDISKNEI VEAIIDSFTS    1320
KNIFWLPKNI ELQKVDNKNI FAIDTSKWFE VETPSDLRDI GIATIQYKID NNSRPKVRVK    1380
LDYVIDDDSK INYFMNHSLL KSRYPDKVLE ILKQSTIIEF HSSGFNKTIK EMLGMKLAGI    1440
YNETSNN                                                            1447

SEQ ID NO: 66              moltype = AA  length = 1447
FEATURE                    Location/Qualifiers
REGION                     1..1447
                           note = FnCas9 truncations
source                     1..1447
                           mol_type = protein
                           organism = synthetic construct
SEQUENCE: 66
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE    1020
VFTKDIFSQI KITDNEFSDK KLVRKKAIEG FNTHRQMTRD GIYAENYLPI LIHKELNEVR    1080
KGYTWKNSEE IKIFKGKKYD IQQLNNLVYC LKFVDKPISI DIQISTLEEL RNILTTNNIA    1140
ATAEYYYINL KTQKLHEYYI ENYNTALGYK KYSKEMEFLR SLAYRSRRVK IKSIDDVKQV    1200
LDKDSNFIIG KITLPFKKEW QRLYREWQNT TIKDDYEFLK SFFNVKSITK LHKKVRKDFS    1260
LPISTNHGKF LVKRKTWDNN FIYQILNDSD SRADGTKPFI PAFDISKNEI VEAIIDSFTS    1320
KNIFWLPKNI ELQKVDNKNI FAIDTSKWFE VETPSDLRDI GIATIQYKID NNSTPKVRVK    1380
LDYVIDDDSK INYFMNHSLL KSRYPDKVLE ILKQSTIIEF ESSGFNKTIK EMLGMKLAGI    1440
YNETSNN                                                            1447

SEQ ID NO: 67              moltype = AA  length = 1447
FEATURE                    Location/Qualifiers
REGION                     1..1447
                           note = FnCas9 truncations
source                     1..1447
                           mol_type = protein
                           organism = synthetic construct
SEQUENCE: 67
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE    1020
VFTKDIFSQI KITDNEFSDK YLVRKKAIEG FNTHRQMTRD GIYAENYLPI LIHKELNEVR    1080
KGYTWKNSEE IKIFKGKKYD IQQLNNLVYC LKFVDKPISI DIQISTLEEL RNILTTNNIA    1140
ATAEYYYINL KTQKLHEYYI ENYNTALGYK KYSKEMEFLR SLAYRSERVK IKSIDDVKQV    1200
LDKDSNFIIG KITLPFKKEW QRLYREWQNT TIKDDYEFLK SFFNVKSITK LHKKVRKDFS    1260
```

```
LPISTNEGKF LVKRKTWDNN FIYQILNDSD SRADGTKPFI PAFDISKNEI VEAIIDSFTS  1320
KNIFWLPKNI ELQKVDNKNI FAIDTSKWFE VETPSDLRDI GIATIQYKID NNSRPKVRVK  1380
LDYVIDDDSK INYFMNHSLL KSRYPDKVLE ILKQSTIIEF ESSGFNKTIK EMLGMKLAGI  1440
YNETSNN                                                           1447

SEQ ID NO: 68           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 68
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YGGGSVNKIK  120
SEMASGGRHR SQYFQEITNV LDENNHQEGY LKNFCENLHN KKYSNLSVKN LVNLIGNLSN  180
LELKPLRKYF NDKIHAKADH WDEQKFTETY CHWILGEWRG GVKDQDKKDG AKYSYKDLCN  240
ELKQKVTKAG LVDFLLELDP CRTIPPYLDN NNRKPPKCQS LILNPKFLDN QYPNWQQYLQ  300
ELKKLQSIQN YLDSFETDLK VLKSSKDQPY FVEYKSSNQQ IASGQRDYKD LDARILQFIF  360
DRVKASDELL LNEIYFQAKK LKQKASSELE KLESSKKLDE VIANSQLSQI LKSQHTNGIF  420
EQGTFLHLVC KYYKQRQRAR DSRLYIMPEY RYDKKLHKYN NTGRFDDDNQ LLTYCNHKPR  480
QKRYQLLNDL AGVLQVSPNF LKDKIGSDDD LFISKWLVEH IRGFKKACED SLKIQKDNRG  540
LLNHKINIAR NTKGKCEKEI FNLICKIEGS EDKKGNYKHG LAYELGVLLF GEPNEASKPE  600
FDRKIKKFNS IYSFAQIQQI AFAERKGNAN TCAVCSADNA HRMQQIKITE PVEDNKDKII  660
LSAKAQRLPA IPTRIVDGAV KKMATILAKN IVDDNWQNIK QVLSAKHQLH IPIITESNAF  720
EFEPALADVK GKSLKDRRKK ALERISPENI FKDKNNRIKE FAKGISAYSG ANLTDGDFDG  780
AKEELDHIIP RSHKKYGTLN DEANLICVTR GDNKNKGNRI FCLRDLADNY KLKQFETTDD  840
LEIEKKIADT IWDANKKDFK FGNYRSFINL TPQEQKAFRH ALFLADENPI KQAVIRAINN  900
RNRTFVNGTQ RYFAEVLANN IYLRAKKENL NTDKISFDYF GIPTIGNGRG IAEIRQLYEK  960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSERVK IKSIDDVKQV 1200
LDKSNFIIG KITLPFKKEW QRLYREWQNT TIKDDYEFLK SFPNVKSITL LHKKVRKDFS 1260
LPISTNEGKF LVKRKTWDNN FIYQILNDSD SRFDGTKPFI PAFDISKNEI VEAIIDSFTS 1320
KNIFWLPKNI ELQKVDNKNI FAIDTSKWFE VETPSDLRDI GIATIQYKID NNSRPKVRVK 1380
LDYVIDDDSK INYFMNHSLL KSRYPDKVLE ILKQSTIIEF ESSGFNKTIK EMLGMKLAGI 1440
YNETSNN                                                           1447

SEQ ID NO: 69           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 69
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YGGGSVNKIK  120
SEMASGGRHR SQYFQEITNV LDENNHQEGY LKNFCENLHN KKYSNLSVKN LVNLIGNLSN  180
LELKPLRKYF NDKIHAKADH WDEQKFTETY CHWILGEWRG GVKDQDKKDG AKYSYKDLCN  240
ELKQKVTKAG LVDFLLELDP CRTIPPYLDN NNRKPPKCQS LILNPKFLDN QYPNWQQYLQ  300
ELKKLQSIQN YLDSFETDLK VLKSSKDQPY FVEYKSSNQQ IASGQRDYKD LDARILQFIF  360
DRVKASDELL LNEIYFQAKK LKQKASSELE KLESSKKLDE VIANSQLSQI LKSQHTNGIF  420
EQGTFLHLVC KYYKQRQRAR DSRLYIMPEY RYDKKLHKYN NTGRFDDDNQ LLTYCNHKPR  480
QKRYQLLNDL AGVLQVSPNF LKDKIGSDDD LFISKWLVEH IRGFKKACED SLKIQKDNRG  540
LLNHKINIAR NTKGKCEKEI FNLICKIEGS EDKKGNYKHG LAYELGVLLF GEPNEASKPE  600
FDRKIKKFNS IYSFAQIQQI AFAERKGNAN TCAVCSADNA HRMQQIKITE PVEDNKDKII  660
LSAKAQRLPA IPTRIVDGAV KKMATILAKN IVDDNWQNIK QVLSAKHQLH IPIITESNAF  720
EFEPALADVK GKSLKDRRKK ALERISPENI FKDKNNRIKE FAKGISAYSG ANLTDGDFDG  780
AKEELDHIIP RSHKKYGTLN DEANLICVTR GDNKNKGNRI FCLRDLADNY KLKQFETTDD  840
LEIEKKIADT IWDANKKDFK FGNYRSFINL TPQEQKAFRH ALFLADENPI KQAVIRAINN  900
RNRTFVNGTQ RYFAEVLANN IYLRAKKENL NTDKISFDYF GIPTIGNGRG IAEIRQLYEK  960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSERVK IKSIDDVKQV 1200
LDKSNFIIG KITLPFKKEW QRLYREWQNT TIKDDYEFLK SFPNVKSITL LHKKVRKDFS 1260
LPISTNEGKF LVKRKTWDNN FIYQILNDSD SRADGTKPFI PAFDISKNEI VEAIIDHFTS 1320
KNIFWLPKNI ELQKVDNKNI FAIDTSKWFE VETPSDLRDI GIATIQYKID NNSRPKVRVK 1380
LDYVIDDDSK INYFMNHSLL KSRYPDKVLE ILKQSTIIEF ESSGFNKTIK EMLGMKLAGI 1440
YNETSNN                                                           1447

SEQ ID NO: 70           moltype = AA  length = 1447
FEATURE                 Location/Qualifiers
REGION                  1..1447
                        note = FnCas9 truncations
source                  1..1447
                        mol_type = protein
```

```
                         organism = synthetic construct
SEQUENCE: 70
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKDG AKYSYKDLCN    240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE  1020
VFTKDIFSQI KITDNEFSDK KLVRKKAIEG FNTHRQMTRD GIYAENYLPI LIHKELNEVR  1080
KGYTWKNSEE IKIFKGKKYD IQQLNNLVYC LKFVDKPISI DIQISTLEEL RNILTTNNIA  1140
ATAEYYYINL KTQKLHEYYI ENYNTALGYK KYSKEMEFLR SLAYRSERVK IKSIDDVKQV  1200
LDKDSNFIIG KITLPFKKEW QRLYREWQNT TIKDDYEFLK SFFNVKSITK LHKKVRKDFS  1260
LPISTNEGKF LVKRKTWDNN FIYQILNDSD SRADGTKPFI PAFDISKNEI VEAIIDSFTS  1320
KNIFWLPKNI ELQKVDNKNI FAIDTSKWFE VETPSDLRDI GIATIQYKID NNSRPKVRVK  1380
LDYVIDDDSK INYFMNHRLL KSRYPDKVLE ILKQSTIIEF ESSGFNKTIK EMLGMKLAGI  1440
YNETSNN                                                          1447

SEQ ID NO: 71            moltype = AA  length = 1447
FEATURE                  Location/Qualifiers
REGION                   1..1447
                         note = FnCas9 truncations
source                   1..1447
                         mol_type = protein
                         organism = synthetic construct
SEQUENCE: 71
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKDG AKYSYKDLCN    240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE  1020
VFTKDIFSQI KITDNEFSDK KLVRKKAIEG FNTHRQMTRD GIYAENYLPI LIHKELNEVR  1080
KGYTWKNSEE IKIFKGKKYD IQQLNNLVYC LKFVDKPISI DIQISTLEEL RNILTTNNIA  1140
ATAEYYYINL KTQKLHEYYI ENYNTALGYK KYSKEMEFLR SLAYRSERVK IKSIDDVKQV  1200
LDKDSNFIIG KITLPFKKEW QRLYREWQNT TIKDDYEFLK SFFNVKSITK LHKKVRKDFS  1260
LPISTNEGKF LVKRKTWDNN FIYQILNDSD SRADGTKPFI PAFDISKNEI VEAIIDSFTS  1320
KNIFWLPKNI ELQKVDNKNI FAIDTSKWFE VETPSDLRDI GIATIQYKID NNSRPKVRVK  1380
LDYVIDDDSK INYFMNHSLL RSRYPDKVLE ILKQSTIIEF ESSGFNKTIK EMLGMKLAGI  1440
YNETSNN                                                          1447

SEQ ID NO: 72            moltype = AA  length = 1447
FEATURE                  Location/Qualifiers
REGION                   1..1447
                         note = FnCas9 truncations
source                   1..1447
                         mol_type = protein
                         organism = synthetic construct
SEQUENCE: 72
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKDG AKYSYKDLCN    240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
```

```
LLNHKINIAR NTKGKCEKEI FNLICKIEGS EDKKGNYKHG LAYELGVLLF GEPNEASKPE  600
FDRKIKKFNS IYSFAQIQQI AFAERKGNAN TCAVCSADNA HRMQQIKITE PVEDNKDKII  660
LSAKAQRLPA IPTRIVDGAV KKMATILAKN IVDDNWQNIK QVLSAKHQLH IPIITESNAF  720
EFEPALADVK GKSLKDRRKK ALERISPENI FKDKNNRIKE FAKGISAYSG ANLTDGDFDG  780
AKEELDHIIP RSHKKYGTLN DEANLICVTR GDNKNKGNRI FCLRDLADNY KLKQFETTDD  840
LEIEKKIADT IWDANKKDFK FGNYRSFINL TPQEQKAFRH ALFLADENPI KQAVIRAINN  900
RNRTFVNGTQ RYFAEVLANN IYLRAKKENL NTDKISFDYF GIPTIGNGRG IAEIRQLYEK  960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSERVK IKSIDDVKQV 1200
LDKDSNFIIG KITLPFKKEW QRLYREWQNT TIKDDYEFLK SFFNVKSITK LHKKVRKDFS 1260
LPISTNEGKF LVKRKTWDNN FIYQILNDSD SRADGTKPFI PAFDISKNEI VEAIIDSFTS 1320
KNIFWLPKNI ELQKVDNKNI FAIDTSKWFE VETPSDLRDI GIATIQYKID NNSRPKVRVK 1380
LDYVIDDDSK INYFMNHSLL KSRYPDKVLE ILKQSTIIEF ESSGFNVTIK EMLGMKLAGI 1440
YNETSNN                                                         1447

SEQ ID NO: 73           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 73
MNFKILPIAI DLGVKNTGVF SAFYQKGTSL ERLDNKNGKV YELSKDSYTL LMNNRTARRH  60
QRRGIDRKQL VKRLFKLIWT EQLNLEWDKD TQQAISFLFN RRGFSFITDG YGGGSVNKIK 120
SEMASGGRHR SQYFQEITNV LDENNHQEGY LKNFCENLHN KKYSNLSVKN LVNLIGNLSN 180
LELKPLRKYF NDKIHAKADH WDEQKFTETY CHWILGEWRV GVKDQDKKDG AKYSYKDLCN 240
ELKQKVTKAG LVDFLLELDP CRTIPPYLDN NNRKPPKCQS LILNPKFLDN QYPNWQQYLQ 300
ELKKLQSIQN YLDSFETDLK VLKSSKDQPY FVEYKSSNQQ IASGQRDYKD LDARILQFIF 360
DRVKASDELL LNEIYFQAKK LKQKASSELE KLESSKKLDE VIANSQLSQI LKSQHTNGIF 420
EQGTFLHLVC KYYKQRQRAR DSRLYIMPEY RYDKKLHKYN NTGRFDDDNQ LLTYCNHKPR 480
QKRYQLLNDL AGVLQVSPNF LKDKIGSDDD LFISKWLVEH IRGFKKACED SLKIQKDNRG 540
LLNHKINIAR NTKGKCEKEI FNLICKIEGS EDKKGNYKHG LAYELGVLLF GEPNEASKPE 600
FDRKIKKFNS IYSFAQIQQI AFAERKGNAN TCAVCSADNA HRMQQIKITE PVEDNKDKII 660
LSAKAQRLPA IPTRIVDGAV KKMATILAKN IVDDNWQNIK QVLSAKHQLH IPIITESNAF 720
EFEPALADVK GKSLKDRRKK ALERISPENI FKDKNNRIKE FAKGISAYSG ANLTDGDFDG 780
AKEELDHIIP RSHKKYGTLN DEANLICVTR GDNKNKGNRI FCLRDLADNY KLKQFETTDD 840
LEIEKKIADT IWDANKKDFK FGNYRSFINL TPQEQKAFRH ALFLADENPI KQAVIRAINN 900
RNRTFVNGTQ RYFAEVLANN IYLRAKKENL NTDKISFDYF GIPTIGNGRG IAEIRQLYEK 960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSERVK IKSIDDVKQV 1200
LDKDSNFIIG KITLPFKKEW QRLYREWQNT TIKDDYEFLK SFFNVKSITK LHKKVRKDFS 1260
LPISTNEGKF LVKRKTWDNN FIYQILNDSD SRADGTKPFI PAFDISKNEI VEAIIDSFTS 1320
KNIFWLPKNI ELQKVDNKNI FAIDTSKWFE VETPSDLRDI GIATIQYKID NNSRPKVRVK 1380
LDYVIDDDSK INYFMNHSLL KSRYPDKVLE ILKQSTIIEF ESSGFNSTIK EMLGMKLAGI 1440
YNETSNN                                                         1447

SEQ ID NO: 74           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 74
MNFKILPIAI DLGVKNTGVF SAFYQKGTSL ERLDNKNGKV YELSKDSYTL LMNNRTARRH  60
QRRGIDRKQL VKRLFKLIWT EQLNLEWDKD TQQAISFLFN RRGFSFITDG YGGGSVNKIK 120
SEMASGGRHR SQYFQEITNV LDENNHQEGY LKNFCENLHN KKYSNLSVKN LVNLIGNLSN 180
LELKPLRKYF NDKIHAKADH WDEQKFTETY CHWILGEWRV GVKDQDKKDG AKYSYKDLCN 240
ELKQKVTKAG LVDFLLELDP CRTIPPYLDN NNRKPPKCQS LILNPKFLDN QYPNWQQYLQ 300
ELKKLQSIQN YLDSFETDLK VLKSSKDQPY FVEYKSSNQQ IASGQRDYKD LDARILQFIF 360
DRVKASDELL LNEIYFQAKK LKQKASSELE KLESSKKLDE VIANSQLSQI LKSQHTNGIF 420
EQGTFLHLVC KYYKQRQRAR DSRLYIMPEY RYDKKLHKYN NTGRFDDDNQ LLTYCNHKPR 480
QKRYQLLNDL AGVLQVSPNF LKDKIGSDDD LFISKWLVEH IRGFKKACED SLKIQKDNRG 540
LLNHKINIAR NTKGKCEKEI FNLICKIEGS EDKKGNYKHG LAYELGVLLF GEPNEASKPE 600
FDRKIKKFNS IYSFAQIQQI AFAERKGNAN TCAVCSADNA HRMQQIKITE PVEDNKDKII 660
LSAKAQRLPA IPTRIVDGAV KKMATILAKN IVDDNWQNIK QVLSAKHQLH IPIITESNAF 720
EFEPALADVK GKSLKDRRKK ALERISPENI FKDKNNRIKE FAKGISAYSG ANLTDGDFDG 780
AKEELDHIIP RSHKKYGTLN DEANLICVTR GDNKNKGNRI FCLRDLADNY KLKQFETTDD 840
LEIEKKIADT IWDANKKDFK FGNYRSFINL TPQEQKAFRH ALFLADENPI KQAVIRAINN 900
RNRTFVNGTQ RYFAEVLANN IYLRAKKENL NTDKISFDYF GIPTIGNGRG IAEIRQLYEK 960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSERVK IKSIDDVKQV 1200
```

```
LDKDSNFIIG KITLPFKKEW QRLYREWQNT TIKDDYEFLK SFFNVKSITK LHKKVRKDFS   1260
LPISTNEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNNTIK EMLGMKLAGI   1440
YNETSNN                                                              1447

SEQ ID NO: 75           moltype = AA   length = 1447
FEATURE                 Location/Qualifiers
REGION                  1..1447
                        note = FnCas9 truncations
source                  1..1447
                        mol_type = protein
                        organism = synthetic construct
SEQUENCE: 75
MNFKILPIAI DLGVKNTGVF SAFYQKGTSL ERLDNKNGKV YELSKDSYTL LMNNRTARRH   60
QRRGIDRKQL VKRLFKLIWT EQLNEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE   1020
VPFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSERVK IKSIDDVKQV   1200
LDKDSNFIIG KITLPFKKEW QRLYREWQNT TIKDDYEFLK SFFNVKSITK LHKKVRKDFS   1260
LPISTNEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESFGFNKTIK EMLGMKLAGI   1440
YNETSNN                                                              1447

SEQ ID NO: 76           moltype = AA   length = 1447
FEATURE                 Location/Qualifiers
REGION                  1..1447
                        note = FnCas9 truncations
source                  1..1447
                        mol_type = protein
                        organism = synthetic construct
SEQUENCE: 76
MNFKILPIAI DLGVKNTGVF SAFYQKGTSL ERLDNKNGKV YELSKDSYTL LMNNRTARRH   60
QRRGIDRKQL VKRLFKLIWT EQLNEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE   1020
VPFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSERVK IKSIDDVKQV   1200
LDKDSNFIIG KITLPFKKEW QRLYREWQNT TIKDDYEFLK SFFNVKSITK LHKKVRKDFS   1260
LPISTNEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESRGFNKTIK EMLGMKLAGI   1440
YNETSNN                                                              1447

SEQ ID NO: 77           moltype = AA   length = 1448
FEATURE                 Location/Qualifiers
REGION                  1..1448
                        note = FnCas9 truncations
source                  1..1448
```

```
                        mol_type = protein
                        organism = synthetic construct
SEQUENCE: 77
MNFKILPIAI DLGVKNTGVF SAFYQKGTSL ERLDKNGKV  YELSKDSYTL LMNNRTARRH   60
QRRGIDRKQL VKRLFKLIWT EQLNLEWDKD TQQAISFLFN RRGFSFITDG YGGGSVNKIK  120
SEMASGGRHR SQYFQEITNV LDENNHQEGY LKNFCENLHN KKYSNLSVKN LVNLIGNLSN  180
LELKPLRKYF NDKIHAKADH WDEQKFTETY CHWILGEWRV GVKDQDKKDG AKYSYKDLCN  240
ELKQKVTKAG LVDFLLELDP CRTIPPYLDN NNRKPPKCQS LILNPKFLDN QYPNWQQYLQ  300
ELKKLQSIQN YLDSFETDLK VLKSSKDQPY FVEYKSSNQQ IASGQRDYKD LDARILQFIF  360
DRVKASDELL LNEIYFQAKK LKQKASSELE KLESSKKLDE VIANSQLSQI LKSQHTNGIF  420
EQGTFLHLVC KYYKQRQRAR DSRLYIMPEY RYDKKLHKYN NTGRFDDDNQ LLTYCNHKPR  480
QKRYQLLNDL AGVLQVSPNF LKDKIGSDDD LFISKWLVEH IRGFKKACED SLKIQKDNRG  540
LLNHKINIAR NTKGKCEKEI FNLICKIEGS EDKKGNYKHG LAYELGVLLF GEPNEASKPE  600
FDRKIKKFNS IYSFAQIQQI AFAERKGNAN TCAVCSADNA HRMQQIKITE PVEDNKDKII  660
LSAKAQRLPA IPTRIVDGAV KKMATILAKN IVDDNWQNIK QVLSAKHQLH IPIITESNAF  720
EFEPALADVK GKSLKDRRKK ALERISPENI FKDKNNRIKE FAKGISAYSG ANLTDGDFDG  780
AKEELDHIIP RSHKKYGTLN DEANLICVTR GDNKNKGNRI FCLRDLADNY KLKQFETTDD  840
LEIEKKIADT IWDANKKDFK FGNYRSFINL TPQEQKAFRH ALFLADENPI KQAVIRAINN  900
RNRTFVNGTQ RYFAEVLANN IYLRAKKENL NTDKISFDYF GIPTIGNRG  IAEIRQLYEK  960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSERVK IKSIDDVKQV 1200
LDKDRSNFII GKITLPFKKE WQRLYREWQN TTIKDDYEFL KSFFNVKSIT KLHKKVRKDF 1260
SLPISTNEGK FLVKRKTWDN NFIYQILNDS DSRADGTKPF IPAFDISKNE IVEAIIDSFT 1320
SKNIFWLPKN IELQKVDNKN IFAIDTSKWF EVETPSDLRD IGIATIQYKI DNNSRPKVRV 1380
KLDYVIDDDS KINYFMNHSL LKSRYPDKVL EILKQSTIIE FESSGFNKTI KEMLGMKLAG 1440
IYNETSNN                                                         1448

SEQ ID NO: 78          moltype = AA  length = 1447
FEATURE                Location/Qualifiers
REGION                 1..1447
                       note = FnCas9 truncations
source                 1..1447
                       mol_type = protein
                       organism = synthetic construct
SEQUENCE: 78
MNFKILPIAI DLGVKNTGVF SAFYQKGTSL ERLDKNGKV  YELSKDSYTL LMNNRTARRH   60
QRRGIDRKQL VKRLFKLIWT EQLNLEWDKD TQQAISFLFN RRGFSFITDG YGGGSVNKIK  120
SEMASGGRHR SQYFQEITNV LDENNHQEGY LKNFCENLHN KKYSNLSVKN LVNLIGNLSN  180
LELKPLRKYF NDKIHAKADH WDEQKFTETY CHWILGEWRV GVKDQDKKDG AKYSYKDLCN  240
ELKQKVTKAG LVDFLLELDP CRTIPPYLDN NNRKPPKCQS LILNPKFLDN QYPNWQQYLQ  300
ELKKLQSIQN YLDSFETDLK VLKSSKDQPY FVEYKSSNQQ IASGQRDYKD LDARILQFIF  360
DRVKASDELL LNEIYFQAKK LKQKASSELE KLESSKKLDE VIANSQLSQI LKSQHTNGIF  420
EQGTFLHLVC KYYKQRQRAR DSRLYIMPEY RYDKKLHKYN NTGRFDDDNQ LLTYCNHKPR  480
QKRYQLLNDL AGVLQVSPNF LKDKIGSDDD LFISKWLVEH IRGFKKACED SLKIQKDNRG  540
LLNHKINIAR NTKGKCEKEI FNLICKIEGS EDKKGNYKHG LAYELGVLLF GEPNEASKPE  600
FDRKIKKFNS IYSFAQIQQI AFAERKGNAN TCAVCSADNA HRMQQIKITE PVEDNKDKII  660
LSAKAQRLPA IPTRIVDGAV KKMATILAKN IVDDNWQNIK QVLSAKHQLH IPIITESNAF  720
EFEPALADVK GKSLKDRRKK ALERISPENI FKDKNNRIKE FAKGISAYSG ANLTDGDFDG  780
AKEELDHIIP RSHKKYGTLN DEANLICVTR GDNKNKGNRI FCLRDLADNY KLKQFETTDD  840
LEIEKKIADT IWDANKKDFK FGNYRSFINL TPQEQKAFRH ALFLADENPI KQAVIRAINN  900
RNRTFVNGTQ RYFAEVLANN IYLRAKKENL NTDKISFDYF GIPTIGNRG  IAEIRQLYEK  960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSERVK IKSIDDVKQV 1200
LDKDSNFIIG KITLPFKKEW QRLYREWQNT TIKDDYEFLK SFFNVKSITK LHKKVRKDFS 1260
LPISTNEGKF LVKRKTWDNN FIYQILNDSD SRADGTKPFI PAFDISKNEI VEAIIDSFTS 1320
KNIFWLPKNI ELQKVDNKNI FAIDTSKWFE VETPSDLRDI GIATIQYKID NNSRPKVRVK 1380
LDYVIDDDSK INYFMNHSLL KSRHPDKVLE ILKQSTIIEF HSSGFNKTIK EMLGMKLAGI 1440
YNETSNN                                                          1447

SEQ ID NO: 79          moltype = AA  length = 1447
FEATURE                Location/Qualifiers
REGION                 1..1447
                       note = FnCas9 truncations
source                 1..1447
                       mol_type = protein
                       organism = synthetic construct
SEQUENCE: 79
MNFKILPIAI DLGVKNTGVF SAFYQKGTSL ERLDKNGKV  YELSKDSYTL LMNNRTARRH   60
QRRGIDRKQL VKRLFKLIWT EQLNLEWDKD TQQAISFLFN RRGFSFITDG YGGGSVNKIK  120
SEMASGGRHR SQYFQEITNV LDENNHQEGY LKNFCENLHN KKYSNLSVKN LVNLIGNLSN  180
LELKPLRKYF NDKIHAKADH WDEQKFTETY CHWILGEWRV GVKDQDKKDG AKYSYKDLCN  240
ELKQKVTKAG LVDFLLELDP CRTIPPYLDN NNRKPPKCQS LILNPKFLDN QYPNWQQYLQ  300
ELKKLQSIQN YLDSFETDLK VLKSSKDQPY FVEYKSSNQQ IASGQRDYKD LDARILQFIF  360
DRVKASDELL LNEIYFQAKK LKQKASSELE KLESSKKLDE VIANSQLSQI LKSQHTNGIF  420
EQGTFLHLVC KYYKQRQRAR DSRLYIMPEY RYDKKLHKYN NTGRFDDDNQ LLTYCNHKPR  480
```

```
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSERVK IKSIDDVKQV   1200
LDKDSNFIIK KITLPFKKEW QRLYREWQNT TIKDDYEFLK SFFNVKSITK LHKKVRKDFS   1260
LPISTYEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                            1447

SEQ ID NO: 80           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 80
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN TNGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD TIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSRRVK IKSIDDVKQV   1200
LDKDSNFIIG KITLPFKKEW QRLYREWQNT TIKDDYEFLK SFFNVKSITK LHKKVRKDFS   1260
LPISTNHGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                            1447

SEQ ID NO: 81           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 81
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSKKLDE VIANSQLSQI LKSQHTNGIF    420
EQGTFLHLVC KYYKQRQRAR DSRLYIMPEY RYDKKLHKYN TNGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
```

```
ATAEYYYINL KTQKLHEYYI ENYNTALGYK KYSKEMEFLR SLAYRSRRVK IKSIDDVKQV   1200
LDKDSNFIIK KITLPFKKEW QRLYREWQNT TIKDDYEFLK SFFNVKSITK LHKKVRKDFS   1260
LPISTNHGKF LVKRKTWDNN FIYQILNDSD SRADGTKPFI PAFDISKNEI VEAAIIDSFTS  1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                              1447

SEQ ID NO: 82          moltype = AA  length = 1447
FEATURE                Location/Qualifiers
REGION                 1..1447
                       note = FnCas9 truncations
source                 1..1447
                       mol_type = protein
                       organism = synthetic construct
SEQUENCE: 82
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNRG IAEIRQLYEK   960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSRRVK IKSIDDVKQV   1200
LDKDSNFIIG KITLPFKKEW QRLYREWQNT TIKDDYEFLK SFFNVKSITK LHKKVRKDFS   1260
LPISTYHGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                              1447

SEQ ID NO: 83          moltype = AA  length = 1447
FEATURE                Location/Qualifiers
REGION                 1..1447
                       note = FnCas9 truncations
source                 1..1447
                       mol_type = protein
                       organism = synthetic construct
SEQUENCE: 83
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNRG IAEIRQLYEK   960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSRRVK IKSIDDVKQV   1200
LDKDSNFIIG KITLPFKKEW QRLYREWQNT TIKDDYEFLK SFFNVKSITK LHKKVRKDFS   1260
LPISTNEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF HSSGFNKTIK EMLGMKLAGI   1440
YNETSNN                                                              1447

SEQ ID NO: 84          moltype = AA  length = 1447
FEATURE                Location/Qualifiers
REGION                 1..1447
                       note = FnCas9 truncations
```

| source | 1..1447 |
| --- | --- |
| | mol_type = protein |
| | organism = synthetic construct |

SEQUENCE: 84

```
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YGGGSVNKIK  120
SEMASGGRHR SQYFQEITNV LDENNHQEGY LKNFCENLHN KKYSNLSVKN LVNLIGNLSN  180
LELKPLRKYF NDKIHAKADH WDEQKFTETY CHWILGEWRV GVKDQDKKDG AKYSYKDLCN  240
ELKQKVTKAG LVDFLLELDP CRTIPPYLDN NNRKPPKCQS LILNPKFLDN QYPNWQQYLQ  300
ELKKLQSIQN YLDSFETDLK VLKSSKDQPY FVEYKSSNQQ IASGQRDYKD LDARILQFIF  360
DRVKASDELL LNEIYFQAKK LKQKASSELE KLESSKKLDE VIANSQLSQI LKSQHTNGIF  420
EQGTFLHLVC KYYKQRQRAR DSRLYIMPEY RYDKKLHKYN NTGRFDDDNQ LLTYCNHKPR  480
QKRYQLLNDL AGVLQVSPNF LKDKIGSDDD LFISKWLVEH IRGFKKACED SLKIQKDNRG  540
LLNHKINIAR NTKGKCEKEI FNLICKIEGS EDKKGNYKHG LAYELGVLLF GEPNEASKPE  600
FDRKIKKFNS IYSFAQIQQI AFAERKGNAN TCAVCSADNA HRMQQIKITE PVEDNKDKII  660
LSAKAQRLPA IPTRIVDGAV KKMATILAKN IVDDNWQNIK QVLSAKHQLH IPIITESNAF  720
EFEPALADVK GKSLKDRRKK ALERISPENI FKDKNNRIKE FAKGISAYSG ANLTDGDFDG  780
AKEELDHIIP RSHKKYGTLN DEANLICVTR GDNKNKGNRI FCLRDLADNY KLKQFETTDD  840
LEIEKKIADT IWDANKKDFK FGNYRSFINL TPQEQKAFRH ALFLADENPI KQAVIRAINN  900
RNRTFVNGTQ RYFAEVLANN IYLRAKKENL NTDKISFDYF GIPTIGNGRG IAEIRQLYEK  960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSRRVK IKSIDDVKQV 1200
LDKDSNFIIK KITLPFKKEW QRLYREWQNT TIKDDYEFLK SFFNVKSITK LHKKVRKDFS 1260
LPISTNEGKF LVKRKTWDNN FIYQILNDSD SRADGTKPFI PAFDISKNEI VEAIIDSFTS 1320
KNIFWLPKNI ELQKVDNKNI FAIDTSKWFE VETPSDLRDI GIATIQYKID NNSRPKVRVK 1380
LDYVIDDDSK INYFMNHSLL KSRYPDKVLE ILKQSTIIEF ESSGFNKTIK EMLGMKLAGI 1440
YNETSNN                                                          1447
```

| SEQ ID NO: 85 | moltype = AA  length = 1447 |
| --- | --- |
| FEATURE | Location/Qualifiers |
| REGION | 1..1447 |
| | note = FnCas9 truncations |
| source | 1..1447 |
| | mol_type = protein |
| | organism = synthetic construct |

SEQUENCE: 85

```
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YGGGSVNKIK  120
SEMASGGRHR SQYFQEITNV LDENNHQEGY LKNFCENLHN KKYSNLSVKN LVNLIGNLSN  180
LELKPLRKYF NDKIHAKADH WDEQKFTETY CHWILGEWRV GVKDQDKKDG AKYSYKDLCN  240
ELKQKVTKAG LVDFLLELDP CRTIPPYLDN NNRKPPKCQS LILNPKFLDN QYPNWQQYLQ  300
ELKKLQSIQN YLDSFETDLK VLKSSKDQPY FVEYKSSNQQ IASGQRDYKD LDARILQFIF  360
DRVKASDELL LNEIYFQAKK LKQKASSELE KLESSKKLDE VIANSQLSQI LKSQHTNGIF  420
EQGTFLHLVC KYYKQRQRAR DSRLYIMPEY RYDKKLHKYN NTGRFDDDNQ LLTYCNHKPR  480
QKRYQLLNDL AGVLQVSPNF LKDKIGSDDD LFISKWLVEH IRGFKKACED SLKIQKDNRG  540
LLNHKINIAR NTKGKCEKEI FNLICKIEGS EDKKGNYKHG LAYELGVLLF GEPNEASKPE  600
FDRKIKKFNS IYSFAQIQQI AFAERKGNAN TCAVCSADNA HRMQQIKITE PVEDNKDKII  660
LSAKAQRLPA IPTRIVDGAV KKMATILAKN IVDDNWQNIK QVLSAKHQLH IPIITESNAF  720
EFEPALADVK GKSLKDRRKK ALERISPENI FKDKNNRIKE FAKGISAYSG ANLTDGDFDG  780
AKEELDHIIP RSHKKYGTLN DEANLICVTR GDNKNKGNRI FCLRDLADNY KLKQFETTDD  840
LEIEKKIADT IWDANKKDFK FGNYRSFINL TPQEQKAFRH ALFLADENPI KQAVIRAINN  900
RNRTFVNGTQ RYFAEVLANN IYLRAKKENL NTDKISFDYF GIPTIGNGRG IAEIRQLYEK  960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSRRVK IKSIDDVKQV 1200
LDKDSNFIIG KITLPFKKEW QRLYREWQNT TIKDDYEFLK SFFNVKSITK LHKKVRKDFS 1260
LPISTREGKF LVKRKTWDNN FIYQILNDSD SRADGTKPFI PAFDISKNEI VEAIIDSFTS 1320
KNIFWLPKNI ELQKVDNKNI FAIDTSKWFE VETPSDLRDI GIATIQYKID NNSRPKVRVK 1380
LDYVIDDDSK INYFMNHSLL KSRYPDKVLE ILKQSTIIEF ESSGFNKTIK EMLGMKLAGI 1440
YNETSNN                                                          1447
```

| SEQ ID NO: 86 | moltype = AA  length = 1447 |
| --- | --- |
| FEATURE | Location/Qualifiers |
| REGION | 1..1447 |
| | note = FnCas9 truncations |
| source | 1..1447 |
| | mol_type = protein |
| | organism = synthetic construct |

SEQUENCE: 86

```
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YGGGSVNKIK  120
SEMASGGRHR SQYFQEITNV LDENNHQEGY LKNFCENLHN KKYSNLSVKN LVNLIGNLSN  180
LELKPLRKYF NDKIHAKADH WDEQKFTETY CHWILGEWRV GVKDQDKKDG AKYSYKDLCN  240
ELKQKVTKAG LVDFLLELDP CRTIPPYLDN NNRKPPKCQS LILNPKFLDN QYPNWQQYLQ  300
ELKKLQSIQN YLDSFETDLK VLKSSKDQPY FVEYKSSNQQ IASGQRDYKD LDARILQFIF  360
DRVKASDELL LNEIYFQAKK LKQKASSELE KLESSKKLDE VIANSQLSQI LKSQHTNGIF  420
```

```
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSRRVK IKSIDDVKQV   1200
LDKDSNFIIG KITLPFKKEW QRLYREWQNT TIKDDYEFLK SFFNVKSITK LHKKVRKDFS   1260
LPISTYEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                            1447

SEQ ID NO: 87          moltype = AA  length = 1447
FEATURE                Location/Qualifiers
REGION                 1..1447
                       note = FnCas9 truncations
source                 1..1447
                       mol_type = protein
                       organism = synthetic construct
SEQUENCE: 87
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSSKLDK VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSRRVK IKSIDDVKQV   1200
LDKDSNFIIG KITLPFKKEW QRLYREWQNT TIKDDYEFLK SFFNVKSITK LHKKVRKDFS   1260
LPISTNEGKF LVKRKTWDNN FIYQILNDSD SRFDGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                            1447

SEQ ID NO: 88          moltype = AA  length = 1447
FEATURE                Location/Qualifiers
REGION                 1..1447
                       note = FnCas9 truncations
source                 1..1447
                       mol_type = protein
                       organism = synthetic construct
SEQUENCE: 88
MNFKILPIAI DLGVKNTGVF SAFYQKGTSL ERLDNKNGKV YELSKDSYTL LMNNRTARRH     60
QRRGIDRKQL VKRLFKLIWT EQLNLEWDKD TQQAISFLFN RRGFSFITDG YGGGSVNKIK    120
SEMASGGRHR SQYFQEITNV LDENNHQEGY LKNFCENLHN KKYSNLSVKN LVNLIGNLSN    180
LELKPLRKYF NDKIHAKADH WDEQKFTETY CHWILGEWRV GVKDQDKKDG AKYSYKDLCN    240
ELKQKVTKAG LVDFLLELDP CRTIPPYLDN NNRKPPKCQS LILNPKFLDN QYPNWQQYLQ    300
ELKKLQSIQN YLDSFETDLK VLKSSKDQPY FVEYKSSNQQ IASGQRDYKD LDARILQFIF    360
DRVKASDELL LNEIYFQAKK LKQKASSELE KLESSSKLDK VIANSQLSQI LKSQHTNGIF    420
EQGTFLHLVC KYYKQRQRAR DSRLYIMPEY RYDKKLHKYN NTGRFDDDNQ LLTYCNHKPR    480
QKRYQLLNDL AGVLQVSPNF LKDKIGSDDD LFISKWLVEH IRGFKKACED SLKIQKDNRG    540
LLNHKINIAR NTKGKCEKEI FNLICKIEGS EDKKGNYKHG LAYELGVLLF GEPNEASKPE    600
FDRKIKKFNS IYSFAQIQQI AFAERKGNAN TCAVCSADNA HRMQQIKITE PVEDNKDKII    660
LSAKAQRLPA IPTRIVDGAV KKMATILAKN IVDDNWQNIK QVLSAKHQLH IPIITESNAF    720
EFEPALADVK GKSLKDRRKK ALERISPENI FKDKNNRIKE FAKGISAYSG ANLTDGDFDG    780
AKEELDHIIP RSHKKYGTLN DEANLICVTR GDNKNKGNRI FCLRDLADNY KLKQFETTDD    840
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNGRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
```

```
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSRRVK IKSIDDVKQV   1200
LDKDSNFIIG KITLPFKKEW QRLYREWQNT TIKDDYEFLK SFFNVKSITK LHKKVRKDFS   1260
LPISTNEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHRLL KSRYPDKVLE ILKQSTIIEF ESSGFNKTIK EMLGMKLAGI   1440
YNETSNN                                                            1447

SEQ ID NO: 89           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 89
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD TIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSRRVK IKSIDDVKQV   1200
LDKDSNFIIG KITLPFKKEW QRLYREWQNT TIKDDYEFLK SFFNVKSITK LHKKVRKDFS   1260
LPISTNEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF ESSGFNKTIK EMLGMKLAGI   1440
YNETSNN                                                            1447

SEQ ID NO: 90           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 90
MNFKILPIAI DLGVKNTGVF SAFYQKGTSL ERLDNKNGKV YELSKDSYTL LMNNRTARRH   60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD TIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSRRVK IKSIDDVKQV   1200
LDKDSNFIIG KITLPFKKEW QRLYREWQNT TIKDDYEFLK SFFNVKSITK LHKKVRKDFS   1260
LPISTNEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSQPKVRVK   1380
LDYVIDDDSK INYFMNHSLL KSRYPDKVLE ILKQSTIIEF ESSGFNKTIK EMLGMKLAGI   1440
YNETSNN                                                            1447

SEQ ID NO: 91           moltype = AA  length = 1629
FEATURE                 Location/Qualifiers
REGION                  1..1629
```

```
                        note = FnCas9 truncations
source                  1..1629
                        mol_type = protein
                        organism = synthetic construct
SEQUENCE: 91
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSITDG YSPEYLNIVP    120
EQVKAILMDI FDDYNGEDDL DSYLKLATEQ ESKISEIYNK LMQKILEFKL MKLCTDIKDD   180
KVSTKTLKEI TSYEFELLAD YLANYSESLK TQKFSYTDKQ GNLKELSYYH HDKYNIQEFL   240
KRHATINDRI LDTLLTDDLD IWNFNFEKFD FDKNEEKLQN QEDKDHIQAH LHHFVFAVNK   300
IKSEMASGGR HRSQYFQEIT NVLDENNHQE GYLKNFCENL HNKKYSNLSV KNLVNLIGNL   360
SNLELKPLRK YFNDKIHAKA DHWDEQKFTE TYCHWILGEW RVGVKDQDKK DGAKYSYKDL   420
CNELKQKVTK AGLVDFLLEL DPCRTIPPYL DNNNRKPPKC QSLILNPKFL DNQYPNWQQY   480
LQELKKLQSI QNYLDSFETD LKVLKSSKDQ PYFVEYKSSN QQIASGQRDY KDLDARILQF   540
IFDRVKASDE LLLNEIYFQA KKLKQKASSE LEKLESSKKL DEVIANSQLS QILKSQHTNG   600
IFEQGTFLHL VCKYYKQRQR ARDSRLYIMP EYRYDKKLHK YNNTGRFDDD NQLLTYCNHK   660
PRQKRYQLLN DLAGVLQVSP NFLKDKIGSD DDLFISKWLV EHIRGFKKAC EDSLKIQKDN   720
RGLLNHKINI ARNTKGKCEK EIFNLICKIE GSEDKKGNYK HGLAYELGVL LFGEPNEASK   780
PEFDRKIKKF NSIYSFAQIQ QIAFAERKGN ANTCAVCSAD NAHRMQQIKI TEPVEDNKDK   840
IILSAKAQRL PAIPTRIVDG AVKKMATILA KNIVDDNWQN IKQVLSAKHQ LHIPIITESN   900
AFEFEPALAD VKGKSLKDRR KKALERISPE NIFKDKNNRI KEFAKGISAY SGANLTDGDF   960
DGAKEELDHI IPRSHKKYGT LNDEANLICV TRGDNKNKGN RIFCLRDLAD NYKLKQFETT   1020
DDLEIEKKIA DTIWDANKKD FKFGNYRSFI NLTPQEQKAF RHALFLADEN PIKQAVIRAI   1080
NNRNRTFVNG TQRYFAEVLA NNIYLRAKKE NLNTDKISFD YFGIPTIGNG RGIAEIRQLY   1140
EKVDSDIQAY AKGDKPQASY SHLIDAMLAF CIAADEHRND GSIGLEIDKN YSLYPLDKNT   1200
GEVFTKDIFS QIKITDNEFS DKKLVRKKAI EGFNTHRQMT RDGIYAENYL PILIHKELNE   1260
VRKGYTWKNS EEIKIFKGKK YDIQQLNNLV YCLKFVDKPI SIDIQISTLE ELRNILTTNN   1320
IAATAEYYYI NLKTQKLHEY YIENYNTALG YKKYSKEMEF LRSLAYRSER VKIKSIDDVK   1380
QVLDKDSNFI IKKITLPFKK EWQRLYREWQ NTTIKDDYEF LKSFFNVKSI TKLHKKVRKD   1440
FSLPISTNEG KFLVKRKTWD NNFIYQILND SDSRADGTKP FIPAFDISKN EIVEAIIDSF   1500
TSKNIFWLPK NIELQKVDNK NIFAIDTSKW FEVETPSDLR DIGIATIQYK IDNNSRPKVR   1560
VKLDYVIDDD SKINYFMNHS LLKSRYPDKV LEILKQSTII EFHSSGFNKT IKEMLGMKLA   1620
GIYNETSNN                                                           1629

SEQ ID NO: 92           moltype = AA   length = 1447
FEATURE                 Location/Qualifiers
REGION                  1..1447
                        note = FnCas9 truncations
source                  1..1447
                        mol_type = protein
                        organism = synthetic construct
SEQUENCE: 92
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSITDG YGGGSVNKIK    120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNKGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNGRG IAEIRQLYEK   960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSERVK IKSIDDVKQV   1200
LDKDSNFIIG KITLPFKKEW QRLYREWQNT TIKDDYEFLK SFFNVKSITK LHKKVRKDFS   1260
LPISTREGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHSLL KSRYPDKVLE ILKQSTIIEF HSSGFNKTIK EMLGMKLAGI   1440
YNETSNN                                                             1447

SEQ ID NO: 93           moltype = AA   length = 1447
FEATURE                 Location/Qualifiers
REGION                  1..1447
                        note = FnCas9 truncations
source                  1..1447
                        mol_type = protein
                        organism = synthetic construct
SEQUENCE: 93
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSITDG YGGGSVNKIK    120
SEMASGGRHR SQYFQEITNV LDENNHQEGY LKNFCENLHN KKYSNLSVKN LVNLIGNLSN   180
```

```
LELKPLRKYF NDKIHAKADH WDEQKFTETY CHWILGEWRV GVKDQDKKDG AKYSYKDLCN      240
ELKQKVTKAG LVDFLLELDP CRTIPPYLDN NNRKPPKCQS LILNPKFLDN QYPNWQQYLQ      300
ELKKLQSIQN YLDSFETDLK VLKSSKDQPY FVEYKSSNQQ IASGQRDYKD LDARILQFIF      360
DRVKASDELL LNEIYFQAKK LKQKASSELE KLESSKKLDE VIANSQLSQI LKSQHTNGIF      420
EQGTFLHLVC KYYKQRQRAR DSRLYIMPEY RYDKKLHKYN NTGRFDDDNQ LLTYCNHKPR      480
QKRYQLLNDL AGVLQVSPNF LKDKIGSDDD LFISKWLVEH IRGFKKACED SLKIQKDNRG      540
LLNHKINIAR NTKGKCEKEI FNLICKIEGS EDKKGNYKHG LAYELGVLLF GEPNEASKPE      600
FDRKIKKFNS IYSFAQIQQI AFAERKGNAN TCAVCSADNA HRMQQIKITE PVEDNKDKII      660
LSAKAQRLPA IPTRIVDGAV KKMATILAKN IVDDNWQNIK QVLSAKHQLH IPIITESNAF      720
EFEPALADVK GKSLKDRRKK ALERISPENI FKDKNNRIKE FAKGISAYSG ANLTDGDFDG      780
AKEELDHIIP RSHKKYGTLN DEANLICVTR GDNKNKGNRI FCLRDLADNY KLKQFETTDD      840
LEIEKKIADT IWDANKKDFK FGNYRSFINL TPQEQKAFRH ALFLADENPI KQAVIRAINN      900
RNRTFVNGTQ RYFAEVLANN IYLRAKKENL NTDKISFDYF GIPTIGNGRG IAEIRQLYEK      960
VDSDIQAYAK GDKPQASYSH LIDAMLAFCI AADEHRNDGS IGLEIDKNYS LYPLDKNTGE     1020
VFTKDIFSQI KITDNEFSDK KLVRKKAIEG FNTHRQMTRD GIYAENYLPI LIHKELNEVR     1080
KGYTWKNSEE IKIFKGKKYD IQQLNNLVYC LKFVDKPISI DIQISTLEEL RNILTTNNIA     1140
ATAEYYYINL KTQKLHEYYI ENYNTALGYK KYSKEMEFLR SLAYRSERVK IKSIDDVKQV     1200
LDKDSNFIIG KITLPFKKEW QRLYREWQNT TIKDDYEFLK SFFNVKSITK LHKKVRKDFS     1260
LPISTYEGKF LVKRKTWDNN FIYQILNDSD SRADGTKPFI PAPDISKNEI VEAAIIDSFTS     1320
KNIFWLPKNI ELQKVDNKNI FAIDTSKWFE VETPSDLRDI GIATIQYKID NNSRPKVRVK     1380
LDYVIDDDSK INYFMNHSLL KSRYPDKVLE ILKQSTIIEF HSSGFNKTIK EMLGMKLAGI     1440
YNETSNN                                                              1447

SEQ ID NO: 94           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 94
MNFKILPIAI DLGVKNTGVF SAFYQKGTSL ERLDNKNGKV YELSKDSYTL LMNNRTARRH       60
QRRGIDRKQL VKRLFKLIWT EQLNLEWDKD TQQAISFLFN RRGFSFITDG YGGGSVNKIK      120
SEMASGGRHR SQYFQEITNV LDENNHQEGY LKNFCENLHK KKYSNLSVKN LVNLIGNLSN      180
LELKPLRKYF NDKIHAKADH WDEQKFTETY CHWILGEWRV GVKDQDKKDG AKYSYKDLCN      240
ELKQKVTKAG LVDFLLELDP CRTIPPYLDN NNRKPPKCQS LILNPKFLDN QYPNWQQYLQ      300
ELKKLQSIQN YLDSFETDLK VLKSSKDQPY FVEYKSSNQQ IASGQRDYKD LDARILQFIF      360
DRVKASDELL LNEIYFQAKK LKQKASSELE KLESSKKLDE VIANSQLSQI LKSQHTNGIF      420
EQGTFLHLVC KYYKQRQRAR DSRLYIMPEY RYDKKLHKYN NTGRFDDDNQ LLTYCNHKPR      480
QKRYQLLNDL AGVLQVSPNF LKDKIGSDDD LFISKWLVEH IRGFKKACED SLKIQKDNRG      540
LLNHKINIAR NTKGKCEKEI FNLICKIEGS EDKKGNYKHG LAYELGVLLF GEPNEASKPE      600
FDRKIKKFNS IYSFAQIQQI AFAERKGNAN TCAVCSADNA HRMQQIKITE PVEDNKDKII      660
LSAKAQRLPA IPTRIVDGAV KKMATILAKN IVDDNWQNIK QVLSAKHQLH IPIITESNAF      720
EFEPALADVK GKSLKDRRKK ALERISPENI FKDKNNRIKE FAKGISAYSG ANLTDGDFDG      780
AKEELDHIIP RSHKKYGTLN DEANLICVTR GDNKNKGNRI FCLRDLADNY KLKQFETTDD      840
LEIEKKIADT IWDANKKDFK FGNYRSFINL TPQEQKAFRH ALFLADENPI KQAVIRAINN      900
RNRTFVNGTQ RYFAEVLANN IYLRAKKENL NTDKISFDYF GIPTIGNGRG IAEIRQLYEK      960
VDSDIQAYAK GDKPQASYSH LIDAMLAFCI AADEHRNDGS IGLEIDKNYS LYPLDKNTGE     1020
VFTKDIFSQI KITDNEFSDK KLVRKKAIEG FNTHRQMTRD GIYAENYLPI LIHKELNEVR     1080
KGYTWKNSEE IKIFKGKKYD IQQLNNLVYC LKFVDKPISI DIQISTLEEL RNILTTNNIA     1140
ATAEYYYINL KTQKLHEYYI ENYNTALGYK KYSKEMEFLR SLAYRSERVK IKSIDDVKQV     1200
LDKDSNFIIG KITLPFKKEW QRLYREWQNT TIKDDYEFLK SFFNVKSITK LHKKVRKDFS     1260
LPISTNEGKF LVKRKTWDNN FIYQILNDSD SRFDGTKPFI PAPDISKNEI VEAAIIDSFTS    1320
KNIFWLPKNI ELQKVDNKNI FAIDTSKWFE VETPSDLRDI GIATIQYKID NNSRPKVRVK     1380
LDYVIDDDSK INYFMNHSLL KSRYPDKVLE ILKQSTIIEF HSSGFNKTIK EMLGMKLAGI     1440
YNETSNN                                                              1447

SEQ ID NO: 95           moltype = AA  length = 1447
FEATURE                 Location/Qualifiers
REGION                  1..1447
                        note = FnCas9 truncations
source                  1..1447
                        mol_type = protein
                        organism = synthetic construct
SEQUENCE: 95
MNFKILPIAI DLGVKNTGVF SAFYQKGTSL ERLDNKNGKV YELSKDSYTL LMNNRTARRH       60
QRRGIDRKQL VKRLFKLIWT EQLNLEWDKD TQQAISFLFN RRGFSFITDG YGGGSVNKIK      120
SEMASGGRHR SQYFQEITNV LDENNHQEGY LKNFCENLHK KKYSNLSVKN LVNLIGNLSN      180
LELKPLRKYF NDKIHAKADH WDEQKFTETY CHWILGEWRV GVKDQDKKDG AKYSYKDLCN      240
ELKQKVTKAG LVDFLLELDP CRTIPPYLDN NNRKPPKCQS LILNPKFLDN QYPNWQQYLQ      300
ELKKLQSIQN YLDSFETDLK VLKSSKDQPY FVEYKSSNQQ IASGQRDYKD LDARILQFIF      360
DRVKASDELL LNEIYFQAKK LKQKASSELE KLESSKKLDE VIANSQLSQI LKSQHTNGIF      420
EQGTFLHLVC KYYKQRQRAR DSRLYIMPEY RYDKKLHKYN NTGRFDDDNQ LLTYCNHKPR      480
QKRYQLLNDL AGVLQVSPNF LKDKIGSDDD LFISKWLVEH IRGFKKACED SLKIQKDNRG      540
LLNHKINIAR NTKGKCEKEI FNLICKIEGS EDKKGNYKHG LAYELGVLLF GEPNEASKPE      600
FDRKIKKFNS IYSFAQIQQI AFAERKGNAN TCAVCSADNA HRMQQIKITE PVEDNKDKII      660
LSAKAQRLPA IPTRIVDGAV KKMATILAKN IVDDNWQNIK QVLSAKHQLH IPIITESNAF      720
EFEPALADVK GKSLKDRRKK ALERISPENI FKDKNNRIKE FAKGISAYSG ANLTDGDFDG      780
AKEELDHIIP RSHKKYGTLN DEANLICVTR GDNKNKGNRI FCLRDLADNY KLKQFETTDD      840
```

```
LEIEKKIADT IWDANKKDFK FGNYRSFINL TPQEQKAFRH ALFLADENPI KQAVIRAINN    900
RNRTFVNGTQ RYFAEVLANN IYLRAKKENL NTDKISFDYF GIPTIGNRG IAEIRQLYEK    960
VDSDIQAYAK GDKPQASYSH LIDAMLAFCI AADEHRNDGS IGLEIDKNYS LYPLDKNTGE   1020
VFTKDIFSQI KITDNEFSDK KLVRKKAIEG FNTHRQMTRD GIYAENYLPI LIHKELNEVR   1080
KGYTWKNSEE IKIFKGKKYD IQQLNNLVYC LKFVDKPISI DIQISTLEEL RNILTTNNIA   1140
ATAEYYYINL KTQKLHEYYI ENYNTALGYK KYSKEMEFLR SLAYRSERVK IKSIDDVKQV   1200
LDKDSNFIIG KITLPFKKEW QRLYREWQNT TIKDDYEFLK SFFNVKSITK LHKKVRKDFS   1260
LPISTNEGKF LVKRKTWDNN FIYQILNDSD SRADGTKPFI PAFDISKNEI VEAIIDSFTS   1320
KNIFWLPKNI ELQKVDNKNI FAIDTSKWFE VETPSDLRDI GIATIQYKID NNSRPKVRVK   1380
LDYVIDDDSK INYFMNHRLL KSRYPDKVLE ILKQSTIIEF HSSGFNKTIK EMLGMKLAGI   1440
YNETSNN                                                            1447

SEQ ID NO: 96            moltype = AA   length = 1447
FEATURE                  Location/Qualifiers
REGION                   1..1447
                         note = FnCas9 truncations
source                   1..1447
                         mol_type = protein
                         organism = synthetic construct
SEQUENCE: 96
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNGNRI FCLRDLADNY KLKQFETTDD   840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNRG IAEIRQLYEK    960
VDSDIQAYAK GDKPQASYSH LIDAMLAFCI AADEHRNDGS IGLEIDKNYS LYPLDKNTGE  1020
VFTKDIFSQI KITDNEFSDK KLVRKKAIEG FNTHRQMTRD GIYAENYLPI LIHKELNEVR  1080
KGYTWKNSEE IKIFKGKKYD IQQLNNLVYC LKFVDKPISI DIQISTLEEL RNILTTNNIA  1140
ATAEYYYINL KTQKLHEYYI ENYNTALGYK KYSKEMEFLR SLAYRSERVK IKSIDDVKQV  1200
LDKDSNFIIG KITLPFKKEW QRLYREWQNT TIKDDYEFLK SFFNVKSITK LHKKVRKDFS  1260
LPISTNEGKF LVKRKTWDNN FIYQILNDSD SRADGTKPFI PAFDISKNEI VEAIIDSFTS  1320
KNIFWLPKNI ELQKVDNKNI FAIDTSKWFE VETPSDLRDI GIATIQYKID NNSRPKVRVK  1380
LDYVIDDDSK INYFMNHSLL KSRYPDKVLE ILKQSTIIEF HSSGFNKTIK EMLGMKLAGI  1440
YNETSNN                                                           1447

SEQ ID NO: 97            moltype = AA   length = 1447
FEATURE                  Location/Qualifiers
REGION                   1..1447
                         note = FnCas9 truncations
source                   1..1447
                         mol_type = protein
                         organism = synthetic construct
SEQUENCE: 97
MNFKILPIAI DLGVKNTGVF SAFYQKGTSL ERLDNKNGKV YELSKDSYTL LMNNRTARRH    60
QRRGIDRKQL VKRLFKLIWT EQLNLEWDKD TQQAISFLFN RRGFSFITDG YGGGSVNKIK   120
SEMASGGRHR SQYFQEITNV LDENNHQEGY LKNFCENLHN KKYSNLSVKN LVNLIGNLSN   180
LELKPLRKYF NDKIHAKADH WDEQKFTETY CHWILGEWRV GVKDQDKKDG AKYSYKDLCN   240
ELKQKVTKAG LVDFLLELDP CRTIPPYLDN NNRKPPKCQS LILNPKFLDN QYPNWQQYLQ   300
ELKKLQSIQN YLDSFETDLK VLKSSSKDQPY FVEYKSSNQQ IASGQRDYKD LDARILQFIF   360
DRVKASDELL LNEIYFQAKK LKQKASSELE KLESSKKLDE VIANSQLSQI LKSQHTNGIF   420
EQGTFLHLVC KYYKQRQRAR DSRLYIMPEY RYDKKLHKYN NTGRFDDDNQ LLTYCNHKPR   480
QKRYQLLNDL AGVLQVSPNF LKDKIGSDDD LFISKWLVEH IRGFKKACED SLKIQKDNRG   540
LLNHKINIAR NTKGKCEKEI FNLICKIEGS EDKKGNYKHG LAYELGVLLF GEPNEASKPE   600
FDRKIKKFNS IYSFAQIQQI AFAERKGNAN TCAVCSADNA HRMQQIKITE PVEDNKDKII   660
LSAKAQRLPA IPTRIVDGAV KKMATILAKN IVDDNWQNIK QVLSAKHQLH IPIITESNAF   720
EFEPALADVK GKSLKDRRKK ALERISPENI FKDKNNRIKE FAKGISAYSG ANLTDGDFDG   780
AKEELDHIIP RSHKKYGTLN DEANLICVTR GDNKNGNRI FCLRDLADNY KLKQFETTDD    840
LEIEKKIADT IWDANKKDFK FGNYRSFINL TPQEQKAFRH ALFLADENPI KQAVIRAINN   900
RNRTFVNGTQ RYFAEVLANN IYLRAKKENL NTDKISFDYF GIPTIGNRG IAEIRQLYEK    960
VDSDIQAYAK GDKPQASYSH LIDAMLAFCI AADEHRNDGS IGLEIDKNYS LYPLDKNTGE  1020
VFTKDIFSQI KITDNEFSDK KLVRKKAIEG FNTHRQMTRD GIYAENYLPI LIHKELNEVR  1080
KGYTWKNSEE IKIFKGKKYD IQQLNNLVYC LKFVDKPISI DIQISTLEEL RNILTTNNIA  1140
ATAEYYYINL KTQKLHEYYI ENYNTALGYK KYSKEMEFLR SLAYRSERVK IKSIDDVKQV  1200
LDKDSNFIIG KITLPFKKEW QRLYREWQNT TIKDDYEFLK SFFNVKSITK LHKKVRKDFS  1260
LPISTNEGKF LVKRKTWDNN FIYQILNDSD SRADGTKPFI PAFDISKNEI VEAIIDSFTS  1320
KNIFWLPKNI ELQKVDNKNI FAIDTSKWFE VETPSDLRDI GIATIQYKID NNSQPKVRVK  1380
LDYVIDDDSK INYFMNHSLL KSRYPDKVLE ILKQSTIIEF HSSGFNKTIK EMLGMKLAGI  1440
YNETSNN                                                           1447
```

```
SEQ ID NO: 98          moltype = AA  length = 1446
FEATURE                Location/Qualifiers
REGION                 1..1446
                       note = FnCas9 truncations
source                 1..1446
                       mol_type = protein
                       organism = synthetic construct
SEQUENCE: 98
MNFKILPIAI DLGVKNTGVF SAFYQKGTSL ERLDKNGKV  YELSKDSYTL LMNNRTARRH   60
QRRGIDRKQL VKRLFKLIWT EQLNLEWDKD TQQAISFLFN RRGFSFITDG YGGGSVNKIK  120
SEMASGGRHR SQYFQEITNV LDENNHQEGY LKNFCENLHN KKYSNLSVKN LVNLIGNLSN  180
LELKPLRKYF NDKIHAKADH WDEQKFTETY CHWILGEWRV GVKDQDKKDG AKYSYKDLCN  240
ELKQKVTKAG LVDFLLELDP CRTIPPYLDN NNRKPPKCQS LILNPKFLDN QYPNWQQYLQ  300
ELKKLQSIQN YLDSFETDLK VLKSSKDQPY FVEYKSSNQQ IASGQRDYKD LDARILQFIF  360
DRVKASDELL LNEIYFQAKK LKQKASSELE KLESSKKLDE VIANSQLSQI LKSQHTNGIF  420
EQGTFLHLVC KYYKQRQRAR DSRLYIMPEY RYDKKLHKYN NTGRFDDDNQ LLTYCNHKPR  480
QKRYQLLNDL AGVLQVSPNF LKDKIGSDDD LFISKWLVEH IRGFKKACED SLKIQKDNRG  540
LLNHKINIAR NTKGKCEKEI FNLICKIEGS EDKKGNYKHG LAYELGVLLF GEPNEASKPE  600
FDRKIKKFNS IYSFAQIQQI AFAERKGNAN TCAVCSADNA HRMQQIKITE PVEDNKDKII  660
LSAKAQRLPA IPTRIVDGAV KKMATILAKN IVDDNWQNIK QVLSAKHQLH IPIITESNAF  720
EFEPALADVK GKSLKDRRKK ALERISPENI FKDKNNRIKE FAKGISAYSG ANLTDGDFDG  780
AKEELDHIIP RSHKKYGTLN DEANLICVTR GDNKNKGNRI FCLRDLADNY KLKQFETTDD  840
LEIEKKIADT IWDANKKDFK FGNYRSFINL TPQEQKAFRH ALFLADENPI KQAVIRAINN  900
RNRTFVNGTQ RYFAEVLANN IYLRAKKENL NTDKISFDYF GIPTIGNGRG IAEIRQLYEK  960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSERVK IKSIDDVKQV 1200
LDKDSNFIIG KITLPFKKEW QRLYREWQNT TIKDDYEFLK SFFNVKSITL LHKKVRKDFS 1260
LPISTNEGKF LVKRKTWDNN FIYQILNDSD SRADGTKPFI PAFDISKNEI VEAAIIDSFTS 1320
KNIFWLPKNI ELQKVDKNNI FAIDTSKWPF VETPSDLRDI GIATIQYKID NNSQKVRVKL 1380
DYVIDDDSKI NYFMNHSLLK SRYPDKVLEI KLQSTIIEFE SSGFNKTIKE MLGMKLAGIY 1440
NETSNN                                                          1446

SEQ ID NO: 99          moltype = AA  length = 1447
FEATURE                Location/Qualifiers
REGION                 1..1447
                       note = FnCas9 truncations
source                 1..1447
                       mol_type = protein
                       organism = synthetic construct
SEQUENCE: 99
MNFKILPIAI DLGVKNTGVF SAFYQKGTSL ERLDKNGKV  YELSKDSYTL LMNNRTARRH   60
QRRGIDRKQL VKRLFKLIWT EQLNLEWDKD TQQAISFLFN RRGFSFITDG YGGGSVNKIK  120
SEMASGGRHR SQYFQEITNV LDENNHQEGY LKNFCENLHN KKYSNLSVKN LVNLIGNLSN  180
LELKPLRKYF NDKIHAKADH WDEQKFTETY CHWILGEWRV GVKDQDKKDG AKYSYKDLCN  240
ELKQKVTKAG LVDFLLELDP CRTIPPYLDN NNRKPPKCQS LILNPKFLDN QYPNWQQYLQ  300
ELKKLQSIQN YLDSFETDLK VLKSSKDQPY FVEYKSSNQQ IASGQRDYKD LDARILQFIF  360
DRVKASDELL LNEIYFQAKK LKQKASSELE KLESSKKLDE VIANSQLSQI LKSQHTNGIF  420
EQGTFLHLVC KYYKQRQRAR DSRLYIMPEY RYDKKLHKYN NTGRFDDDNQ LLTYCNHKPR  480
QKRYQLLNDL AGVLQVSPNF LKDKIGSDDD LFISKWLVEH IRGFKKACED SLKIQKDNRG  540
LLNHKINIAR NTKGKCEKEI FNLICKIEGS EDKKGNYKHG LAYELGVLLF GEPNEASKPE  600
FDRKIKKFNS IYSFAQIQQI AFAERKGNAN TCAVCSADNA HRMQQIKITE PVEDNKDKII  660
LSAKAQRLPA IPTRIVDGAV KKMATILAKN IVDDNWQNIK QVLSAKHQLH IPIITESNAF  720
EFEPALADVK GKSLKDRRKK ALERISPENI FKDKNNRIKE FAKGISAYSG ANLTDGDFDG  780
AKEELDHIIP RSHKKYGTLN DEANLICVTR GDNKNKGNRI FCLRDLADNY KLKQFETTDD  840
LEIEKKIADT IWDANKKDFK FGNYRSFINL TPQEQKAFRH ALFLADENPI KQAVIRAINN  900
RNRTFVNGTQ RYFAEVLANN IYLRAKKENL NTDKISFDYF GIPTIGNGRG IAEIRQLYEK  960
VDSDIQAYAK GDKPQASYSH LIDAMLAFCI AADEHRNDGS IGLEIDKNYS LYPLDKNTGE 1020
VFTKDIFSQI KITDNEFSDK KLVRKKAIEG FNTHRQMTRD GIYAENYLPI LIHKELNEVR 1080
KGYTWKNSEE IKIFKGKKYD IQQLNNLVYC LKFVDKPISI DIQISTLEEL RNILTTNNIA 1140
ATAEYYYINL KTQKLHEYYI ENYNTALGYK KYSKEMEFLR SLAYRSRRVK IKSIDDVKQV 1200
LDKDSNFIIG KITLPFKKEW QRLYREWQNT TIKDDYEFLK SFFNVKSITK LHKKVRKDFS 1260
LPISTNHGKF LVKRKTWDNN FIYQILNDSD SRADGTKPFI PAFDISKNEI VEAIIDSFTS 1320
KNIFWLPKNI ELQKVDKNNI FAIDTSKWPF VETPSDLRDI GIATIQYKID NNSQPKVRVK 1380
LDYVIDDDSK INYFMNHSLL KSRYPDKVLE ILKQSTIIEF ESSGFNKTIK EMLGMKLAGI 1440
YNETSNN                                                         1447

SEQ ID NO: 100         moltype = AA  length = 2025
FEATURE                Location/Qualifiers
REGION                 1..2025
                       note = Fn/enFnCas9
source                 1..2025
                       mol_type = protein
                       organism = synthetic construct
SEQUENCE: 100
MSEVEFSHEY WMRHALTLAK RAWDEREVPV GAVLVHNNRV IGEGWNRPIG RHDPTAHAEI   60
MALRQGGLVM QNYRLIDATL YVTLEPCVMC AGAMIHSRIG RVVFGARDAK TGAAGSLMDV  120
```

```
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDDLDIWNF   660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSRRVKIK SIDDVKQVLD KDSNFIIGKI TLPFKKEWQR   1800
LYREWQNTTI KDDYEFLKSF FNVKSITKLH KKVRKDFSLP ISTNEGKFLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFES SGFNKTIKEM LGMKLAGIYN ETSNN                   2025

SEQ ID NO: 101          moltype = AA  length = 2025
FEATURE                 Location/Qualifiers
REGION                  1..2025
                        note = Fn/enFnCas9
source                  1..2025
                        mol_type = protein
                        organism = synthetic construct SEQUENCE: 101
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDDLDIWNF   660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSERVKIK SIDDVKQVLD KDSNFIIGKI TLPFKKEWQR   1800
LYREWQNTTI KDDYEFLKSF FNVKSITKLH KKVRKDFSLP ISTNHGKFLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFES SGFNKTIKEM LGMKLAGIYN ETSNN                   2025

SEQ ID NO: 102          moltype = AA  length = 2025
FEATURE                 Location/Qualifiers
REGION                  1..2025
```

```
                        note = Fn/enFnCas9
source                  1..2025
                        mol_type = protein
                        organism = synthetic construct
SEQUENCE: 102
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGSETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDLDIWNF   660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVGKG SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRR RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSRRVKIK SIDDVKQVLD KDSNFIIGKI TLPFKKEWQR  1800
LYREWQNTTI KDDYEFLKSF FNVKSITKLH KKVRKDFSLP ISTNHGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFES SGFNKTIKEM LGMKLAGIYN ETSNN                 2025

SEQ ID NO: 103          moltype = AA   length = 2025
FEATURE                 Location/Qualifiers
REGION                  1..2025
                        note = Fn/enFnCas9
source                  1..2025
                        mol_type = protein
                        organism = synthetic construct
SEQUENCE: 103
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGSETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDLDIWNF   660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVGKG SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRR RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDTI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTNEGKFLV KRKTWDNNFI  1860
```

```
YQILNDSDSR ADGTKPFPIPA FDISKNEIVE AIIDSFTSKN IFWLPKNIEL QKVDNKNIFA    1920
IDTSKWFEVE TPSDLRDIGI ATIQYKIDNN SRPKVRVKLD YVIDDDSKIN YFMNHSLLKS    1980
RYPDKVLEIL KQSTIIEFES SGFNKTIKEM LGMKLAGIYN ETSNN                   2025

SEQ ID NO: 104           moltype = AA   length = 2025
FEATURE                  Location/Qualifiers
REGION                   1..2025
                         note = Fn/enFnCas9
source                   1..2025
                         mol_type = protein
                         organism = synthetic construct
SEQUENCE: 104
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NPFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IPFKGKKYDIQ  1680
QLNNLVYCLK FVDKPISIDI QISTLEELRN ILTTNNIAAT AEYYYINLKT QKLHEYYIEN   1740
YNTALGYKKY SKEMEFLRSL AYRSYRVKIK SIDDVKQVLD KDSNFIIGKI TLPFKKEWQR   1800
LYREWQNTTI KDDYEFLKSF FNVKSITKLH KKVRKDFSLP ISTNEGKFLV KRKTWDNIYF   1860
YQILNDSDSR ADGTKPFPIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFES SGFNKTIKEM LGMKLAGIYN ETSNN                   2025

SEQ ID NO: 105           moltype = AA   length = 2025
FEATURE                  Location/Qualifiers
REGION                   1..2025
                         note = Fn/enFnCas9
source                   1..2025
                         mol_type = protein
                         organism = synthetic construct
SEQUENCE: 105
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NPFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
```

```
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVIK SIDDVKQVLD KDSNFIIRKI TLPFKKEWQR  1800
LYREWQNTTI KDDYEFLKSF FNVKSITKLH KKVRKDFSLP ISTNEGKFLV KRKTWDNNFI  1860
YQILNDSDSR ADGTKPFIPA FDISKNEIVE AIIDSFTSKN IFWLPKNIEL QKVDNKIFA  1920
IDTSKWFEVE TPSDLRDIGI ATIQYKIDNN SRPKVRVKLD YVIDDDSKIN YFMNHSLLKS  1980
RYPDKVLEIL KQSTIIEFES SGFNKTIKEM LGMKLAGIYN ETSNN              2025

SEQ ID NO: 106       moltype = AA  length = 2025
FEATURE              Location/Qualifiers
REGION               1..2025
                     note = Fn/enFnCas9
source               1..2025
                     mol_type = protein
                     organism = synthetic construct
SEQUENCE: 106
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGSETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVGKS SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVIK SIDDVKQVLD KDSNFIIKKI TLPFKKEWQR  1800
LYREWQNTTI KDDYEFLKSF FNVKSITKLH KKVRKDFSLP ISTNEGKFLV KRKTWDNNFI  1860
YQILNDSDSR ADGTKPFIPA FDISKNEIVE AIIDSFTSKN IFWLPKNIEL QKVDNKIFA  1920
IDTSKWFEVE TPSDLRDIGI ATIQYKIDNN SRPKVRVKLD YVIDDDSKIN YFMNHSLLKS  1980
RYPDKVLEIL KQSTIIEFES SGFNKTIKEM LGMKLAGIYN ETSNN              2025

SEQ ID NO: 107       moltype = AA  length = 2025
FEATURE              Location/Qualifiers
REGION               1..2025
                     note = Fn/enFnCas9
source               1..2025
                     mol_type = protein
                     organism = synthetic construct
SEQUENCE: 107
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGSETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS  1020
```

```
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTREGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFES SGFNKTIKEM LGMKLAGIYN ETSNN                  2025

SEQ ID NO: 108          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 108
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKYDLD ARILQFIFDR VKASDELLLN EIYFQAKLK  960
QKASSELEKL ESSKKLDEVI ANSQLSQILK SQHTNGFIEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTYEGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFES SGFNKTIKEM LGMKLAGIYN ETSNN                  2025

SEQ ID NO: 109          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 109
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITYEF ELLADYLANY  600
```

```
SESLKTQKFS YTDKQGNLKE LSYYHHDKYN IQEFLKRHAT INDRILDTLL TDDLDIWNFN  660
FEKFDFDKNE EKLQNQEDKD HIQAHLHHFV FAVNKIKSEM ASGGRHRSQY FQEITNVLDE  720
NNHQEGYLKN FCENLHNKKY SNLSVKNLVN LIGNLSNLEL KPLRKYFNDK IHAKADHWDE  780
QKFTETYCHW ILGEWRVGVK DQDKKDGAKY SYKDLCNELK QKVTKAGLVD FLLELDPCRT  840
IPPYLDNNNR KPPKCQSLIL NPKFLDNQYP NWQQYLQELK KLQSIQNYLD SFETDLKVLK  900
SSKDQPYFVE YKSSNQQIAS GQRDYKDLDA RILQFIFDRV KASDELLLNE IYFQAKKLKQ  960
KASSELEKLE SSKKLDEVIA NSQLSQILKS QHTNGIFEQG TFLHLVCKYY KQRQRARDSR 1020
LYIMPEYRYD KKLHKYNNTG RFDDDNQLLT YCNHKPRQKR YQLLNDLAGV LQVSPNFLKD 1080
KIGSDDDLFI SKWLVEHIRG FKKACEDSLK IQKDNRGLLN HKINIARNTK GKCEKEIFNL 1140
ICKIEGSEDK KGNYKHGLAY ELGVLLFGEP NEASKPEFDR KIKKFNSIYS FAQIQQIAFA 1200
ERKGNANTCA VCSADNAHRM QQIKITEPVE DNKDKIILSA KAQRLPAIPT RIVDGAVKKM 1260
ATILAKNIVD DNWQNIKQVL SAKHQLHIPI ITESNAFEFE PALADVKGKS LKDRRKKALE 1320
RISPENIFKD KNNRIKEFAK GISAYSGANL TDGDFDGAKE ELDHIIPRSH KKYGTLNDEA 1380
NLICVTRGDN KNKGNRIFCL RDLADNYKLK QFETTDDLEI EKKIADTIWD ANKKDFKFGN 1440
YRSFINLTPQ EQKAFRHALF LADENPIKQA VIRAINNRNR TFVNGTQRYF AEVLANNIYL 1500
RAKKENLNTD KISFDYFGIP TIGNGRGIAE IRQLYEKVDS DIQAYAKGDK PQASYSHLID 1560
AMLAFCIAAD EHRNDGSIGL EIDKNYSLYP LDKNTGEVFT KDIFSQIKIT DNEFSDKKLV 1620
RKKAIEGFNT HRQMTRDGIY AENYLPILIH KELNEVRKGY TWKNSEEIKI FKGKKYDIQQ 1680
LNNLVYCLKF VDKPISIDIQ ISTLEELRNI LTTNNIAATA EYYYINLKTQ KLHEYYIENY 1740
NTALGYKKYS KEMEFLRSLA YRSERVKIKS IDDVKQVLDK DSNFIIGKIT LPFKKEWQRL 1800
YREWQNTTIK DDYEFLKSFF NVKSITKLHK KVRKDFSLPI STNEGKVFLV KRKTWDNNFI 1860
YQILNDSDSR ADGTKPFIPA FDISKNEIVE AIIDSFTSKN IFWLPKNIEL QKVDNKIFA  1920
IDTSKWFEVE TPSDLRDIGI ATIQYKIDNN SRPKVRVKLD YVIDDDSKIN YFMNHSLLKS 1980
RYPDKVLEIL KQSTIIEFES SGFNKTIKEM LGMKLAGIYN ETSNN                2025

SEQ ID NO: 110        moltype = AA  length = 2025
FEATURE               Location/Qualifiers
REGION                1..2025
                      note = Fn/enFnCas9
source                1..2025
                      mol_type = protein
                      organism = synthetic construct
SEQUENCE: 110
MSEVEFSHEY WMRHALTLAK RAWDEREVPV GAVLVHNNRV IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSSGSET 180
PGTSESATPE SSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGGSETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKDGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS 1020
RLYIMPEYRY DKKLHKYNNT GRFDDDNQLL TYCNHKPRQK RYQLLNDLAG VLQVSPNFLK 1080
DKIGSDDDLF ISKWLVEHIR GFKKACEDSL KIQKDNRGLL NHKINIARNT KGKCEKEIFN 1140
LICKIEGSED KKGNYKHGLA YELGVLLFGE PNEASKPEFD RKIKKFNSIY SFAQIQQIAF 1200
AERKGNANTC AVCSADNAHR MQQIKITEPV EDNKDKIILS AKAQRLPAIP TRIVDGAVKK 1260
MATILAKNIV DDNWQNIKQV LSAKHQLHIP IITESNAFEF EPALADVKGK SLKDRRKKAL 1320
ERISPENIFK DKNNRIKEFA KGISAYSGAN LTDGDFDGAK EELDHIIPRS HKKYGTLNDE 1380
ANLICVTRGD NKNKGNRIFC LRDLADNYKL KQFETTDDLE IEKKIADTIW DANKKDFKFG 1440
NYRSFINLTP QEQKAFRHAL FLADENPIKQ AVIRAINNRN RTFVNGTQRY FAEVLANNIY 1500
LRAKKENLNT DKISFDYFGI PTIGNGRGIA EIRQLYEKVD SDIQAYAKGD KPQASYSHLI 1560
DAMLAFCIAA DEHRNDGSIG LEIDKNYSLY PLDKNTGEVF TKDIFSQIKI TDNEFSDKKL 1620
VRKKAIEGFN THRQMTRDGI YAENYLPILI HKELNEVRKG YTWKNSEEIK IFKGKKYDIQ 1680
QLNNLVYCLK FVDKPISIDI QISTLEELRN ILTTNNIAAT AEYYYINLKT QKLHEYYIEN 1740
YNTALGYKKY SKEMEFLRSL AYRSERVKIK SIDDVKQVLD KDSNFIIGKI TLPFKKEWQR 1800
LYREWQNTTI KDDYEFLKSF FNVKSITKLH KKVRKDFSLP ISTNEGKVFL VKRKTWDNNF 1860
IYQILNDSDTR ADGTKPFIPA FDISKNEIVE AIIDSFTSKN IFWLPKNIEL QKVDNKIFA 1920
IDTSKWFEVE TPSDLRDIGI ATIQYKIDNN SRPKVRVKLD YVIDDDSKIN YFMNHSLLKS 1980
RYPDKVLEIL KQSTIIEFES SGFNKTIKEM LGMKLAGIYN ETSNN                2025

SEQ ID NO: 111        moltype = AA  length = 2025
FEATURE               Location/Qualifiers
REGION                1..2025
                      note = Fn/enFnCas9
source                1..2025
                      mol_type = protein
                      organism = synthetic construct
SEQUENCE: 111
MSEVEFSHEY WMRHALTLAK RAWDEREVPV GAVLVHNNRV IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSSGSET 180
```

```
PGTSESATPE SSSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGSETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKDGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTNEGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDVN SRPKVRVKLD YVIDDDSKIN YFMNHSLLKS  1980
RYPDKVLEIL KQSTIIEFES SGFNKTIKEM LGMKLAGIYN ETSNN                 2025

SEQ ID NO: 112          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 112
MSEVEFSHEY WMRHALTLAK RAWDEREVPV GAVLVHNNRV IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLCSDFFR MRRQEIKAQK KAQSSTDSGG SSGGSSGSET  180
PGTSESATPE SSSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGSETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKDGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTNEGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RHPDKVLEIL KQSTIIEFES SGFNKTIKEM LGMKLAGIYN ETSNN                 2025

SEQ ID NO: 113          moltype = AA  length = 2025
FEATURE                 Location/Qualifiers
REGION                  1..2025
                        note = Fn/enFnCas9
```

| source | 1..2025 |
| --- | --- |
| | mol_type = protein |
| | organism = synthetic construct |

SEQUENCE: 113

```
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGSETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDLDIWNF   660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IPFKGKKYDIQ 1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTNEGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RRPDKVLEIL KQSTIIEFES SGFNKTIKEM LGMKLAGIYN ETSNN                 2025
```

| SEQ ID NO: 114 | moltype = AA   length = 2025 |
| --- | --- |
| FEATURE | Location/Qualifiers |
| REGION | 1..2025 |
| | note = Fn/enFnCas9 |
| source | 1..2025 |
| | mol_type = protein |
| | organism = synthetic construct |

SEQUENCE: 114

```
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGSETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDLDIWNF   660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IPFKGKKYDIQ 1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTNEGKFLV KRKTWDNNFI  1860
YQILNDSDSR ADGTKPFIPA FDISKNEIVE AIIDSFTSKN IFWLPKNIEL QKVDNKNIFA  1920
```

```
IDTSKWFEVE TPSDLRDIGI ATIQYKIDNN SRPKVRVKLD YVIDDDSKIN YFMNHSLLKS    1980
RYPDKVLEIL KQSTIIEFHS SGFNKTIKEM LGMKLAGIYN ETSNN                   2025

SEQ ID NO: 115          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 115
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSRRVKIK SIDDVKQVLD KDSNFIIGKI TLPFKKEWQR   1800
LYREWQNTTI KDDYEFLKSF FNVKSITKLH KKVRKDFSLP ISTNHGKFLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN STPKVRVKLD YVIDDDSKIN YFMNHSLLKS   1980
RYPDKVLEIL KQSTIIEFES SGFNKTIKEM LGMKLAGIYN ETSNN                   2025

SEQ ID NO: 116          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 116
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
```

```
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKYL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTNEGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFES SGFNKTIKEM LGMKLAGIYN ETSNN                 2025

SEQ ID NO: 117          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 117
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGETPG TSESATPESS GGSSGGSNFK ILPIAIDLGV KNTGVFSAFY   420
QKGTSLERLD NKNGKVYELS KDSYTLLMNN RTARRHQRPG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKDGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTNEGKFLV KRKTWDNNFI  1860
YQILNDSDSR FDGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFES SGFNKTIKEM LGMKLAGIYN ETSNN                 2025

SEQ ID NO: 118          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 118
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKDGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
```

```
DKIGSDDDLF ISKWLVEHIR GFKKACEDSL KIQKDNRGLL NHKINIARNT KGKCEKEIFN    1140
LICKIEGSED KKGNYKHGLA YELGVLLFGE PNEASKPEFD RKIKKFNSIY SFAQIQQIAF    1200
AERKGNANTC AVCSADNAHR MQQIKITEPV EDNKDKIILS AKAQRLPAIP TRIVDGAVKK    1260
MATILAKNIV DDNWQNIKQV LSAKHQLHIP IITESNAFEF EPALADVKGK SLKDRRKKAL    1320
ERISPENIFK DKNNRIKEFA KGISAYSGAN LTDGDFDGAK EELDHIIPRS HKKYGTLNDE    1380
ANLICVTRGD NKNKGNRIFC LRDLADNYKL KQFETTDDLE IEKKIADTIW DANKKDFKFG    1440
NYRSFINLTP QEQKAFRHAL FLADENPIKQ AVIRAINNRN RTFVNGTQRY FAEVLANNIY    1500
LRAKKENLNT DKISFDYFGI PTIGNGRGIA EIRQLYEKVD SDIQAYAKGD KPQASYSHLI    1560
DAMLAFCIAA DEHRNDGSIG LEIDKNYSLY PLDKNTGEVF TKDIFSQIKI TDNEFSDKKL    1620
VRKKAIEGFN THRQMTRDGI YAENYLPILI HKELNEVRKG YTWKNSEEIK IFKGKKYDIQ    1680
QLNNLVYCLK FVDKPISIDI QISTLEELRN ILTTNNIAAT AEYYYINLKT QKLHEYYIEN    1740
YNTALGYKKY SKEMEFLRSL AYRSERVKIK SIDDVKQVLD KDSNFIIGKI TLPFKKEWQR    1800
LYREWQNTTI KDDYEFLKSF FNVKSITKLH KKVRKDFSLP ISTNEGKFLV KRKTWDNNFI    1860
YQILNDSDSR ADGTKPFIPA FDISKNEIVE AIIDHFTSKN IFWLPKNIEL QKVDNKNIFA    1920
IDTSKWFEVE TPSDLRDIGI ATIQYKIDNN SRPKVRVKLD YVIDDDSKIN YFMNHSLLKS    1980
RYPDKVLEIL KQSTIIEFES SGFNKTIKEM LGMKLAGIYN ETSNN                   2025

SEQ ID NO: 119           moltype = AA  length = 2025
FEATURE                  Location/Qualifiers
REGION                   1..2025
                         note = Fn/enFnCas9
source                   1..2025
                         mol_type = protein
                         organism = synthetic construct
SEQUENCE: 119
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE KKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSERVKIK SIDDVKQVLD KDSNFIIGKI TLPFKKEWQR   1800
LYREWQNTTI KDDYEFLKSF FNVKSITKLH KKVRKDFSLP ISTNEGKFLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHRLLKS   1980
RYPDKVLEIL KQSTIIEFES SGFNKTIKEM LGMKLAGIYN ETSNN                  2025

SEQ ID NO: 120           moltype = AA  length = 2025
FEATURE                  Location/Qualifiers
REGION                   1..2025
                         note = Fn/enFnCas9
source                   1..2025
                         mol_type = protein
                         organism = synthetic construct
SEQUENCE: 120
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
```

```
NPEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKDGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS 1020
RLYIMPEYRY DKKLHKYNNT GRFDDDNQLL TYCNHKPRQK RYQLLNDLAG VLQVSPNFLK 1080
DKIGSDDDLF ISKWLVEHIR GFKKACEDSL KIQKDNRGLL NHKINIARNT KGKCEKEIFN 1140
LICKIEGSED KKGNYKHGLA YELGVLLFGE PNEASKPEFD RKIKKFNSIY SFAQIQQIAF 1200
AERKGNANTC AVCSADNAHR MQQIKITEPV EDNKDKIILS AKAQRLPAIP TRIVDGAVKK 1260
MATILAKNIV DDNWQNIKQV LSAKHQLHIP IITESNAFEF EPALADVKGK SLKDRRKKAL 1320
ERISPENIFK DKNNRIKEFA KGISAYSGAN LTDGDFDGAK EELDHIIPRS HKKYGTLNDE 1380
ANLICVTRGD NKNKGNRIFC LRDLADNYKL KQFETTDDLE IEKKIADTIW DANKKDFKFG 1440
NYRSFINLTP QEQKAFRHAL FLADENPIKQ AVIRAINNRN RTFVNGTQRY FAEVLANNIY 1500
LRAKKENLNT DKISFDYFGI PTIGNGRGIA EIRQLYEKVD SDIQAYAKGD KPQASYSHLI 1560
DAMLAFCIAA DEHRNDGSIG LEIDKNYSLY PLDKNTGEVF TKDIFSQIKI TDNEFSDKKL 1620
VRKKAIEGFN THRQMTRDGI YAENYLPILI HKELNEVRKG YTWKNSEEIK IFKGKKYDIQ 1680
QLNNLVYCLK FVDKPISIDI QISTLEELRN ILTTNNIAAT AEYYYINLKT QKLHEYYIEN 1740
YNTALGYKKY SKEMEFLRSL AYRSERVIK  SIDDVKQVLD KDSNFIIGKI TLPFKKEWQR 1800
LYREWQNTTI KDDYEFLKSF FNVKSITKLH KKVRKDFSLP ISTNEGKFLV KRKTWDNNFI 1860
YQILNDSDSR ADGTKPFIPA FDISKNEIVE AIIDSFTSKN IFWLPKNIEL QKVDNKNIFA 1920
IDTSKWFEVE TPSDLRDIGI ATIQYKIDNN SRPKVRVKLD YVIDDDSKIN YFMNHSLLRS 1980
RYPDKVLEIL KQSTIIEFES SGFNKTIKEM LGMKLAGIYN ETSNN                2025

SEQ ID NO: 121         moltype = AA  length = 2025
FEATURE                Location/Qualifiers
REGION                 1..2025
                       note = Fn/enFnCas9
source                 1..2025
                       mol_type = protein
                       organism = synthetic construct
SEQUENCE: 121
MSEVEFSHEY WMRHALTLAK RAWDEREVPV GAVLVHNNRV IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGSETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKDGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS 1020
RLYIMPEYRY DKKLHKYNNT GRFDDDNQLL TYCNHKPRQK RYQLLNDLAG VLQVSPNFLK 1080
DKIGSDDDLF ISKWLVEHIR GFKKACEDSL KIQKDNRGLL NHKINIARNT KGKCEKEIFN 1140
LICKIEGSED KKGNYKHGLA YELGVLLFGE PNEASKPEFD RKIKKFNSIY SFAQIQQIAF 1200
AERKGNANTC AVCSADNAHR MQQIKITEPV EDNKDKIILS AKAQRLPAIP TRIVDGAVKK 1260
MATILAKNIV DDNWQNIKQV LSAKHQLHIP IITESNAFEF EPALADVKGK SLKDRRKKAL 1320
ERISPENIFK DKNNRIKEFA KGISAYSGAN LTDGDFDGAK EELDHIIPRS HKKYGTLNDE 1380
ANLICVTRGD NKNKGNRIFC LRDLADNYKL KQFETTDDLE IEKKIADTIW DANKKDFKFG 1440
NYRSFINLTP QEQKAFRHAL FLADENPIKQ AVIRAINNRN RTFVNGTQRY FAEVLANNIY 1500
LRAKKENLNT DKISFDYFGI PTIGNGRGIA EIRQLYEKVD SDIQAYAKGD KPQASYSHLI 1560
DAMLAFCIAA DEHRNDGSIG LEIDKNYSLY PLDKNTGEVF TKDIFSQIKI TDNEFSDKKL 1620
VRKKAIEGFN THRQMTRDGI YAENYLPILI HKELNEVRKG YTWKNSEEIK IFKGKKYDIQ 1680
QLNNLVYCLK FVDKPISIDI QISTLEELRN ILTTNNIAAT AEYYYINLKT QKLHEYYIEN 1740
YNTALGYKKY SKEMEFLRSL AYRSERVIK  SIDDVKQVLD KDSNFIIGKI TLPFKKEWQR 1800
LYREWQNTTI KDDYEFLKSF FNVKSITKLH KKVRKDFSLP ISTNEGKFLV KRKTWDNNFI 1860
YQILNDSDSR ADGTKPFIPA FDISKNEIVE AIIDSFTSKN IFWLPKNIEL QKVDNKNIFA 1920
IDTSKWFEVE TPSDLRDIGI ATIQYKIDNN SRPKVRVKLD YVIDDDSKIN YFMNHSLLKS 1980
RYPDKVLEIL KQSTIIEFES SGFNVTIKEM LGMKLAGIYN ETSNN                2025

SEQ ID NO: 122         moltype = AA  length = 2025
FEATURE                Location/Qualifiers
REGION                 1..2025
                       note = Fn/enFnCas9
source                 1..2025
                       mol_type = protein
                       organism = synthetic construct
SEQUENCE: 122
MSEVEFSHEY WMRHALTLAK RAWDEREVPV GAVLVHNNRV IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTLAKRA RDEREVPVGA VLVLNNRVIG  240
```

```
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSERVKIK SIDDVKQVLD KDSNFIIGKI TLPFKKEWQR   1800
LYREWQNTTI KDDYEFLKSF FNVKSITKLH KKVRKDFSLP ISTNEGKFLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFES SGFNSTIKEM LGMKLAGIYN ETSNN                   2025

SEQ ID NO: 123           moltype = AA   length = 2025
FEATURE                  Location/Qualifiers
REGION                   1..2025
                         note = Fn/enFnCas9
source                   1..2025
                         mol_type = protein
                         organism = synthetic construct
SEQUENCE: 123
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS REVEFSHEYW RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSERVKIK SIDDVKQVLD KDSNFIIGKI TLPFKKEWQR   1800
LYREWQNTTI KDDYEFLKSF FNVKSITKLH KKVRKDFSLP ISTNEGKFLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFES SGFNNTIKEM LGMKLAGIYN ETSNN                   2025

SEQ ID NO: 124           moltype = AA   length = 2025
FEATURE                  Location/Qualifiers
REGION                   1..2025
                         note = Fn/enFnCas9
source                   1..2025
```

```
                        mol_type = protein
                        organism = synthetic construct
SEQUENCE: 124
MSEVEFSHEY WMRHALTLAK RAWDEREVPV GAVLHNNRV  IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGGSETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKDGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS 1020
RLYIMPEYRY DKKLHKYNNT GRFDDDNQLL TYCNHKPRQK RYQLLNDLAG VLQVSPNFLK 1080
DKIGSDDDLF ISKWLVEHIR GFKKACEDSL KIQKDNRGLL NHKINIARNT KGKCEKEIFN 1140
LICKIEGSED KKGNYKHGLA YELGVLLFGE PNEASKPEFD RKIKKFNSIY SFAQIQQIAF 1200
AERKGNANTC AVCSADNAHR MQQIKITEPV EDNKDKIILS AKAQRLPAIP TRIVDGAVKK 1260
MATILAKNIV DDNWQNIKQV LSAKHQLHIP IITESNAFEF EPALADVKGK SLKDRRKKAL 1320
ERISPENIFK DKNNRIKEFA KGISAYSGAN LTDGDFDGAK EELDHIIPRS HKKYGTLNDE 1380
ANLICVTRGD NKNKGNRIFC LRDLADNYKL KQFETTDDLE IEKKIADTIW DANKKDFKFG 1440
NYRSFINLTP QEQKAFRHAL FLADENPIKQ AVIRAINNRN RTFVNGTQRY FAEVLANNIY 1500
LRAKKENLNT DKISFDYFGI PTIGNGRGIA EIRQLYEKVD SDIQAYAKGD KPQASYSHLI 1560
DAMLAFCIAA DEHRNDSIG LEIDKNYSLY PLDKNTGEVF TKDIFSQIKI TDNEFSDKKL 1620
VRKKAIEGFN THRQMTRDGI YAENYLPILI HKELNEVRKG YTWKNSEEIK IFKGKKYDIQ 1680
QLNNLVYCLK FVDKPISIDI QISTLEELRN ILTTNNIAAT AEYYYINLKT QKLHEYYIEN 1740
YNTALGYKKY SKEMEFLRSL AYRSERVIK SIDDVKQVLD KDSNFIIGKI TLPFKKEWQR 1800
LYREWQNTTI KDDYEFLKSF FNVKSITKLH KKVRKDFSLP ISTNEGKFLV KRKTWDNNFI 1860
YQILNDSDSR ADGTKPFIPA FDISKNEIVE AIIDSFTSKN IFWLPKNIEL QKVDNKNIFA 1920
IDTSKWFEVE TPSDLRDIGI ATIQYKIDNN SRPKVRVKLD YVIDDDSKIN YFMNHSLLKS 1980
RYPDKVLEIL KQSTIIEFES FGFNKTIKEM LGMKLAGIYN ETSNN                 2025

SEQ ID NO: 125          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 125
MSEVEFSHEY WMRHALTLAK RAWDEREVPV GAVLHNNRV  IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGGSETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKDGAK YSYKDLCNEL KQKVTKAGLV DFLLELDPCR  840
TIPPYLDNNN RKPPKCQSLI LNPKFLDNQY PNWQQYLQEL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS 1020
RLYIMPEYRY DKKLHKYNNT GRFDDDNQLL TYCNHKPRQK RYQLLNDLAG VLQVSPNFLK 1080
DKIGSDDDLF ISKWLVEHIR GFKKACEDSL KIQKDNRGLL NHKINIARNT KGKCEKEIFN 1140
LICKIEGSED KKGNYKHGLA YELGVLLFGE PNEASKPEFD RKIKKFNSIY SFAQIQQIAF 1200
AERKGNANTC AVCSADNAHR MQQIKITEPV EDNKDKIILS AKAQRLPAIP TRIVDGAVKK 1260
MATILAKNIV DDNWQNIKQV LSAKHQLHIP IITESNAFEF EPALADVKGK SLKDRRKKAL 1320
ERISPENIFK DKNNRIKEFA KGISAYSGAN LTDGDFDGAK EELDHIIPRS HKKYGTLNDE 1380
ANLICVTRGD NKNKGNRIFC LRDLADNYKL KQFETTDDLE IEKKIADTIW DANKKDFKFG 1440
NYRSFINLTP QEQKAFRHAL FLADENPIKQ AVIRAINNRN RTFVNGTQRY FAEVLANNIY 1500
LRAKKENLNT DKISFDYFGI PTIGNGRGIA EIRQLYEKVD SDIQAYAKGD KPQASYSHLI 1560
DAMLAFCIAA DEHRNDSIG LEIDKNYSLY PLDKNTGEVF TKDIFSQIKI TDNEFSDKKL 1620
VRKKAIEGFN THRQMTRDGI YAENYLPILI HKELNEVRKG YTWKNSEEIK IFKGKKYDIQ 1680
QLNNLVYCLK FVDKPISIDI QISTLEELRN ILTTNNIAAT AEYYYINLKT QKLHEYYIEN 1740
YNTALGYKKY SKEMEFLRSL AYRSERVIK SIDDVKQVLD KDSNFIIGKI TLPFKKEWQR 1800
LYREWQNTTI KDDYEFLKSF FNVKSITKLH KKVRKDFSLP ISTNEGKFLV KRKTWDNNFI 1860
YQILNDSDSR ADGTKPFIPA FDISKNEIVE AIIDSFTSKN IFWLPKNIEL QKVDNKNIFA 1920
IDTSKWFEVE TPSDLRDIGI ATIQYKIDNN SRPKVRVKLD YVIDDDSKIN YFMNHSLLKS 1980
```

```
                                                            -continued
RYPDKVLEIL  KQSTIIEFES  RGFNKTIKEM  LGMKLAGIYN  ETSNN                      2025

SEQ ID NO: 126            moltype = AA   length = 2026
FEATURE                   Location/Qualifiers
REGION                    1..2026
                          note = Fn/enFnCas9
source                    1..2026
                          mol_type = protein
                          organism = synthetic construct
SEQUENCE: 126
MSEVEFSHEY  WMRHALTLAK  RAWDEREVPV  GAVLVHNNRV  IGEGWNRPIG  RHDPTAHAEI   60
MALRQGGLVM  QNYRLIDATL  YVTLEPCVMC  AGAMIHSRIG  RVVFGARDAK  TGAAGSLMDV  120
LHHPGMNHRV  EITEGILADE  CAALLSDFFR  MRRQEIKAQK  KAQSSTDSGG  SSGGSSGSET  180
PGTSESATPE  SSGGSSGGSS  EVEFSHEYWM  RHALTLAKRA  RDEREVPVGA  VLVLNNRVIG  240
EGWNRAIGLH  DPTAHAEIMA  LRQGGLVMQN  YRLIDATLYS  TFEPCVMCAG  AMIHSRIGRV  300
VFGWRNAKTG  AAGSLMDVLH  YPGMNHRVEI  TEGILADECA  ALLCYFFRMP  RRVFNAQKKA  360
QSSTDSGGSS  GGSSGSETPG  TSESATPESS  GGSSGGSNFK  ILPIAIDLGV  KNTGVFSAFY  420
QKGTSLERLD  NKNGKVYELS  KDSYTLLMNN  RTARRHQRRG  IDRKQLVKRL  FKLIWTEQLN  480
LEWDKDTQQA  ISFLFNRRGF  SFITDGYSPE  YLNIVPEQVK  AILMDIFDDY  NGEDDLDSYL  540
KLATEQESKI  SEIYNKLMQK  ILEFKLMKLC  TDIKDDKVST  KTLKEITSYE  FELLADYLAN  600
YSESLKTQKF  SYTDKQGNLK  ELSYYHHDKY  NIQEFLKRHA  TINDRILDTL  LTDDLDIWNF  660
NFEKFDFDKN  EEKLQNQEDK  DHIQAHLHHF  VFAVNKIKSE  MASGGRHRSQ  YFQEITNVLD  720
ENNHQEGYLK  NFCENLHNKK  YSNLSVKNLV  NLIGNLSNLE  LKPLRKYFND  KIHAKADHWD  780
EQKFTETYCH  WILGEWRVGV  KDQDKKDGAK  YSYKDLCNEL  KQKVTKAGLV  DFLLELDPCR  840
TIPPYLDNNN  RKPPKCQSLI  LNPKFLDNQY  PNWQQYLQEL  KKLQSIQNYL  DSFETDLKVL  900
KSSKDQPYFV  EYKSSNQQIA  SGQRDYKDLD  ARILQFIFDR  VKASDELLLN  EIYFQAKKLK  960
QKASSELEKL  ESSKKLDEVI  ANSQLSQILK  SQHTNGIFEQ  GTFLHLVCKY  YKQRQRARDS  1020
RLYIMPEYRY  DKKLHKYNNT  GRFDDDNQLL  TYCNHKPRQK  RYQLLNDLAG  VLQVSPNFLK  1080
DKIGSDDDLF  ISKWLVEHIR  GFKKACEDSL  KIQKDNRGLL  NHKINIARNT  GKCEKEIFN   1140
LICKIEGSED  KKGNYKHGLA  YELGVLLFGE  PNEASKPEFD  RKIKKFNSIY  SFAQIQQIAF  1200
AERKGNANTC  AVCSADNAHR  MQQIKITEPV  EDNKDKIILS  AKAQRLPAIP  TRIVDGAVKK  1260
MATILAKNIV  DDNWQNIKQV  LSAKHQLHIP  IITESNAFEF  EPALADVGKK  SLKDRRKKAL  1320
ERISPENIFK  DKNNRIKEFA  KGISAYSGAN  LTDGDFDGAK  EELDHIIPRS  HKKYGTLNDE  1380
ANLICVTRGD  NKNKGNRIFC  LRDLADNYKL  KQFETTDDLE  IEKKIADTIW  DANKKDFKFG  1440
NYRSFINLTP  QEQKAFRHAL  FLADENPIKQ  AVIRAINNRN  RTFVNGTQRY  FAEVLANNIY  1500
LRAKKENLNT  DKISFDYFGI  PTIGNGRGIA  EIRQLYEKVD  SDIQAYAKGD  KPQASYSHLI  1560
DAMLAFCIAA  DEHRNDGSIG  LEIDKNYSLY  PLDKNTGEVF  TKDIFSQIKI  TDNEFSDKKL  1620
VRKKAIEGFN  THRQMTRDGI  YAENYLPILI  HKELNEVRKG  YTWKNSEEIK  IFPKGKKYDIQ 1680
QLNNLVYCLK  FVDKPISIDI  QISTLEELRN  ILTTNNIAAT  AEYYYINLKT  QKLHEYYIEN  1740
YNTALGYKKY  SKEMEFLRSL  AYRSERVVIK  SIDDVKQVLD  KDRSNFIIGK  ITLPFKKEWQ  1800
RLYREWQNTT  IKDDYEFLKS  FFNVKSITKL  HKKVRKDFSL  PISTNEGKFL  VKRKTWDNNF  1860
IYQILNDSDS  RADGTKPFIP  AFDISKNEIV  EAIIDSFTSK  NIFWLPKNIE  LQKVDNKNIF  1920
AIDTSKWFEV  ETPSDLRDIG  IATIQYKIDN  NSRPKVRVKL  DYVIDDDSKI  NYFMNHSLLK  1980
SRYPDKVLEI  LKQSTIIEFE  SSGFNKTIKE  MLGMKLAGIY  NETSNN                  2026

SEQ ID NO: 127            moltype = AA   length = 2025
FEATURE                   Location/Qualifiers
REGION                    1..2025
                          note = Fn/enFnCas9
source                    1..2025
                          mol_type = protein
                          organism = synthetic construct
SEQUENCE: 127
MSEVEFSHEY  WMRHALTLAK  RAWDEREVPV  GAVLVHNNRV  IGEGWNRPIG  RHDPTAHAEI   60
MALRQGGLVM  QNYRLIDATL  YVTLEPCVMC  AGAMIHSRIG  RVVFGARDAK  TGAAGSLMDV  120
LHHPGMNHRV  EITEGILADE  CAALLSDFFR  MRRQEIKAQK  KAQSSTDSGG  SSGGSSGSET  180
PGTSESATPE  SSGGSSGGSS  EVEFSHEYWM  RHALTLAKRA  RDEREVPVGA  VLVLNNRVIG  240
EGWNRAIGLH  DPTAHAEIMA  LRQGGLVMQN  YRLIDATLYS  TFEPCVMCAG  AMIHSRIGRV  300
VFGWRNAKTG  AAGSLMDVLH  YPGMNHRVEI  TEGILADECA  ALLCYFFRMP  RRVFNAQKKA  360
QSSTDSGGSS  GGSSGSETPG  TSESATPESS  GGSSGGSNFK  ILPIAIDLGV  KNTGVFSAFY  420
QKGTSLERLD  NKNGKVYELS  KDSYTLLMNN  RTARRHQRRG  IDRKQLVKRL  FKLIWTEQLN  480
LEWDKDTQQA  ISFLFNRRGF  SFITDGYSPE  YLNIVPEQVK  AILMDIFDDY  NGEDDLDSYL  540
KLATEQESKI  SEIYNKLMQK  ILEFKLMKLC  TDIKDDKVST  KTLKEITSYE  FELLADYLAN  600
YSESLKTQKF  SYTDKQGNLK  ELSYYHHDKY  NIQEFLKRHA  TINDRILDTL  LTDDLDIWNF  660
NFEKFDFDKN  EEKLQNQEDK  DHIQAHLHHF  VFAVNKIKSE  MASGGRHRSQ  YFQEITNVLD  720
ENNHQEGYLK  NFCENLHNKK  YSNLSVKNLV  NLIGNLSNLE  LKPLRKYFND  KIHAKADHWD  780
EQKFTETYCH  WILGEWRVGV  KDQDKKDGAK  YSYKDLCNEL  KQKVTKAGLV  DFLLELDPCR  840
TIPPYLDNNN  RKPPKCQSLI  LNPKFLDNQY  PNWQQYLQEL  KKLQSIQNYL  DSFETDLKVL  900
KSSKDQPYFV  EYKSSNQQIA  SGQRDYKDLD  ARILQFIFDR  VKASDELLLN  EIYFQAKKLK  960
QKASSELEKL  ESSKKLDEVI  ANSQLSQILK  SQHTNGIFEQ  GTFLHLVCKY  YKQRQRARDS  1020
RLYIMPEYRY  DKKLHKYNNT  GRFDDDNQLL  TYCNHKPRQK  RYQLLNDLAG  VLQVSPNFLK  1080
DKIGSDDDLF  ISKWLVEHIR  GFKKACEDSL  KIQKDNRGLL  NHKINIARNT  GKCEKEIFN   1140
LICKIEGSED  KKGNYKHGLA  YELGVLLFGE  PNEASKPEFD  RKIKKFNSIY  SFAQIQQIAF  1200
AERKGNANTC  AVCSADNAHR  MQQIKITEPV  EDNKDKIILS  AKAQRLPAIP  TRIVDGAVKK  1260
MATILAKNIV  DDNWQNIKQV  LSAKHQLHIP  IITESNAFEF  EPALADVGKK  SLKDRRKKAL  1320
ERISPENIFK  DKNNRIKEFA  KGISAYSGAN  LTDGDFDGAK  EELDHIIPRS  HKKYGTLNDE  1380
ANLICVTRGD  NKNKGNRIFC  LRDLADNYKL  KQFETTDDLE  IEKKIADTIW  DANKKDFKFG  1440
NYRSFINLTP  QEQKAFRHAL  FLADENPIKQ  AVIRAINNRN  RTFVNGTQRY  FAEVLANNIY  1500
LRAKKENLNT  DKISFDYFGI  PTIGNGRGIA  EIRQLYEKVD  SDIQAYAKGD  KPQASYSHLI  1560
```

```
DAMLAFCIAA DEHRNDGSIG LEIDKNYSLY PLDKNTGEVF TKDIFSQIKI TDNEFSDKKL     1620
VRKKAIEGFN THRQMTRDGI YAENYLPILI HKELNEVRKG YTWKNSEEIK IFKGKKYDIQ     1680
QLNNLVYCLK FVDKPISIDI QISTLEELRN ILTTNNIAAT AEYYYINLKT QKLHEYYIEN     1740
YNTALGYKKY SKEMEFLRSL AYRSERVKIK SIDDVKQVLD KDSNFIIGKI TLPFKKEWQR     1800
LYREWQNTTI KDDYEFLKSF FNVKSITKLH KKVRKDFSLP ISTNEGKFLV KRKTWDNNFI     1860
YQILNDSDSR ADGTKPFIPA FDISKNEIVE AIIDSFTSKN IFWLPKNIEL QKVDNKNIFA     1920
IDTSKWFEVE TPSDLRDIGI ATIQYKIDNN SRPKVRVKLD YVIDDDSKIN YFMNHSLLKS     1980
RHPDKVLEIL KQSTIIEFHS SGFNKTIKEM LGMKLAGIYN ETSNN                    2025

SEQ ID NO: 128          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 128
MSEVEFSHEY WMRHALTLAK RAWDEREVPV GAVLVHNNRV IGEGWNRPIG RHDPTAHAEI       60
MALRQGGLVM QNYRLIDATL YVTLEPCVMC AGAMIHSRIG RVVFGARDAK TGAAGSLMDV      120
LHHPGMNHRV EITEGILADE CAALLSDFFR MRRQEIKAQK KAQSSTDSGG SSGGSSGSET      180
PGTSESATPE SSGGSSGGSS EVEFSHEYWM RHALTLAKRA RDEREVPVGA VLVLNNRVIG      240
EGWNRAIGLH DPTAHAEIMA LRQGGLVMQN YRLIDATLYS TFEPCVMCAG AMIHSRIGRV      300
VFGWRNAKTG AAGSLMDVLH YPGMNHRVEI TEGILADECA ALLCYFFRMP RRVFNAQKKA      360
QSSTDSGGSS GGSSGETPG TSESATPESS GGSSGGSNFK ILPIAIDLGV KNTGVFSAFY      420
QKGTSLERLD NKNGKVYELS KDSYTLLMNN RTARRHQRRG IDRKQLVKRL FKLIWTEQLN      480
LEWDKDTQQA ISFLFNRRGF SFITDGYSPE YLNIVPEQVK AILMDIFDDY NGEDDLDSYL      540
KLATEQESKI SEIYNKLMQK ILEFKLMKLC TDIKDDKVST KTLKEITSYE FELLADYLAN      600
YSESLKTQKF SYTDKQGNLK ELSYYHHDKY NIQEFLKRHA TINDRILDTL LTDDLDIWNF      660
NFEKFDFDKN EEKLQNQEDK DHIQAHLHHF VFAVNKIKSE MASGGRHRSQ YFQEITNVLD      720
ENNHQEGYLK NFCENLHNKK YSNLSVKNLV NLIGNLSNLE LKPLRKYFND KIHAKADHWD      780
EQKFTETYCH WILGEWRVGV KDQDKKDGAK YSYKDLCNEL KQKVTKAGLV DFLLELDPCR      840
TIPPYLDNNN RKPPKCQSLI LNPKFLDNQY PNWQQYLQEL KKLQSIQNYL DSFETDLKVL      900
KSSKDQPYFV EYKSSNQQIA SGQRDYKDLD ARILQFIFDR VKASDELLLN EIYFQAKKLK      960
QKASSELEKL ESSKKLDEVI ANSQLSQILK SQHTNGIFEQ GTFLHLVCKY YKQRQRARDS     1020
RLYIMPEYRY DKKLHKYNNT GRFDDDNQLL TYCNHKPRQK RYQLLNDLAG VLQVSPNFLK     1080
DKIGSDDDLF ISKWLVEHIR GFKKACEDSL KIQKDNRGLL NHKINIARNT KGKCEKEIFN     1140
LICKIEGSED KKGNYKHGLA YELGVLLFGE PNEASKPEFD RKIKKFNSIY SFAQIQQIAF     1200
AERKGNANTC AVCSADNAHR MQQIKITEPV EDNKDKIILS AKAQRLPAIP TRIVDGAVKK     1260
MATILAKNIV DDNWQNIKQV LSAKHQLHIP IITESNAFEF EPALADVGKK SLKDRRKKAL     1320
ERISPENIFK DKNNRIKEFA KGISAYSGAN LTDGDFDGAK EELDHIIPRS HKKYGTLNDE     1380
ANLICVTRGD NKNKGNRIFC LRDLADNYKL KQFETTDDLE IEKKIADTIW DANKKDFKFG     1440
NYRSFINLTP QEQKAFRHAL FLADENPIKQ AVIRAINNRN RTFVNGTQRY FAEVLANNIY     1500
LRAKKENLNT DKISFDYFGI PTIGNGRGIA EIRQLYEKVD SDIQAYAKGD KPQASYSHLI     1560
DAMLAFCIAA DEHRNDGSIG LEIDKNYSLY PLDKNTGEVF TKDIFSQIKI TDNEFSDKKL     1620
VRKKAIEGFN THRQMTRDGI YAENYLPILI HKELNEVRKG YTWKNSEEIK IFKGKKYDIQ     1680
QLNNLVYCLK FVDKPISIDI QISTLEELRN ILTTNNIAAT AEYYYINLKT QKLHEYYIEN     1740
YNTALGYKKY SKEMEFLRSL AYRSERVKIK SIDDVKDSNF IIKKI TLPFKKEWQR         1800
LYREWQNTTI KDDYEFLKSF FNVKSITKLH KKVRKDFSLP ISTYEGKFLV KRKTWDNNFI     1860
YQILNDSDSR ADGTKPFIPA FDISKNEIVE AIIDSFTSKN IFWLPKNIEL QKVDNKNIFA     1920
IDTSKWFEVE TPSDLRDIGI ATIQYKIDNN SRPKVRVKLD YVIDDDSKIN YFMNHSLLKS     1980
RYPDKVLEIL KQSTIIEFES SGFNKTIKEM LGMKLAGIYN ETSNN                    2025

SEQ ID NO: 129          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 129
MSEVEFSHEY WMRHALTLAK RAWDEREVPV GAVLVHNNRV IGEGWNRPIG RHDPTAHAEI       60
MALRQGGLVM QNYRLIDATL YVTLEPCVMC AGAMIHSRIG RVVFGARDAK TGAAGSLMDV      120
LHHPGMNHRV EITEGILADE CAALLSDFFR MRRQEIKAQK KAQSSTDSGG SSGGSSGSET      180
PGTSESATPE SSGGSSGGSS EVEFSHEYWM RHALTLAKRA RDEREVPVGA VLVLNNRVIG      240
EGWNRAIGLH DPTAHAEIMA LRQGGLVMQN YRLIDATLYS TFEPCVMCAG AMIHSRIGRV      300
VFGWRNAKTG AAGSLMDVLH YPGMNHRVEI TEGILADECA ALLCYFFRMP RRVFNAQKKA      360
QSSTDSGGSS GGSSGETPG TSESATPESS GGSSGGSNFK ILPIAIDLGV KNTGVFSAFY      420
QKGTSLERLD NKNGKVYELS KDSYTLLMNN RTARRHQRRG IDRKQLVKRL FKLIWTEQLN      480
LEWDKDTQQA ISFLFNRRGF SFITDGYSPE YLNIVPEQVK AILMDIFDDY NGEDDLDSYL      540
KLATEQESKI SEIYNKLMQK ILEFKLMKLC TDIKDDKVST KTLKEITSYE FELLADYLAN      600
YSESLKTQKF SYTDKQGNLK ELSYYHHDKY NIQEFLKRHA TINDRILDTL LTDDLDIWNF      660
NFEKFDFDKN EEKLQNQEDK DHIQAHLHHF VFAVNKIKSE MASGGRHRSQ YFQEITNVLD      720
ENNHQEGYLK NFCENLHNKK YSNLSVKNLV NLIGNLSNLE LKPLRKYFND KIHAKADHWD      780
EQKFTETYCH WILGEWRVGV KDQDKKDGAK YSYKDLCNEL KQKVTKAGLV DFLLELDPCR      840
TIPPYLDNNN RKPPKCQSLI LNPKFLDNQY PNWQQYLQEL KKLQSIQNYL DSFETDLKVL      900
KSSKDQPYFV EYKSSNQQIA SGQRDYKDLD ARILQFIFDR VKASDELLLN EIYFQAKKLK      960
QKASSELEKL ESSKKLDEVI ANSQLSQILK SQHTNGIFEQ GTFLHLVCKY YKQRQRARDS     1020
RLYIMPEYRY DKKLHKYNNT GRFDDDNQLL TYCNHKPRQK RYQLLNDLAG VLQVSPNFLK     1080
DKIGSDDDLF ISKWLVEHIR GFKKACEDSL KIQKDNRGLL NHKINIARNT KGKCEKEIFN     1140
```

```
LICKIEGSED KKGNYKHGLA YELGVLLFGE PNEASKPEFD RKIKKFNSIY SFAQIQQIAF    1200
AERKGNANTC AVCSADNAHR MQQIKITEPV EDNKDKIILS AKAQRLPAIP TRIVDGAVKK    1260
MATILAKNIV DDNWQNIKQV LSAKHQLHIP IITESNAFEF EPALADVKGK SLKDRRKKAL    1320
ERISPENIFK DKNNRIKEFA KGISAYSGAN LTDGDFDGAK EELDHIIPRS HKKYGTLNDE    1380
ANLICVTRGD NKNKGNRIFC LRDLADNYKL KQFETTDDLE IEKKIADTIW DANKKDFKFG    1440
NYRSFINLTP QEQKAFRHAL FLADENPIKQ AVIRAINNRN RTFVNGTQRY FAEVLANNIY    1500
LRAKKENLNT DKISFDYFGI PTIGNGRGIA EIRQLYEKVD SDIQAYAKGD KPQASYSHLI    1560
DAMLAFCIAA DEHRNDGSIG LEIDKNYSLY PLDKNTGEVF TKDIFSQIKI TDNEFSDKKL    1620
VRKKAIEGFN THRQMTRDTI YAENYLPILI HKELNEVRKG YTWKNSEEIK IPFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSRRVKIK SIDDVKQVLD KDSNFIIGKI TLPFKKEWQR   1800
LYREWQNTTI KDDYEFLKSF FNVKSITKLH KKVRKDFSLP ISTNHGKFLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFES SGFNKTIKEM LGMKLAGIYN ETSNN                   2025

SEQ ID NO: 130          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 130
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVKAGLV  DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IPFKGKKYDIQ  1680
QLNNLVYCLK FVDKPISIDI QISTLEELRN ILTTNNIAAT AEYYYINLKT QKLHEYYIEN   1740
YNTALGYKKY SKEMEFLRSL AYRSRRVKIK SIDDVKQVLD KDSNFIIKKI TLPFKKEWQR   1800
LYREWQNTTI KDDYEFLKSF FNVKSITKLH KKVRKDFSLP ISTNHGKFLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFES SGFNKTIKEM LGMKLAGIYN ETSNN                   2025

SEQ ID NO: 131          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 131
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
```

```
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVGKG SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSRRVKIK SIDDVKQVLD KDSNFIIGKI TLPFKKEWQR  1800
LYREWQNTTI KDDYEFLKSF FNVKSITKLH KKVRKDFSLP ISTYHGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFES SGFNKTIKEM LGMKLAGIYN ETSNN                  2025

SEQ ID NO: 132          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 132
MSEVEFSHEY WMRHALTLAK RAWDEREVPV GAVLVHNNRV IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFRMP RRVFNAQKKA  360
QSSTDSGGSS GGSSGGSETP TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDVKST KTLKEITSYE FELLADYLAN  600
YSESLKTQKF SYTDKQGNLK ELSYYHHDKY NIQEFLKRTA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVGKG SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSRRVKIK SIDDVKQVLD KDSNFIIGKI TLPFKKEWQR  1800
LYREWQNTTI KDDYEFLKSF FNVKSITKLH KKVRKDFSLP ISTNEGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFHS SGFNKTIKEM LGMKLAGIYN ETSNN                  2025

SEQ ID NO: 133          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 133
MSEVEFSHEY WMRHALTLAK RAWDEREVPV GAVLVHNNRV IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTLAKRA RDEREVPVGA VLVLNNRVIG  240
EGWNRAIGLH DPTAHAEIMA LRQGGLVMQN YRLIDATLYS TFEPCVMCAG AMIHSRIGRV  300
```

```
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVGKG SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSRRVKIK SIDDVKQVLD KDSNFIIKKI TLPFKKEWQR   1800
LYREWQNTTI KDDYEFLKSF FNVKSITKLH KKVRKDFSLP ISTNEGKFLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFES SGFNKTIKEM LGMKLAGIYN ETSNN                   2025

SEQ ID NO: 134           moltype = AA  length = 2025
FEATURE                  Location/Qualifiers
REGION                   1..2025
                         note = Fn/enFnCas9
source                   1..2025
                         mol_type = protein
                         organism = synthetic construct
SEQUENCE: 134
MSEVEFSHEY WMRHALTLAK RAWDEREVPV GAVLHNNRV  IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPVGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVGKG SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSRRVKIK SIDDVKQVLD KDSNFIIKKI TLPFKKEWQR   1800
LYREWQNTTI KDDYEFLKSF FNVKSITKLH KKVRKDFSLP ISTREGKFLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFES SGFNKTIKEM LGMKLAGIYN ETSNN                   2025

SEQ ID NO: 135           moltype = AA  length = 2025
FEATURE                  Location/Qualifiers
REGION                   1..2025
                         note = Fn/enFnCas9
source                   1..2025
                         mol_type = protein
```

```
                    organism = synthetic construct
SEQUENCE: 135
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGSETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDDLDIWNF  660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IPFKGKKYDIQ 1680
QLNNLVYCLK FVDKPISIDI QISTLEELRN ILTTNNIAAT AEYYYINLKT QKLHEYYIEN  1740
YNTALGYKKY SKEMEFLRSL AYRSRRVKIK SIDDVKQVLD KDSNFIIGKI TLPFKKEWQR  1800
LYREWQNTTI KDDYEFLKSF FNVKSITKLH KKVRKDFSLP ISTYEGKFLV KRKTWDNNFI  1860
YQILNDSDSR ADGTKPFIPA FDISKNEIVE AIIDSFTKSN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFES SGFNKTIKEM LGMKLAGIYN ETSNN                 2025

SEQ ID NO: 136      moltype = AA   length = 2025
FEATURE             Location/Qualifiers
REGION              1..2025
                    note = Fn/enFnCas9
source              1..2025
                    mol_type = protein
                    organism = synthetic construct
SEQUENCE: 136
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGSETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDDLDIWNF  660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IPFKGKKYDIQ 1680
QLNNLVYCLK FVDKPISIDI QISTLEELRN ILTTNNIAAT AEYYYINLKT QKLHEYYIEN  1740
YNTALGYKKY SKEMEFLRSL AYRSRRVKIK SIDDVKQVLD KDSNFIIGKI TLPFKKEWQR  1800
LYREWQNTTI KDDYEFLKSF FNVKSITKLH KKVRKDFSLP ISTNEGKFLV KRKTWDNNFI  1860
YQILNDSDSR FDGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFES SGFNKTIKEM LGMKLAGIYN ETSNN                 2025
```

```
SEQ ID NO: 137          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 137
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGSETPG TSESATPESS GGSSGGSNFK ILPIAIDLGV KNTGVFSAFY   420
QKGTSLERLD NKNGKVYELS KDSYTLLMNN RTARRHQRGF IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDLDIWNF   660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVGKG SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSRRVKIK SIDDVKQVLD KDSNFIIGKI TLPFKKEWQR  1800
LYREWQNTTI KDDYEFLKSF FNVKSITKLH KKVRKDFSLP ISTNEGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHRLLKS  1980
RYPDKVLEIL KQSTIIEFES SGFNKTIKEM LGMKLAGIYN ETSNN                  2025

SEQ ID NO: 138          moltype = AA  length = 2025
FEATURE                 Location/Qualifiers
REGION                  1..2025
                        note = Fn/enFnCas9
source                  1..2025
                        mol_type = protein
                        organism = synthetic construct
SEQUENCE: 138
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGSETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDLDIWNF   660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVGKG SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
```

```
VRKKAIEGFN THRQMTRDTI YAENYLPILI HKELNEVRKG YTWKNSEEIK IFKGKKYDIQ    1680
QLNNLVYCLK FVDKPISIDI QISTLEELRN ILTTNNIAAT AEYYYINLKT QKLHEYYIEN    1740
YNTALGYKKY SKEMEFLRSL AYRSRRVKIK SIDDVKQVLD KDSNFIIGKI TLPFKKEWQR    1800
LYREWQNTTI KDDYEFLKSF FNVKSITKLH KKVRKDFSLP ISTNEGKFLV KRKTWDNNFI    1860
YQILNDSDSR ADGTKPFIPA FDISKNEIVE AIIDSFTSKN IFWLPKNIEL QKVDNKNIFA    1920
IDTSKWFEVE TPSDLRDIGI ATIQYKIDNN SRPKVRVKLD YVIDDDSKIN YFMNHSLLKS    1980
RYPDKVLEIL KQSTIIEFES SGFNKTIKEM LGMKLAGIYN ETSNN                   2025

SEQ ID NO: 139          moltype = AA   length = 2025
FEATURE                 Location/Qualifiers
REGION                  1..2025
                        note = Fn/enFnCas9
source                  1..2025
                        mol_type = protein
                        organism = synthetic construct
SEQUENCE: 139
MSEVEFSHEY WMRHALTLAK RAWDEREVPV GAVLVHNNRV IGEGWNRPIG RHDPTAHAEI      60
MALRQGGLVM QNYRLIDATL YVTLEPCVMC AGAMIHSRIG RVVFGARDAK TGAAGSLMDV     120
LHHPGMNHRV EITEGILADE CAALLSDFFR MRRQEIKAQK KAQSSTDSGG SSGGSSGSET     180
PGTSESATPE SSGGSSGGSS EVEFSHEYWM RHALTLAKRA RDEREVPVGA VLVLNNRVIG     240
EGWNRAIGLH DPTAHAEIMA LRQGGLVMQN YRLIDATLYS TFEPCVMCAG AMIHSRIGRV     300
VFGWRNAKTG AAGSLMDVLH YPGMNHRVEI TEGILADECA ALLCYFFRMP RRVFNAQKKA     360
QSSTDSGGSS GGSSGSETPG TSESATPESS GGSSGGSNFK ILPIAIDLGV KNTGVFSAFY     420
QKGTSLERLD NKNGKVYELS KDSYTLLMNN RTARRHQRRG IDRKQLVKRL FKLIWTEQLN     480
LEWDKDTQQA ISFLFNRRGF SFITDGYSPE YLNIVPEQVK AILMDIFDDY NGEDDLDSYL     540
KLATEQESKI SEIYNKLMQK ILEFKLMKLC TDIKDDKVST KTLKEITSYE FELLADYLAN     600
YSESLKTQKF SYTDKQGNLK ELSYYHHDKY NIQEFLKRHA TINDRILDTL LTDDLDIWNF     660
NPFEKFDFDKN EEKLQNQEDK DHIQAHLHHF VFAVNKIKSE MASGGRHRSQ YFQEITNVLD     720
ENNHQEGYLK NFCENLHNKK YSNLSVKNLV NLIGNLSNLE LKPLRKYFND KIHAKADHWD     780
EQKFTETYCH WILGEWRVGV KDQDKKDGAK YSYKDLCNEK KQKVTKAGLV DFLLELEDPCR     840
TIPPYLDNNN RKPPKCQSLI LNPKFLDNQY PNWQQYLQEL KKLQSIQNYL DSFETDLKVL     900
KSSKDQPYFV EYKSSNQQIA SGQRDYKDLD ARILQFIFDR VKASDELLLN EIYFQAKKLK     960
QKASSELEKL ESSKKLDEVI ANSQLSQILK SQHTNGIFEQ GTFLHLVCKY YKQRQRARDS    1020
RLYIMPEYRY DKKLHKYNNT GRFDDDNQLL TYCNHKPRQK RYQLLNDLAG VLQVSPNFLK    1080
DKIGSDDDLF ISKWLVEHIR GFKKACEDSL KIQKDNRGLL NHKINIARNT KGKCEKEIFN    1140
LICKIEGSED KKGNYKHGLA YELGVLLFGE PNEASKPEFD RKIKKFNSIY SFAQIQQIAF    1200
AERKGNANTC AVCSADNAHR MQQIKITEPV EDNKDKIILS AKAQRLPAIP TRIVDGAVKK    1260
MATILAKNIV DDNWQNIKQV LSAKHQLHIP IITESNAFEF EPALADVKGK SLKDRRKKAL    1320
ERISPENIFK DKNNRIKEFA KGISAYSGAN LTDGDFDGAK EELDHIIPRS HKKYGTLNDE    1380
ANLICVTRGD NKNKGNRIFC LRDLADNYKL KQFETTDDLE IEKKIADTIW DANKKDFKFG    1440
NYRSFINLTP QEQKAFRHAL FLADENPIKQ AVIRAINNRN RTFVNGTQRY FAEVLANNIY    1500
LRAKKENLNT DKISFDYFGI PTIGNGRGIA EIRQLYEKVD SDIQAYAKGD KPQASYSHLI    1560
DAMLAFCIAA DEHRNDGSIG LEIDKNYSLY PLDKNTGEVF TKDIFSQIKI TDNEFSDKKL    1620
VRKKAIEGFN THRQMTRDGI YAENYLPILI HKELNEVRKG YTWKNSEEIK IFKGKKYDIQ    1680
QLNNLVYCLK FVDKPISIDI QISTLEELRN ILTTNNIAAT AEYYYINLKT QKLHEYYIEN    1740
YNTALGYKKY SKEMEFLRSL AYRSRRVKIK SIDDVKQVLD KDSNFIIGKI TLPFKKEWQR    1800
LYREWQNTTI KDDYEFLKSF FNVKSITKLH KKVRKDFSLP ISTNEGKFLV KRKTWDNNFI    1860
YQILNDSDSR ADGTKPFIPA FDISKNEIVE AIIDSFTSKN IFWLPKNIEL QKVDNKNIFA    1920
IDTSKWFEVE TPSDLRDIGI ATIQYKIDNN SQPKVRVKLD YVIDDDSKIN YFMNHSLLKS    1980
RYPDKVLEIL KQSTIIEFES SGFNKTIKEM LGMKLAGIYN ETSNN                   2025

SEQ ID NO: 140          moltype = AA   length = 2025
FEATURE                 Location/Qualifiers
REGION                  1..2025
                        note = Fn/enFnCas9
source                  1..2025
                        mol_type = protein
                        organism = synthetic construct
SEQUENCE: 140
MSEVEFSHEY WMRHALTLAK RAWDEREVPV GAVLVHNNRV IGEGWNRPIG RHDPTAHAEI      60
MALRQGGLVM QNYRLIDATL YVTLEPCVMC AGAMIHSRIG RVVFGARDAK TGAAGSLMDV     120
LHHPGMNHRV EITEGILADE CAALLSDFFR MRRQEIKAQK KAQSSTDSGG SSGGSSGSET     180
PGTSESATPE SSGGSSGGSS EVEFSHEYWM RHALTLAKRA RDEREVPVGA VLVLNNRVIG     240
EGWNRAIGLH DPTAHAEIMA LRQGGLVMQN YRLIDATLYS TFEPCVMCAG AMIHSRIGRV     300
VFGWRNAKTG AAGSLMDVLH YPGMNHRVEI TEGILADECA ALLCYFFRMP RRVFNAQKKA     360
QSSTDSGGSS GGSSGSETPG TSESATPESS GGSSGGSNFK ILPIAIDLGV KNTGVFSAFY     420
QKGTSLERLD NKNGKVYELS KDSYTLLMNN RTARRHQRRG IDRKQLVKRL FKLIWTEQLN     480
LEWDKDTQQA ISFLFNRRGF SFITDGYSPE YLNIVPEQVK AILMDIFDDY NGEDDLDSYL     540
KLATEQESKI SEIYNKLMQK ILEFKLMKLC TDIKDDKVST KTLKEITSYE FELLADYLAN     600
YSESLKTQKF SYTDKQGNLK ELSYYHHDKY NIQEFLKRHA TINDRILDTL LTDDLDIWNF     660
NPFEKFDFDKN EEKLQNQEDK DHIQAHLHHF VFAVNKIKSE MASGGRHRSQ YFQEITNVLD     720
ENNHQEGYLK NFCENLHNKK YSNLSVKNLV NLIGNLSNLE LKPLRKYFND KIHAKADHWD     780
EQKFTETYCH WILGEWRVGV KDQDKKDGAK YSYKDLCNEK KQKVTKAGLV DFLLELEDPCR     840
TIPPYLDNNN RKPPKCQSLI LNPKFLDNQY PNWQQYLQEL KKLQSIQNYL DSFETDLKVL     900
KSSKDQPYFV EYKSSNQQIA SGQRDYKDLD ARILQFIFDR VKASDELLLN EIYFQAKKLK     960
QKASSELEKL ESSKKLDEVI ANSQLSQILK SQHTNGIFEQ GTFLHLVCKY YKQRQRARDS    1020
RLYIMPEYRY DKKLHKYNNT GRFDDDNQLL TYCNHKPRQK RYQLLNDLAG VLQVSPNFLK    1080
DKIGSDDDLF ISKWLVEHIR GFKKACEDSL KIQKDNRGLL NHKINIARNT KGKCEKEIFN    1140
LICKIEGSED KKGNYKHGLA YELGVLLFGE PNEASKPEFD RKIKKFNSIY SFAQIQQIAF    1200
```

```
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIKKI TLPFKKEWQR  1800
LYREWQNTTI KDDYEFLKSF FNVKSITKLH KKVRKDFSLP ISTNEGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFHS SGFNKTIKEM LGMKLAGIYN ETSNN                2025

SEQ ID NO: 141            moltype = AA   length = 2025
FEATURE                   Location/Qualifiers
REGION                    1..2025
                          note = Fn/enFnCas9
source                    1..2025
                          mol_type = protein
                          organism = synthetic construct
SEQUENCE: 141
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFMRP RRVFNAQKKA  360
QSSTDSGGSS GGSSGSETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
EQKFTETYCH WILGEWRVGV KDQDKKGDAK YSYKDLCNEL KQKVTKAGLV DFLLELDPCR  840
TIPPYLDNNN RKPPKCQSLI LNPKFLDNQY PNWQQYLAGL KKLQSIQNYL DSFETDLKVL  900
KSSKDQPYFV EYKSSNQQIA SGQRDYKDLD ARILQFIFDR VKASDELLLN EIYFQAKKLK  960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTREGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SRPKVRVKLD YVIDDDSKIN YFMNHSLLKS  1980
RYPDKVLEIL KQSTIIEFHS SGFNKTIKEM LGMKLAGIYN ETSNN                2025

SEQ ID NO: 142            moltype = AA   length = 2025
FEATURE                   Location/Qualifiers
REGION                    1..2025
                          note = Fn/enFnCas9
source                    1..2025
                          mol_type = protein
                          organism = synthetic construct
SEQUENCE: 142
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSHEYWM RHALTAKRA RDEREVPVGA VLVLNNRVIG  240
EGWNRAIGLH DPTAHAEIMA LRQGGLVMQN YRLIDATLYS TFEPCVMCAG AMIHSRIGRV  300
VFGWRNAKTG AAGSLMDVLH YPGMNHRVEI TEGILADECA ALLCYFFMRP RRVFNAQKKA  360
QSSTDSGGSS GGSSGSETPG TSESATPESS GGSSGGSNFK ILPIAIDLGV KNTGVFSAFY  420
QKGTSLERLD NKNGKVYELS KDSYTLLMNN RTARRHQRRG IDRKQLVKRL FKLIWTEQLN  480
LEWDKDTQQA ISFLFNRRGF SFITDGYSPE YLNIVPEQVK AILMDIFDDY NGEDDLDSYL  540
KLATEQESKI SEIYNKLMQK ILEFKLMKLC TDIKDDKVST KTLKEITSYE FELLADYLAN  600
YSESLKTQKF SYTDKQGNLK ELSYYHHDKY NIQEFLKRHA TINDRILDTL LTDDLDIWNF  660
NFEKFDFDKN EEKLQNQEDK DHIQAHLHHF VFAVNKIKSE MASGGRHRSQ YFQEITNVLD  720
ENNHQEGYLK NFCENLHNKK YSNLSVKNLV NLIGNLSNLE LKPLRKYFND KIHAKADHWD  780
```

```
EQKFTETYCH WILGEWRVGV KDQDKKDGAK YSYKDLCNEL KQKVTKAGLV DFLLELDPCR      840
TIPPYLDNNN RKPPKCQSLI LNPKFLDNQY PNWQQYLQEL KKLQSIQNYL DSFETDLKVL      900
KSSSKDQPYFV EYKSSNQQIA SGQRDYKDLD ARILQFIFDR VKASDELLLN EIYFQAKKLK     960
QKASSELEKL ESSKKLDEVI ANSQLSQILK SQHTNGIFEQ GTFLHLVCKY YKQRQRARDS     1020
RLYIMPEYRY DKKLHKYNNT GRFDDDNQLL TYCNHKPRQK RYQLLNDLAG VLQVSPNFLK     1080
DKIGSDDDLF ISKWLVEHIR GFKKACEDSL KIQKDNRGLL NHKINIARNT KGKCEKEIFN     1140
LICKIEGSED KKGNYKHGLA YELGVLLFGE PNEASKPEFD RKIKKFNSIY SFAQIQQIAF     1200
AERKGNANTC AVCSADNAHR MQQIKITEPV EDNKDKIILS AKAQRLPAIP TRIVDGAVKK     1260
MATILAKNIV DDNWQNIKQV LSAKHQLHIP IITESNAFEF EPALADVKGK SLKDRRKKAL     1320
ERISPENIFK DKNNRIKEFA KGISAYSGAN LTDGDFDGAK EELDHIIPRS HKKYGTLNDE     1380
ANLICVTRGD NKNKGNRIFC LRDLADNYKL KQFETTDDLE IEKKIADTIW DANKKDFKFG     1440
NYRSFINLTP QEQKAFRHAL FLADENPIKQ AVIRAINNRN RTFVNGTQRY FAEVLANNIY     1500
LRAKKENLNT DKISFDYFGI PTIGNGRGIA EIRQLYEKVD SDIQAYAKGD KPQASYSHLI     1560
DAMLAFCIAA DEHRNDGSIG LEIDKNYSLY PLDKNTGEVF TKDIFSQIKI TDNEFSDKKL     1620
VRKKAIEGFN THRQMTRDGI YAENYLPILI HKELNEVRKG YTWKNSEEIK IFKGKKYDIQ     1680
QLNNLVYCLK FVDKPISIDI QISTLEELRN ILTTNNIAAT AEYYYINLKT QKLHEYYIEN     1740
YNTALGYKKY SKEMEFLRSL AYRSERVKIK SIDDVKQVLD KDSNFIIGKI TLPFKKEWQR     1800
LYREWQNTTI KDDYEFLKSL AYRSERVKIK STIYEGKFLV KRKTWDNNFI                1860
YQILNDSDSR ADGTKPFIPA FDISKNEIVE AIIDSFTSKN IFWLPKNIEL QKVDNKNIFA     1920
IDTSKWFEVE TPSDLRDIGI ATIQYKIDNN SRPKVRVKLD YVIDDDSKIN YFMNHSLLKS     1980
RYPDKVLEIL KQSTIIEFHS SGFNKTIKEM LGMKLAGIYN ETSNN                     2025

SEQ ID NO: 143         moltype = AA   length = 2025
FEATURE                Location/Qualifiers
REGION                 1..2025
                       note = Fn/enFnCas9
source                 1..2025
                       mol_type = protein
                       organism = synthetic construct
SEQUENCE: 143
MSEVEFSHEY WMRHALTLAK RAWDEREVPV GAVLVHNNRV IGEGWNRPIG RHDPTAHAEI       60
MALRQGGLVM QNYRLIDATL YVTLEPCVMC AGAMIHSRIG RVVFGARDAK TGAAGSLMDV      120
LHHPGMNHRV EITEGILADE CAALLSDFFR MRRQEIKAQK KAQSSTDSGG SSGGSSGSET      180
PGTSESATPE SSGGSSGGSS EVEFSHEYWM RHALTLAKRA DEREVPVGA VLVLNNRVIG       240
EGWNRAIGLH DPTAHAEIMA LRQGGLVMQN YRLIDATLYS TFEPCVMCAG AMIHSRIGRV      300
VFGWRNAKTG AAGSLMDVLH YPGMNHRVEI TEGILADECA ALLCYFFRMP RRVFNAQKKA      360
QSSTDSGGGS GGSSGGSETP GTSESATPESS GGSSGGSNFK ILPIAIDLGV KNTGVFSAFY     420
QKGTSLERLD NKNGKVYELS KDSYTLLMNN RTARRHQRRG IRKQLVKRL FKLIWTEQLN      480
LEWDKDTQQA ISFLFNRRGF SFITDGYSPE YLNIVPEQVK AILMDIFDDY NGEDDLDSYL     540
KLATEQESKI SEIYNKLMQK ILEFKLMKLC TDIKDDKVST KTLKEITSYE FELLADYLAN     600
YSESLKTQKF SYTDKQGNLK ELSYYHHDKY NIQEFLKRHA TINDRILDTL LTDDLDIWNF     660
NFEKFDFDKN EEKLQNQEDK DHIQAHLHHF VFAVNKIKSE MASGGRHRSQ YFQEITNVLD     720
ENNHQEGYLK NFCENLHNKK YSNLSVKNLV NLIGNLSENL KIHAKADHWD KIHAKADHWD     780
EQKFTETYCH WILGEWRVGV KDQDKKDGAK YSYKDLCNEL KQKVTKAGLV DFLLELDPCR     840
TIPPYLDNNN RKPPKCQSLI LNPKFLDNQY PNWQQYLQEL KKLQSIQNYL DSFETDLKVL     900
KSSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEEIK IFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSERVKIK SIDDVKQVLD KDSNFIIGKI TLPFKKEWQR   1800
LYREWQNTTI KDDYEFLKSF FNVKSITKLH KKVRKDFSLP ISTNEGKFLV KRKTWDNNFI   1860
YQILNDSDSR FDGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFHS SGFNKTIKEM LGMKLAGIYN ETSNN                   2025

SEQ ID NO: 144         moltype = AA   length = 2025
FEATURE                Location/Qualifiers
REGION                 1..2025
                       note = Fn/enFnCas9
source                 1..2025
                       mol_type = protein
                       organism = synthetic construct
SEQUENCE: 144
MSEVEFSHEY WMRHALTLAK RAWDEREVPV GAVLVHNNRV IGEGWNRPIG RHDPTAHAEI       60
MALRQGGLVM QNYRLIDATL YVTLEPCVMC AGAMIHSRIG RVVFGARDAK TGAAGSLMDV      120
LHHPGMNHRV EITEGILADE CAALLSDFFR MRRQEIKAQK KAQSSTDSGG SSGGSSGSET      180
PGTSESATPE SSGGSSGGSS EVEFSHEYWM RHALTLAKRA RDEREVPVGA VLVLNNRVIG      240
EGWNRAIGLH DPTAHAEIMA LRQGGLVMQN YRLIDATLYS TFEPCVMCAG AMIHSRIGRV      300
VFGWRNAKTG AAGSLMDVLH YPGMNHRVEI TEGILADECA ALLCYFFRMP RRVFNAQKKA      360
```

```
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLQQEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDGI YAENYLPILI HKELNEVRKG YTWKNSEIK IFKGKKYDIQ    1680
QLNNLVYCLK FVDKPISIDI QISTLEELRN ILTTNNIAAT AEYYYINLKT QKLHEYYIEN   1740
YNTALGYKKY SKEMEFLRSL AYRSERVIK SIDDVKQVLD KDSNFIIGKI TLPFKKEWQR    1800
LYREWQNTTI KDDYEFLKSF FNVKSITKLH KKVRKDFSLP ISTNEGKPLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHRLLKS   1980
RYPDKVLEIL KQSTIIEFHS SGFNKTIKEM LGMKLAGIYN ETSNN                  2025

SEQ ID NO: 145        moltype = AA   length = 2025
FEATURE               Location/Qualifiers
REGION                1..2025
                      note = Fn/enFnCas9
source                1..2025
                      mol_type = protein
                      organism = synthetic construct
SEQUENCE: 145
MSEVEFSHEY WMRHALTLAK RAWDEREVPV GAVLVHNNRV IGEGWNRPIG RHDPTAHAEI     60
MALRQGGLVM QNYRLIDATL YVTLEPCVMC AGAMIHSRIG RVVFGARDAK TGAAGSLMDV    120
LHHPGMNHRV EITEGILADE CAALLSDFFR MRRQEIKAQK KAQSSTDSGG SSGGSSGSET    180
PGTSESATPE SSGGSSGGSS EVEFSHEYWM RHALTLAKRA RDEREVPGA VLVLNNRVIG    240
EGWNRAIGLH DPTAHAEIMA LRQGGLVMQN YRLIDATLYS TFEPCVMCAG AMIHSRIGRV    300
VFGWRNAKTG AAGSLMDVLH YPGMNHRVEI TEGILADECA ALLCYFFRMP RRVFNAQKKA    360
QSSTDSGGSS GGSSGSETPG TSESATPESS GGSSGGSNFK ILPIAIDLGV KNTGVFSAFY    420
QKGTSLERLD NKNGKVYELS KDSYTLLMNN RTARRHQRRG IDRKQLVKRL FKLIWTEQLN    480
LEWDKDTQQA ISFLFNRRGF SFITDGYSPE YLNIVPEQVK AILMDIFDDY NGEDDLDSYL    540
KLATEQESKI SEIYNKLMQK ILEFKLMKLC TDIKDDKVST KTLKEITSYE FELLADYLAN    600
YSESLKTQKF SYTDKQGNLK ELSYYHHDKY NIQEFLKRHA TINDRILDTL LTDDLDIWNF    660
NFEKFDFDKN EEKLQNQEDK DHIQAHLHHF VFAVNKIKSE MASGGRHRSQ YFQEITNVLD    720
ENNHQEGYLK NFCENLHNKK YSNLSVKNLV NLIGNLSNLE LKPLRKYFND KIHAKADHWD    780
EQKFTETYCH WILGEWRVGV KDQDKKDGAK YSYKDLCNEL KQKVTKAGLV DFLLELDPCR    840
TIPPYLDNNN RKPPKCQSLI LNPKFLDNQY PNWQQYLQEL KKLQSIQNYL DSFETDLKVL    900
KSSKDQPYFV EYKSSNQQIA SGQRDYKDLD ARILQFIFDR VKASDELLLN EIYFQAKKLK    960
QKASSELEKL ESSKKLDEVI ANSQLSQILK SQHTNGIFEQ GTFLHLVCKY YKQRQRARDS   1020
RLYIMPEYRY DKKLHKYNNT GRFDDDNQLL TYCNHKPRQK RYQLLNDLAG VLQVSPNFLK   1080
DKIGSDDDLF ISKWLVEHIR GFKKACEDSL KIQKDNRGLL NHKINIARNT KGKCEKEIFN   1140
LICKIEGSED KKGNYKHGLA YELGVLLFGE PNEASKPEFD RKIKKFNSIY SFAQIQQIAF   1200
AERKGNANTC AVCSADNAHR MQQIKITEPV EDNKDKIILS AKAQRLPAIP TRIVDGAVKK   1260
MATILAKNIV DDNWQNIKQV LSAKHQLHIP IITESNAFEF EPALADVKGK SLKDRRKKAL   1320
ERISPENIFK DKNNRIKEFA KGISAYSGAN LTDGDFDGAK EELDHIIPRS HKKYGTLNDE   1380
ANLICVTRGD NKNKGNRIFC LRDLADNYKL KQFETTDDLE IEKKIADTIW DANKKDFKFG   1440
NYRSFINLTP QEQKAFRHAL FLADENPIKQ AVIRAINNRN RTFVNGTQRY FAEVLANNIY   1500
LRAKKENLNT DKISFDYFGI PTIGNGRGIA EIRQLYEKVD SDIQAYAKGD KPQASYSHLI   1560
DAMLAFCIAA DEHRNDGSIG LEIDKNYSLY PLDKNTGEVF TKDIFSQIKI TDNEFSDKKL   1620
VRKKAIEGFN THRQMTRDTI YAENYLPILI HKELNEVRKG YTWKNSEEIK IFKGKKYDIQ   1680
QLNNLVYCLK FVDKPISIDI QISTLEELRN ILTTNNIAAT AEYYYINLKT QKLHEYYIEN   1740
YNTALGYKKY SKEMEFLRSL AYRSERVIK SIDDVKQVLD KDSNFIIGKI TLPFKKEWQR    1800
LYREWQNTTI KDDYEFLKSF FNVKSITKLH KKVRKDFSLP ISTNEGKPLV KRKTWDNNFI   1860
YQILNDSDSR ADGTKPFIPA FDISKNEIVE AIIDSFTSKN IFWLPKNIEL QKVDNKNIFA   1920
IDTSKWFEVE TPSDLRDIGI ATIQYKIDNN SRPKVRVKLD YVIDDDSKIN YFMNHSLLKS   1980
RYPDKVLEIL KQSTIIEFHS SGFNKTIKEM LGMKLAGIYN ETSNN                  2025

SEQ ID NO: 146        moltype = AA   length = 2025
FEATURE               Location/Qualifiers
REGION                1..2025
                      note = Fn/enFnCas9
source                1..2025
                      mol_type = protein
                      organism = synthetic construct
```

```
SEQUENCE: 146
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGSETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDLDIWNF   660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVGKG SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYINLKT QKLHEYYIEN   1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTNEGKPLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SQPKVRVKLD YVIDDDSKIN YFMNHSLLKS  1980
RYPDKVLEIL KQSTIIEFHS SGFNKTIKEM LGMKLAGIYN ETSNN                 2025

SEQ ID NO: 147         moltype = AA  length = 2024
FEATURE                Location/Qualifiers
REGION                 1..2024
                       note = Fn/enFnCas9
source                 1..2024
                       mol_type = protein
                       organism = synthetic construct
SEQUENCE: 147
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGSETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDLDIWNF   660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVGKG SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDFKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYINLKT QKLHEYYIEN   1740
YNTALGYKKY SKEMEFLRSL AYRSERVKIK SIDDVKQVLD KDSNFIIGKI TLPFKKEWQR  1800
LYREWQNTTI KDDYEFLKSF FNVKSITKLH KKVRKDFSLP ISTNEGKPLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SQPKVRVKLD YVIDDDSKIN YFMNHSLLKSR 1980
YPDKVLEILK QSTIIEFESS GFNKTIKEML GMKLAGIYNE TSNN                   2024
```

-continued

```
SEQ ID NO: 148         moltype = AA  length = 2025
FEATURE                Location/Qualifiers
REGION                 1..2025
                       note = Fn/enFnCas9
source                 1..2025
                       mol_type = protein
                       organism = synthetic construct
SEQUENCE: 148
MSEVEFSHEY WMRHALTLAK RAWDEREVPV GAVLVHNNRV IGEGWNRPIG RHDPTAHAEI    60
MALRQGGLVM QNYRLIDATL YVTLEPCVMC AGAMIHSRIG RVVFGARDAK TGAAGSLMDV   120
LHHPGMNHRV EITEGILADE CAALLSDFFR MRRQEIKAQK KAQSSTDSGG SSGGSSGSET   180
PGTSESATPE SSGGSSGGSS EVEFSHEYWM RHALTLAKRA RDEREVPVGA VLVLNNRVIG   240
EGWNRAIGLH DPTAHAEIMA LRQGGLVMQN YRLIDATLYS TFEPCVMCAG AMIHSRIGRV   300
VFGWRNAKTG AAGSLMDVLH YPGMNHRVEI TEGILADECA ALLCYFFRMP RRVFNAQKKA   360
QSSTDSGGSS GGSSGGSETPG TSESATPESS GGSSGGSNFK ILPIAIDLGV KNTGVFSAFY   420
QKGTSLERLD NKNGKVYELS KDSYTLLMNN RTARRHQRRG IDRKQLVKRL FKLIWTEQLN   480
LEWDKDTQQA ISFLFNRRGF SFITDGYSPE YLNIVPEQVK AILMDIFDDY NGEDDLDSYL   540
KLATEQESKI SEIYNKLMQK ILEFKLMKLC TDIKDDKVST KTLKEITSYE FELLADYLAN   600
YSESLKTQKF SYTDKQGNLK ELSYYHHDKY NIQEFLKRHA TINDRILDTL LTDDLDIWNF   660
NFEKFDFDKN EEKLQNQEDK DHIQAHLHHF VFAVNKIKSE MASGGRHRSQ YFQEITNVLD   720
ENNHQEGYLK NFCENLHNKK YSNLSVKNLV NLIGNLSNLE LKPLRKYFND KIHAKADHWD   780
EQKFTETYCH WILGEWRVGV KDQDKKDGAK YSYKDLCNEL KQKVTKAGLV DFLLELDPCR   840
TIPPYLDNNN RKPPKCQSLI LNPKFLDNQY PNWQQYLQEL KKLQSIQNYL DSFETDLKVL   900
KSSKDQPYFV EYKSSNQQIA SGQRDYKDLD ARILQFIFDR VKASDELLLN EIYFQAKKLK   960
QKASSELEKL ESSKKLDEVI ANSQLSQILK SQHTNGIFEQ GTFLHLVCKY YKQRQRARDS  1020
RLYIMPEYRY DKKLHKYNNT GRFDDDNQLL TYCNHKPRQK RYQLLNDLAG VLQVSPNFLK  1080
DKIGSDDDLF ISKWLVEHIR GFKKACEDSL KIQKDNRGLL NHKINIARNT KGKCEKEIFN  1140
LICKIEGSED KKGNYKHGLA YELGVLLFGE PNEASKPEFD RKIKKFNSIY SFAQIQQIAF  1200
AERKGNANTC AVCSADNAHR MQQIKITEPV EDNKDKIILS AKAQRLPAIP TRIVDGAVKK  1260
MATILAKNIV DDNWQNIKQV LSAKHQLHIP IITESNAFEF EPALADVKGK SLKDRRKKAL  1320
ERISPENIFK DKNNRIKEFA KGISAYSGAN LTDGDFDGAK EELDHIIPRS HKKYGTLNDE  1380
ANLICVTRGD NKNKGNRIFC LRDLADNYKL KQFETTDDLE IEKKIADTIW DANKKDPKFG  1440
NYRSFINLTP QEQKAFRHAL FLADENPIKQ AVIRAINNRN RTFVNGTQRY FAEVLANNIY  1500
LRAKKENLNT DKISFDYFGI PTIGNGRGIA EIRQLYEKVD SDIQAYAKGD KPQASYSHLI  1560
DAMLAFCIAA DEHRNDGSIG LEIDKNYSLY PLDKNTGEVF TKDIFSQIKI TDNEFSDKKL  1620
VRKKAIEGFN THRQMTRDGI YAENYLPILI HKELNEVRKG YTWKNSEEIK IFKGKKYDIQ  1680
QLNNLVYCLK FVDKPISIDI QISTLEELRN ILTTNNIAAT AEYYYINLKT QKLHEYYIEN  1740
YNTALGYKKY SKEMEFLRSL AYRSRRVKIK SIDDVKQVLD KDSNFIIGKI TLPFKKEWQR  1800
LYREWQNTTI KDDYEFLKSF FNVKSITKLH KKVRKDFSLP ISTNHGKFLV KRKTWDNNFI  1860
YQILNDSDSR ADGTKPFIPA FDISKNEIVE AIIDSFTSKN IFWLPKNIEL QKVDNKNIFA  1920
IDTSKWFEVE TPSDLRDIGI ATIQYKIDNN SQPKVRVKLD YVIDDDSKIN YFMNHSLLKS  1980
RYPDKVLEIL KQSTIIEFES SGFNKTIKEM LGMKLAGIYN ETSNN                  2025

SEQ ID NO: 149         moltype = AA  length = 2074
FEATURE                Location/Qualifiers
REGION                 1..2074
                       note = Fn/enFnCas9
source                 1..2074
                       mol_type = protein
                       organism = synthetic construct
SEQUENCE: 149
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSRRV KIKSIDDVKQ VLDKDSNFII GKITLPFKKE WQRLYREWQN TTIKDDYEFL  1680
```

```
KSFFNVKSIT KLHKKVRKDF SLPISTNEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FESSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 150           moltype = AA  length = 2074
FEATURE                  Location/Qualifiers
REGION                   1..2074
                         note = Fn/enFnCas9
source                   1..2074
                         mol_type = protein
                         organism = synthetic construct
SEQUENCE: 150
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKDF DKNEEKLQNQ   540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTNHGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FESSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 151           moltype = AA  length = 2074
FEATURE                  Location/Qualifiers
REGION                   1..2074
                         note = Fn/enFnCas9
source                   1..2074
                         mol_type = protein
                         organism = synthetic construct
SEQUENCE: 151
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKDF DKNEEKLQNQ   540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
```

| | | | | | |
|---|---|---|---|---|---|
| KQVLSAKHQL | HIPIITESNA | FEFEPALADV | KGKSLKDRRK | KALERISPEN | IFKDKNNRIK | 1200
| EFAKGISAYS | GANLTDGDFD | GAKEELDHII | PRSHKKYGTL | NDEANLICVT | RGDNKNKGNR | 1260
| IFCLRDLADN | YKLKQFETTD | DLEIEKKIAD | TIWDANKKDF | KFGNYRSFIN | LTPQEQKAFR | 1320
| HALFLADENP | IKQAVIRAIN | NRNRTFVNGT | QRYFAEVLAN | NIYLRAKKEN | LNTDKISFDY | 1380
| FGIPTIGNGR | GIAEIRQLYE | KVDSDIQAYA | KGDKPQASYS | HLIDAMLAFC | IAADEHRNDG | 1440
| SIGLEIDKNY | SLYPLDKNTG | EVFTKDIFSQ | IKITDNEFSD | KKLVRKKAIE | GFNTHRQMTR | 1500
| DGIYAENYLP | ILIHKELNEV | RKGYTWKNSE | EIKIFKGKKY | DIQQLNNLVY | CLKFVDKPIS | 1560
| IDIQISTLEE | LRNILTTNNI | AATAEYYYIN | LKTQKLHEYY | IENYNTALGY | KKYSKEMEFL | 1620
| RSLAYRSRRV | KIKSIDDVKQ | VLDKDSNFII | GKITLPFKKE | WQRLYREWQN | TTIKDDYEFL | 1680
| KSFFNVKSIT | KLHKKVRKDF | SLPISTNHGK | FLVKRKTWDN | NFIYQILNDS | DSRADGTKPF | 1740
| IPAFDISKNE | IVEAIIDSFT | SKNIFWLPKN | IELQKVDNKN | IFAIDTSKWF | EVETPSDLRD | 1800
| IGIATIQYKI | DNNSRPKVRV | KLDYVIDDDS | KINYFMNHSL | LKSRYPDKVL | EILKQSTIIE | 1860
| FESSGFNKTI | KEMLGMKLAG | IYNETSNNSG | GSGGSGGSTN | LSDIIEKETG | KQLVIQESIL | 1920
| MLPEEVEEVI | GNKPESDILV | HTAYDESTDE | NVMLLTSDAP | EYKPWALVIQ | DSNGENKIKM | 1980
| LSGGGSGGSGG | STNLSDIIEK | ETGKQLVIQE | SILMLPEEVE | EVIGNKPESD | ILVHTAYDES | 2040
| TDENVMLLTS | DAPEYKPWAL | VIQDSNGENK | IKML | | | 2074

SEQ ID NO: 152                moltype = AA   length = 2074
FEATURE                       Location/Qualifiers
REGION                        1..2074
                              note = Fn/enFnCas9
source                        1..2074
                              mol_type = protein
                              organism = synthetic construct
SEQUENCE: 152

| | | | | | |
|---|---|---|---|---|---|
| SSETGPVAVD | PTLRRRIEPH | EFEVFFDPRE | LAAETCLLYE | INWGGRHSIW | RHTSQNTNKH | 60
| VEVNFIEKFT | TERYFCPNTR | CSITWFLSWS | PCGECSRAIT | EFLSRYPHVT | LFIYIARLYH | 120
| HADPRNQGL | RDLISSGVTI | QIMTEQESGY | CWRNFVNYSP | SNEAHWPRYP | HLWVRLYVLE | 180
| LYCIILGLPP | CLNILRRKQP | QLTFFTIALQ | SCHYQRLPPH | ILWATGLKSG | GSSGGSSGSE | 240
| TPGTSESATP | ESSGGSSGGS | NFKILPIAID | LGVKNTGVFS | AFYQKGTSLE | RLDNKNGKVY | 300
| ELSKDSYTLL | MNNRTARRHQ | RRGIDRKQLV | KRLFKIWTE | QLNLEWDKDT | QQAISFLFNR | 360
| RGFSFITDGY | SPEYLNIVPE | QVKAILMDIF | DDYNGEDDLD | SYLKLATEQE | SKISEIYNKL | 420
| MQKILEFKLM | KLCTDIKDDK | VSTKTLKEIT | SYEFELLADY | LANYSESLKT | QKFSYTDKQG | 480
| NLKELSYYHH | DKYNIQEFLK | RHATINDRIL | DTLLTDDLDI | WNFNEFKDF | DKNEEKLQNQ | 540
| EDKDHIQAHL | HHFVFAVNKI | KSEMASGGRH | RSQYFQEITN | VLDENNHQEG | YLKNFCENLH | 600
| NKKYSNLSVK | NLVNLIGNLS | NLELKPLRKY | FNDKIHAKAD | HWDEQKFTET | YCHWILGEWR | 660
| VGVKDQDKKD | GAKYSYKDLC | NELKQKVTKA | GLVDFLLELD | PCRTIPPYLD | NNNRKPPKCQ | 720
| SLILNPKFLD | NQYPNWQQYL | QELKKLQSIQ | NYLDSFETDL | KVLKSSKDQP | YFVEYKSSNQ | 780
| QIASGQRDYK | DLDARILQFI | FDRVKASDEL | LLNEIYFQAK | KLKQKASSEL | EKLESSKKLD | 840
| EVIANSQLSQ | ILKSQHTNGI | FEQGTFLHLV | CKYYKQRQRA | RDSRLYIMPE | YRYDKKLHKY | 900
| NNTGRFDDDN | QLLTYCNHKP | RQKRYQLLND | LAGVLQVSPN | FLKDKIGSDD | DLFISKWLVE | 960
| HIRGFKKACE | DSLKIQKDNR | GLLNHKINIA | RNTKGKCEKE | IPNLICKIEG | SEDKKGNYKH | 1020
| GLAYELGVLL | FGEPNEASKP | EFDRKIKKFN | SIYSFAQIQQ | IAFAERKGNA | NTCAVCSADN | 1080
| AHRMQQIKIT | EPVEDNKDKI | ILSAKAQRLP | AIPTRIVDGA | VKKMATILAK | NIVDDNWQNI | 1140
| KQVLSAKHQL | HIPIITESNA | FEFEPALADV | KGKSLKDRRK | KALERISPEN | IFKDKNNRIK | 1200
| EFAKGISAYS | GANLTDGDFD | GAKEELDHII | PRSHKKYGTL | NDEANLICVT | RGDNKNKGNR | 1260
| IFCLRDLADN | YKLKQFETTD | DLEIEKKIAD | TIWDANKKDF | KFGNYRSFIN | LTPQEQKAFR | 1320
| HALFLADENP | IKQAVIRAIN | NRNRTFVNGT | QRYFAEVLAN | NIYLRAKKEN | LNTDKISFDY | 1380
| FGIPTIGNGR | GIAEIRQLYE | KVDSDIQAYA | KGDKPQASYS | HLIDAMLAFC | IAADEHRNDG | 1440
| SIGLEIDKNY | SLYPLDKNTG | EVFTKDIFSQ | IKITDNEFSD | KKLVRKKAIE | GFNTHRQMTR | 1500
| DTIYAENYLP | ILIHKELNEV | RKGYTWKNSE | EIKIFKGKKY | DIQQLNNLVY | CLKFVDKPIS | 1560
| IDIQISTLEE | LRNILTTNNI | AATAEYYYIN | LKTQKLHEYY | IENYNTALGY | KKYSKEMEFL | 1620
| RSLAYRSERV | KIKSIDDVKQ | VLDKDSNFII | GKITLPFKKE | WQRLYREWQN | TTIKDDYEFL | 1680
| KSFFNVKSIT | KLHKKVRKDF | SLPISTNEGK | FLVKRKTWDN | NFIYQILNDS | DSRADGTKPF | 1740
| IPAFDISKNE | IVEAIIDSFT | SKNIFWLPKN | IELQKVDNKN | IFAIDTSKWF | EVETPSDLRD | 1800
| IGIATIQYKI | DNNSRPKVRV | KLDYVIDDDS | KINYFMNHSL | LKSRYPDKVL | EILKQSTIIE | 1860
| FESSGFNKTI | KEMLGMKLAG | IYNETSNNSG | GSGGSGGSTN | LSDIIEKETG | KQLVIQESIL | 1920
| MLPEEVEEVI | GNKPESDILV | HTAYDESTDE | NVMLLTSDAP | EYKPWALVIQ | DSNGENKIKM | 1980
| LSGGGSGGSGG | STNLSDIIEK | ETGKQLVIQE | SILMLPEEVE | EVIGNKPESD | ILVHTAYDES | 2040
| TDENVMLLTS | DAPEYKPWAL | VIQDSNGENK | IKML | | | 2074

SEQ ID NO: 153                moltype = AA   length = 2074
FEATURE                       Location/Qualifiers
REGION                        1..2074
                              note = Fn/enFnCas9
source                        1..2074
                              mol_type = protein
                              organism = synthetic construct
SEQUENCE: 153

| | | | | | |
|---|---|---|---|---|---|
| SSETGPVAVD | PTLRRRIEPH | EFEVFFDPRE | LAAETCLLYE | INWGGRHSIW | RHTSQNTNKH | 60
| VEVNFIEKFT | TERYFCPNTR | CSITWFLSWS | PCGECSRAIT | EFLSRYPHVT | LFIYIARLYH | 120
| HADPRNQGL | RDLISSGVTI | QIMTEQESGY | CWRNFVNYSP | SNEAHWPRYP | HLWVRLYVLE | 180
| LYCIILGLPP | CLNILRRKQP | QLTFFTIALQ | SCHYQRLPPH | ILWATGLKSG | GSSGGSSGSE | 240
| TPGTSESATP | ESSGGSSGGS | NFKILPIAID | LGVKNTGVFS | AFYQKGTSLE | RLDNKNGKVY | 300
| ELSKDSYTLL | MNNRTARRHQ | RRGIDRKQLV | KRLFKIWTE | QLNLEWDKDT | QQAISFLFNR | 360
| RGFSFITDGY | SPEYLNIVPE | QVKAILMDIF | DDYNGEDDLD | SYLKLATEQE | SKISEIYNKL | 420
| MQKILEFKLM | KLCTDIKDDK | VSTKTLKEIT | SYEFELLADY | LANYSESLKT | QKFSYTDKQG | 480
| NLKELSYYHH | DKYNIQEFLK | RHATINDRIL | DTLLTDDLDI | WNFNEFKDF | DKNEEKLQNQ | 540
| EDKDHIQAHL | HHFVFAVNKI | KSEMASGGRH | RSQYFQEITN | VLDENNHQEG | YLKNFCENLH | 600

```
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLKDKIGSDD DLFISKWLVE    960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTGDFD GAKEELDHII PRSHKKYGTL NDEANLICVT RGDNKNKGNR    1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSYRV KIKSIDDVKQ VLDKDSNFII GKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074

SEQ ID NO: 154          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 154
SSETGPVAVD PTLRRRIEPH EFEVFFDPRE LAAETCLLYE INWGGRHSIW RHTSQNTNKH     60
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLKSG GSSGGSSGSE    240
TPGTSESATP ESSGGSSGGS NFKILPIAID LGVKNTGVFS AFYQKGTSLE RLDNKNGKVY    300
ELSKDSYTLL MNNRTARRHQ RRGIDRKQLV KRLFKLIWTE QLNLEWDKDT QQAISFLFNR    360
RGFSFITDGY SPEYLNIVPE QVKAILMDIF DDYNGEDDLD SYLKLATEQE SKISEIYNKL    420
MQKILEFKLM KLCTDIKDDK VSTKTLKEIT SYEFELLADY LANYSESLKT QKFSYTDKQG    480
NLKELSYYHH DKYNIQEFLK RHATINDRIL DTLLTDDLDI WNFNFEKFDF DKNEEKLQNQ    540
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLKDKIGSDD DLFISKWLVE    960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTGDFD GAKEELDHII PRSHKKYGTL NDEANLICVT RGDNKNKGNR    1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSERV KIKSIDDVKQ VLDKDSNFII RKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074

SEQ ID NO: 155          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 155
SSETGPVAVD PTLRRRIEPH EFEVFFDPRE LAAETCLLYE INWGGRHSIW RHTSQNTNKH     60
```

```
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLKSG GSSGGSSGSE    240
TPGTSESATP ESSGGSSGGS NFKILPIAID LGVKNTGVFS AFYQKGTSLE RLDNKNGKVY    300
ELSKDSYTLL MNNRTARRHQ RRGIDRKQLV KRLFKLIWTE QLNLEWDKDT QQAISFLFNR    360
RGFSFITDGY SPEYLNIVPE QVKAILMDIF DDYNGEDDLD SYLKLATEQE SKISEIYNKL    420
MQKILEFKLM KLCTDIKDDK VSTKTLKEIT SYEFELLADY LANYSESLKT QKFSYTDKQG    480
NLKELSYYHH DKYNIQEFLK RHATINDRIL DTLLTDDLDI WNFNFEKFDF DKNEEKLQNQ    540
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLKDKIGSDD DLFISKWLVE    960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTDGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSERV KIKSIDDVKQ VLDKDSNFII KKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGS STNLSDIIEK ETGKQLVIQE SILMLPEEVE EVIGNKPESD ILVHTAYDES   2040
TDENVMLLTS DAPEYKPWAL VIQDSNGENK IKML                                2074

SEQ ID NO: 156         moltype = AA  length = 2074
FEATURE                Location/Qualifiers
REGION                 1..2074
                       note = Fn/enFnCas9
source                 1..2074
                       mol_type = protein
                       organism = synthetic construct
SEQUENCE: 156
SSETGPVAVD PTLRRRIEPH EFEVFFDPRE LAAETCLLYE INWGGRHSIW RHTSQNTNKH     60
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLKSG GSSGGSSGSE    240
TPGTSESATP ESSGGSSGGS NFKILPIAID LGVKNTGVFS AFYQKGTSLE RLDNKNGKVY    300
ELSKDSYTLL MNNRTARRHQ RRGIDRKQLV KRLFKLIWTE QLNLEWDKDT QQAISFLFNR    360
RGFSFITDGY SPEYLNIVPE QVKAILMDIF DDYNGEDDLD SYLKLATEQE SKISEIYNKL    420
MQKILEFKLM KLCTDIKDDK VSTKTLKEIT SYEFELLADY LANYSESLKT QKFSYTDKQG    480
NLKELSYYHH DKYNIQEFLK RHATINDRIL DTLLTDDLDI WNFNFEKFDF DKNEEKLQNQ    540
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLKDKIGSDD DLFISKWLVE    960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTDGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSERV KIKSIDDVKQ VLDKDSNFII GKITLPFKKE WQRLYREWQN TTIKDDYEFL   1680
KSFFNVKSIT KLHKKVRKDF SLPISTREGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGS STNLSDIIEK ETGKQLVIQE SILMLPEEVE EVIGNKPESD ILVHTAYDES   2040
TDENVMLLTS DAPEYKPWAL VIQDSNGENK IKML                                2074
```

```
SEQ ID NO: 157          moltype = AA  length = 2074
FEATURE                 Location/Qualifiers
REGION                  1..2074
                        note = Fn/enFnCas9
source                  1..2074
                        mol_type = protein
                        organism = synthetic construct
SEQUENCE: 157
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKPDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTYEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FESSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 158          moltype = AA  length = 2075
FEATURE                 Location/Qualifiers
REGION                  1..2075
                        note = Fn/enFnCas9
source                  1..2075
                        mol_type = protein
                        organism = synthetic construct
SEQUENCE: 158
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKPDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
```

```
RSLAYRSERV KIKSIDDVKQ VLDKDSNFII GKITLPFKKE WQRLYREWQN TTIKDDYEFL     1680
KSFFNVKSIT KLHKKVRKDF SLPISTNEGK VFLVKRKTWD NNFIYQILND  SDSRADGTKP    1740
FIPAFDISKN EIVEAIIDSF TSKNIFWLPK NIELQKVDNK NIFAIDTSKW  FEVETPSDLR    1800
DIGIATIQYK IDNNSRPKVR VKLDYVIDDD SKINYFMNHS LLKSRYPDKV  LEILKQSTII    1860
EFESSGFNKT IKEMLGMKLA GIYNETSNNS GGSGGSGGST NLSDIIEKET  GKQLVIQESI    1920
LMLPEEVEEV IGNKPESDIL VHTAYDESTD ENVMLLTSDA PEYKPWALVI  QDSNGENKIK    1980
MLSGGSGGSG GSTNLSDIIE KETGKQLVIQ ESILMLPEEV EEVIGNKPES  DILVHTAYDE    2040
STDENVMLLT SDAPEYKPWA LVIQDSNGEN KIKML                                2075

SEQ ID NO: 159          moltype = AA  length = 2074
FEATURE                 Location/Qualifiers
REGION                  1..2074
                        note = Fn/enFnCas9
source                  1..2074
                        mol_type = protein
                        organism = synthetic construct
SEQUENCE: 159
SSETGPVAVD PTLRRRIEPH EFEVFFDPRE LAAETCLLYE INWGGRHSIW RHTSQNTNKH       60
VEVNFIEKFT TERYFCPNTR CSITWFLSWS PCGECSRAIT EFLSRYPHVT LFIYIARLYH      120
HADPRNRQGL RDLISSGVTI QIMTEQESGY CWRNFVNYSP SNEAHWPRYP HLWVRLYVLE      180
LYCIILGLPP CLNILRRKQP QLTFFTIALQ SCHYQRLPPH ILWATGLKSG GSSGGSSGSE      240
TPGTSESATP ESSGGSSGGS NFKILPIAID LGVKNTGVFS AFYQKGTSLE RLDNKNGKVY      300
ELSKDSYTLL MNNRTARRHQ RRGIDRKQLV KRLFKLIWTE QLNLEWDKDT QQAISFLFNR      360
RGFSFITDGY SPEYLNIVPE QVKAILMDIF DDYNGEDDLD SYLKLATEQE SKISEIYNKL      420
MQKILEFKLM KLCTDIKDDK VSTKTLKEIT SYEFELLADY LANYSESLKT QKFSYTDKQG      480
NLKELSYYHH DKYNIQEFLK RHATINDRIL DTLLTDDLDI WNFNFEKPDF DKNEEKLQNQ      540
EDKDHIQAHL HHFVFAVNKI KSEMASGGRH RSQYFQEITN VLDENNHQEG YLKNFCENLH      600
NKKYSNLSVK NLVNLIGNLS NLELKPLRKY FNDKIHAKAD HWDEQKFTET YCHWILGEWR      660
VGVKDQDKKD GAKYSYKDLC NELKQKVTKA GLVDFLLELD PCRTIPPYLD NNNRKPPKCQ      720
SLILNPKFLD NQYPNWQQYL QELKKLQSIQ NYLDSFETDL KVLKSSKDQP YFVEYKSSNQ      780
QIASGQRDYK DLDARILQFI FDRVKASDEL LLNEIYFQAK KLKQKASSEL EKLESSKKLD      840
EVIANSQLSQ ILKSQHTNGI FEQGTFLHLV CKYYKQRQRA RDSRLYIMPE YRYDKKLHKY      900
NNTGRFDDDN QLLTYCNHKP RQKRYQLLND LAGVLQVSPN FLKDKIGSDD DLFISKWLVE     960
HIRGFKKACE DSLKIQKDNR GLLNHKINIA RNTKGKCEKE IFNLICKIEG SEDKKGNYKH     1020
GLAYELGVLL FGEPNEASKP EFDRKIKKFN SIYSFAQIQQ IAFAERKGNA NTCAVCSADN     1080
AHRMQQIKIT EPVEDNKDKI ILSAKAQRLP AIPTRIVDGA VKKMATILAK NIVDDNWQNI     1140
KQVLSAKHQL HIPIITESNA FEFEPALADV KGKSLKDRRK KALERISPEN IFKDKNNRIK     1200
EFAKGISAYS GANLTDGFGD GAKEELDHII PRSHKKYGTL NDEANLICVT RGDNKNKGNR     1260
IFCLRDLADN YKLKQFETTD DLEIEKKIAD TIWDANKKDF KFGNYRSFIN LTPQEQKAFR     1320
HALFLADENP IKQAVIRAIN NRNRTFVNGT QRYFAEVLAN NIYLRAKKEN LNTDKISFDY     1380
FGIPTIGNGR GIAEIRQLYE KVDSDIQAYA KGDKPQASYS HLIDAMLAFC IAAADEHRNDG    1440
SIGLEIDKNY SLYPLDKNTG EVFTKDIFSQ IKITDNEFSD KKLVRKKAIE GFNTHRQMTR     1500
DGIYAENYLP ILIHKELNEV RKGYTWKNSE EIKIFKGKKY DIQQLNNLVY CLKFVDKPIS     1560
IDIQISTLEE LRNILTTNNI AATAEYYYIN LKTQKLHEYY IENYNTALGY KKYSKEMEFL     1620
RSLAYRSERV KIKSIDDVKQ VLDKDSNFII GKITLPFKKE WQRLYREWQN TTIKDDYEFL     1680
KSFFNVKSIT KLHKKVRKDF SLPISTNEGK FLVKRKTWDN NFIYQILNDS DTRADGTKPF     1740
IPAFDISKNE IVEAIIDSFT SKNIFWLPKN IELQKVDNKN IFAIDTSKWF EVETPSDLRD     1800
IGIATIQYKI DNNSRPKVRV KLDYVIDDDS KINYFMNHSL LKSRYPDKVL EILKQSTIIE     1860
FESSGFNKTI KEMLGMKLAG IYNETSNNSG GSGGSGGSTN LSDIIEKETG KQLVIQESIL     1920
MLPEEVEEVI GNKPESDILV HTAYDESTDE NVMLLTSDAP EYKPWALVIQ DSNGENKIKM     1980
LSGGSGGSGG STNLSDIIEK ETGKQLVIQE SILMLPEEVE EVIGNKPESD ILVHTAYDES     2040
TDENVMLLTS DAPEYKPWAL VIQDSNGENK IKML                                 2074

SEQ ID NO: 160          moltype = AA  length = 2074
FEATURE                 Location/Qualifiers
REGION                  1..2074
                        note = Fn/enFnCas9
source                  1..2074
                        mol_type = protein
                        organism = synthetic construct
SEQUENCE: 160
SSETGPVAVD PTLRRRIEPH EFEVFFDPRE LAAETCLLYE INWGGRHSIW RHTSQNTNKH       60
VEVNFIEKFT TERYFCPNTR CSITWFLSWS PCGECSRAIT EFLSRYPHVT LFIYIARLYH      120
HADPRNRQGL RDLISSGVTI QIMTEQESGY CWRNFVNYSP SNEAHWPRYP HLWVRLYVLE      180
LYCIILGLPP CLNILRRKQP QLTFFTIALQ SCHYQRLPPH ILWATGLKSG GSSGGSSGSE      240
TPGTSESATP ESSGGSSGGS NFKILPIAID LGVKNTGVFS AFYQKGTSLE RLDNKNGKVY      300
ELSKDSYTLL MNNRTARRHQ RRGIDRKQLV KRLFKLIWTE QLNLEWDKDT QQAISFLFNR      360
RGFSFITDGY SPEYLNIVPE QVKAILMDIF DDYNGEDDLD SYLKLATEQE SKISEIYNKL      420
MQKILEFKLM KLCTDIKDDK VSTKTLKEIT SYEFELLADY LANYSESLKT QKFSYTDKQG      480
NLKELSYYHH DKYNIQEFLK RHATINDRIL DTLLTDDLDI WNFNFEKPDF DKNEEKLQNQ      540
EDKDHIQAHL HHFVFAVNKI KSEMASGGRH RSQYFQEITN VLDENNHQEG YLKNFCENLH      600
NKKYSNLSVK NLVNLIGNLS NLELKPLRKY FNDKIHAKAD HWDEQKFTET YCHWILGEWR      660
VGVKDQDKKD GAKYSYKDLC NELKQKVTKA GLVDFLLELD PCRTIPPYLD NNNRKPPKCQ      720
SLILNPKFLD NQYPNWQQYL QELKKLQSIQ NYLDSFETDL KVLKSSKDQP YFVEYKSSNQ      780
QIASGQRDYK DLDARILQFI FDRVKASDEL LLNEIYFQAK KLKQKASSEL EKLESSKKLD      840
EVIANSQLSQ ILKSQHTNGI FEQGTFLHLV CKYYKQRQRA RDSRLYIMPE YRYDKKLHKY      900
NNTGRFDDDN QLLTYCNHKP RQKRYQLLND LAGVLQVSPN FLKDKIGSDD DLFISKWLVE      960
HIRGFKKACE DSLKIQKDNR GLLNHKINIA RNTKGKCEKE IFNLICKIEG SEDKKGNYKH     1020
GLAYELGVLL FGEPNEASKP EFDRKIKKFN SIYSFAQIQQ IAFAERKGNA NTCAVCSADN     1080
```

```
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTNEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DVNSRPKVRV KLDYVIDDDS KINYFMNHSL LKSRYPDKVL EILKQSTIIE  1860
FESSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 161          moltype = AA  length = 2074
FEATURE                 Location/Qualifiers
REGION                  1..2074
                        note = Fn/enFnCas9
source                  1..2074
                        mol_type = protein
                        organism = synthetic construct
SEQUENCE: 161
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH LIWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKFDF DKNEEKLQNQ  540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH 1020
GLAYELGVLL FGEPNEASKP EFDRKIKKFN SIYSFAQIQQ IAFAERKGNA NTCAVCSADN 1080
AHRMQQIKIT EPVEDNKDKI ILSAKAQRLP AIPTRIVDGA VKKMATILAK NIVDDNWQNI 1140
KQVLSAKHQL HIPIITESNA FEFEPALADV KGKSLKDRRK KALERISPEN IFKDKNNRIK 1200
EFAKGISAYS GANLTDGDFD GAKEELDHII PRSHKKYGTL NDEANLICVT RGDNKNKGNR 1260
IFCLRDLADN YKLKQFETTD DLEIEKKIAD TIWDANKKDF KFGNYRSFIN LTPQEQKAFR 1320
HALFLADENP IKQAVIRAIN NRNRTFVNGT QRYFAEVLAN NIYLRAKKEN LNTDKISFDY 1380
FGIPTIGNGR GIAEIRQLYE KVDSDIQAYA KGDKPQASYS HLIDAMLAFC IAADEHRNDG 1440
SIGLEIDKNY SLYPLDKNTG EVFTKDIFSQ IKITDNEFSD KKLVRKKAIE GFNTHRQMTR 1500
DGIYAENYLP ILIHKELNEV RKGYTWKNSE EIKIFKGKKY DIQQLNNLVY CLKFVDKPIS 1560
IDIQISTLEE LRNILTTNNI AATAEYYYIN LKTQKLHEYY IENYNTALGY KKYSKEMEFL 1620
RSLAYRSERV KIKSIDDVKQ VLDKDSNFII GKITLPFKKE WQRLYREWQN TTIKDDYEFL 1680
KSFFNVKSIT KLHKKVRKDF SLPISTNEGK FLVKRKTWDN NFIYQILNDS DSRADGTKPF 1740
IPAFDISKNE IVEAIIDSFT SKNIFWLPKN IELQKVDNKN IFAIDTSKWF EVETPSDLRD 1800
IGIATIQYKI DNNSRPKVRV KLDYVIDDDS KINYFMNHSL LKSRHPDKVL EILKQSTIIE 1860
FESSGFNKTI KEMLGMKLAG IYNETSNNSG GSGGSGGSTN LSDIIEKETG KQLVIQESIL 1920
MLPEEVEEVI GNKPESDILV HTAYDESTDE NVMLLTSDAP EYKPWALVIQ DSNGENKIKM 1980
LSGGSGGSGG STNLSDIIEK ETGKQLVIQE SILMLPEEVE EVIGNKPESD ILVHTAYDES 2040
TDENVMLLTS DAPEYKPWAL VIQDSNGENK IKML                              2074

SEQ ID NO: 162          moltype = AA  length = 2074
FEATURE                 Location/Qualifiers
REGION                  1..2074
                        note = Fn/enFnCas9
source                  1..2074
                        mol_type = protein
                        organism = synthetic construct
SEQUENCE: 162
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKFDF DKNEEKLQNQ  540
```

```
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLKDKIGSDD DLFISKWLVE    960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTDGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSERV KIKSIDDVKQ VLDKDSNFII GKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRRPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 163          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 163
SSETGPVAVD PTLRRRIEPH EFEVFFDPRE LAAETCLLYE INWGGRHSIW RHTSQNTNKH     60
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLKSG GSSGGSSGSE    240
TPGTSESATP ESSGGSSGGS NFKILPIAID LGVKNTGVFS AFYQKGTSLE RLDNKNGKVY    300
ELSKDSYTLL MNNRTARRHQ RRGIDRKQLV KRLFKLIWTE QLNLEWDKDT QQAISFLFNR    360
RGFSFITDGY SPEYLNIVPE QVKAILMDIF DDYNGEDDLD SYLKLATEQE SKISEIYNKL    420
MQKILEFKLM KLCTDIKDDK VSTKTLKEIT SYEFELLADY LANYSESLKT QKFSYTDKQG    480
NLKELSYYHH DKYNIQEFLK RHATINDRIL DTLLTDDLDI WNFNFEKPDF DKNEEKLQNQ    540
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLKDKIGSDD DLFISKWLVE    960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTDGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSERV KIKSIDDVKQ VLDKDSNFII GKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FHSSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 164          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 164
```

```
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNQGL  RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSRRV KIKSIDDVKQ VLDKDSNFII GKITLPFKKE WQRLYREWQN TTIKDDYEFL  1680
KSFFNVKSIT KLHKKVRKDF SLPISTNHGK FLVRKTWDN  NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSTPKVRV KLDYVIDDDS KINYFMNHSL LKSRYPDKVL EILKQSTIIE  1860
FESSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                             2074

SEQ ID NO: 165         moltype = AA  length = 2074
FEATURE                Location/Qualifiers
REGION                 1..2074
                       note = Fn/enFnCas9
source                 1..2074
                       mol_type = protein
                       organism = synthetic construct
SEQUENCE: 165
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNQGL  RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KYLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTNEGK FLVRKTWDN  NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FESSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                             2074
```

```
SEQ ID NO: 166           moltype = AA  length = 2074
FEATURE                  Location/Qualifiers
REGION                   1..2074
                         note = Fn/enFnCas9
source                   1..2074
                         mol_type = protein
                         organism = synthetic construct
SEQUENCE: 166
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKFDF DKNEEKLQNQ  540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH 1020
GLAYELGVLL FGEPNEASKP EFDRKIKKFN SIYSFAQIQQ IAFAERKGNA NTCAVCSADN 1080
AHRMQQIKIT EPVEDNKDKI ILSAKAQRLP AIPTRIVDGA VKKMATILAK NIVDDNWQNI 1140
KQVLSAKHQL HIPIITESNA FEFEPALADV KGKSLKDRRK KALERISPEN IFKDKNNRIK 1200
EFAKGISAYS GANLTDGDFD GAKEELDHII PRSHKKYGTL NDEANLICVT RGDNKNKGNR 1260
IFCLRDLADN YKLKQFETTD DLEIEKKIAD TIWDANKKDF KFGNYRSFIN LTPQEQKAFR 1320
HALFLADENP IKQAVIRAIN NRNRTFVNGT QRYFAEVLAN NIYLRAKKEN LNTDKISFDY 1380
FGIPTIGNGR GIAEIRQLYE KVDSDIQAYA KGDKPQASYS HLIDAMLAFC IAADEHRNDG 1440
SIGLEIDKNY SLYPLDKNTG EVFTKDIFSQ IKITDNEFSD KKLVRKKAIE GFNTHRQMTR 1500
DGIYAENYLP ILIHKELNEV RKGYTWKNSE EIKIFKGKKY DIQQLNNLVY CLKFVDKPIS 1560
IDIQISTLEE LRNILTTNNI AATAEYYYIN LKTQKLHEYY IENYNTALGY KKYSKEMEFL 1620
RSLAYRSERV KIKSIDDVKQ VLDKDSNFII GKITLPFKKE WQRLYREWQN TTIKDDYEFL 1680
KSFFNVKSIT KLHKKVRKDF SLPISTNEGK FLVKRKTWDN NFIYQILNDS DSRFDGTKPF 1740
IPAFDISKNE IVEAIIDSFT SKNIFWLPKN IELQKVDNKN IFAIDTSKWF EVETPSDLRD 1800
IGIATIQYKI DNNSRPKVRV KLDYVIDDDS KINYFMNHSL LKSRYPDKVL EILKQSTIIE 1860
FESSGFNKTI KEMLGMKLAG IYNETSNNSG GSGGSGGSTN LSDIIEKETG KQLVIQESIL 1920
MLPEEVEEVI GNKPESDILV HTAYDESTDE NVMLLTSDAP EYKPWALVIQ DSNGENKIKM 1980
LSGGSGGSGG STNLSDIIEK ETGKQLVIQE SILMLPEEVE EVIGNKPESD ILVHTAYDES 2040
TDENVMLLTS DAPEYKPWAL VIQDSNGENK IKML                             2074

SEQ ID NO: 167           moltype = AA  length = 2074
FEATURE                  Location/Qualifiers
REGION                   1..2074
                         note = Fn/enFnCas9
source                   1..2074
                         mol_type = protein
                         organism = synthetic construct
SEQUENCE: 167
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKFDF DKNEEKLQNQ  540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH 1020
GLAYELGVLL FGEPNEASKP EFDRKIKKFN SIYSFAQIQQ IAFAERKGNA NTCAVCSADN 1080
AHRMQQIKIT EPVEDNKDKI ILSAKAQRLP AIPTRIVDGA VKKMATILAK NIVDDNWQNI 1140
KQVLSAKHQL HIPIITESNA FEFEPALADV KGKSLKDRRK KALERISPEN IFKDKNNRIK 1200
EFAKGISAYS GANLTDGDFD GAKEELDHII PRSHKKYGTL NDEANLICVT RGDNKNKGNR 1260
IFCLRDLADN YKLKQFETTD DLEIEKKIAD TIWDANKKDF KFGNYRSFIN LTPQEQKAFR 1320
HALFLADENP IKQAVIRAIN NRNRTFVNGT QRYFAEVLAN NIYLRAKKEN LNTDKISFDY 1380
FGIPTIGNGR GIAEIRQLYE KVDSDIQAYA KGDKPQASYS HLIDAMLAFC IAADEHRNDG 1440
SIGLEIDKNY SLYPLDKNTG EVFTKDIFSQ IKITDNEFSD KKLVRKKAIE GFNTHRQMTR 1500
DGIYAENYLP ILIHKELNEV RKGYTWKNSE EIKIFKGKKY DIQQLNNLVY CLKFVDKPIS 1560
```

-continued

```
IDIQISTLEE LRNILTTNNI AATAEYYYIN LKTQKLHEYY IENYNTALGY KKYSKEMEFL   1620
RSLAYRSERV KIKSIDDVKQ VLDKDSNFII GKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDHFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074

SEQ ID NO: 168        moltype = AA   length = 2074
FEATURE               Location/Qualifiers
REGION                1..2074
                      note = Fn/enFnCas9
source                1..2074
                      mol_type = protein
                      organism = synthetic construct
SEQUENCE: 168
SSETGPVAVD PTLRRRIEPH EFEVFFDPRE LAAETCLLYE INWGGRHSIW RHTSQNTNKH     60
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLKSG GSSGGSSGSE    240
TPGTSESATP ESSGGSSGGS NFKILPIAID LGVKNTGVFS AFYQKGTSLE RLDNKNGKVY    300
ELSKDSYTLL MNNRTARRHQ RRGIDRKQLV KRLFKLIWTE QLNLEWDKDT QQAISFLFNR    360
RGFSFITDGY SPEYLNIVPE QVKAILMDIF DDYNGEDDLD SYLKLATEQE SKISEIYNKL    420
MQKILEFKLM KLCTDIKDDK VSTKTLKEIT SYEFELLADY LANYSESLKT QKFSYTDKQG    480
NLKELSYYHH DKYNIQEFLK RHATINDRIL DTLLTDDLDI WNFNFEKFDF DKNEEKLQNQ    540
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLKDKIGSDD DLFISKWLVE    960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTDGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSERV KIKSIDDVKQ VLDKDSNFII GKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHRL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074

SEQ ID NO: 169        moltype = AA   length = 2074
FEATURE               Location/Qualifiers
REGION                1..2074
                      note = Fn/enFnCas9
source                1..2074
                      mol_type = protein
                      organism = synthetic construct
SEQUENCE: 169
SSETGPVAVD PTLRRRIEPH EFEVFFDPRE LAAETCLLYE INWGGRHSIW RHTSQNTNKH     60
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLKSG GSSGGSSGSE    240
TPGTSESATP ESSGGSSGGS NFKILPIAID LGVKNTGVFS AFYQKGTSLE RLDNKNGKVY    300
ELSKDSYTLL MNNRTARRHQ RRGIDRKQLV KRLFKLIWTE QLNLEWDKDT QQAISFLFNR    360
RGFSFITDGY SPEYLNIVPE QVKAILMDIF DDYNGEDDLD SYLKLATEQE SKISEIYNKL    420
MQKILEFKLM KLCTDIKDDK VSTKTLKEIT SYEFELLADY LANYSESLKT QKFSYTDKQG    480
NLKELSYYHH DKYNIQEFLK RHATINDRIL DTLLTDDLDI WNFNFEKFDF DKNEEKLQNQ    540
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLKDKIGSDD DLFISKWLVE    960
HIRGFKKACE DSLKIQKDNR GLLNHKINIA RNTKGKCEKE IFNLICKIEG SEDKKGNYKH   1020
```

```
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTNEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LRSRYPDKVL EILKQSTIIE  1860
FESSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 170          moltype = AA  length = 2074
FEATURE                 Location/Qualifiers
REGION                  1..2074
                        note = Fn/enFnCas9
source                  1..2074
                        mol_type = protein
                        organism = synthetic construct
SEQUENCE: 170
SSETGPVAVD PTLRRRIEPH EFEVFFDPRE LAAETCLLYE INWGGRHSIW RHTSQNTNKH  60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKPDF DKNEEKLQNQ  540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTGKCEKEK IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTNEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FESSGFNVTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 171          moltype = AA  length = 2074
FEATURE                 Location/Qualifiers
REGION                  1..2074
                        note = Fn/enFnCas9
source                  1..2074
                        mol_type = protein
                        organism = synthetic construct
SEQUENCE: 171
SSETGPVAVD PTLRRRIEPH EFEVFFDPRE LAAETCLLYE INWGGRHSIW RHTSQNTNKH  60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
```

```
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTNEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FESSGFNSTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 172         moltype = AA  length = 2074
FEATURE                Location/Qualifiers
REGION                 1..2074
                       note = Fn/enFnCas9
source                 1..2074
                       mol_type = protein
                       organism = synthetic construct
SEQUENCE: 172
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTNEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FESSGFNNTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 173         moltype = AA  length = 2074
FEATURE                Location/Qualifiers
source                 1..2074
                       mol_type = protein
                       organism = synthetic construct
SEQUENCE: 173
SSETGPVAVD PTLRRRIEPH EFEVFFDPRE LAAETCLLYE INWGGRHSIW RHTSQNTNKH    60
```

```
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLKSG GSSGGSSGSE    240
TPGTSESATP ESSGGSSGGS NFKILPIAID LGVKNTGVFS AFYQKGTSLE RLDNKNGKVY    300
ELSKDSYTLL MNNRTARRHQ RRGIDRKQLV KRLFKLIWTE QLNLEWDKDT QQAISFLFNR    360
RGFSFITDGY SPEYLNIVPE QVKAILMDIF DDYNGEDDLD SYLKLATEQE SKISEIYNKL    420
MQKILEFKLM KLCTDIKDDK VSTKTLKEIT SYEFELLADY LANYSESLKT QKFSYTDKQG    480
NLKELSYYHH DKYNIQEFLK RHATINDRIL DTLLTDDLDI WNFNFEKFDF DKNEEKLQNQ    540
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLKDKIGSDD DLFISKWLVE    960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSERV KIKSIDDVKQ VLDKDSNFII GKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESFGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074

SEQ ID NO: 174         moltype = AA  length = 2074
FEATURE                Location/Qualifiers
REGION                 1..2074
                       note = Fn/enFnCas9
source                 1..2074
                       mol_type = protein
                       organism = synthetic construct
SEQUENCE: 174
SSETGPVAVD PTLRRRIEPH EFEVFFDPRE LAAETCLLYE INWGGRHSIW RHTSQNTNKH     60
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLKSG GSSGGSSGSE    240
TPGTSESATP ESSGGSSGGS NFKILPIAID LGVKNTGVFS AFYQKGTSLE RLDNKNGKVY    300
ELSKDSYTLL MNNRTARRHQ RRGIDRKQLV KRLFKLIWTE QLNLEWDKDT QQAISFLFNR    360
RGFSFITDGY SPEYLNIVPE QVKAILMDIF DDYNGEDDLD SYLKLATEQE SKISEIYNKL    420
MQKILEFKLM KLCTDIKDDK VSTKTLKEIT SYEFELLADY LANYSESLKT QKFSYTDKQG    480
NLKELSYYHH DKYNIQEFLK RHATINDRIL DTLLTDDLDI WNFNFEKFDF DKNEEKLQNQ    540
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLKDKIGSDD DLFISKWLVE    960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSERV KIKSIDDVKQ VLDKDSNFII GKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESRGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074
```

```
SEQ ID NO: 175           moltype = AA   length = 2075
FEATURE                  Location/Qualifiers
REGION                   1..2075
                         note = Fn/enFnCas9
source                   1..2075
                         mol_type = protein
                         organism = synthetic construct
SEQUENCE: 175
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKPDF DKNEEKLQNQ  540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH 1020
GLAYELGVLL FGEPNEASKP EFDRKIKKFN SIYSFAQIQQ IAFAERKGNA NTCAVCSADN 1080
AHRMQQIKIT EPVEDNKDKI ILSAKAQRLP AIPTRIVDGA VKKMATILAK NIVDDNWQNI 1140
KQVLSAKHQL HIPIITESNA FEFEPALADV KGKSLKDRRK KALERISPEN IFKDKNNRIK 1200
EFAKGISAYS GANLTDGDFD GAKEELDHII PRSHKKYGTL NDEANLICVT RGDNKNKGNR 1260
IFCLRDLADN YKLKQFETTD DLEIEKKIAD TIWDANKKDF KFGNYRSFIN LTPQEQKAFR 1320
HALFLADENP IKQAVIRAIN NRNRTFVNGT QRYFAEVLAN NIYLRAKKEN LNTDKISFDY 1380
FGIPTIGNGR GIAEIRQLYE KVDSDIQAYA KGDKPQASYS HLIDAMLAFC IAADEHRNDG 1440
SIGLEIDKNY SLYPLDKNTG EVFTKDIFSQ IKITDNEFSD KKLVRKKAIE GFNTHRQMTR 1500
DGIYAENYLP ILIHKELNEV RKGYTWKNSE EIKIFKGKKY DIQQLNNLVY CLKFVDKPIS 1560
IDIQISTLEE LRNILTTNNI AATAEYYYIN LKTQKLHEYY IENYNTALGY KKYSKEMEFL 1620
RSLAYRSERV KIKSIDDVKQ VLDKDRSNFI IGKITLPFKK EWQRLYREWQ NTTIKDDYEF 1680
LKSFFNVKSI TKLHKKVRKD FSLPISTNEG KFLVKRKTWD NNFIYQILND SDSRADGTKP 1740
FIPAFDISKN EIVEAIIDSF TSKNIFWLPK NIELQVKDNK NIFAIDTSKW FEVETPSDLR 1800
DIGIATIQYK IDNNSRPKVR VKLDYVIDDD SKINYFMNHS LLKSRYPDKV LEILKQSTII 1860
EFESSGFNKT IKEMLGMKLA GIYNETSNNS GGSSGSGGST NLSDIIEKET GKQLVIQESI 1920
LMLPEEVEEV IGNKPESDIL VHTAYDESTD ENVMLLTSDA PEYKPWALVI QDSNGENKIK 1980
MLSGGSGGSS GSTNLSDIIE KETGKQLVIQ ESILMLPEEV EEVIGNKPES DILVHTAYDE 2040
STDENVMLLT SDAPEYKPWA LVIQDSNGEN KIKML                           2075

SEQ ID NO: 176           moltype = AA   length = 2074
FEATURE                  Location/Qualifiers
REGION                   1..2074
                         note = Fn/enFnCas9
source                   1..2074
                         mol_type = protein
                         organism = synthetic construct
SEQUENCE: 176
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKPDF DKNEEKLQNQ  540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH 1020
GLAYELGVLL FGEPNEASKP EFDRKIKKFN SIYSFAQIQQ IAFAERKGNA NTCAVCSADN 1080
AHRMQQIKIT EPVEDNKDKI ILSAKAQRLP AIPTRIVDGA VKKMATILAK NIVDDNWQNI 1140
KQVLSAKHQL HIPIITESNA FEFEPALADV KGKSLKDRRK KALERISPEN IFKDKNNRIK 1200
EFAKGISAYS GANLTDGDFD GAKEELDHII PRSHKKYGTL NDEANLICVT RGDNKNKGNR 1260
IFCLRDLADN YKLKQFETTD DLEIEKKIAD TIWDANKKDF KFGNYRSFIN LTPQEQKAFR 1320
HALFLADENP IKQAVIRAIN NRNRTFVNGT QRYFAEVLAN NIYLRAKKEN LNTDKISFDY 1380
FGIPTIGNGR GIAEIRQLYE KVDSDIQAYA KGDKPQASYS HLIDAMLAFC IAADEHRNDG 1440
SIGLEIDKNY SLYPLDKNTG EVFTKDIFSQ IKITDNEFSD KKLVRKKAIE GFNTHRQMTR 1500
DGIYAENYLP ILIHKELNEV RKGYTWKNSE EIKIFKGKKY DIQQLNNLVY CLKFVDKPIS 1560
IDIQISTLEE LRNILTTNNI AATAEYYYIN LKTQKLHEYY IENYNTALGY KKYSKEMEFL 1620
```

```
RSLAYRSERV KIKSIDDVKQ VLDKDSNFII GKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRHPDKVL EILKQSTIIE   1860
FHSSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                               2074

SEQ ID NO: 177          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 177
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNEKFDF DKNEEKLQNQ    540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTDGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSERV KIKSIDDVKQ VLDKDSNFII KKITLPFKKE WQRLYREWQN TTIKDDYEFL   1680
KSFFNVKSIT KLHKKVRKDF SLPISTYEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                               2074

SEQ ID NO: 178          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 178
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNEKFDF DKNEEKLQNQ    540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
```

```
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTDGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DTIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSRRV KIKSIDDVKQ VLDKDSNFII GKITLPFKKE WQRLYREWQN TTIKDDYEFL   1680
KSFFNVKSIT KLHKKVRKDF SLPISTNHGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074

SEQ ID NO: 179         moltype = AA  length = 2074
FEATURE                Location/Qualifiers
REGION                 1..2074
                       note = Fn/enFnCas9
source                 1..2074
                       mol_type = protein
                       organism = synthetic construct
SEQUENCE: 179
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTDGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSRRV KIKSIDDVKQ VLDKDSNFII KKITLPFKKE WQRLYREWQN TTIKDDYEFL   1680
KSFFNVKSIT KLHKKVRKDF SLPISTNHGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074

SEQ ID NO: 180         moltype = AA  length = 2074
FEATURE                Location/Qualifiers
REGION                 1..2074
                       note = Fn/enFnCas9
source                 1..2074
                       mol_type = protein
                       organism = synthetic construct
SEQUENCE: 180
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
```

```
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH 1020
GLAYELGVLL FGEPNEASKP EFDRKIKKFN SIYSFAQIQQ IAFAERKGNA NTCAVCSADN 1080
AHRMQQIKIT EPVEDNKDKI ILSAKAQRLP AIPTRIVDGA VKKMATILAK NIVDDNWQNI 1140
KQVLSAKHQL HIPIITESNA FEFEPALADV KGKSLKDRRK KALERISPEN IFKDKNNRIK 1200
EFAKGISAYS GANLTDGDFD GAKEELDHII PRSHKKYGTL NDEANLICVT RGDNKNKGNR 1260
IFCLRDLADN YKLKQFETTD DLEIEKKIAD TIWDANKKDF KFGNYRSFIN LTPQEQKAFR 1320
HALFLADENP IKQAVIRAIN NRNRTFVNGT QRYFAEVLAN NIYLRAKKEN LNTDKISFDY 1380
FGIPTIGNGR GIAEIRQLYE KVDSDIQAYA KGDKPQASYS HLIDAMLAFC IAADEHRNDG 1440
SIGLEIDKNY SLYPLDKNTG EVFTKDIFSQ IKITDNEFSD KKLVRKKAIE GFNTHRQMTR 1500
DGIYAENYLP ILIHKELNEV RKGYTWKNSE EIKIFKGKKY DIQQLNNLVY CLKFVDKPIS 1560
IDIQISTLEE LRNILTTNNI AATAEYYYIN LKTQKLHEYY IENYNTALGY KKYSKEMEFL 1620
RSLAYRSRRV KIKSIDDVKQ VLDKDSNFII GKITLPFKKE WQRLYREWQN TTIKDDYEFL 1680
KSFFNVKSIT KLHKKVRKDF SLPISTYHGK FLVKRKTWDN NFIYQILNDS DSRADGTKPF 1740
IPAFDISKNE IVEAIIDSFT SKNIFWLPKN IELQKVDNKN IFAIDTSKWF EVETPSDLRD 1800
IGIATIQYKI DNNSRPKVRV KLDYVIDDDS KINYFMNHSL LKSRYPDKVL EILKQSTIIE 1860
FESSGFNKTI KEMLGMKLAG IYNETSNNSG GSGGSGGSTN LSDIIEKETG KQLVIQESIL 1920
MLPEEVEEVI GNKPESDILV HTAYDESTDE NVMLLTSDAP EYKPWALVIQ DSNGENKIKM 1980
LSGGSGGSGG STNLSDIIEK ETGKQLVIQE SILMLPEEVE EVIGNKPESD ILVHTAYDES 2040
TDENVMLLTS DAPEYKPWAL VIQDSNGENK IKML                           2074

SEQ ID NO: 181         moltype = AA   length = 2074
FEATURE                Location/Qualifiers
REGION                 1..2074
                       note = Fn/enFnCas9
source                 1..2074
                       mol_type = protein
                       organism = synthetic construct
SEQUENCE: 181
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKPDF DKNEEKLQNQ  540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH 1020
GLAYELGVLL FGEPNEASKP EFDRKIKKFN SIYSFAQIQQ IAFAERKGNA NTCAVCSADN 1080
AHRMQQIKIT EPVEDNKDKI ILSAKAQRLP AIPTRIVDGA VKKMATILAK NIVDDNWQNI 1140
KQVLSAKHQL HIPIITESNA FEFEPALADV KGKSLKDRRK KALERISPEN IFKDKNNRIK 1200
EFAKGISAYS GANLTDGDFD GAKEELDHII PRSHKKYGTL NDEANLICVT RGDNKNKGNR 1260
IFCLRDLADN YKLKQFETTD DLEIEKKIAD TIWDANKKDF KFGNYRSFIN LTPQEQKAFR 1320
HALFLADENP IKQAVIRAIN NRNRTFVNGT QRYFAEVLAN NIYLRAKKEN LNTDKISFDY 1380
FGIPTIGNGR GIAEIRQLYE KVDSDIQAYA KGDKPQASYS HLIDAMLAFC IAADEHRNDG 1440
SIGLEIDKNY SLYPLDKNTG EVFTKDIFSQ IKITDNEFSD KKLVRKKAIE GFNTHRQMTR 1500
DGIYAENYLP ILIHKELNEV RKGYTWKNSE EIKIFKGKKY DIQQLNNLVY CLKFVDKPIS 1560
IDIQISTLEE LRNILTTNNI AATAEYYYIN LKTQKLHEYY IENYNTALGY KKYSKEMEFL 1620
RSLAYRSRRV KIKSIDDVKQ VLDKDSNFII GKITLPFKKE WQRLYREWQN TTIKDDYEFL 1680
KSFFNVKSIT KLHKKVRKDF SLPISTNEGK FLVKRKTWDN NFIYQILNDS DSRADGTKPF 1740
IPAFDISKNE IVEAIIDSFT SKNIFWLPKN IELQKVDNKN IFAIDTSKWF EVETPSDLRD 1800
IGIATIQYKI DNNSRPKVRV KLDYVIDDDS KINYFMNHSL LKSRYPDKVL EILKQSTIIE 1860
FHSSGFNKTI KEMLGMKLAG IYNETSNNSG GSGGSGGSTN LSDIIEKETG KQLVIQESIL 1920
MLPEEVEEVI GNKPESDILV HTAYDESTDE NVMLLTSDAP EYKPWALVIQ DSNGENKIKM 1980
LSGGSGGSGG STNLSDIIEK ETGKQLVIQE SILMLPEEVE EVIGNKPESD ILVHTAYDES 2040
TDENVMLLTS DAPEYKPWAL VIQDSNGENK IKML                           2074

SEQ ID NO: 182         moltype = AA   length = 2074
FEATURE                Location/Qualifiers
REGION                 1..2074
                       note = Fn/enFnCas9
source                 1..2074
                       mol_type = protein
                       organism = synthetic construct
SEQUENCE: 182
```

```
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNQGL  RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKFDF DKNEEKLQNQ  540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH 1020
GLAYELGVLL FGEPNEASKP EFDRKIKKFN SIYSFAQIQQ IAFAERKGNA NTCAVCSADN 1080
AHRMQQIKIT EPVEDNKDKI ILSAKAQRLP AIPTRIVDGA VKKMATILAK NIVDDNWQNI 1140
KQVLSAKHQL HIPIITESNA FEFEPALADV KGKSLKDRRK KALERISPEN IFKDKNNRIK 1200
EFAKGISAYS GANLTDGDFD GAKEELDHII PRSHKKYGTL NDEANLICVT RGDNKNKGNR 1260
IFCLRDLADN YKLKQFETTD DLEIEKKIAD TIWDANKKDF KFGNYRSFIN LTPQEQKAFR 1320
HALFLADENP IKQAVIRAIN NRNRTFVNGT QRYFAEVLAN NIYLRAKKEN LNTDKISFDY 1380
FGIPTIGNGR GIAEIRQLYE KVDSDIQAYA KGDKPQASYS HLIDAMLAFC IAADEHRNDG 1440
SIGLEIDKNY SLYPLDKNTG EVFTKDIFSQ IKITDNEFSD KKLVRKKAIE GFNTHRQMTR 1500
DGIYAENYLP ILIHKELNEV RKGYTWKNSE EIKIFKGKKY DIQQLNNLVY CLKFVDKPIS 1560
IDIQISTLEE LRNILTTNNI AATAEYYYIN LKTQKLHEYY IENYNTALGY KKYSKEMEFL 1620
RSLAYRSRRV KIKSIDDVKQ VLDKDSNFII KKITLPFKKE WQLRYREWQN TTIKDDYEFL 1680
KSFFNVKSIT KLHKKVRKDF SLPISTNEGK FLVKRKTWDN NFIYQILNDS DSRADGTKPF 1740
IPAFDISKNE IVEAIIDSFT SKNIFWLPKN IELQKVDNKN IFAIDTSKWF EVETPSDLRD 1800
IGIATIQYKI DNNSRPKVRV KLDYVIDDDS KINYFMNHSL LKSRYPDKVL EILKQSTIIE 1860
FESSGFNKTI KEMLGMKLAG IYNETSNNSG GSGGSGGSTN LSDIIEKETG KQLVIQESIL 1920
MLPEEVEEVI GNKPESDILV HTAYDESTDE NVMLLTSDAP EYKPWALVIQ DSNGENKIKM 1980
LSGGSGGSGG STNLSDIIEK ETGKQLVIQE SILMLPEEVE EVIGNKPESD ILVHTAYDES 2040
TDENVMLLTS DAPEYKPWAL VIQDSNGENK IKML                            2074

SEQ ID NO: 183          moltype = AA  length = 2074
FEATURE                 Location/Qualifiers
REGION                  1..2074
                        note = Fn/enFnCas9
source                  1..2074
                        mol_type = protein
                        organism = synthetic construct
SEQUENCE: 183
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNQGL  RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKFDF DKNEEKLQNQ  540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTKGKCEKE IFNLICKIEG SEDKKGNYKH 1020
GLAYELGVLL FGEPNEASKP EFDRKIKKFN SIYSFAQIQQ IAFAERKGNA NTCAVCSADN 1080
AHRMQQIKIT EPVEDNKDKI ILSAKAQRLP AIPTRIVDGA VKKMATILAK NIVDDNWQNI 1140
KQVLSAKHQL HIPIITESNA FEFEPALADV KGKSLKDRRK KALERISPEN IFKDKNNRIK 1200
EFAKGISAYS GANLTDGDFD GAKEELDHII PRSHKKYGTL NDEANLICVT RGDNKNKGNR 1260
IFCLRDLADN YKLKQFETTD DLEIEKKIAD TIWDANKKDF KFGNYRSFIN LTPQEQKAFR 1320
HALFLADENP IKQAVIRAIN NRNRTFVNGT QRYFAEVLAN NIYLRAKKEN LNTDKISFDY 1380
FGIPTIGNGR GIAEIRQLYE KVDSDIQAYA KGDKPQASYS HLIDAMLAFC IAADEHRNDG 1440
SIGLEIDKNY SLYPLDKNTG EVFTKDIFSQ IKITDNEFSD KKLVRKKAIE GFNTHRQMTR 1500
DGIYAENYLP ILIHKELNEV RKGYTWKNSE EIKIFKGKKY DIQQLNNLVY CLKFVDKPIS 1560
IDIQISTLEE LRNILTTNNI AATAEYYYIN LKTQKLHEYY IENYNTALGY KKYSKEMEFL 1620
RSLAYRSRRV KIKSIDDVKQ VLDKDSNFII GKITLPFKKE WQLRYREWQN TTIKDDYEFL 1680
KSFFNVKSIT KLHKKVRKDF SLPISTREGK FLVKRKTWDN NFIYQILNDS DSRADGTKPF 1740
IPAFDISKNE IVEAIIDSFT SKNIFWLPKN IELQKVDNKN IFAIDTSKWF EVETPSDLRD 1800
IGIATIQYKI DNNSRPKVRV KLDYVIDDDS KINYFMNHSL LKSRYPDKVL EILKQSTIIE 1860
FESSGFNKTI KEMLGMKLAG IYNETSNNSG GSGGSGGSTN LSDIIEKETG KQLVIQESIL 1920
MLPEEVEEVI GNKPESDILV HTAYDESTDE NVMLLTSDAP EYKPWALVIQ DSNGENKIKM 1980
LSGGSGGSGG STNLSDIIEK ETGKQLVIQE SILMLPEEVE EVIGNKPESD ILVHTAYDES 2040
TDENVMLLTS DAPEYKPWAL VIQDSNGENK IKML                            2074
```

-continued

```
SEQ ID NO: 184          moltype = AA  length = 2074
FEATURE                 Location/Qualifiers
REGION                  1..2074
                        note = Fn/enFnCas9
source                  1..2074
                        mol_type = protein
                        organism = synthetic construct
SEQUENCE: 184
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSRRV KIKSIDDVKQ VLDKDSNFII GKITLPFKKE WQRLYREWQN TTIKDDYEFL  1680
KSFFNVKSIT KLHKKVRKDF SLPISTYEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FESSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                             2074

SEQ ID NO: 185          moltype = AA  length = 2074
FEATURE                 Location/Qualifiers
REGION                  1..2074
                        note = Fn/enFnCas9
source                  1..2074
                        mol_type = protein
                        organism = synthetic construct
SEQUENCE: 185
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
```

```
IDIQISTLEE LRNILTTNNI AATAEYYYIN LKTQKLHEYY IENYNTALGY KKYSKEMEFL    1620
RSLAYRSRRV KIKSIDDVKQ VLDKDSNFII GKITLPFKKE WQRLYREWQN TTIKDDYEFL    1680
KSFFNVKSIT KLHKKVRKDF SLPISTNEGK FLVKRKTWDN NFIYQILNDS DSRFDGTKPF    1740
IPAFDISKNE IVEAIIDSFT SKNIFWLPKN IELQKVDNKN IFAIDTSKWF EVETPSDLRD    1800
IGIATIQYKI DNNSRPKVRV KLDYVIDDDS KINYFMNHSL LKSRYPDKVL EILKQSTIIE    1860
FESSGFNKTI KEMLGMKLAG IYNETSNNSG GSGGSGGSTN LSDIIEKETG KQLVIQESIL    1920
MLPEEVEEVI GNKPESDILV HTAYDESTDE NVMLLTSDAP EYKPWALVIQ DSNGENKIKM    1980
LSGGSGGSGG STNLSDIIEK ETGKQLVIQE SILMLPEEVE EVIGNKPESD ILVHTAYDES    2040
TDENVMLLTS DAPEYKPWAL VIQDSNGENK IKML                                2074

SEQ ID NO: 186          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 186
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLKSG GSSGGSSGSE    240
TPGTSESATP ESSGGSSGGS NFKILPIAID LGVKNTGVFS AFYQKGTSLE RLDNKNGKVY    300
ELSKDSYTLL MNNRTARRHQ RRGIDRKQLV KRLFKLIWTE QLNLEWDKDT QQAISFLFNR    360
RGFSFITDGY SPEYLNIVPE QVKAILMDIF DDYNGEDDLD SYLKLATEQE SKISEIYNKL    420
MQKILEFKLM KLCTDIKDDK VSTKTLKEIT SYEFELLADY LANYSESLKT QKFSYTDKQG    480
NLKELSYYHH DKYNIQEFLK RHATINDRIL DTLLTDDLDI WNFNFEKFDF DKNEEKLQNQ    540
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLDKIGSDD DLFISKWLVE    960
HIRGFKKACE DSLKIQKDNR GLLNHKINIA RNTKGKCEKE IFNLICKIEG SEDKKGNYKH    1020
GLAYELGVLL FGEPNEASKP EFDRKIKKFN SIYSFAQIQQ IAFAERKGNA NTCAVCSADN    1080
AHRMQQIKIT EPVEDNKDKI ILSAKAQRLP AIPTRIVDGA VKKMATILAK NIVDDNWQNI    1140
KQVLSAKHQL HIPIITESNA FEFEPALADV KGKSLKDRRK KALERISPEN IFKDKNNRIK    1200
EFAKGISAYS GANLTDGDFD GAKEELDHII PRSHKKYGTL NDEANLICVT RGDNKNKGNR    1260
IFCLRDLADN YKLKQFETTD DLEIEKKIAD TIWDANKKDF KFGNYRSFIN LTPQEQKAFR    1320
HALFLADENP IKQAVIRAIN NRNRTFVNGT QRYFAEVLAN NIYLRAKKEN LNTDKISFDY    1380
FGIPTIGNGR GIAEIRQLYE KVDSDIQAYA KGDKPQASYS HLIDAMLAFC IAADEHRNDG    1440
SIGLEIDKNY SLYPLDKNTG EVFTKDIFSQ IKITDNEFSD KKLVRKKAIE GFNTHRQMTR    1500
DGIYAENYLP ILIHKELNEV RKGYTWKNSE EIKIFKGKKY DIQQLNNLVY CLKFVDKPIS    1560
IDIQISTLEE LRNILTTNNI AATAEYYYIN LKTQKLHEYY IENYNTALGY KKYSKEMEFL    1620
RSLAYRSRRV KIKSIDDVKQ VLDKDSNFII GKITLPFKKE WQRLYREWQN TTIKDDYEFL    1680
KSFFNVKSIT KLHKKVRKDF SLPISTNEGK FLVKRKTWDN NFIYQILNDS DSRADGTKPF    1740
IPAFDISKNE IVEAIIDSFT SKNIFWLPKN IELQKVDNKN IFAIDTSKWF EVETPSDLRD    1800
IGIATIQYKI DNNSRPKVRV KLDYVIDDDS KINYFMNHRL LKSRYPDKVL EILKQSTIIE    1860
FESSGFNKTI KEMLGMKLAG IYNETSNNSG GSGGSGGSTN LSDIIEKETG KQLVIQESIL    1920
MLPEEVEEVI GNKPESDILV HTAYDESTDE NVMLLTSDAP EYKPWALVIQ DSNGENKIKM    1980
LSGGSGGSGG STNLSDIIEK ETGKQLVIQE SILMLPEEVE EVIGNKPESD ILVHTAYDES    2040
TDENVMLLTS DAPEYKPWAL VIQDSNGENK IKML                                2074

SEQ ID NO: 187          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 187
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLKSG GSSGGSSGSE    240
TPGTSESATP ESSGGSSGGS NFKILPIAID LGVKNTGVFS AFYQKGTSLE RLDNKNGKVY    300
ELSKDSYTLL MNNRTARRHQ RRGIDRKQLV KRLFKLIWTE QLNLEWDKDT QQAISFLFNR    360
RGFSFITDGY SPEYLNIVPE QVKAILMDIF DDYNGEDDLD SYLKLATEQE SKISEIYNKL    420
MQKILEFKLM KLCTDIKDDK VSTKTLKEIT SYEFELLADY LANYSESLKT QKFSYTDKQG    480
NLKELSYYHH DKYNIQEFLK RHATINDRIL DTLLTDDLDI WNFNFEKFDF DKNEEKLQNQ    540
EDKDHIQAHL HHFVFAVNKI KSEMASGGRH RSQYFQEITN VLDENNHQEG YLKNFCENLH    600
NKKYSNLSVK NLVNLIGNLS NLELKPLRKY FNDKIHAKAD HWDEQKFTET YCHWILGEWR    660
VGVKDQDKKD GAKYSYKDLC NELKQKVTKA GLVDFLLELD PCRTIPPYLD NNNRKPPKCQ    720
SLILNPKFLD NQYPNWQQYL QELKKLQSIQ NYLDSFETDL KVLKSSKDQP YFVEYKSSNQ    780
QIASGQRDYK DLDARILQFI FDRVKASDEL LLNEIYFQAK KLKQKASSEL EKLESSKKLD    840
EVIANSQLSQ ILKSQHTNGI FEQGTFLHLV CKYYKQRQRA RDSRLYIMPE YRYDKKLHKY    900
NNTGRFDDDN QLLTYCNHKP RQKRYQLLND LAGVLQVSPN FLDKIGSDD DLFISKWLVE    960
HIRGFKKACE DSLKIQKDNR GLLNHKINIA RNTKGKCEKE IFNLICKIEG SEDKKGNYKH    1020
```

```
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTDGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DTIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSRRV KIKSIDDVKQ VLDKDSNFII GKITLPFKKE WQRLYREWQN TTIKDDYEFL   1680
KSFFNVKSIT KLHKKVRKDF SLPISTNEGK FLVKRKTWDN NFIYQILNDS DSRADGTKPF   1740
IPAFDISKNE IVEAIIDSFT SKNIFWLPKN IELQKVDNKN IFAIDTSKWF EVETPSDLRD   1800
IGIATIQYKI DNNSRPKVRV KLDYVIDDDS KINYFMNHSL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074

SEQ ID NO: 188          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 188
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
NLKELSYYHH DKYNIQEFLK RHATINDRIL DTLLTDDLDI WNFNFEKPDF DKNEEKLQNQ  540
EDKDHIQAHL HHFVFAVNKI KSEMASGGRH RSQYFQEITN VLDENNHQEG YLKNFCENLH  600
NKKYSNLSVK NLVNLIGNLS NLELKPLRKY FNDKIHAKAD HWDEQKFTET YCHWILGEWR  660
VGVKDQDKKD GAKYSYKDLC NELKQKVTKA GLVDFLLELD PCRTIPPYLD NNNRKPPKCQ  720
SLILNPKFLD NQYPNWQQYL QELKKLQSIQ NYLDSFETDL KVLKSSKDQP YFVEYKSSNQ  780
QIASGQRDYK DLDARILQFI FDRVKASDEL LLNEIYFQAK KLKQKASSEL EKLESSKKLD  840
EVIANSQLSQ ILKSQHTNGI FEQGTFLHLV CKYYKQRQRA RDSRLYIMPE YRYDKKLHKY  900
NNTGRFDDDN QLLTYCNHKP RQKRYQLLND LAGVLQVSPN FLKDKIGSDD DLFISKWLVE  960
HIRGFKKACE DSLKIQKDNR GLLNHKINIA RNTGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTDGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSRRV KIKSIDDVKQ VLDKDSNFII GKITLPFKKE WQRLYREWQN TTIKDDYEFL  1680
KSFFNVKSIT KLHKKVRKDF SLPISTNEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSQPKVRV KLDYVIDDDS KINYFMNHSL LKSRYPDKVL EILKQSTIIE  1860
FESSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 189          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 189
SSETGPVAVD PTLRRRIEPH EFEVFFDPRE LAAETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLKSG GSSGGSSGSE  240
TPGTSESATP ESSGGSSGGS NFKILPIAID LGVKNTGVFS AFYQKGTSLE RLDNKNGKVY  300
ELSKDSYTLL MNNRTARRHQ RRGIDRKQLV KRLFKLIWTE QLNLEWDKDT QQAISFLFNR  360
RGFSFITDGY SPEYLNIVPE QVKAILMDIF DDYNGEDDLD SYLKLATEQE SKISEIYNKL  420
MQKILEFKLM KLCTDIKDDK VSTKTLKEIT SYEFELLADY LANYSESLKT QKFSYTDKQG  480
```

```
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII KKITLPFKKE WQRLYREWQN TTIKDDYEFL  1680
KSFFNVKSIT KLHKKVRKDF SLPISTNEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FHSSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 190         moltype = AA  length = 2074
FEATURE                Location/Qualifiers
REGION                 1..2074
                       note = Fn/enFnCas9
source                 1..2074
                       mol_type = protein
                       organism = synthetic construct
SEQUENCE: 190
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWTE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTGDFD GAKEELDHII PRSHKKYGTL NDEANLICVT RGDNKNKGNR  1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTREGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FHSSGFNKTI KEMLGMKLAG IYNETSNNSG GSGGSGGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 191         moltype = AA  length = 2074
FEATURE                Location/Qualifiers
REGION                 1..2074
                       note = Fn/enFnCas9
source                 1..2074
                       mol_type = protein
                       organism = synthetic construct
```

```
SEQUENCE: 191
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKIWTE QLNLEWDKDT QQAISFLFNR    360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTYEGK FLVKRKTWDN NFIYQILNDS DSRADGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FHSSGFNKTI KEMLGMKLAG IYNETSNNSG GSGGSGSGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
TDENVMLLTS DAPEYKPWAL VIQDSNGENK IKML                              2074

SEQ ID NO: 192       moltype = AA  length = 2074
FEATURE              Location/Qualifiers
REGION               1..2074
                     note = Fn/enFnCas9
source               1..2074
                     mol_type = protein
                     organism = synthetic construct SEQUENCE: 192
SSETGPVAVD PTLRRRIEPH EFEVFFDPRE LAAETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKIWTE QLNLEWDKDT QQAISFLFNR    360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTNGI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH  1020
GLAYELGVLL FGEPNEASKP EFDRKIKKFN SIYSFAQIQQ IAFAERKGNA NTCAVCSADN  1080
AHRMQQIKIT EPVEDNKDKI ILSAKAQRLP AIPTRIVDGA VKKMATILAK NIVDDNWQNI  1140
KQVLSAKHQL HIPIITESNA FEFEPALADV KGKSLKDRRK KALERISPEN IFKDKNNRIK  1200
EFAKGISAYS GANLTGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR  1320
HALFLADENP IKQAVIRAIN NRNRTFVNGT QRYFAEVLAN NIYLRAKKEN LNTDKISFDY  1380
FGIPTIGNGR GIAEIRQLYE KVDSDIQAYA KGDKPQASYS HLIDAMLAFC IAADEHRNDG  1440
SIGLEIDKNY SLYPLDKNTG EVFTKDIFSQ IKITDNEFSD KKLVRKKAIE GFNTHRQMTR  1500
DGIYAENYLP ILIHKELNEV RKGYTWKNSE EIKIFKGKKY DIQQLNNLVY CLKFVDKPIS  1560
IDIQISTLEE LRNILTTNNI AATAEYYYIN LKTQKLHEYY IENYNTALGY KKYSKEMEFL  1620
RSLAYRSERV KIKSIDDVKQ VLDKDSNFII GKITLPFKKE WQRLYREWQN TTIKDDYEFL  1680
KSFFNVKSIT KLHKKVRKDF SLPISTNEGK FLVKRKTWDN NFIYQILNDS DSRFDGTKPF  1740
IPAFDISKNE IVEAIIDSFT SKNIFWLPKN IELQKVDNKN IFAIDTSKWF EVETPSDLRD  1800
IGIATIQYKI DNNSRPKVRV KLDYVIDDDS KINYFMNHSL LKSRYPDKVL EILKQSTIIE  1860
FHSSGFNKTI KEMLGMKLAG IYNETSNNSG GSGGSGSGSTN LSDIIEKETG KQLVIQESIL  1920
MLPEEVEEVI GNKPESDILV HTAYDESTDE NVMLLTSDAP EYKPWALVIQ DSNGENKIKM  1980
LSGGSGGSGG STNLSDIIEK ETGKQLVIQE SILMLPEEVE EVIGNKPESD ILVHTAYDES  2040
```

-continued

```
TDENVMLLTS DAPEYKPWAL VIQDSNGENK IKML                                  2074

SEQ ID NO: 193          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 193
SSETGPVAVD PTLRRRIEPH EFEVFFDPRE LAAETCLLYE INWGGRHSIW RHTSQNTNKH       60
VEVNFIEKFT TERYFCPNTR CSITWFLSWS PCGECSRAIT EFLSRYPHVT LFIYIARLYH       120
HADPRNRQGL RDLISSGVTI QIMTEQESGY CWRNFVNYSP SNEAHWPRYP HLWVRLYVLE       180
LYCIILGLPP CLNILRRKQP QLTFFTIALQ SCHYQRLPPH ILWATGLKSG GSSGGSSGSE       240
TPGTSESATP ESSGGSSGGS NFKILPIAID LGVKNTGVFS AFYQKGTSLE RLDNKNGKVY       300
ELSKDSYTLL MNNRTARRHQ RRGIDRKQLV KRLFKLIWTE QLNLEWDKDT QQAISFLFNR       360
RGFSFITDGY SPEYLNIVPE QVKAILMDIF DDYNGEDDLD SYLKLATEQE SKISEIYNKL       420
MQKILEFKLM KLCTDIKDDK VSTKTLKEIT SYEFELLADY LANYSESLKT QKFSYTDKQG       480
NLKELSYYHH DKYNIQEFLK RHATINDRIL DTLLTDDLDI WNFNFEKFDF DKNEEKLQNQ       540
EDKDHIQAHL HHFVFAVNKI KSEMASGGRH RSQYFQEITN VLDENNHQEG YLKNFCENLH       600
NKKYSNLSVK NLVNLIGNLS NLELKPLRKY FNDKIHAKAD HWDEQKFTET YCHWILGEWR       660
VGVKDQDKKD GAKYSYKDLC NELKQKVTKA GLVDFLLELD PCRTIPPYLD NNNRKPPKCQ       720
SLILNPKFLD NQYPNWQQYL QELKKLQSIQ NYLDSFETDL KVLKSSKDQP YFVEYKSSNQ       780
QIASGQRDYK DLDARILQFI FDRVKASDEL LLNEIYFQAK KLKQKASSEL EKLESSKKLD       840
EVIANSQLSQ ILKSQHTNGI FEQGTFLHLV CKYYKQRQRA RDSRLYIMPE YRYDKKLHKY       900
NNTGRFDDDN QLLTYCNHKP RQKRYQLLND LAGVLQVSPN FLKDKIGSDD DLFISKWLVE       960
HIRGFKKACE DSLKIQKDNR GLLNHKINIA RNTKGKCEKE IFNLICKIEG SEDKKGNYKH       1020
GLAYELGVLL FGEPNEASKP EFDRKIKKFN SIYSFAQIQQ IAFAERKGNA NTCAVCSADN      1080
AHRMQQIKIT EPVEDNKDKI ILSAKAQRLP AIPTRIVDGA VKKMATILAK NIVDDNWQNI      1140
KQVLSAKHQL HIPIITESNA FEFEPALADV KGKSLKDRRK KALERISPEN IFKDKNNRIK      1200
EFAKGISAYS GANLTDGDFD GAKEELDHII PRSHKKYGTL NDEANLICVT RGDNKNKGNR      1260
IFCLRDLADN YKLKQFETTD DLEIEKKIAD TIWDANKKDF KFGNYRSFIN LTPQEQKAFR      1320
HALFLADENP IKQAVIRAIN NRNRTFVNGT QRYFAEVLAN NIYLRAKKEN LNTDKISFDY      1380
FGIPTIGNGR GIAEIRQLYE KVDSDIQAYA KGDKPQASYS HLIDAMLAFC IAADEHRNDG      1440
SIGLEIDKNY SLYPLDKNTG EVFTKDIFSQ IKITDNEFSD KKLVRKKAIE GFNTHRQMTR      1500
DGIYAENYLP ILIHKELNEV RKGYTWKNSE EIKIFKGKKY DIQQLNNLVY CLKFVDKPIS      1560
IDIQISTLEE LRNILTTNNI AATAEYYYIN LKTQKLHEYY IENYNTALGY KKYSKEMEFL      1620
RSLAYRSERV KIKSIDDVKQ VLDKDSNFII GKITLPFKKE WQRLYREWQN TTIKDDYEFL      1680
KSFFNVKSIT KLHKKVRKDF SLPISTNEGK FLVRKTWDN NFIYQILNDS DSRADGTKPF      1740
IPAFDISKNE IVEAIIDSFT SKNIFWLPKN IELQKVDNKN IFAIDTSKWF EVETPSDLRD      1800
IGIATIQYKI DNNSRPKVRV KLDYVIDDDS KINYFMNHRL LKSRYPDKVL EILKQSTIIE      1860
FHSSGFNKTI KEMLGMKLAG IYNETSNNSG GSGGSGGSTN LSDIIEKETG KQLVIQESIL      1920
MLPEEVEEVI GNKPESDILV HTAYDESTDE NVMLLTSDAP EYKPWALVIQ DSNGENKIKM      1980
LSGGSGGSGG STNLSDIIEK ETGKQLVIQE SILMLPEEVE EVIGNKPESD ILVHTAYDES      2040
TDENVMLLTS DAPEYKPWAL VIQDSNGENK IKML                                  2074

SEQ ID NO: 194          moltype = AA   length = 2074
FEATURE                 Location/Qualifiers
REGION                  1..2074
                        note = Fn/enFnCas9
source                  1..2074
                        mol_type = protein
                        organism = synthetic construct
SEQUENCE: 194
SSETGPVAVD PTLRRRIEPH EFEVFFDPRE LAAETCLLYE INWGGRHSIW RHTSQNTNKH       60
VEVNFIEKFT TERYFCPNTR CSITWFLSWS PCGECSRAIT EFLSRYPHVT LFIYIARLYH       120
HADPRNRQGL RDLISSGVTI QIMTEQESGY CWRNFVNYSP SNEAHWPRYP HLWVRLYVLE       180
LYCIILGLPP CLNILRRKQP QLTFFTIALQ SCHYQRLPPH ILWATGLKSG GSSGGSSGSE       240
TPGTSESATP ESSGGSSGGS NFKILPIAID LGVKNTGVFS AFYQKGTSLE RLDNKNGKVY       300
ELSKDSYTLL MNNRTARRHQ RRGIDRKQLV KRLFKLIWTE QLNLEWDKDT QQAISFLFNR       360
RGFSFITDGY SPEYLNIVPE QVKAILMDIF DDYNGEDDLD SYLKLATEQE SKISEIYNKL       420
MQKILEFKLM KLCTDIKDDK VSTKTLKEIT SYEFELLADY LANYSESLKT QKFSYTDKQG       480
NLKELSYYHH DKYNIQEFLK RHATINDRIL DTLLTDDLDI WNFNFEKFDF DKNEEKLQNQ       540
EDKDHIQAHL HHFVFAVNKI KSEMASGGRH RSQYFQEITN VLDENNHQEG YLKNFCENLH       600
NKKYSNLSVK NLVNLIGNLS NLELKPLRKY FNDKIHAKAD HWDEQKFTET YCHWILGEWR       660
VGVKDQDKKD GAKYSYKDLC NELKQKVTKA GLVDFLLELD PCRTIPPYLD NNNRKPPKCQ       720
SLILNPKFLD NQYPNWQQYL QELKKLQSIQ NYLDSFETDL KVLKSSKDQP YFVEYKSSNQ       780
QIASGQRDYK DLDARILQFI FDRVKASDEL LLNEIYFQAK KLKQKASSEL EKLESSKKLD       840
EVIANSQLSQ ILKSQHTNGI FEQGTFLHLV CKYYKQRQRA RDSRLYIMPE YRYDKKLHKY       900
NNTGRFDDDN QLLTYCNHKP RQKRYQLLND LAGVLQVSPN FLKDKIGSDD DLFISKWLVE       960
HIRGFKKACE DSLKIQKDNR GLLNHKINIA RNTKGKCEKE IFNLICKIEG SEDKKGNYKH      1020
GLAYELGVLL FGEPNEASKP EFDRKIKKFN SIYSFAQIQQ IAFAERKGNA NTCAVCSADN      1080
AHRMQQIKIT EPVEDNKDKI ILSAKAQRLP AIPTRIVDGA VKKMATILAK NIVDDNWQNI      1140
KQVLSAKHQL HIPIITESNA FEFEPALADV KGKSLKDRRK KALERISPEN IFKDKNNRIK      1200
EFAKGISAYS GANLTDGDFD GAKEELDHII PRSHKKYGTL NDEANLICVT RGDNKNKGNR      1260
IFCLRDLADN YKLKQFETTD DLEIEKKIAD TIWDANKKDF KFGNYRSFIN LTPQEQKAFR      1320
HALFLADENP IKQAVIRAIN NRNRTFVNGT QRYFAEVLAN NIYLRAKKEN LNTDKISFDY      1380
FGIPTIGNGR GIAEIRQLYE KVDSDIQAYA KGDKPQASYS HLIDAMLAFC IAADEHRNDG      1440
SIGLEIDKNY SLYPLDKNTG EVFTKDIFSQ IKITDNEFSD KKLVRKKAIE GFNTHRQMTR      1500
```

```
DTIYAENYLP ILIHKELNEV RKGYTWKNSE EIKIFKGKKY DIQQLNNLVY CLKFVDKPIS 1560
IDIQISTLEE LRNILTTNNI AATAEYYYIN LKTQKLHEYY IENYNTALGY KKYSKEMEFL 1620
RSLAYRSERV KIKSIDDVKQ VLDKDSNFII GKITLPFKKE WQRLYREWQN TTIKDDYEFL 1680
KSFFNVKSIT KLHKKVRKDF SLPISTNEGK FLVKRKTWDN NFIYQILNDS DSRADGTKPF 1740
IPAFDISKNE IVEAIIDSFT SKNIFWLPKN IELQKVRKDN IFAIDTSKWF EVETPSDLRD 1800
IGIATIQYKI DNNSRPKVRV KLDYVIDDDS KINYFMNHSL LKSRYPDKVL EILKQSTIIE 1860
FHSSGFNKTI KEMLGMKLAG IYNETSNNSG GSGGSGGSTN LSDIIEKETG KQLVIQESIL 1920
MLPEEVEEVI GNKPESDILV HTAYDESTDE NVMLLTSDAP EYKPWALVIQ DSNGENKIKM 1980
LSGGSGGSGG STNLSDIIEK ETGKQLVIQE SILMLPEEVE EVIGNKPESD ILVHTAYDES 2040
TDENVMLLTS DAPEYKPWAL VIQDSNGENK IKML                              2074

SEQ ID NO: 195            moltype = AA  length = 2074
FEATURE                   Location/Qualifiers
REGION                    1..2074
                          note = Fn/enFnCas9
source                    1..2074
                          mol_type = protein
                          organism = synthetic construct
SEQUENCE: 195
SSETGPVAVD PTLRRRIEPH EFEVFFDPRE LAAETCLLYE INWGGRHSIW RHTSQNTNKH 60
VEVNFIEKFT TERYFCPNTR CSITWFLSWS PCGECSRAIT EFLSRYPHVT LFIYIARLYH 120
HADPRNRQGL RDLISSGVTI QIMTEQESGY CWRNFVNYSP SNEAHWPRYP HLWVRLYVLE 180
LYCIILGLPP CLNILRRKQP QLTFFTIALQ SCHYQRLPPH ILWATGLKSG GSSGGSSGSE 240
TPGTSESATP ESSGGSSGGS NFKILPIAID LGVKNTGVFS AFYQKGTSLE RLDNKNGKVY 300
ELSKDSYTLL MNNRTARRHQ RRGIDRKQLV KRLFKLIWTE QLNLEWDKDT QQAISFLFNR 360
RGFSFITDGY SPEYLNIVPE QVKAILMDIF DDYNGEDDLD SYLKLATEQE SKISEIYNKL 420
MQKILEFKLM KLCTDIKDDK VSTKTLKEIT SYEFELLADY LANYSESLKT QKFSYTDKQG 480
NLKELSYYHH DKYNIQEFLK RHATINDRIL DTLLTDDLDI WNFNFEKFDF DKNEEKLQNQ 540
EDKDHIQAHL HHFVFAVNKI KSEMASGGRH RSQYFQEITN VLDENNHQEG YLKNFCENLH 600
NKKYSNLSVK NLVNLIGNLS NLELKPLRKY FNDKIHAKAD HWDEQKFTET YCHWILGEWR 660
VGVKDQDKKD GAKYSYKDLC NELKQKVTKA GLVDFLLELD PCRTIPPYLD NNNRKPPKCQ 720
SLILNPKFLD NQYPNWQQYL QELKKLQSIQ NYLDSFETDL KVLKSSKDQP YFVEYKSSNQ 780
QIASGQRDYK DLDARILQFI FDRVKASDEL LLNEIYFQAK KLKQKASSEL EKLESSKKLD 840
EVIANSQLSQ ILKSQHTNGI FEQGTFLHLV CKYYKQRQRA RDSRLYIMPE YRYDKKLHKY 900
NNTGRFDDDN QLLTYCNHKP RQKRYQLLND LAGVLQVSPN FLKDKIGSDD DLFISKWLVE 960
HIRGFKKACE DSLKIQKDNR GLLNHKINIA RNTKGKCEKE IFNLICKIEG SEDKKGNYKH 1020
GLAYELGVLL FGEPNEASKP EFDRKIKKFN SIYSFAQIQQ IAFAERKGNA NTCAVCSADN 1080
AHRMQQIKIT EPVEDNKDKI ILSAKAQRLP AIPTRIVDGA VKKMATILAK NIVDDNWQNI 1140
KQVLSAKHQL HIPIITESNA FEFEPALADV KGKSLKDRRK KALERISPEN IFKDKNNRIK 1200
EFAKGISAYS GANLTGDFD GAKEELDHII PRSHKKYGTL NDEANLICVT RGDNKNKGNR 1260
IFCLRDLADN YKLKQFETTD DLEIEKKIAD TIWDANKKDF KFGNYRSFIN LTPQEQKAFR 1320
HALFLADENP IKQAVIRAIN NRNRTFVNGT QRYFAEVLAN NIYLRAKKEN LNTDKISFDY 1380
FGIPTIGNGR GIAEIRQLYE KVDSDIQAYA KGDKPQASYS HLIDAMLAFC IAADEHRNDG 1440
SIGLEIDKNY SLYPLDKNTG EVFTKDIFSQ IKITDNEFSD KKLVRKKAIE GFNTHRQMTR 1500
DGIYAENYLP ILIHKELNEV RKGYTWKNSE EIKIFKGKKY DIQQLNNLVY CLKFVDKPIS 1560
IDIQISTLEE LRNILTTNNI AATAEYYYIN LKTQKLHEYY IENYNTALGY KKYSKEMEFL 1620
RSLAYRSERV KIKSIDDVKQ VLDKDSNFII GKITLPFKKE WQRLYREWQN TTIKDDYEFL 1680
KSFFNVKSIT KLHKKVRKDF SLPISTNEGK FLVKRKTWDN NFIYQILNDS DSRADGTKPF 1740
IPAFDISKNE IVEAIIDSFT SKNIFWLPKN IELQKVDKN IFAIDTSKWF EVETPSDLRD 1800
IGIATIQYKI DNNSQPKVRV KLDYVIDDDS KINYFMNHSL LKSRYPDKVL EILKQSTIIE 1860
FHSSGFNKTI KEMLGMKLAG IYNETSNNSG GSGGSGGSTN LSDIIEKETG KQLVIQESIL 1920
MLPEEVEEVI GNKPESDILV HTAYDESTDE NVMLLTSDAP EYKPWALVIQ DSNGENKIKM 1980
LSGGSGGSGG STNLSDIIEK ETGKQLVIQE SILMLPEEVE EVIGNKPESD ILVHTAYDES 2040
TDENVMLLTS DAPEYKPWAL VIQDSNGENK IKML                              2074

SEQ ID NO: 196            moltype = AA  length = 2074
FEATURE                   Location/Qualifiers
REGION                    1..2074
                          note = Fn/enFnCas9
source                    1..2074
                          mol_type = protein
                          organism = synthetic construct
SEQUENCE: 196
SSETGPVAVD PTLRRRIEPH EFEVFFDPRE LAAETCLLYE INWGGRHSIW RHTSQNTNKH 60
VEVNFIEKFT TERYFCPNTR CSITWFLSWS PCGECSRAIT EFLSRYPHVT LFIYIARLYH 120
HADPRNRQGL RDLISSGVTI QIMTEQESGY CWRNFVNYSP SNEAHWPRYP HLWVRLYVLE 180
LYCIILGLPP CLNILRRKQP QLTFFTIALQ SCHYQRLPPH ILWATGLKSG GSSGGSSGSE 240
TPGTSESATP ESSGGSSGGS MNFKILPIAI DLGVKNTGVF SAFYQKGTSL ERLDNKNGKV 300
YELSKDSYTL LMNNRTARRH QRRGIDRKQL VKRLFKLIWT EQLNLEWDKD TQQAISFLFN 360
RRGFSFITDG YSPEYLNIVP EQVKAILMDI FDDYNGEDDL DSYLKLATEQ ESKISEIYNK 420
LMQKILEFKL MKLCTDIKDD KVSTKTLKEI TSYEFELLAD YLANYSESLK TQKFSYTDKQ 480
GNLKELSYYH HDKYNIQEFL KRHATINDRI LDTLLTDDLD IWNFNFEKFD FDKNEEKLQN 540
QEDKDHIQAH LHHFVFAVNK IKSEMASGGR HRSQYFQEIT NVLDENNHQE GYLKNFCENL 600
HNKKYSNLSV KNLVNLIGNL SNLELKPLRK YFNDKIHAKA DHWDEQKFTE TYCHWILGEW 660
RVGVKDQDKK DGAKYSYKDL CNELKQKVTK AGLVDFLLEL DPCRTIPPYL DNNNRKPPKC 720
QSLILNPKFL DNQYPNWQQY LQELKKLQSI QNYLDSFETD LKVLKSSKDQ PYFVEYKSSN 780
QQIASGQRDY KDLDARILQF IFDRVKASDE LLLNEIYFQA KKLKQKASSE LEKLESSKKL 840
DEVIANSQLS QILKSQHTNG IFEQGTFLHL VCKYYKQRQR ARDSRLYIMP EYRYDKKLHK 900
YNNTGRFDDD NQLLTYCNHK PRQKRYQLLN DLAGVLQVSP NFLKDKIGSD DDLFISKWLV 960
```

```
EHIRGFKKAC EDSLKIQKDN RGLLNHKINI ARNTKGKCEK EIFNLICKIE GSEDKKGNYK   1020
HGLAYELGVL LFGEPNEASK PEFDRKIKKF NSIYSFAQIQ QIAFAERKGN ANTCAVCSAD   1080
NAHRMQQIKI TEPVEDNKDK IILSAKAQRL PAIPTRIVDG AVKKMATILA KNIVDDNWQN   1140
IKQVLSAKHQ LHIPIITESN AFEFEPALAD VKGKSLKDRR KKALERISPE NIFKDKNNRI   1200
KEFAKGISAY SGANLTGDPF DGAKEELDHI IPRSHKKYGT LNDEANLICV TRGDNKNKGN   1260
RIFCLRDLAD NYKLKQFETT DDLEIEKKIA DTIWDANKKD FKFGNYRSFI NLTPQEQKAF   1320
RHALFLADEN PIKQAVIRAI NNRNRTFVNG TQRYFAEVLA NNIYLRAKKE NLNTDKISFD   1380
YFGIPTIGNG RGIAEIRQLY EKVDSDIQAY AKGDKPQASY SHLIDAMLAF CIAADEHRND   1440
GSIGLEIDKN YSLYPLDKNT GEVFTKDIFS QIKITDNEFS DKKLVRKKAI EGFNTHRQMT   1500
RDGIYAENYL PILIHKELNE VRKGYTWKNS EEIKIFKGKK YDIQQLNNLV YCLKFVDKPI   1560
SIDIQISTLE ELRNILTTNN IAATAEYYYI NLKTQKLHEY YIENYNTALG YKKYSKEMEF   1620
LRSLAYRSER VKIKSIDDVK QVLDKDSNFI IGKITLPFKK EWQRLYREWQ NTTIKDDYEF   1680
LKSFFNVKSI TKLHKKVRKD FSLPISTNEG KFLVKRKTWD NNFIYQILND SDRADGTKP   1740
FIPAPFDISKN EIVEAIIDSF TSKNIFWLPK NIELQKVDNK NIFAIDTSKW FEVETPSDLR   1800
DIGIATIQYK IDNNSQKVRV KLDYVIDDDS KINYFMNHSL LKSRYPDKVL EILKQSTIIE   1860
FESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074

SEQ ID NO: 197           moltype = AA  length = 2074
FEATURE                  Location/Qualifiers
REGION                   1..2074
                         note = Fn/enFnCas9
source                   1..2074
                         mol_type = protein
                         organism = synthetic construct
SEQUENCE: 197
SSETGPVAVD PTLRRRIEPH EFEVFFDPRE LAAETCLLYE INWGGRHSIW RHTSQNTNKH     60
VEVNFIEKFT TERYFCPNTR CSITWFLSWS PCGECSRAIT EFLSRYPHVT LPFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLKSG GSSGGSSGSE   240
TPGTSESATP ESSGGSSGGS NFKILPIAID LGVKNTGVFS AFYQKGTSLE RLDNKNGKVY   300
ELSKDSYTLL MNNRTARRHQ RRGIDRKQLV KRLFKLIWRE QLNLEWDKDT QQAISFLFNR   360
RGFSFITDGY SPEYLNIVPE QVKAILMDIF DDYNGEDDLD SYLKLATEQE SKISEIYNKL   420
MQKILEFKLM KLCTDIKDDK VSTKTLKEIT SYEFELLADY LANYSESLKT QKFSYTDKQG   480
NLKELSYYHH DKYNIQEFLK RHATINDRIL DTLLTDDLDI WNFNFEKFDF DKNEEKLQNQ   540
EDKDHIQAHL HHFVFAVNKI KSEMASGGRH RSQYFQEITN VLDENNHQEG YLKNFCENLH   600
NKKYSNLSVK NLVNLIGNLS NLELKPLRKY FNDKIHAKAD HWDEQKFTET YCHWILGEWR   660
VGVKDQDKKD GAKYSYKDLC NELKQKVTKA GLVDFLLELD PCRTIPPYLD NNNRKPPKCQ   720
SLILNPKFLD NQYPNWQQYL QELKKLQSIQ NYLDSFETDL KVLKSSKDQP YFVEYKSSNQ   780
QIASGQRDYK DLDARILQFI FDRVKASDEL LLNEIYFQAK KLKQKASSEL EKLESSKKLD   840
EVIANSQLSQ ILKSQHTLVI FEQGTFLHLV CKYYKQRQRA RDSRLYIMPE YRYDKKLHKY   900
NNTGRFDDDN QLLTYCNHKP RQKRYQLLND LAGVLQVSPN FLKDKIGSDD DLFISKWLVE   960
HIRGFKKACE DSLKIQKDNR GLLNHKINIA RNTKGKCEKE IFNLICKIEG SEDKKGNYKH   1020
GLAYELGVLL FGEPNEASKP EFDRKIKKFN SIYSFAQIQQ IAFAERKGNA NTCAVCSADN   1080
AHRMQQIKIT EPVEDNKDKI ILSAKAQRLP AIPTRIVDGA VKKMATILAK NIVDDNWQNI   1140
KQVLSAKHQL HIPIITESNA FEFEPALADV KGKSLKDRRK KALERISPEN IFKDKNNRIK   1200
EFAKGISAYS GANLTGDFD GAKEELDHII PRSHKKYGTL NDEANLICVT RGDNKNKGNR   1260
IFCLRDLADN YKLKQFETTD DLEIEKKIAD TIWDANKKDF KFGNYRSFIN LTPQEQKAFR   1320
HALFLADENP IKQAVIRAIN NRNRTFVNGT QRYFAEVLAN NIYLRAKKEN LNTDKISFDY   1380
FGIPTIGNGR GIAEIRQLYE KVDSDIQAYA KGDKPQASYS HLIDAMLAFC IAADEHRNDG   1440
SIGLEIDKNY SLYPLDKNTG EVFTKDIFSQ IKITDNEFSD KKLVRKKAIE GFNTHRQMTR   1500
DGIYAENYLP ILIHKELNEV RKGYTWKNSE EIKIFKGKKY DIQQLNNLVY CLKFVDKPIS   1560
IDIQISTLEE LRNILTTNNI AATAEYYYIN LKTQKLHEYY IENYNTALGY KKYSKEMEFL   1620
RSLAYRSRV KIKSIDDVKQ VLDKDSNFII GKITLPFKKE WQRLYREWQN TTIKDDYEFL   1680
KSFFNVKSIT KLHKKVRKDF SLPISTNHGK FLVKRKTWDN NFIYQILNDS DRADGTKPF   1740
IPAPFDISKNE IVEAIIDSFT SKNIFWLPKN IELQKVDNKN IFAIDTSKWF EVETPSDLRD   1800
IGIATIQYKI DNNSQKVRVK LDYVIDDDSK INYFMNHSLL KSRYPDKVLE ILKQSTIIEF   1860
ESSGFNKTI KEMLGMKLAG IYNETSNNSG GSGGSGGSTN LSDIIEKETG KQLVIQESIL   1920
MLPEEVEEVI GNKPESDILV HTAYDESTDE NVMLLTSDAP EYKPWALVIQ DSNGENKIKM   1980
LSGGSGGSGG STNLSDIIEK ETGKQLVIQE SILMLPEEVE EVIGNKPESD ILVHTAYDES   2040
TDENVMLLTS DAPEYKPWAL VIQDSNGENK IKML                              2074

SEQ ID NO: 198           moltype = DNA  length = 72
FEATURE                  Location/Qualifiers
source                   1..72
                         mol_type = other DNA
                         organism = Homo sapiens
SEQUENCE: 198
taatacgact cactataggg aattaggtgc gcttggcgtt tcagttgcgc cgaaaggcgc     60
tctgtaatca tt                                                       72

SEQ ID NO: 199           moltype = DNA  length = 73
FEATURE                  Location/Qualifiers
source                   1..73
                         mol_type = other DNA
                         organism = Homo sapiens
SEQUENCE: 199
```

```
taatacgact cactataggg aaattaggtg cgcttggcgt ttcagttgcg ccgaaaggcg    60
ctctgtaatc att                                                       73

SEQ ID NO: 200           moltype = DNA  length = 74
FEATURE                  Location/Qualifiers
source                   1..74
                         mol_type = other DNA
                         organism = Homo sapiens
SEQUENCE: 200
taatacgact cactataggg gaaattaggt gcgcttggcg tttcagttgc gccgaaaggc    60
gctctgtaat catt                                                      74

SEQ ID NO: 201           moltype = DNA  length = 75
FEATURE                  Location/Qualifiers
source                   1..75
                         mol_type = other DNA
                         organism = Homo sapiens
SEQUENCE: 201
taatacgact cactataggg ggaaattagg tgcgcttggc gtttcagttg cgccgaaagg    60
cgctctgtaa tcatt                                                     75

SEQ ID NO: 202           moltype = DNA  length = 76
FEATURE                  Location/Qualifiers
source                   1..76
                         mol_type = other DNA
                         organism = Homo sapiens
SEQUENCE: 202
taatacgact cactataggg gggaaattag gtgcgcttgg cgtttcagtt gcgccgaaag    60
gcgctctgta atcatt                                                    76

SEQ ID NO: 203           moltype = DNA  length = 20
FEATURE                  Location/Qualifiers
source                   1..20
                         mol_type = other DNA
                         organism = Homo sapiens
SEQUENCE: 203
gagtccgagc agaagaagaa                                                20

SEQ ID NO: 204           moltype = DNA  length = 20
FEATURE                  Location/Qualifiers
source                   1..20
                         mol_type = other DNA
                         organism = Homo sapiens
SEQUENCE: 204
gagttagagc agaagaagaa                                                20

SEQ ID NO: 205           moltype = DNA  length = 20
FEATURE                  Location/Qualifiers
source                   1..20
                         mol_type = other DNA
                         organism = Homo sapiens
SEQUENCE: 205
gagtctaagc agaagaagaa                                                20

SEQ ID NO: 206           moltype = DNA  length = 20
FEATURE                  Location/Qualifiers
source                   1..20
                         mol_type = other DNA
                         organism = Homo sapiens
SEQUENCE: 206
gtaacggcag acttctcctc                                                20

SEQ ID NO: 207           moltype = DNA  length = 20
FEATURE                  Location/Qualifiers
source                   1..20
                         mol_type = other DNA
                         organism = Homo sapiens
SEQUENCE: 207
ggaaaggcag acttctcctt                                                20

SEQ ID NO: 208           moltype = DNA  length = 20
FEATURE                  Location/Qualifiers
misc_feature             1..20
                         note = DNA sequence for transcribing crispr RNA
source                   1..20
                         mol_type = other DNA
                         organism = synthetic construct
SEQUENCE: 208
gcattttcag gaggaagcga                                                20
```

```
SEQ ID NO: 209          moltype = DNA  length = 20
FEATURE                 Location/Qualifiers
misc_feature            1..20
                        note = DNA sequence for transcribing crispr RNA
source                  1..20
                        mol_type = other DNA
                        organism = synthetic construct
SEQUENCE: 209
gcattttcag aaggaagcaa                                              20

SEQ ID NO: 210          moltype = DNA  length = 20
FEATURE                 Location/Qualifiers
source                  1..20
                        mol_type = other DNA
                        organism = Homo sapiens
SEQUENCE: 210
gctgcagaag ggattccatg                                              20

SEQ ID NO: 211          moltype = DNA  length = 20
FEATURE                 Location/Qualifiers
misc_feature            1..20
                        note = DNA sequence for transcribing crispr RNA
source                  1..20
                        mol_type = other DNA
                        organism = synthetic construct
SEQUENCE: 211
gctgcagaag ggattccaag                                              20

SEQ ID NO: 212          moltype = DNA  length = 20
FEATURE                 Location/Qualifiers
misc_feature            1..20
                        note = DNA sequence for transcribing crispr RNA
source                  1..20
                        mol_type = other DNA
                        organism = synthetic construct
SEQUENCE: 212
gctattggtc aaggcaaggc                                              20

SEQ ID NO: 213          moltype = DNA  length = 21
FEATURE                 Location/Qualifiers
misc_feature            1..21
                        note = DNA sequence for transcribing crispr RNA
source                  1..21
                        mol_type = other DNA
                        organism = synthetic construct
SEQUENCE: 213
ggctattggt caaggcaagg c                                            21

SEQ ID NO: 214          moltype = DNA  length = 20
FEATURE                 Location/Qualifiers
misc_feature            1..20
                        note = DNA sequence for transcribing crispr RNA
source                  1..20
                        mol_type = other DNA
                        organism = synthetic construct
SEQUENCE: 214
tttatcacag gctccaggaa                                              20

SEQ ID NO: 215          moltype = DNA  length = 20
FEATURE                 Location/Qualifiers
misc_feature            1..20
                        note = DNA sequence for transcribing crispr RNA
source                  1..20
                        mol_type = other DNA
                        organism = synthetic construct
SEQUENCE: 215
ttttatcaca ggctccagga                                              20

SEQ ID NO: 216          moltype = DNA  length = 34
FEATURE                 Location/Qualifiers
source                  1..34
                        mol_type = other DNA
                        organism = Francisella novicida
SEQUENCE: 216
cgacgcgtga agatcaaaa gtattgacga tgtc                               34

SEQ ID NO: 217          moltype = DNA  length = 30
FEATURE                 Location/Qualifiers
```

```
source                  1..30
                        mol_type = other DNA
                        organism = Francisella novicida
SEQUENCE: 217
agacctacct caggaactct aagccaggga                                        30

SEQ ID NO: 218          moltype = DNA   length = 34
FEATURE                 Location/Qualifiers
source                  1..34
                        mol_type = other DNA
                        organism = Francisella novicida
SEQUENCE: 218
cacggcaagt ttctggtgaa gagaaaaact tggg                                   34

SEQ ID NO: 219          moltype = DNA   length = 33
FEATURE                 Location/Qualifiers
source                  1..33
                        mol_type = other DNA
                        organism = Francisella novicida
SEQUENCE: 219
gtttgtactg atgggcagag agaagtcttt ccg                                    33

SEQ ID NO: 220          moltype = DNA   length = 33
FEATURE                 Location/Qualifiers
misc_feature            1..33
                        note = SDM primer
source                  1..33
                        mol_type = other DNA
                        organism = synthetic construct
SEQUENCE: 220
cgccccaagg tgcgagtcaa actggattac gtg                                    33

SEQ ID NO: 221          moltype = DNA   length = 33
FEATURE                 Location/Qualifiers
source                  1..33
                        mol_type = other DNA
                        organism = Francisella novicida
SEQUENCE: 221
acaatctatg cagagaatta cctgcctatc ctg                                    33

SEQ ID NO: 222          moltype = DNA   length = 35
FEATURE                 Location/Qualifiers
source                  1..35
                        mol_type = other DNA
                        organism = Francisella novicida
SEQUENCE: 222
atccctagtc atctgtctgt gtgtgtgtta aaccc                                  35

SEQ ID NO: 223          moltype = DNA   length = 34
FEATURE                 Location/Qualifiers
source                  1..34
                        mol_type = other DNA
                        organism = Francisella novicida
SEQUENCE: 223
tatcgcgtga aagatcaaaa gtattgacga tgtc                                   34

SEQ ID NO: 224          moltype = DNA   length = 34
FEATURE                 Location/Qualifiers
source                  1..34
                        mol_type = other DNA
                        organism = Francisella novicida
SEQUENCE: 224
cgaaagatca cactgcccctt caagaaagag tggc                                  34

SEQ ID NO: 225          moltype = DNA   length = 34
FEATURE                 Location/Qualifiers
source                  1..34
                        mol_type = other DNA
                        organism = Francisella novicida
SEQUENCE: 225
gcaggtcctg gacaaggatt caaacttcat catc                                   34

SEQ ID NO: 226          moltype = DNA   length = 34
FEATURE                 Location/Qualifiers
source                  1..34
                        mol_type = other DNA
                        organism = Francisella novicida
SEQUENCE: 226
aaaaagatca cactgcccctt caagaaagag tggc                                  34
```

```
SEQ ID NO: 227         moltype = DNA  length = 35
FEATURE                Location/Qualifiers
source                 1..35
                       mol_type = other DNA
                       organism = Francisella novicida
SEQUENCE: 227
agggagggca agtttctggt gaagagaaaa acttg                                35

SEQ ID NO: 228         moltype = DNA  length = 33
FEATURE                Location/Qualifiers
source                 1..33
                       mol_type = other DNA
                       organism = Francisella novicida
SEQUENCE: 228
tgtactgatg ggcagagaga agtctttccg gac                                  33

SEQ ID NO: 229         moltype = DNA  length = 35
FEATURE                Location/Qualifiers
source                 1..35
                       mol_type = other DNA
                       organism = Francisella novicida
SEQUENCE: 229
tacgagggca agtttctggt gaagagaaaa acttg                                35

SEQ ID NO: 230         moltype = DNA  length = 35
FEATURE                Location/Qualifiers
source                 1..35
                       mol_type = other DNA
                       organism = Francisella novicida
SEQUENCE: 230
gtgtttctgg tgaagagaaa aacttgggat aataa                                35

SEQ ID NO: 231         moltype = DNA  length = 33
FEATURE                Location/Qualifiers
source                 1..33
                       mol_type = other DNA
                       organism = Francisella novicida
SEQUENCE: 231
gccctcgttt gtactgatgg gcagagagaa gtc                                  33

SEQ ID NO: 232         moltype = DNA  length = 34
FEATURE                Location/Qualifiers
source                 1..34
                       mol_type = other DNA
                       organism = Francisella novicida
SEQUENCE: 232
accagggcag acgggactaa acccttcatt cctg                                 34

SEQ ID NO: 233         moltype = DNA  length = 31
FEATURE                Location/Qualifiers
source                 1..31
                       mol_type = other DNA
                       organism = Francisella novicida
SEQUENCE: 233
atctgagtca ttcagaatct ggtagatgaa g                                    31

SEQ ID NO: 234         moltype = DNA  length = 33
FEATURE                Location/Qualifiers
source                 1..33
                       mol_type = other DNA
                       organism = Francisella novicida
SEQUENCE: 234
gtgaactcac gccccaaggt gcgagtcaaa ctg                                  33

SEQ ID NO: 235         moltype = DNA  length = 31
FEATURE                Location/Qualifiers
source                 1..31
                       mol_type = other DNA
                       organism = Francisella novicida
SEQUENCE: 235
cggcattgct accattcagt acaagatcga c                                    31

SEQ ID NO: 236         moltype = DNA  length = 33
FEATURE                Location/Qualifiers
source                 1..33
                       mol_type = other DNA
                       organism = Francisella novicida
SEQUENCE: 236
```

-continued

```
caccccgaca aagtcctgga gatcctgaag cag                              33

SEQ ID NO: 237          moltype = DNA  length = 34
FEATURE                 Location/Qualifiers
source                  1..34
                        mol_type = other DNA
                        organism = Francisella novicida
SEQUENCE: 237
ccggctcttc agcagtgagt gattcatgaa atag                             34

SEQ ID NO: 238          moltype = DNA  length = 33
FEATURE                 Location/Qualifiers
source                  1..33
                        mol_type = other DNA
                        organism = Francisella novicida
SEQUENCE: 238
cggcccgaca aagtcctgga gatcctgaag cag                              33

SEQ ID NO: 239          moltype = DNA  length = 33
FEATURE                 Location/Qualifiers
source                  1..33
                        mol_type = other DNA
                        organism = Francisella novicida
SEQUENCE: 239
cacagttcag ggtttaacaa aactattaag gag                              33

SEQ ID NO: 240          moltype = DNA  length = 33
FEATURE                 Location/Qualifiers
source                  1..33
                        mol_type = other DNA
                        organism = Francisella novicida
SEQUENCE: 240
gaactcaatg attgtgctct gcttcaggat ctc                              33

SEQ ID NO: 241          moltype = DNA  length = 33
FEATURE                 Location/Qualifiers
source                  1..33
                        mol_type = other DNA
                        organism = Francisella novicida
SEQUENCE: 241
actcccaagg tgcgagtcaa actggattac gtg                              33

SEQ ID NO: 242          moltype = DNA  length = 33
FEATURE                 Location/Qualifiers
source                  1..33
                        mol_type = other DNA
                        organism = Francisella novicida
SEQUENCE: 242
tgagttattg tcgatcttgt actgaatggt agc                              33

SEQ ID NO: 243          moltype = DNA  length = 32
FEATURE                 Location/Qualifiers
source                  1..32
                        mol_type = other DNA
                        organism = Francisella novicida
SEQUENCE: 243
tataacacac acagacagat gactagggat gg                               32

SEQ ID NO: 244          moltype = DNA  length = 31
FEATURE                 Location/Qualifiers
source                  1..31
                        mol_type = other DNA
                        organism = Francisella novicida
SEQUENCE: 244
cccttcaata gctttctttc tgaccagttt c                                31

SEQ ID NO: 245          moltype = DNA  length = 34
FEATURE                 Location/Qualifiers
source                  1..34
                        mol_type = other DNA
                        organism = Francisella novicida
SEQUENCE: 245
tttgacggga ctaaaccctt cattcctgcc tttg                             34

SEQ ID NO: 246          moltype = DNA  length = 34
FEATURE                 Location/Qualifiers
source                  1..34
                        mol_type = other DNA
                        organism = Francisella novicida
```

```
SEQUENCE: 246
cctgctatct gagtcattca gaatctggta gatg                                      34

SEQ ID NO: 247         moltype = DNA  length = 32
FEATURE                Location/Qualifiers
source                 1..32
                       mol_type = other DNA
                       organism = Francisella novicida
SEQUENCE: 247
catttcacct caaaaaacat cttttggctg cc                                        32

SEQ ID NO: 248         moltype = DNA  length = 32
FEATURE                Location/Qualifiers
source                 1..32
                       mol_type = other DNA
                       organism = Francisella novicida
SEQUENCE: 248
gtcaatgatg gcttccacaa tctcgttctt gc                                        32

SEQ ID NO: 249         moltype = DNA  length = 33
FEATURE                Location/Qualifiers
source                 1..33
                       mol_type = other DNA
                       organism = Francisella novicida
SEQUENCE: 249
cgtctgctga agagccggta tcccgacaaa gtc                                       33

SEQ ID NO: 250         moltype = DNA  length = 34
FEATURE                Location/Qualifiers
source                 1..34
                       mol_type = other DNA
                       organism = Francisella novicida
SEQUENCE: 250
gtgattcatg aaatagttaa tcttgctgtc atcg                                      34

SEQ ID NO: 251         moltype = DNA  length = 33
FEATURE                Location/Qualifiers
source                 1..33
                       mol_type = other DNA
                       organism = Francisella novicida
SEQUENCE: 251
cgtagccggt atcccgacaa agtcctggag atc                                       33

SEQ ID NO: 252         moltype = DNA  length = 35
FEATURE                Location/Qualifiers
source                 1..35
                       mol_type = other DNA
                       organism = Francisella novicida
SEQUENCE: 252
cagcagtgag tgattcatga aatagttaat cttgc                                     35

SEQ ID NO: 253         moltype = DNA  length = 34
FEATURE                Location/Qualifiers
source                 1..34
                       mol_type = other DNA
                       organism = Francisella novicida
SEQUENCE: 253
gtgactatta aggagatgct gggaatgaag ctgg                                      34

SEQ ID NO: 254         moltype = DNA  length = 34
FEATURE                Location/Qualifiers
source                 1..34
                       mol_type = other DNA
                       organism = Francisella novicida
SEQUENCE: 254
gttaaaccct gaactttcga actcaatgat tgtg                                      34

SEQ ID NO: 255         moltype = DNA  length = 34
FEATURE                Location/Qualifiers
source                 1..34
                       mol_type = other DNA
                       organism = Francisella novicida
SEQUENCE: 255
tctactatta aggagatgct gggaatgaag ctgg                                      34

SEQ ID NO: 256         moltype = DNA  length = 34
FEATURE                Location/Qualifiers
source                 1..34
                       mol_type = other DNA
```

```
                       organism = Francisella novicida
SEQUENCE: 256
aacactatta aggagatgct gggaatgaag ctgg                              34

SEQ ID NO: 257         moltype = DNA   length = 35
FEATURE                Location/Qualifiers
source                 1..35
                       mol_type = other DNA
                       organism = Francisella novicida
SEQUENCE: 257
tttgggttta acaaaactat taaggagatg ctggg                             35

SEQ ID NO: 258         moltype = DNA   length = 34
FEATURE                Location/Qualifiers
source                 1..34
                       mol_type = other DNA
                       organism = Francisella novicida
SEQUENCE: 258
actttcgaac tcaatgattg tgctctgctt cagg                              34

SEQ ID NO: 259         moltype = DNA   length = 35
FEATURE                Location/Qualifiers
source                 1..35
                       mol_type = other DNA
                       organism = Francisella novicida
SEQUENCE: 259
cgtgggttta acaaaactat taaggagatg ctggg                             35

SEQ ID NO: 260         moltype = DNA   length = 34
FEATURE                Location/Qualifiers
source                 1..34
                       mol_type = other DNA
                       organism = Francisella novicida
SEQUENCE: 260
cgttcaaact tcatcatcgg aaagatcaca ctgc                              34

SEQ ID NO: 261         moltype = DNA   length = 35
FEATURE                Location/Qualifiers
source                 1..35
                       mol_type = other DNA
                       organism = Francisella novicida
SEQUENCE: 261
tctcttgtcc aggacctgct tgacatcgtc aatac                             35

SEQ ID NO: 262         moltype = DNA   length = 33
FEATURE                Location/Qualifiers
source                 1..33
                       mol_type = other DNA
                       organism = Francisella novicida
SEQUENCE: 262
cagcccaagg tgcgagtcaa actggattac gtg                               33

SEQ ID NO: 263         moltype = DNA   length = 35
FEATURE                Location/Qualifiers
source                 1..35
                       mol_type = other DNA
                       organism = Francisella novicida
SEQUENCE: 263
ctggcttata ggtctaggcg cgtgaagatc aaaag                             35

SEQ ID NO: 264         moltype = DNA   length = 35
FEATURE                Location/Qualifiers
source                 1..35
                       mol_type = other DNA
                       organism = Francisella novicida
SEQUENCE: 264
cttttgatct tcacgcgcct agacctataa gccag                             35

SEQ ID NO: 265         moltype = DNA   length = 44
FEATURE                Location/Qualifiers
source                 1..44
                       mol_type = other DNA
                       organism = Francisella novicida
SEQUENCE: 265
cagagcacaa tcattgagtt ccacagttca gggtttaaca aaac                   44

SEQ ID NO: 266         moltype = DNA   length = 44
FEATURE                Location/Qualifiers
source                 1..44
```

```
                        mol_type = other DNA
                        organism = Francisella novicida
SEQUENCE: 266
gttttgttaa accctgaact gtggaactca atgattgtgc tctg              44

SEQ ID NO: 267          moltype = DNA  length = 35
FEATURE                 Location/Qualifiers
source                  1..35
                        mol_type = other DNA
                        organism = Francisella novicida
SEQUENCE: 267
ctggcttata ggtctaggcg cgtgaagatc aaaag                        35

SEQ ID NO: 268          moltype = DNA  length = 35
FEATURE                 Location/Qualifiers
source                  1..35
                        mol_type = other DNA
                        organism = Francisella novicida
SEQUENCE: 268
cttttgatct tcacgcgcct agacctataa gccag                        35

SEQ ID NO: 269          moltype = DNA  length = 44
FEATURE                 Location/Qualifiers
source                  1..44
                        mol_type = other DNA
                        organism = Francisella novicida
SEQUENCE: 269
cagagcacaa tcattgagtt ccacagttca gggtttaaca aaac              44

SEQ ID NO: 270          moltype = DNA  length = 44
FEATURE                 Location/Qualifiers
source                  1..44
                        mol_type = other DNA
                        organism = Francisella novicida
SEQUENCE: 270
gttttgttaa accctgaact gtggaactca atgattgtgc tctg              44

SEQ ID NO: 271          moltype = DNA  length = 38
FEATURE                 Location/Qualifiers
misc_feature            1..38
                        note = Mammalian sequence for insertion to engineered
                        backbone
source                  1..38
                        mol_type = other DNA
                        organism = synthetic construct
SEQUENCE: 271
gacagatgac tagggatacc atctatgcag agaattac                     38

SEQ ID NO: 272          moltype = DNA  length = 38
FEATURE                 Location/Qualifiers
misc_feature            1..38
                        note = Mammalian sequence for insertion to engineered
                        backbone
source                  1..38
                        mol_type = other DNA
                        organism = synthetic construct
SEQUENCE: 272
gtaattctct gcatagatgg tatccctagt catctgtc                     38

SEQ ID NO: 273          moltype = DNA  length = 39
FEATURE                 Location/Qualifiers
misc_feature            1..39
                        note = Mammalian sequence for insertion to engineered
                        backbone
source                  1..39
                        mol_type = other DNA
                        organism = synthetic construct
SEQUENCE: 273
ctgcccatca gtacaaacca cggcaagttt ctggtgaag                    39

SEQ ID NO: 274          moltype = DNA  length = 39
FEATURE                 Location/Qualifiers
misc_feature            1..39
                        note = Mammalian sequence for insertion to engineered
                        backbone
source                  1..39
                        mol_type = other DNA
                        organism = synthetic construct
SEQUENCE: 274
```
cttcaccaga aacttgccgt ggtttgtact gatgggcag                                   39

SEQ ID NO: 275          moltype = DNA   length = 36
FEATURE                 Location/Qualifiers
source                  1..36
                        mol_type = other DNA
                        organism = Francisella novicida
SEQUENCE: 275
gccaccacta tagccgtcag taataaaaga gaatcc                                      36

SEQ ID NO: 276          moltype = DNA   length = 38
FEATURE                 Location/Qualifiers
source                  1..38
                        mol_type = other DNA
                        organism = Francisella novicida
SEQUENCE: 276
ggttcagcag tcaataagat caaaagcgag atggcatc                                    38

SEQ ID NO: 277          moltype = DNA   length = 72
FEATURE                 Location/Qualifiers
misc_feature            1..72
                        note = SDM primer
source                  1..72
                        mol_type = other DNA
                        organism = synthetic construct
SEQUENCE: 277
taatacgact cactatagta acggcagact tctcctcgtt tcagttgcgc cgaaaggcgc            60
tctgtaatca tt                                                                72

SEQ ID NO: 278          moltype = DNA   length = 20
FEATURE                 Location/Qualifiers
misc_feature            1..20
                        note = oligonucleotide
source                  1..20
                        mol_type = other DNA
                        organism = synthetic construct
SEQUENCE: 278
tctccacatg cccagtttct                                                        20

SEQ ID NO: 279          moltype = DNA   length = 20
FEATURE                 Location/Qualifiers
misc_feature            1..20
                        note = oligonucleotide
source                  1..20
                        mol_type = other DNA
                        organism = synthetic construct
SEQUENCE: 279
agtcagggca gagccatcta                                                        20

SEQ ID NO: 280          moltype = DNA   length = 73
FEATURE                 Location/Qualifiers
misc_feature            1..73
                        note = oligonucleotide
source                  1..73
                        mol_type = other DNA
                        organism = synthetic construct
SEQUENCE: 280
cagacgtgtc aaacagaggt ccgttcaaaa tacttttaaa tgattacaga gcgcctttcg            60
gcgcaactga aac                                                               73

SEQ ID NO: 281          moltype = DNA   length = 30
FEATURE                 Location/Qualifiers
source                  1..30
                        mol_type = other DNA
                        organism = Homo sapiens
SEQUENCE: 281
tgtgggtgag tgagtgtgtg cgtgtggggt                                             30

SEQ ID NO: 282          moltype = DNA   length = 30
FEATURE                 Location/Qualifiers
source                  1..30
                        mol_type = other DNA
                        organism = Homo sapiens
SEQUENCE: 282
accccacacg cacacactca ctcacccaca                                             30

SEQ ID NO: 283          moltype = DNA   length = 20
FEATURE                 Location/Qualifiers
source                  1..20

```
                        mol_type = other DNA
                        organism = Homo sapiens
SEQUENCE: 283
actcctaagc cagtgccaga                                              20

SEQ ID NO: 284          moltype = DNA   length = 21
FEATURE                 Location/Qualifiers
source                  1..21
                        mol_type = other DNA
                        organism = Homo sapiens
SEQUENCE: 284
ggcagagaga gtcagtgcct a                                            21

SEQ ID NO: 285          moltype = DNA   length = 53
FEATURE                 Location/Qualifiers
source                  1..53
                        mol_type = other DNA
                        organism = Homo sapiens
SEQUENCE: 285
tcgtcggcag cgtcagatgt gtataagaga caggcctcct gagtttctca tct         53

SEQ ID NO: 286          moltype = DNA   length = 54
FEATURE                 Location/Qualifiers
source                  1..54
                        mol_type = other DNA
                        organism = Homo sapiens
SEQUENCE: 286
gtctcgtggg ctcggagatg tgtataagag acaggttgcc caccctagtc attg        54

SEQ ID NO: 287          moltype = DNA   length = 54
FEATURE                 Location/Qualifiers
source                  1..54
                        mol_type = other DNA
                        organism = Homo sapiens
SEQUENCE: 287
tcgtcggcag cgtcagatgt gtataagaga cagccatctt ggggttacag aaag        54

SEQ ID NO: 288          moltype = DNA   length = 58
FEATURE                 Location/Qualifiers
source                  1..58
                        mol_type = other DNA
                        organism = Homo sapiens
SEQUENCE: 288
gtctcgtggg ctcggagatg tgtataagag acaggaaaca tttaccatag actatcac    58

SEQ ID NO: 289          moltype = DNA   length = 53
FEATURE                 Location/Qualifiers
source                  1..53
                        mol_type = other DNA
                        organism = Homo sapiens
SEQUENCE: 289
tcgtcggcag cgtcagatgt gtataagaga cagtctccac atgcccagtt tct         53

SEQ ID NO: 290          moltype = DNA   length = 54
FEATURE                 Location/Qualifiers
source                  1..54
                        mol_type = other DNA
                        organism = Homo sapiens
SEQUENCE: 290
gtctcgtggg ctcggagatg tgtataagag acagagtcag ggcagagcca tcta        54

SEQ ID NO: 291          moltype = DNA   length = 53
FEATURE                 Location/Qualifiers
source                  1..53
                        mol_type = other DNA
                        organism = Homo sapiens
SEQUENCE: 291
tcgtcggcag cgtcagatgt gtataagaga caggaggggt tgctttcttg tga         53

SEQ ID NO: 292          moltype = DNA   length = 54
FEATURE                 Location/Qualifiers
source                  1..54
                        mol_type = other DNA
                        organism = Homo sapiens
SEQUENCE: 292
gtctcgtggg ctcggagatg tgtataagag acagatgcac acagtggagc cttc        54

SEQ ID NO: 293          moltype = DNA   length = 52
FEATURE                 Location/Qualifiers
```

```
source                  1..52
                        mol_type = other DNA
                        organism = Homo sapiens
SEQUENCE: 293
tcgtcggcag cgtcagatgt gtataagaga cagtagggct agaggggtga gg          52

SEQ ID NO: 294          moltype = DNA   length = 54
FEATURE                 Location/Qualifiers
source                  1..54
                        mol_type = other DNA
                        organism = Homo sapiens
SEQUENCE: 294
gtctcgtggg ctcggagatg tgtataagag acagaagcac tgtgggtacg aagg        54

SEQ ID NO: 295          moltype = DNA   length = 53
FEATURE                 Location/Qualifiers
source                  1..53
                        mol_type = other DNA
                        organism = Homo sapiens
SEQUENCE: 295
tcgtcggcag cgtcagatgt gtataagaga caggcatgat actttggggg aga         53

SEQ ID NO: 296          moltype = DNA   length = 57
FEATURE                 Location/Qualifiers
source                  1..57
                        mol_type = other DNA
                        organism = Homo sapiens
SEQUENCE: 296
gtctcgtggg ctcggagatg tgtataagag acagcccaga aatttaattc caatcac     57

SEQ ID NO: 297          moltype = DNA   length = 52
FEATURE                 Location/Qualifiers
source                  1..52
                        mol_type = other DNA
                        organism = Homo sapiens
SEQUENCE: 297
tcgtcggcag cgtcagatgt gtataagaga cagccaggtg ctgacgtagg ta          52

SEQ ID NO: 298          moltype = DNA   length = 54
FEATURE                 Location/Qualifiers
source                  1..54
                        mol_type = other DNA
                        organism = Homo sapiens
SEQUENCE: 298
gtctcgtggg ctcggagatg tgtataagag acagtagcat tgcagagagg cgta        54

SEQ ID NO: 299          moltype = DNA   length = 53
FEATURE                 Location/Qualifiers
source                  1..53
                        mol_type = other DNA
                        organism = Homo sapiens
SEQUENCE: 299
tcgtcggcag cgtcagatgt gtataagaga cagcccactc tctcctgttc tgg         53

SEQ ID NO: 300          moltype = DNA   length = 54
FEATURE                 Location/Qualifiers
source                  1..54
                        mol_type = other DNA
                        organism = Homo sapiens
SEQUENCE: 300
gtctcgtggg ctcggagatg tgtataagag acagcccatt tctgtctcca cctc        54

SEQ ID NO: 301          moltype = DNA   length = 53
FEATURE                 Location/Qualifiers
misc_feature            1..53
                        note = for use in amplicon sequencing
source                  1..53
                        mol_type = other DNA
                        organism = synthetic construct
SEQUENCE: 301
tcgtcggcag cgtcagatgt gtataagaga cagttcccca cactatctca atg         53

SEQ ID NO: 302          moltype = DNA   length = 54
FEATURE                 Location/Qualifiers
misc_feature            1..54
                        note = for use in amplicon sequencing
source                  1..54
                        mol_type = other DNA
                        organism = synthetic construct
```

```
SEQUENCE: 302
gtctcgtggg ctcggagatg tgtataagag acagtattct tcatccctag ccag        54

SEQ ID NO: 303          moltype = DNA  length = 55
FEATURE                 Location/Qualifiers
misc_feature            1..55
                        note = for use in amplicon sequencing
source                  1..55
                        mol_type = other DNA
                        organism = synthetic construct
SEQUENCE: 303
tcgtcggcag cgtcagatgt gtataagaga caggccagaa aagagatatg gcatc        55

SEQ ID NO: 304          moltype = DNA  length = 53
FEATURE                 Location/Qualifiers
misc_feature            1..53
                        note = for use in amplicon sequencing
source                  1..53
                        mol_type = other DNA
                        organism = synthetic construct
SEQUENCE: 304
gtctcgtggg ctcggagatg tgtataagag acagccaccg atggagaggt ctg          53

SEQ ID NO: 305          moltype = RNA  length = 61
FEATURE                 Location/Qualifiers
misc_feature            1..61
                        note = trans-activating crispr RNA (tracrRNA)
source                  1..61
                        mol_type = other RNA
                        organism = synthetic construct
SEQUENCE: 305
gtaattaatg ctctgtaatc atttaaaagt attttgaacg gacctctgtt tgacacgtct  60
t                                                                  61
```